US009546207B2

(12) United States Patent
Kaempfer et al.

(10) Patent No.: US 9,546,207 B2
(45) Date of Patent: *Jan. 17, 2017

(54) BROAD-SPECTRUM IN-VIVO EFFECTIVE SUPERANTIGEN TOXIN ANTAGONISTS BASED ON THE INTERACTION BETWEEN CD28 AND THE SUPERANTIGEN AND USES THEREOF

(71) Applicant: Yissum Research Development Company of the Hebrew University of Jerusalem Ltd., Jerusalem (IL)

(72) Inventors: Raymond Kaempfer, Jerusalem (IL); Gila Arad, Mevasseret Zion (IL)

(73) Assignee: YISSUM RESEARCH DEVELOPMENT COMPANY OF THE HEBREW UNIVERSITY OF JERUSALEM LTD., Jerusalem (IL)

( * ) Notice: Subject to any disclaimer, the term of this patent is extended or adjusted under 35 U.S.C. 154(b) by 541 days.

This patent is subject to a terminal disclaimer.

(21) Appl. No.: 14/028,117

(22) Filed: Sep. 16, 2013

(65) Prior Publication Data

US 2014/0011731 A1 Jan. 9, 2014

Related U.S. Application Data

(60) Division of application No. 10/958,765, filed on Oct. 4, 2004, now Pat. No. 8,535,672, which is a continuation-in-part of application No. PCT/IL03/00278, filed on Apr. 3, 2003, and a continuation-in-part of application No. PCT/IL03/00839, filed on Oct. 15, 2003, and a continuation-in-part of application No. PCT/IL2004/000299, filed on Apr. 1, 2004.

(30) Foreign Application Priority Data

Apr. 4, 2002 (IL) .......................... 148993

(51) Int. Cl.
  C07K 16/28 (2006.01)
  C07K 14/74 (2006.01)
  A61K 39/395 (2006.01)
  C07K 14/705 (2006.01)

(52) U.S. Cl.
  CPC .............. C07K 14/70521 (2013.01)

(58) Field of Classification Search
  None
  See application file for complete search history.

(56) References Cited

U.S. PATENT DOCUMENTS

| 5,770,572 | A | 6/1998 | Gershoni |
| 5,932,556 | A | 8/1999 | Tam |
| 6,337,316 | B1 | 1/2002 | El Tayar et al. |
| 2003/0147908 | A1 | 8/2003 | Kaempfer |

FOREIGN PATENT DOCUMENTS

| CA | 2 389 911 A1 | 12/2003 |
| JP | 2003-377682 A | 7/2003 |
| WO | 92/15671 A1 | 9/1992 |
| WO | 97/37687 A1 | 10/1997 |
| WO | 98/29444 A1 | 7/1998 |
| WO | 02/074803 A2 | 9/2002 |
| WO | 02/096941 A2 | 12/2002 |
| WO | 03/084995 A1 | 10/2003 |
| WO | 03/084995 A2 | 10/2003 |

OTHER PUBLICATIONS

Eckert et al, "Inhibiting HIV-1 entry: discovery of D-peptide inhibitors that target the gp41 coiled-coil pocket," Cell 99 (1):103-115(1999).
Florquin et al, "Persistent production of TH2-type cytokines and polyclonal B cell activation after chronic administration of staphylococcal enterotoxin B in mice," J Autoimmun 9(5):609-615 (1996).
Fraser JD, "High-affinity binding of staphylococcal enterotoxins A and B to HLA-DR," Nature 339(6221 ):221-223 (1989).
Freeman et al, "Abstract B7-1 and B7-2 do not deliver identical costimulatory signals, since B7-2 but not B7-1 preferentially costimulates the initial production of IL-4," Immunity 2(5):523-532 (1995).
Friedler et al, "Development of a functional backbone cyclic mimetic of the HIV-1 Tat arginine-rich motif," J Bioi Chem 275 (31 ):23783-23789 (2000).
Gerez et al, "Hyperinducible expression of the interferon-gamma (IFN-gamma) gene and its suppression in systemic lupus erythematosus (SLE)," Clin Exp Immunol 109(2):296-303 (1997).
Gerez et al, "Regulation of interleukin-2 and interferon-gamma gene expression in renal failure," Kidney Int 40 (2):266-272 (1991).
Gerez et al, "Aberrant regulation of interleukin-2 but not of interferon-gamma gene expression in Down syndrome (trisomy 21)," Clin Immunol Immunopathol 58(2):251-266 (1991).

(Continued)

Primary Examiner — Robert A Zeman
(74) Attorney, Agent, or Firm — Browdy and Neimark, PLLC

(57) ABSTRACT

Disclosed are methods and compositions for the inhibition of modulation of T cell costimulatory pathway by a pathogenic agent, particularly, the inhibition of activation of a T cell costimulatory pathway by a pyrogenic exotoxin. The direct interaction of a superantigen with a specific site within the dimer interface of a CD28 family member is inhibited using immunomodulatory peptides. Specific antagonist immunomodulatory peptides comprise amino acid sequences derived from a dimer interface of a T cell costimulatory pathway member, or peptides which comprise an amino acid sequence which specifically binds to an amino acid sequence within the dimer interface of a T cell costimulatory pathway member. Compositions comprising said peptides and methods for the treatment of immune-related disorders are also disclosed. Such molecules may be used in screening for a test substance which specifically binds to the CD28 molecule and is capable of antagonizing pyrogenic exotoxin-mediated activation of Th1 lymphocytes.

3 Claims, 39 Drawing Sheets

(56) References Cited

OTHER PUBLICATIONS

Gilon et al, "Backbone cyclization: A new method for conferring conformational constraint on peptides," Biopolymers 31(6):745-750 (1991).
Grakoui et al, "The immunological synapse: a molecular machine controlling T cell activation," Science 285 (5425):221-227 ( 1999).
Greenfield et al, "CD28/B7 costimulation: a review," Crit Rev Immunol18(5):389-418 (1998).
Guinan et al, "Transplantation of anergic histoincompatible bone marrow allografts," N Engl J Med 340(22):1704-1714 (1999).
Guy et al, "No abstract Trifluoroacetic acid cleavage and deprotection of resin-bound peptides following synthesis by Fmoc chemistry," Methods Enzymol 289:67-83 (1997).
Hackett et al, "Superantigens associated with staphylococcal and streptococcal toxic shock syndrome are potent inducers of tumor necrosis factor-beta synthesis," J Infect Dis 168(1 ):232-235 (1993).
Hanawa et al, "A novel costimulatory signaling in human T lymphocytes by a splice variant of CD28," Blood 99 (6):2138-2145 (2002).
Hoffman M, "'Superantigens' may shed light on immune puzzle," Science 248(4956):685-686 (1990).
Hudson et al, "Staphylococcal enterotoxin A has two cooperative binding sites on major histocompatibility complex class II," J Exp Med 182(3):711-720 (1995).
Hutloff et al, "I COS is an inducible T-cell co-stimulator structurally and functionally related to CD28," Nature 397 (6716):263-266 (1999).
Ikejima et al, "Free in PMC Induction of human interleukin-1 by a product of *Staphylococcus aureus* associated with toxic shock syndrome," J Clin Invest 73(5):1312-1312 (May 1984).
Ikemizu et al, "Structure and dimerization of a soluble form of 87-1," Immunity 12(1 ):51-60 (2000).
Janeway et al, "Abstract Innate immune recognition," Annu Rev Immunol20:197-216 (2002).
Janeway et al, "T-cell responses to MIs and to bacterial proteins that mimic its behavior," Immunol Rev 107:61-88 (1989).
Jeannin et al, "Abstract Soluble CD86 is a costimulatory molecule for human T lymphocytes," Immunity 13 (3):303-312 (2000).
Jeti et al, "Identification of staphylococcal enterotoxin B sequences important for induction of lymphocyte proliferation by using synthetic peptide fragments of the toxin," Infect Immun 62(8):3408-3415 (1994).
Kaempfer et al, "Prediction of response to treatment in superficial bladder carcinoma through pattern of interleukin-2 gene expression," J Clin Oncol14(6):1778-1786 (1996).
Muraille et al, "Costimulation regulates the kinetics of interleukin-2 response to bacterial superantigens," Immunology 89(2):245-249 (1996).
Muraille et al, "87.2 provides co-stimulatory functions in vivo in response to staphylococcal enterotoxin B," Eur J Immunol25(7):2111-2114 (1995).
Muraille et al, "Co-stimulation lowers the threshold for activation of naive T cells by bacterial superantigens," Int Immunol 7(2):295-304 (1995).
Murray et al, "Staphylococcal and streptococcal superantigens: their role in human disease," ASM News 61 (5):229-235 (1995).
Nagelkerken et al, "Role of transforming growth factor-beta in the preferential induction ofT helper cells of type 1 by staphylococcal enterotoxin B," Eur J Immuno123(9):2306-2310 (1993).
Oosterom et al, "Conformation of the core sequence in melanocortin peptides directs selectivity for the melanocortin MC3 and MC4 receptors," J Bioi Chern 274(24):16853-16860 (1999).
Oosterwegel et al, "CTLA-4 and T cell activation," Curr Opin Immunoll 1(3):294-300 (1999).
Ostrov et al, "Structure of murine CTLA-4 and its role in modulating T cell responsiveness," Science 290 (5492):816-981 (2000).
Papageorgiou et al, "Structural basis for the recognition of superantigen streptococcal pyrogenic exotoxin a (SpeA1) by MHC class II molecules and T-cell receptors," EMBO J 18(1):9-21 (1999).
Papageorgiou et al. "Crystal structure of microbial superantigen staphylococcal enterotoxin Bat 1.5 A resolution: implications for superantigen recognition by MHC class II molecules and T-cell receptors," J Mol Biol277(1):61-79 D (1998).
Pappenheimer et al, "Free in PMC Intestinal absorption and excretion of octapeptides composed of D amino acids," Proc Natl Acad Sci USA 91(5):1942-1945 (1994).
Pinto et al, "Suppression of the in vivo humoral and cellular immune response by staphylococcal enterotoxin B (SEB)," Transplantation 25(6):320-323 (1978).
Poindexter et al, "Suppression of immunoglobulin-secreting cells from human peripheral blood by toxic-shock-syndrome toxin-1 ," J Infect Dis 153(4):772-779 (1986).
Ptachcinski et al, "Clinical pharmacokinetics of cyclosporin," Clin Pharmacokinet 11 (2): 107-132 (1986).
Redpath et al, "Cutting edge: trimolecular interaction of TCR with MHC class II and bacterial superantigen shows a similar affinity to MHC:peptide ligands," J Immunol163(1):6-10 (1999).
Rudd et al, "Unifying concepts in CD28, ICOS and CTLA4 co-receptor signalling," Nat Rev Immunol 3(7):544-556 (2003).
Saha et al, "Protection against lethal toxic shock by targeted disruption of the CD28 gene," J Exp Med 183 (6):2675-2680 (1996).
Salomon et al, "Complexities of CD28/B7: CTLA-4 costimulatory pathways in autoimmunity and transplantation," Annu Rev Immunol19:225-252 (2001).
Sancho et al, "CD3-zeta surface expression is required for CD4-p561ck-mediated upregulation ofT cell antigen receptor-CD3 signaling in T cells," J Bioi Chern 267(11 ):7871-7879 (1992).
Sansom et al, "What's the difference between CD80 and CD86?," Trends Immunol24(6):314-319 (2003).
Schad et al, "Crystal structure of the superantigen staphylococcal enterotoxin type A," EMBO J 14(14):3292-3301 (1995).
Schlievert PM, "Will therapeutic peplides be kryptonite for superantigens?," Nat Med 6(4):378-379 (2000).
Schlievert PM, "Role of superantigens in human disease," J Infect Dis 167(5):997-1002 (1993).
Schnolzer et al, In situ neutralization in Soc-chemistry solid phase peptide synthesis. Rapid, high yield assembly of difficult sequences, in! J Pep! Protein Res 40(3-4):180-193 (1992).
Scholl et al, "Toxic shock syndrome toxin 1 binds to major histocompatibility complex class II molecules," Proc Nail Acad Sci USA 86(11):4210-4214 (1989).
Schroeijers et al, "The Mr 193,000 vault protein is up-regulated in mullidrug-resistant cancer cell lines," Cancer Res 60(4):1104-1110 (2000).
Abrahmsen et al, "Characterization of two distinct MHC class II binding sites in the superantigen staphylococcal enterotoxin A," EMBO J 14(13):2978-2986 (1995).
Acuto et al, "CD28-mediated co-stimulation: a quantitative support for TCR signalling," Nat Rev Immunol 3 (12):939-951 (2003).
Akira et al, "Toll-like receptors: critical proteins linking innate and acquired immunity," Nat Immunol 2(8):675-680 (2001).
Altstein et al, "Backbone cyclic peptide antagonists, derived from the insect pheromone biosynthesis activating neuropeptide, inhibit sex pheromone biosynthesis in moths," Bioi Chem 274(25):17573-17579 (1999).
Andersen et al, "Role of the T cell receptor ligand affinity in T cell activation by bacterial superantigens," J Bioi Chern 276(36):33452-33457 (2001).
Arad et al, "Superantigen antagonist blocks Th1 cytokine gene induction and lethal shock," J Leukoc Bioi 69 (6):921-927 (2001).
Arad et al, "Superantigen antagonist protects against lethal shock and defines a new domain forT-cell activation," Nat Med 6(4):414-421 (2000).
Arad et al, "Transient expression of human interleukin-2 and interferon-gamma genes is regulated by interaction between distinct cell subsets," CellImmunol160(2):240-247 (1995).

(56) References Cited

OTHER PUBLICATIONS

Aruffo et al, "Molecular cloning of a CD28 eDNA by a high-efficiency COS cell expression system, "Proc Natl Acad Sci USA 84(23):8573-8577 (1987).
Ben-Asouli et al, "Human interferon-gamma mRNA autoregulates its translation through a pseudoknot that activates the interferon-inducible protein kinase PKR, "Cell108(2):221-232 (2002).
Bitan et al, "Backbone cyclization of the C-terminal part of substance P. Part 1: The important role of the sulphur in position 11 ," J Pep! Sci 2(4):261-269 (1996).
Bohach et al, "Staphylococcal and streptococcal pyrogenic toxins involved in toxic shock syndrome and related illnesses," Crit Rev Microbiol17(4):251-272 (1990).
Brocke et al, "Induction of relapsing paralysis in experimental autoimmune encephalomyelitis by bacterial superantigen," Nature 365(6447):642-644 (1993).
Byk et al, "Synthesis and biological activity of NK-1 selective, N-backbone cyclic analogs of the C-terminal hexapeptide of substance P," J Med Chern 39(16):3174-3168 (1996).
Cardell et al, "Manipulation of the superantigen-induced lymphokine response. Selective induction of interleukin-10 or interferon-gamma synthesis in small resting CD4+ T cells," Eur J Immunol 23(2):523-529 (1993).
Carreno et al. "The 87 family of ligands and its receptors: new pathways for costimulation and inhibition of immune responses," Annu Rev Immunol 20:29-53 (2002).
Chang et al, in Signal Transduction Pathways in Autoimmunity, vol. 5, A. Altman (Ed.), Basel, Karger, pp. 113-130 (2002).
Choi et al, "Residues of the variable region of the T-cell-receptor beta-chain that interact with S. au reus toxin superantigens," Nature 346(6283):471-473 (1990).
Chomczynski et al, "Single-step method of RNA isolation by acid guanidinium thiocyanate-phenol-chloroform extraction," Anal Biochem 162(1):156-159 (1987).
Chorev et al, "Toward nonpeptidal substance P mimetic analogues: design, synthesis, and biological activity," Biopolymers 31(6):725-733 (1991).
Collins et al, "The interaction properties of costimulatory molecules revisited," Immunity 17(2):201-210 (2002).
Coyle et al, "The CD28-related molecule ICOS is required for effective T cell-dependent immune responses," Immunity 13(1 ):95-1 05 (2000).
De Samblanx et al, "Antifungal activity of synthetic 15-mer peptides based on the Rs-AFP2 (Raphanus sativus antifungal protein 2) sequence," Pep! Res 9(6):262-268 (1996).
Dintzis et al, "A comparison of the immunogen icily of a pair of enantiomeric proteins," Proteins 16(3):306-308 (1993).
Hemalatha et al.: "Superantigens- concepts, clinical disease and therapy." Indian Journal of Medical Microbiology pp. 204-211 (2004).
Bowie et al (Science, 1990, 257:1306-1310).
Greenspan et al. (Nature Biotechnology 7: 936-937, 1999.
Life et al. "CD28 functions as an adhesion molecule and is involved in the regulation of human IgE synthesis" Eur. J. D Immunol., 25:333-339 (1995).
Kapsogeorgou et al. "Functional Expression of a Costimulatory B7.2 (CD86) Protein on Human Salivary Gland Epithelial Cells that Interacts with the CD28 Receptor, but Has Reduced Binding to CTLA41" J. Immunol D 166:3107-3113 (2001).
Muraille et al., "Short Communication Activation of Murine T Cells by Bacterial Superantigens Requires B7-Mediated Costimulation" Cellular Immunol., 162:315-320 (1995).
Peach et al., "Complementarity Determining Region 1 (CDR1 )-and CDR3-analogous Regions in CTLA-4 and CD28 D Determine the Binding to B7-1" J. Exp. Med., 180:2049-2058 (1994).
Bork (Genome Research, 2000,1 0:398-400).
Schumacher et al, "Identification of D-peptide ligands through mirror-image phage display," Science 271 (5257):1854-1857 (1996).

Schwartz et al, "Structural basis for co-stimulation by the human CTLA-4/B7-2 complex," Nature 41 0 (6828):604-608 (2001).
Seth et al, "Binary and ternary complexes between T-cell receptor, class II MHC and superantigen in vitro," Nature 369(6478):324-327 (1994).
Sharpe et al, "The B7-CD28 superfamily," Nat Rev Immunol2(2):116-126 (2002).
Slootstra et al, "Structural aspects of antibody-antigen interaction revealed through small random peptide libraries," Mol Divers 1(2):87-96 (1996).
Smith et al, "The effect of staphylococcal enterotoxins on the primary in vitro immune response," J Immunol 115 (2):575-578 (1975).
Stamper et al, Crystal structure of the B7-1/CTLA-4 complex that inhibits human immune responses, Nature 410 (6828):608-611 (2001).
Sundberg et al, "Structures of two streptococcal superantigens bound to TCR bela chains reveal diversity in the architecture ofT cell signaling complexes," Structure 10(5):687-699 (2002).
Sundberg et al, "So many ways of getting in the way: diversity in the molecular architecture of superantigen-dependent T-cell signaling complexes," Curr Opin Immunol14(1):36-44 (2002).
Taylor et al, "Emetic action of staphylococcal enterotoxin A on weanling pigs," Infect Immun 36(3):1263-1266 (1982).
Toniolo C, "Conformationally restricted peplides through short-range cyclizations," In! J Pep! Protein Res 35 (4):287-300 (1990).
Tseng et al. "Humoral immunity to aerosolized staphylococcal enterotoxin B (SEB), a superantigen, in monkeys vaccinated with SEB toxoid-containing microspheres," Infect Immun 63(8):2880-2885 (1995).
Uchiyama et al, "Activation of murine T cells by toxic shock syndrome toxin-1. The toxin-binding structures expressed on murine accessory cells are MHC class II molecules," J Immunol 143(10):3175-3182 (1989).
Visvanathan et al, "Inhibition of bacterial superantigens by peptides and antibodies," Infect Immun 69(2):875-884 (2001).
Wahl et al, "Improved radioimaging and tumor localization with monoclonal F(ab')2," J Nucl Med 24(4):316-325 (1983).
Wang et al, "CD28 ligation prevents bacterial toxin-induced septic shock in mice by inducing IL-10 expression," J Immunol158(6):2856-2861 (1997).
Zhou et al, "T cells of staphylococcal enterotoxin B-tolerized autoimmune MRL-Ipr/Ipr mice require co-stimulation through the B7-CD28/CTLA-4 pathway for activation and can be reanergized in vivo by stimulation of the T cell D receptor in the absence of this co-stimulatory signal," Eur J Immunol24(5):1019-1025 (1994).
Kast et al, "Protection against lethal Sendai virus infection by in vivo priming of virus-specific cytotoxic T lymphocytes with a free synthetic peptide," Proc Nail Acad Sci USA 88(6):2283-2287 (1991).
Kast et al, "Eradication of adenovirus E1-induced tumors by EtA-specific cytotoxic T lymphocytes," Cell 59 (4):603-614 (1989).
Ketzinel et al, Regulation of human interleukin-2 and interferon-gamma gene expression by suppressor T lymphocytes, Scand J Immunol33(5):593-605 (1991).
Khoury et al, "The roles of the new negative T cell costimulatory pathways in regulating autoimmunity," Immunity 20(5):529-538 (2004).
Kieke et al, "High affinity T cell receptors from yeast display libraries block T cell activation by superantigens," J Mol Biol307(5):1305-1315 (2001).
Kline et al, "Analysis of the interaction between the bacterial superantigen streptococcal pyrogenic exotoxin a (SpeA) and the human T-cell receptor," Mol Microbiol 24(1 ):191-202 (1997).
Kohm et al, "Cutting edge: CD4+CD25+ regulatory T cells suppress antigen-specific autoreactive immune responses and central nervous system inftammation during active experimental autoimmune encephalomyelitis," J Immunol D 169(9):4712-16 (2002).
Krakauer T, "Differential inhibitory effects of interleukin-10, interleukin-4, and dexamethasone on staphylococcal enterotoxin-induced cytokine production and T cell activation," J Leukoc Bioi 57(3):450-454 (1995).

(56) References Cited

OTHER PUBLICATIONS

Krummel et al, "Superantigen responses and co-stimulation: CD28 and CTLA-4 have opposing effects on T cell expansion in vitro and in vivo," In! Immunol8(4):519-523 (1996).

Kuchroo et al, "87-1 and 87-2 costimulatory molecules activate differentially the Th1/Th2 developmental pathways: application to autoimmune disease therapy," Cell80(5):707-718 91995).

Langeveld et al, "First peptide vaccine providing protection against viral infection in the target animal: studies of canine parvovirus in dogs," J Virol68(7):4506-4513 (1994).

Leder et al, A mutational analysis of the binding of staphylococcal enterotoxins Band C3 to the T cell receptor beta chain and major histocompatibility complex class II, J Exp Med 187(6):823-833 (1998).

Len Schow et al, "CD28/B7 system ofT cell costimulation," Annu Rev Immunol14:233-258 (1996).

Li et al, "Structure-function studies ofT-cell receptor-superantigen interactions," Immunol Rev 163:177-186 ( 1998).

Linsley et al, "Binding stoichiometry of the cytotoxic T lymphocyte-associated molecule-4 (CTLA-4). A disulfide-linked homodimer binds two CD86 molecules," J Bioi Chern 270(25):15417-15424 (1995).

Lition et al, "Abstract Early expression of cytokines in lymph nodes after treatment in vivo with Staphylococcus enterotoxin B," J Immunol Methods 175(1):47-58 (1994).

Lowell et al, "Intranasal and intramuscular proteosome-staphylococcal enterotoxin B (SEB) toxoid vaccines: immunogenicity and efficacy against lethal SEB intoxication in mice," Infect Immun 64(5):1706-1713 (1996).

Luhder et al, "Topological requirements and signaling properties ofT cell-activating, anti-CD28 antibody superagonists," J Exp Med 197(8):955-966 (2003).

Marrack et al, "The staphylococcal enterotoxins and their relatives," Science 248(4956):705-711 (1990).

Marrack et al, "The toxicity of staphylococcal enterotoxin Bin mice is mediated by T cells," J Exp Med 171 (2):455-464 (1990).

Miethke et al, "T cell-mediated lethal shock triggered in mice by the superantigen staphylococcal enterotoxin B: critical role of tumor necrosis factor," J Exp Med 175(1):91-98 (1992).

Miller et al, Probing the structural basis of the catalytic activity of HIV-1 PR through total chemical protein synthesis J Molec Struc (Theochem) 423:137-152 (1998).

Mittrucker et al. "Induction of unresponsiveness and impaired T cell expansion by staphylococcal enterotoxin B in CD28-deficient mice." J Exp Med 183(6):2481-2488 (1996).

Mosmann et al. "TH1 and TH2 cells: different patterns of lymphokine secretion lead to different functional properties," Annu Rev Immunol7:145-173 (1989).

Friedler et al, "Backbone cyclic peptide, which mimics the nuclear localization signal of human immunodeficiency virus type 1 matrix protein, inhibits nuclear import and virus production in nondividing cells," Biochemistry 37 (16):5616-5622 (1998).

Zhang et al, "Structural and functional analysis of the costimulatory receptor programmed death-1," Immunity 20 (3):337-347 (2004).

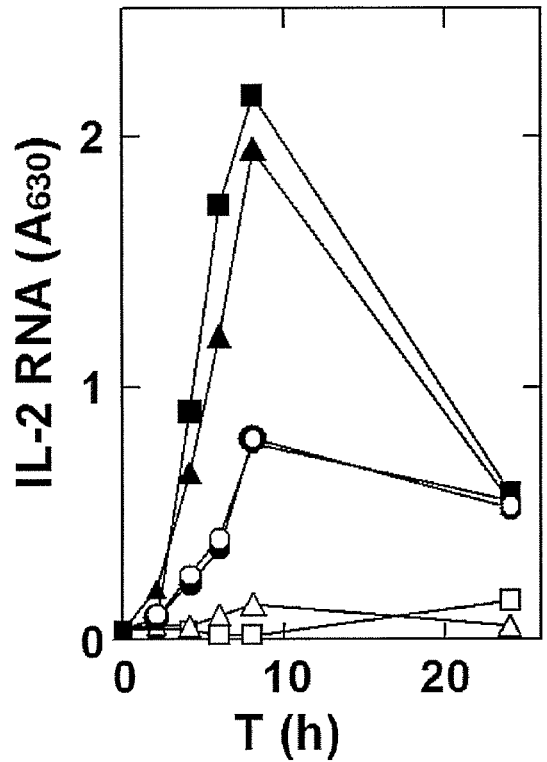
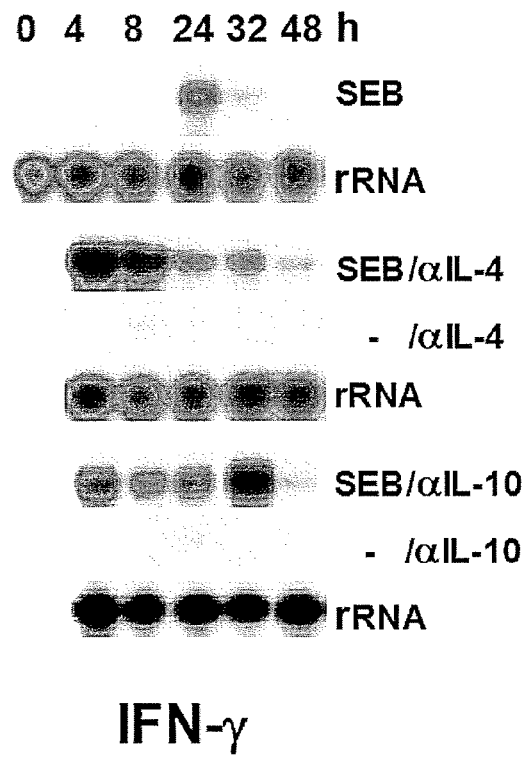
Fig. 2A
Fig. 2C
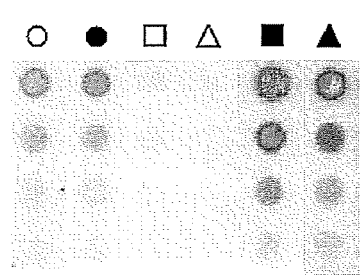
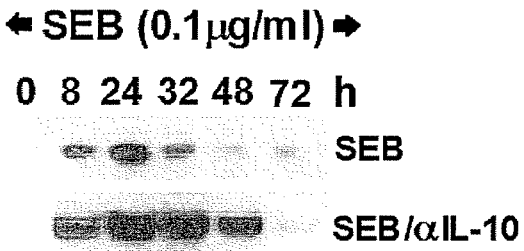
Fig. 2B
Fig. 2D

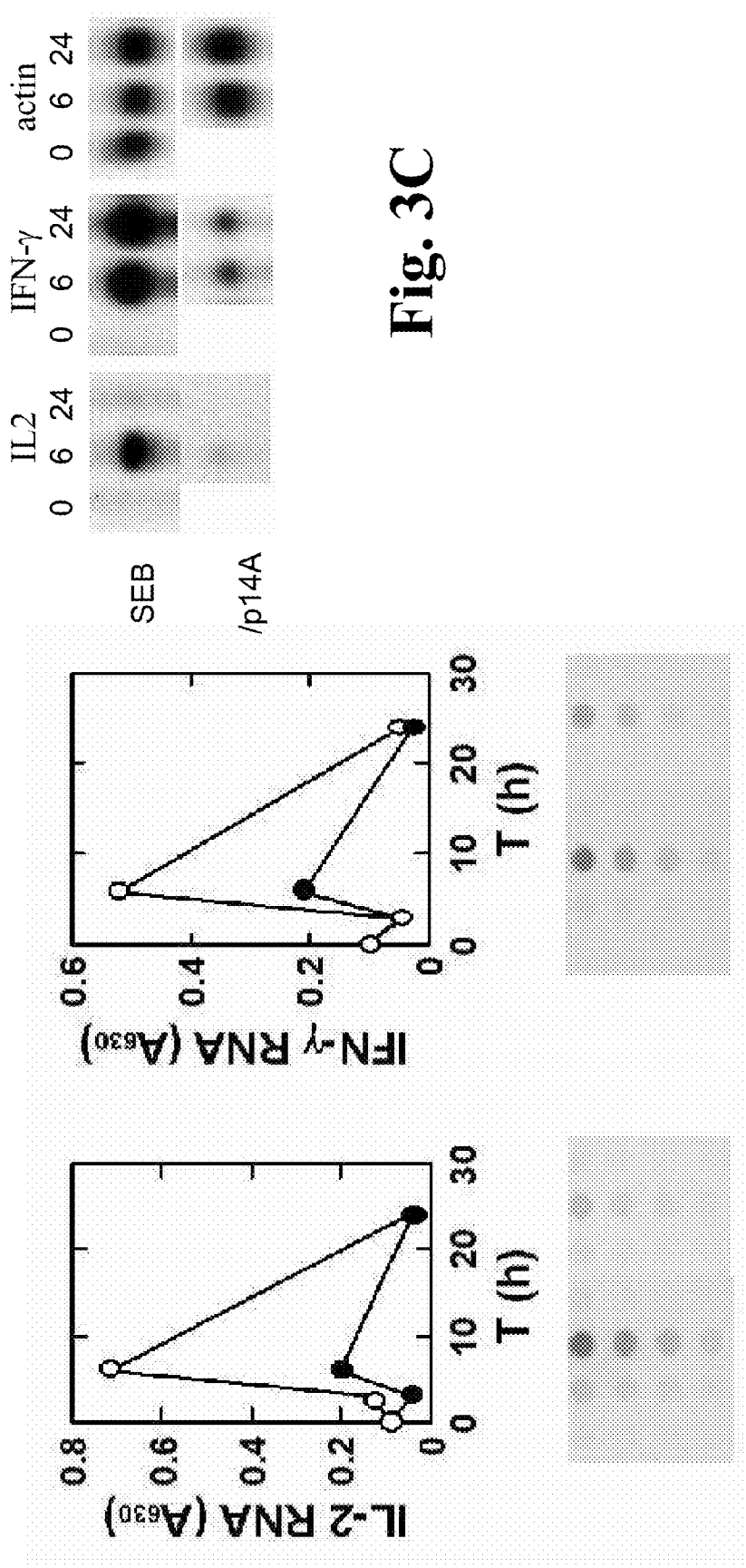

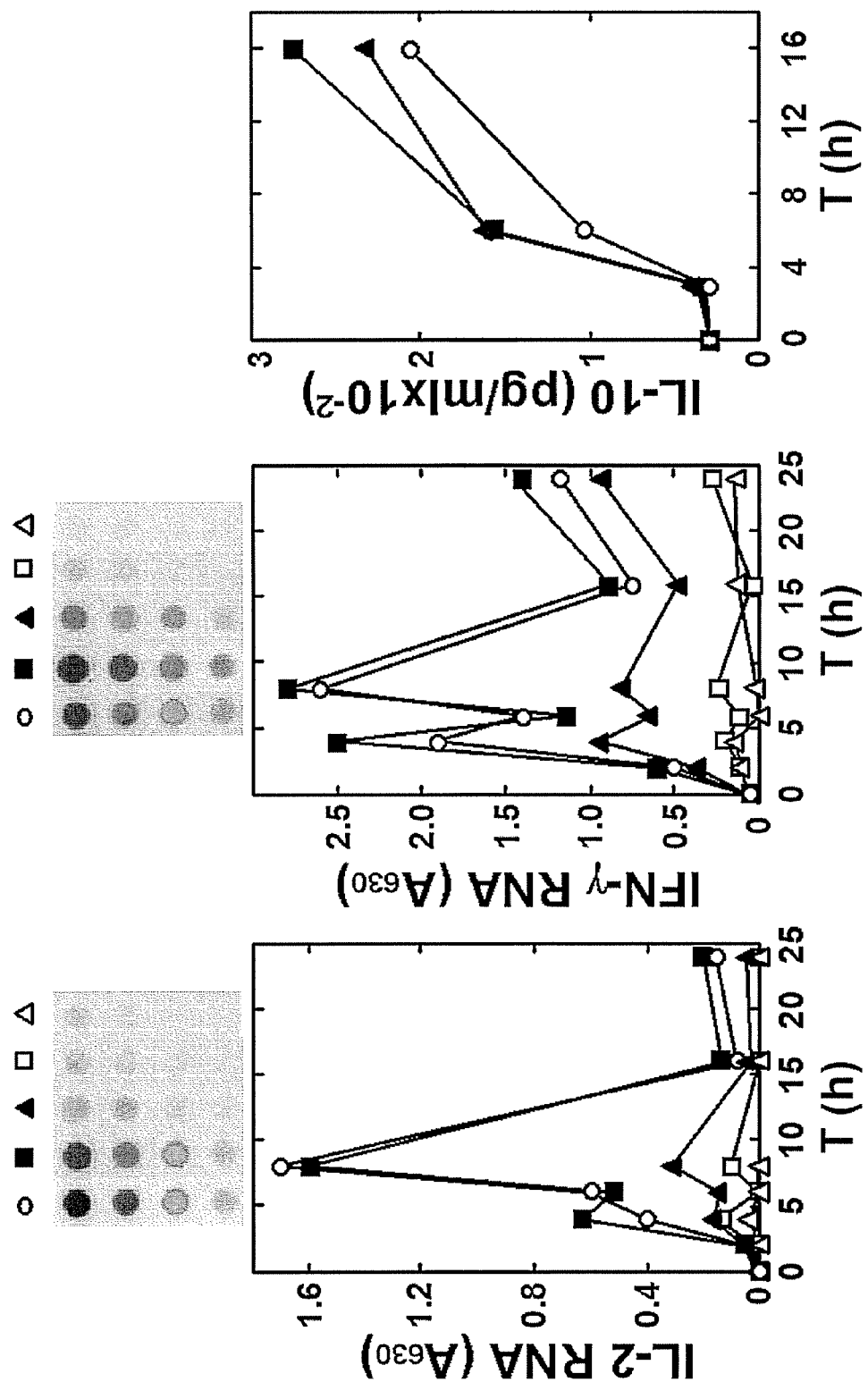

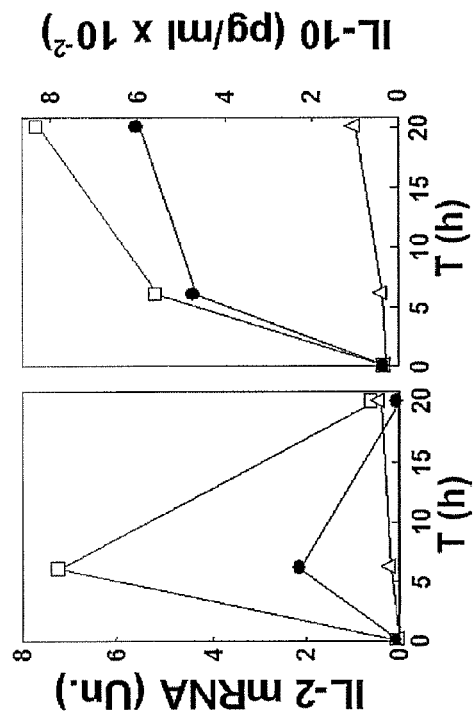
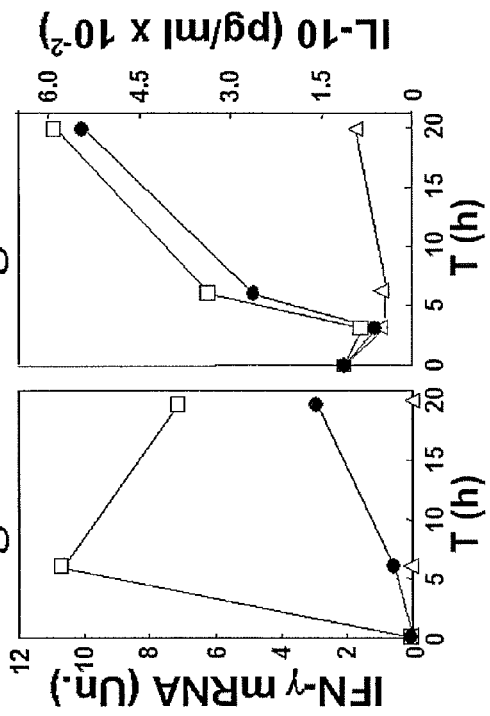
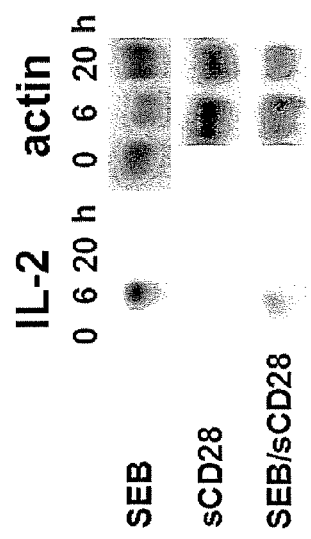
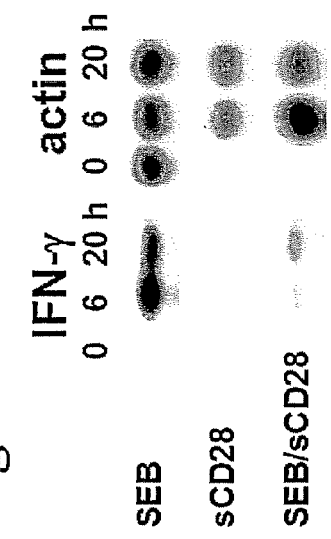
Fig. 7A  Fig. 7B  Fig. 7C
Fig. 7D  Fig. 7E  Fig. 7F

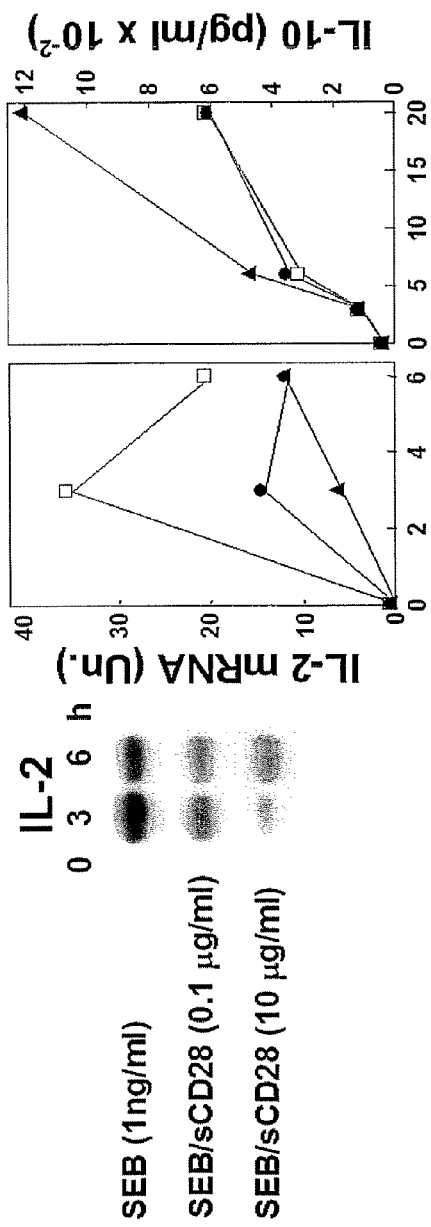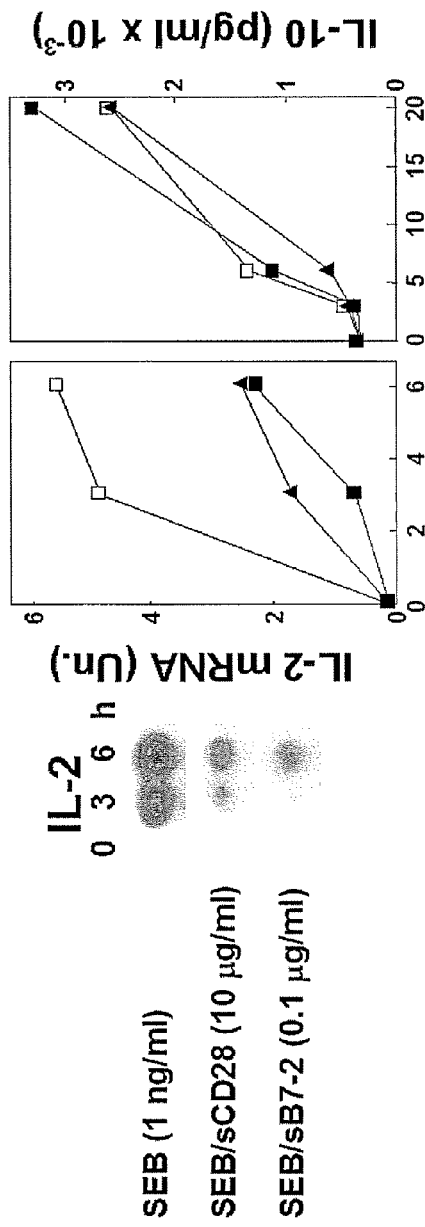
Fig. 8A
Fig. 8B
Fig. 8C
Fig. 8D
Fig. 8E
Fig. 8F

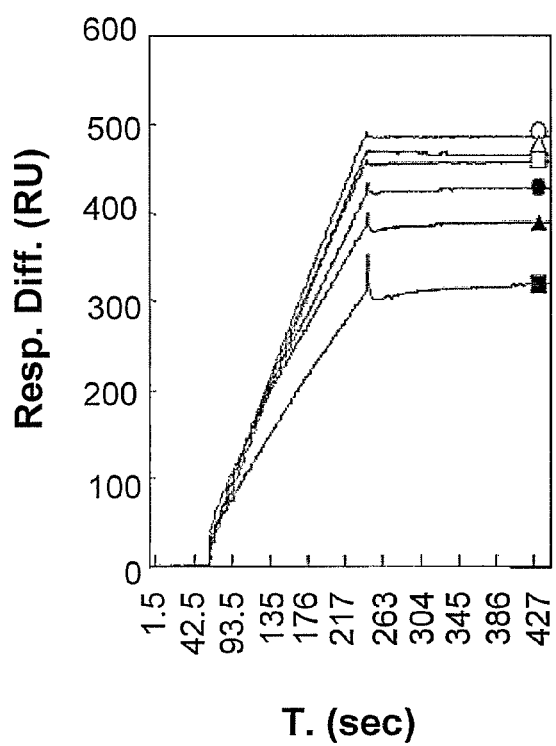
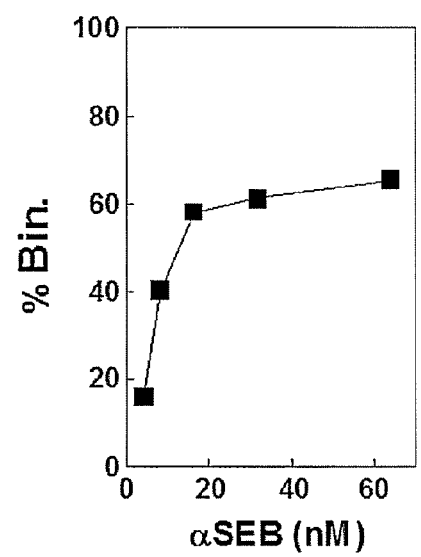
| αSEB (nM) | (RU) αSEB | (RU) αSEB/sCD28 | %Bin. |
|---|---|---|---|
| 4 | 242 | 39 | 16 |
| 8 | 445 | 179 | 40 |
| 16 | 810 | 469 | 58 |
| 32 | 1440 | 877 | 61 |
| 64 | 2346 | 1533 | 65 |
Fig. 18A     Fig. 18B

| No. | sCD28 conc. |
|---|---|
| 1 | 0.24 pg/ml |
| 2 | 2.4 pg/ml |
| 3 | 24 pg/ml |
| 5 | 2.4 ng/ml |
| 6 | 24 ng/ml |

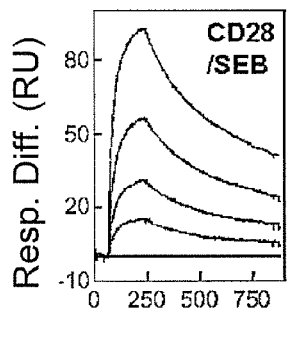
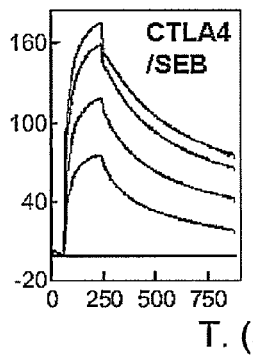
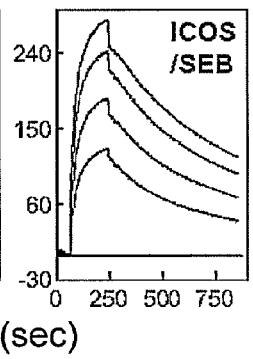
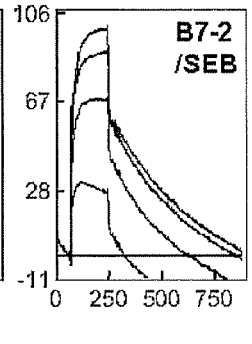
Fig. 22A   Fig. 22B   Fig. 22C   Fig. 22D
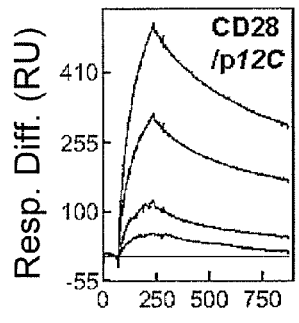
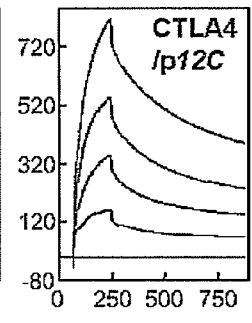
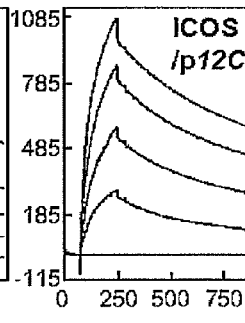
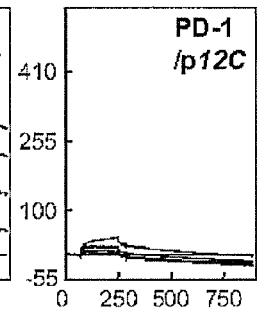
Fig. 22E   Fig. 22F   Fig. 22G   Fig. 22H
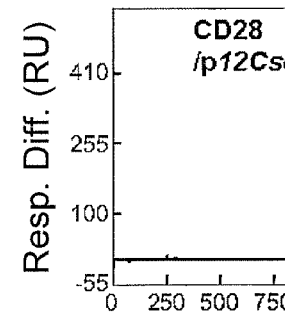
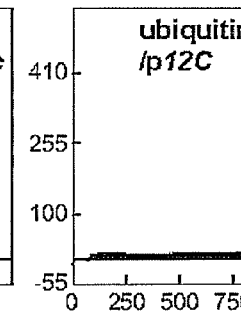
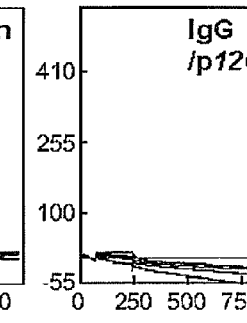
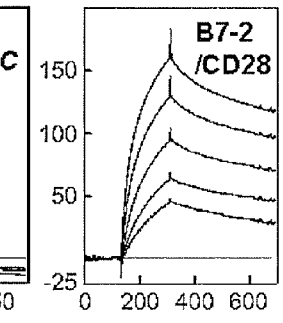
Fig. 22I   Fig. 22J   Fig. 22K   Fig. 22L

```
           1       8    15
hCD28    NKILVKQSPMLVAYDNAVN-LSCKYSYNLFSREFRASLHKGLDSAV-EVCVVYGNYSQQLQVYSK
mCD28    NKILVKQSPLLVVDSNEVS-LSCRYSYNLLAKEFRASLYKGVNSDV-EVCVGNGNFTYQPQFRSN
hCTLA4   KAMHVAQPAVVLASSRGIASFVCEYASPGKATEVRVTVLRQADSQVTEVCAATYMMGNELTFLDD
mCTLA4   EAIQVTQPSVVLASSHGVASFPCEYSPSHNTDEVRVTVLRQTNDQMTEVCATTFTEKNTVGFLDY
                                  97        105        116       124
hCD28    TGFNCDGKLGNESVTFYLQNLYVNQTDIYFCKIEVMYPPPYLDNEKSNGTII▓▓▓▓LCPSPL
mCD28    AEFNCDGDFDNETVTFRLWNLHVNHTDIYFCKIEFMYPPPYLDNERSNGTII▓▓▓▓LCHTQS
hCTLA4   S--ICTGTSSGNQVNLTIQGLRAMDTGLYICKVELMYPPPYYLG-IGNGTQI▓▓▓▓PCPDSD
mCTLA4   P--FCSGTFNESRVNLTIQGLRAVDTGLYLCKVELMYPPPYFVG-MGNGTQI▓▓▓▓PCPDSD
```

Fig. 24A

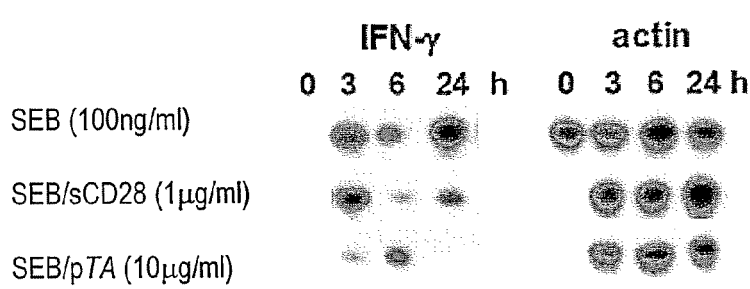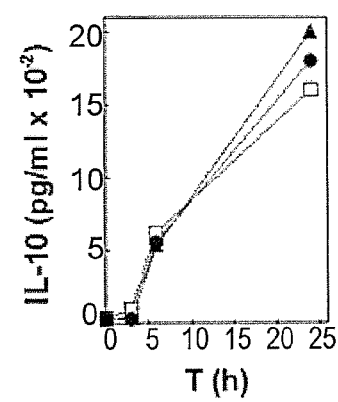
Fig. 25A
Fig. 25B
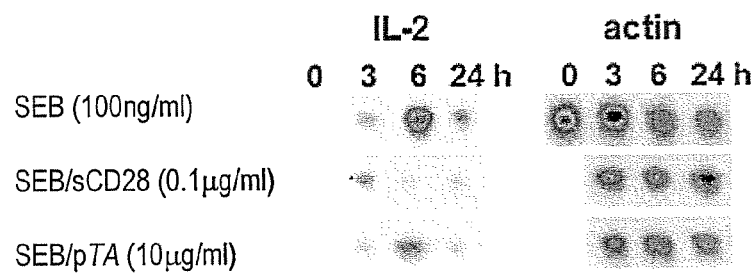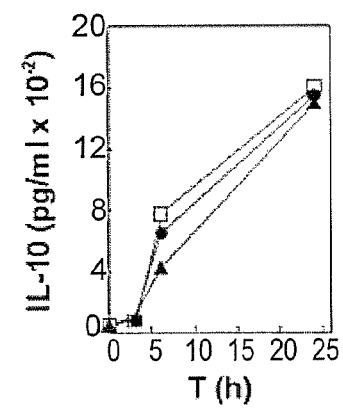
Fig. 25C
Fig. 25D

```
         1                8        15
hICOS    LRIKVLTGEINGSANYEMFIEHNGGVQILCKYPDIVQQ--EKMQLLKGGQILCDLTKTKGSNT----VSIK
mICOS    LRIKVLTGEINGSANYEMFIEHNGGVQILCKYPDIVQQ--EKMQLLKGGQILCDLTKTKGSNT----VSIK
hCD28    FLIRLLTGEINGSADHRMFSFHNGGVQISCKYPETVQQ---LKMRLFREREVLCELTKTKGSGNA----VSIK
mCD28    NKILVKQSPMLVAYDNA--------VNLSCKYSYNLFSREFRASLHKGLDSAVEVCVVY--GNYSQQLQVYSK
hCTLA4   NKILVKQSPILVVDSNE--------VSLSCRYSYNLLAKEFRASLYKGVNSDVEVCVGN--GNFTYQPQFRSN
mCTLA4   KAMHVAQPAVVLASSRGIASFVCEYASPGKATEVRVTVLRQADSQVTEVCAATYMMGNELTFLDD
         EAIQVTQPSVVLASSHGVASFPCEYSPSHNTDEVRVTVLRQTNDQMTEVCATTFTEKNTVGFLDY 97          105         116    124
hICOS    SLKFCHSQLSNNSVSEFLYNLDHSHANYYFCNLSIFDPPPFKVTLTGGYLHIYESQLCCQLKFW
mICOS    NPMLCLYHLSNNSVSFFLNNPDSSQGSYYFCSLSIFDPPFQERNLSGGYLHIYESQLCCQLKLW
hCD28    TGFNCDGKLGNESVTFYLQNLYVNQTDIYFCKIEVMYPPPYLDNEKSNGTIIHVKGKHLCPSPL
mCD28    AEFNCDGDFDNETVTFRLWNLHVNHTDIYFCKIEFMYPPPYLDNERSNGTIIHIKEKHLCHTQS
hCTLA4   S--ICTGTSSGNQVNLTIQGLRAMDTGLYICKVELMYPPPYYLG-IGNGTQIYVIDPEPCPDSD
mCTLA4   P--FCSGTFNESRVNLTIQGLRAVDTGLYLCKVELMYPPPYFVG-MGNGTQIYVIDPFPCPDSD
```

Fig. 26C

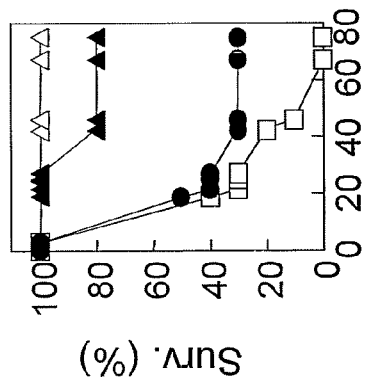
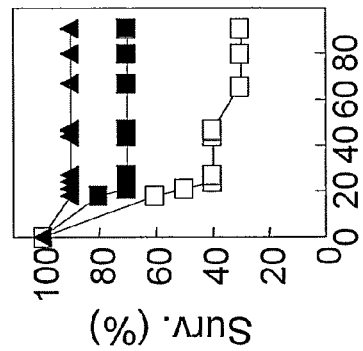
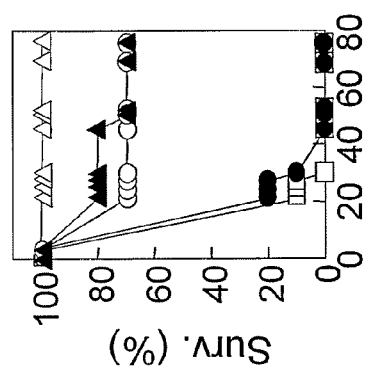
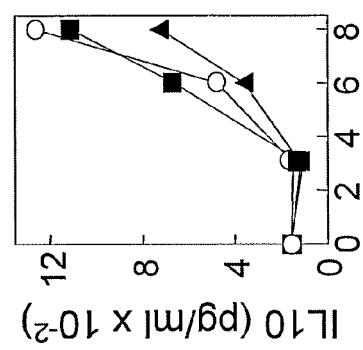
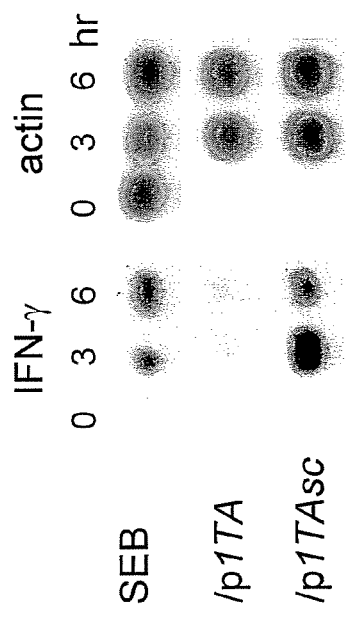
Fig. 27A
Fig. 27B
Fig. 27C
Fig. 27D
Fig. 27E
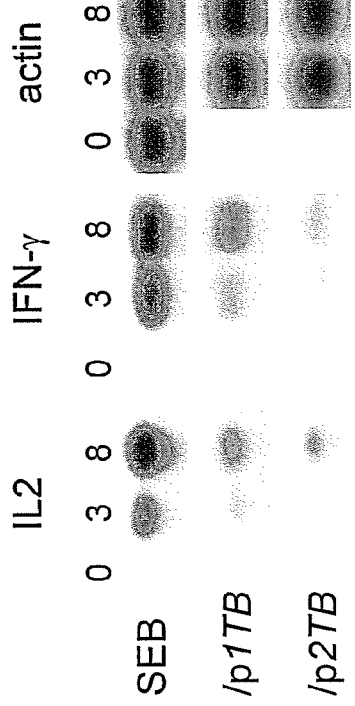
Fig. 27F

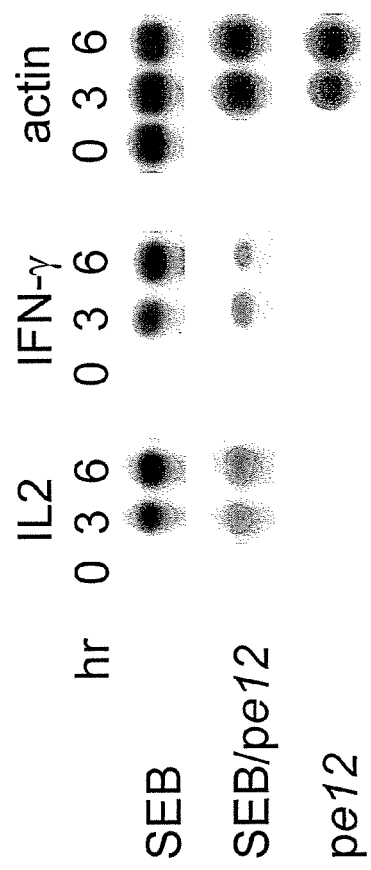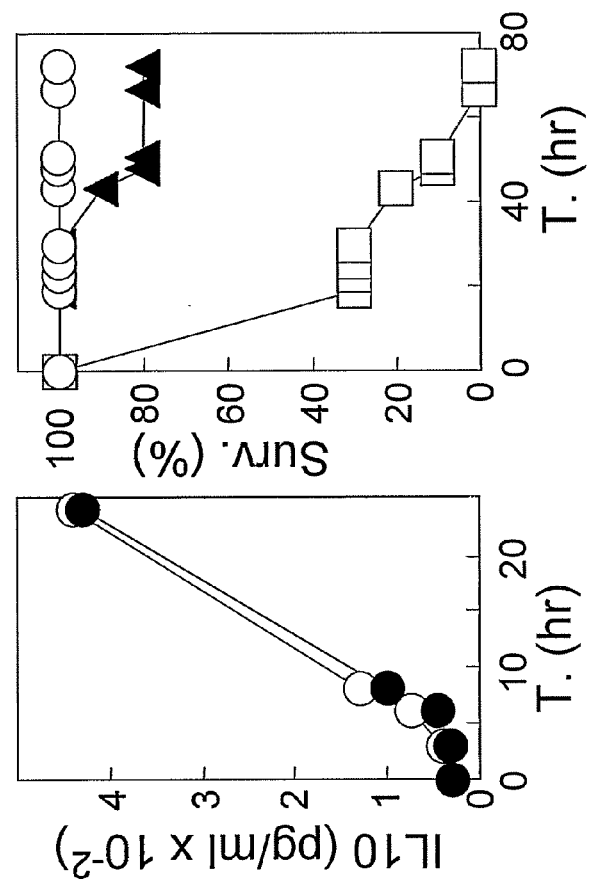
Fig. 28B  Fig. 28C  Fig. 28D

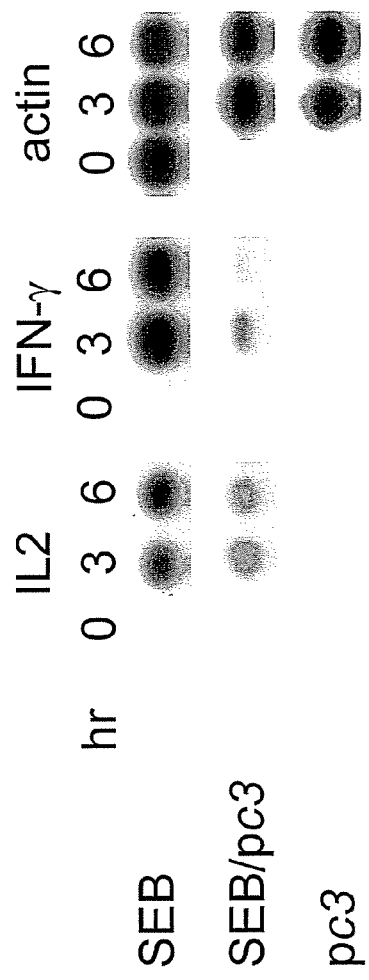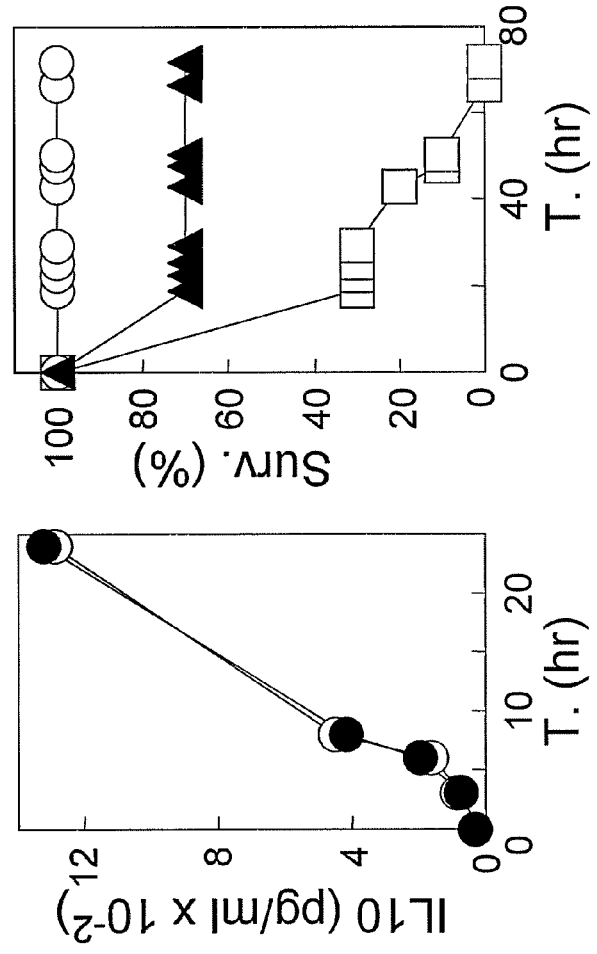
Fig. 29A  Fig. 29B  Fig. 29C

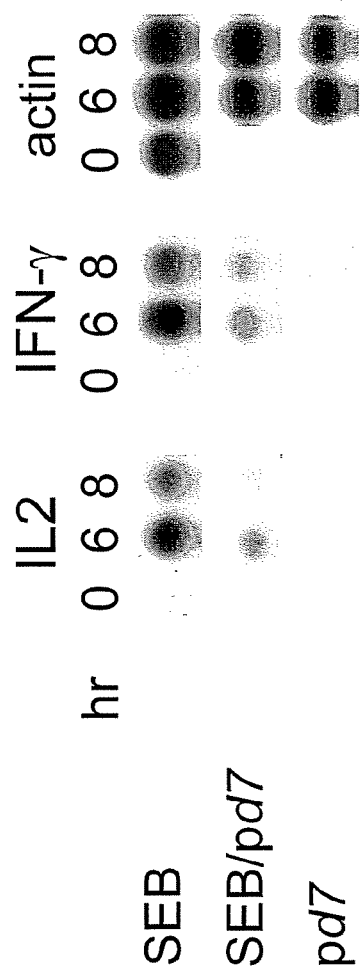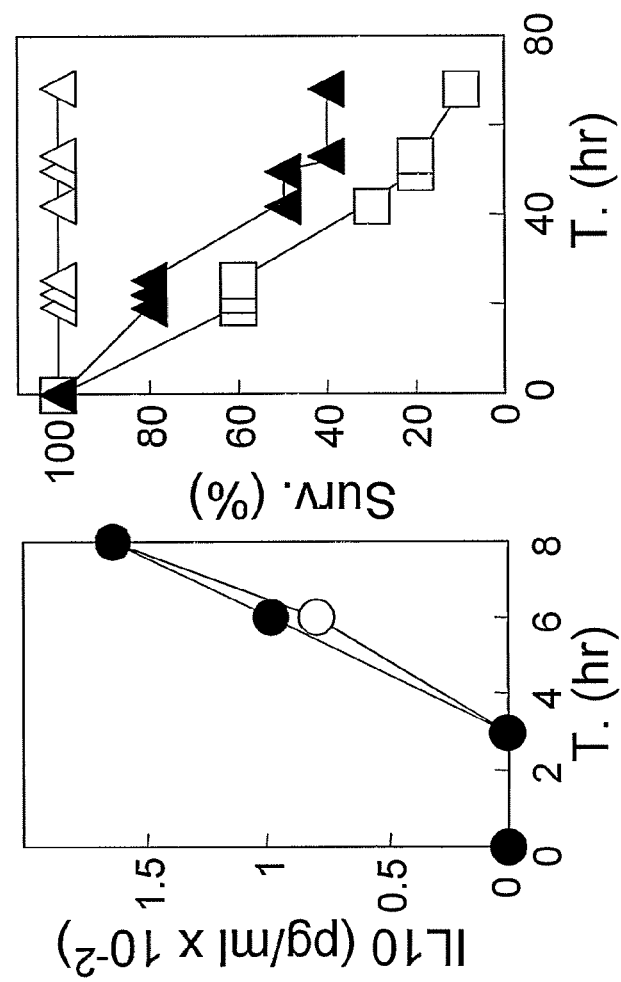

BROAD-SPECTRUM IN-VIVO EFFECTIVE SUPERANTIGEN TOXIN ANTAGONISTS BASED ON THE INTERACTION BETWEEN CD28 AND THE SUPERANTIGEN AND USES THEREOF

CROSS REFERENCE TO RELATED APPLICATIONS

This application is a division of U.S. application Ser. No. 10/958,765, now U.S. Pat. No. 8,535,672, which was a continuation-in-part of PCT International Application Nos. PCT/IL03/00278, filed Apr. 3, 2003; PCT/IL03/00839, filed Oct. 15, 2003; and PCT/IL04/000299, filed Apr. 1, 2004, all of which designate the United States of America and claim priority of Israeli Application No. 148993, filed Apr. 4, 2002, the entire contents all of which are hereby incorporated by reference into the present application The U.S. Government has a nonexclusive, nontransferable, irrevocable paid-up license to practice or have practiced this invention for or on its behalf as provided for by the terms of Grant N65236-98-1-5402 awarded by the Defense Advanced Research Projects Agency and Grant DAMD17-02-2-0030 awarded by the United States Army Medical Research and Material Command.

FIELD OF THE INVENTION

The invention relates to methods and compositions for the inhibition of modulation of T cell costimulatory pathway by a pathogenic agent, particularly the inhibition of activation of a T cell costimulatory pathway, preferably, the CD28/B7 pathway, by a pyrogenic exotoxin, by inhibiting the direct interaction of a superantigen with a specific binding site within the dimer interface of a CD28 family member, using peptides derived from said dimer interface or peptides which specifically bind to said dimer interface. The invention further relates to use of the CD28 molecule or any fragments thereof, comprising said superantigen binding site in a method of screening for a test substance which specifically binds to the CD28 molecule and is capable of antagonizing pyrogenic exotoxin-mediated activation of Th1 lymphocytes. The invention further provides specific antagonist immunomodulatory peptides, compositions thereof and also methods for the treatment of immune-related disorders.

BACKGROUND OF THE INVENTION

Throughout this application, various publications are referred to. These publications, and references included therein, are incorporated herein in their entirety.

Regulation of T-cell activity is dependent on antigen-independent co-stimulatory signals provided by the T-cell surface receptors, CD28 and CTLA-4 (CD152). Engagement of CD28 with B7-1 (CD80) and B7-2 (CD86) ligands expressed on antigen-presenting cells provides a stimulatory signal for T-cell activation, whereas subsequent engagement of CTLA-4 with these same ligands results in attenuation of the response [reviewed by Oosterwegel et al., Curr. Opin. Immunol. 11:294-300 (1999); Lenschow et al., Annu. Rev. Immunol. 14:233-258 (1996); Greenfield et al., Crit. Rev. Immunol. 18:389-418 (1998)]. Altering these interactions has profound effects on immune responses in experimental disease models. CTLA-4- and CD28-associated signaling pathways are primary therapeutic targets for preventing autoimmune disease, graft versus host disease, graft rejection and promoting tumor immunity [reviewed by Oosterwegel (1999) ibid.; Ikemizu et al., Immunity 12:51-60 (2000)]. Enhanced anti-tumor immune responses result from transfecting B7-1 into murine tumors or from using anti-CTLA-4 antibodies to block CTLA-4 interactions with B7-1 and B7-2. Conversely, inhibition of B7/CD28 interactions results in general immunosuppression, reduced autoantibody production, and enhanced skin and cardiac allograft survival. There is, therefore, considerable interest in manipulating human B7 interactions, and such approaches have already shown promise [Guinan et al., N. Engl. J. Med. 340:1704-1714 (1999); reviewed by Ikemizu (2000) ibid.].

B7-1 and B7-2 are glycoproteins, each consisting of single V-like and C-like immunoglobulin superfamily (IgSF) domains. Their ligands, CD28 and CTLA-4, are also structurally related and expressed at the cell surface as disulfide-linked homodimers of single V-like IgSF domains. A third CD28-like molecule, ICOS, interacts with another B7-related molecule, but the analysis of transgenic mice indicates that B7-1 and B7-2 are the only functional ligands of CD28 and CTLA-4. The affinities of these interactions differ substantially: human CTLA-4 binds B7-1 with a solution Kd of 0.2-0.4 µM, whereas the affinity of CD28 for B7-2 is 40- to 100-fold lower (B7-1/CD28 and B7-2/CTLA-4 interactions each have intermediate affinities [Kd=4 µM]) [reviewed by Ikemizu (2000) ibid.].

Expression of B7-1, B7-2, CD28 and CTLA-4 is tightly regulated: whereas CD28 is constitutively expressed on resting human T cells and B7-2 is rapidly induced on antigen-presenting cells early in immune responses, the expression of both B7-1 and CTLA-4 is considerably delayed [reviewed by Lenschow (1996) ibid.]. Interactions of the B7 molecules with CD28 generate costimulatory signals amplifying T cell receptor (TCR) signaling and preventing anergy, whereas interactions with CTLA-4 induce powerful inhibitory signals in T cells. CD28-dependent costimulation is poorly understood, but recent work implicates the bulk recruitment of cell surface molecules and kinase-rich rafts to the site of TCR engagement, favoring receptor phosphorylation and signaling. Conversely, CTLA-4 inhibits signal transduction by inducing the dephosphorylation of TCR and RAS signaling pathway components and by interfering with distal events in the CD28 signaling pathway [reviewed by Ikemizu (2000) ibid.].

While the opposing effects of CD28 and CTLA-4 are clear-cut, distinct functions for B7-1 and B7-2 have yet to be defined. A role of Th0, Th1, or Th2 differentiation has been proposed [Freeman et al., Immunity 2:523-532 (1995); Kuchroo et al., Cell 80:707-718 (1995)] but other work suggests that B7-1 and B7-2 determine the magnitude of costimulatory signals rather than the outcome of Th subset differentiation. Moreover, gene disruption studies reveal considerable overlap in the costimulatory functions of B7-1 and B7-2. It has been suggested that rather than having distinct CD28-dependent costimulatory roles, the key functional differences between B7-1 and B7-2 concern strength and/or mode of their binding to CD28 and CTLA-4 [reviewed by Ikemizu (2000) ibid.]. In addition, the differential timing of the expression of B7-2 and B7-1, as well as of CD28 and CTLA-4, already referred to above, is likely to be critical in the early events during a cellular immune response [reviewed by Lenschow (1996) ibid.].

Full T cell activation requires, as said, both an antigen-specific and a second, antigen-independent costimulatory signal. A unique group of antigens is comprised of a family of pyrogenic exotoxins, also known as superantigen toxins, produced by *Staphylococcus aureus* and *Streptococcus pyo-*

*genes*. The exotoxins comprised of the *S. aureus* enterotoxins (SEs) cause the majority of human food poisoning cases manifested by vomiting and diarrhea after ingestion [Schlievert, J. Infect. Dis. 167:997 (1993)]. *S. aureus* is found widespread in nature, often in association with humans. Among the major serological types within the family of SEs (including but not limited to SEA to SEE and SEG), SEB is prominent [Marrack and Kappler, Science 248:705 (1990)]. SEB has also been recognized as a leading cause of human cases of non-menstrual toxic shock syndrome that can accompany surgical or injurious wound infections, as well as viral infections of the respiratory tract of influenza patients to which children are especially vulnerable [Schlievert (1993) ibid.; Tseng et al., Infect. Immun. 63:2880 (1995)]. Toxic shock syndrome, in its most severe form, causes shock and death [Murray et al., ASM News 61:229 (1995); Schlievert (1993) ibid.]. More generally, members of the staphylococcal exotoxin family, including SEA to SEE and toxic shock syndrome toxin 1 (TSST-1), have been implicated in toxic shock syndrome, in atopic dermatitis [Schlievert (1993) ibid.] and in Kawasaki's syndrome [Bohach et al., Crit. Rev. Microbiol. 17:251 (1990)].

Because of the potential for causing lethal shock in humans after aerosol exposure and because of the relative ease with which superantigen toxins can be produced in large amounts, there is concern that these toxins, alone or in combination, could be used as a biological weapon [Lowell et al., Infect. Immun. 64:1706 (1996)]. SEB is thought to be a potential biological weapon mainly in view of its lethal potential. However, through their exquisite ability to induce vomiting and diarrhea, staphylococcal and streptococcal superantigens are also incapacitating agents that could severely impair the effectiveness of a fighting force, even temporarily, thereby enhancing vulnerability to conventional military means. Moreover, mass incapacitation of civilians, accompanied by high morbidity if low mortality, constitutes a serious bio-terror threat. Needless to say, the harmful effects of SEB, and of other members of the superantigen exotoxin family, need to be generally attacked, and not only in connection with the military aspect.

Superantigens are toxic mitogens that trigger a paradoxical response in the infected organism: a vast stimulation of the immune system on the one hand and, on the other hand, a profound immunosuppression that may allow the multiplication of the infecting bacteria, unimpeded by an immune response [Hoffman, Science 248:685 (1990); Smith and Johnson J. Immunol. 115:575 (1975); Marrack et al., J. Exp. Med. 171:455 (1990); Pinto et al., Transplantation 25:320 (1978)]. During the cellular immune response, a dynamic interplay is induced, by antigens or mitogens, between activation of Th1 type cytokine gene expression, exemplified by interleukin-2 (IL-2), interferon-γ (IFN-γ) and tumor necrosis factor-β (TNF-β), and on the other hand, its cell-mediated suppression by CD8 cells and other cell subsets [Ketzinel et al., Scand. J. Immunol. 33:593 (1991); Arad et al., Cell Immunol 160:240 (1995)], and by the inhibitory cytokines from Th2 cells, IL-4 and IL-10 [Mosmann and Coffman, Annu. Rev. Immunol. 7:145 (1989)].

Bacterial superantigens are exotoxins that stimulate a 5- to 50-thousandfold greater proportion of rodent or human T cells than do ordinary antigens. Thus, SEB activates 30-40% of all T cells in some mice to divide and produce cytokines [Marrack and Kappler (1990) ibid.]. Indeed, toxicity of SEB requires T cells; mice that lack T cells or SEB-reactive T cells are not affected by doses of SEB that cause weight loss and death in normal animals [Marrack et al. (1990) ibid.; Marrack and Kappler (1990) ibid.]. Bypassing the restricted presentation of conventional antigens, superantigens produced by *S. aureus* and *Streptococcus pyogenes* bind directly to most major histocompatibility (MHC) class II molecules and activate virtually all T cells bearing particular domains in the variable portion of the T-cell receptor (TCR) β chain, without need for processing by antigen-presenting cells [Scholl, P. et al., Proc. Natl. Acad. Sci. USA 86:4210-4214 (1989); Fraser, J. D. Nature 339(6221):221-3 (1989); Choi, Y. W. et al., Nature 346(6283):471-3 (1990); Janeway, C. A. Jr. et al., Immunol. Rev. 107:61-88 (1989)]. This results in an excessive induction of T helper 1 (Th1) cytokines interleukin-2 (IL2), interferon-γ (IFN-γ) and tumor necrosis factor β, mediators of toxic shock [Marrack, P. and Kappler, J. Science 248:705-711 (1990a); Marrack, P. et al., J. Exp. Med. 171(2):455-64 (1990b); Miethke, T. et al., J. Exp. Med. 175(1):91-8 (1992); Hackett, S. P. and Stevens, D. L. J. Infect. Dis. 168:232-235 (1993); Arad, G. et al., Nat. Med. 6(4):414-21 (2000)]. Superantigens thus use the same ligands as conventional antigens but do so distinctly [Sundberg, E. J. et al., Structure (Camb) 10:687-699 (2002a); Sundberg, E. J. et al., Curr. Opin. Immunol. 14:36-44 (2002b)].

The toxicity of SEB and related exotoxins is thought to be related to the capacity of these molecules to stimulate a rapid and excessive production of cytokines, especially of IL-2, IFN-γ and tumor necrosis factors (TNFs). IL-2, IFN-γ, and TNF-β are secreted from activated T helper type 1 (Th1) cells while TNF-α is secreted by Th1 cells, monocytes and macrophages. High levels of these cytokines, suddenly produced, have been implicated as a central pathogenic factor in toxin-related toxicity [Schad et al., EMBO J. 14:3292 (1995)] and are thought to cause a rapid drop in blood pressure leading to toxic shock.

While investigation has produced a plausible explanation for the vast stimulation of T cells by SEs, it is not yet clear why these toxins are also strongly immunosuppressive. They induce a decline in both primary T and B cell responses, including the production of antibodies and the generation of plaque-forming cells [Hoffman (1990) ibid.; Smith and Johnson (1975) ibid.; Marrack (1990) ibid.; Pinto (1978) ibid.; Ikejima et al., J. Clin. Invest. 73:1312 (1984); Poindexter & Schlievert, J. Infect. Dis. 153:772 (1986)].

The sensitivity of humans to staphylococcal toxins exceeds that of mice by a factor of 100. Thus, the toxic shock syndrome toxin 1, TSST-1, another pyrogenic exotoxin from *S. aureus*, stimulates human T cells to express the key cytokines, IL-2, IFN-γ and TNF-β at <0.1 pg/ml, while murine cells require approximately 10 pg/ml [Uchiyama et al., J. Immunol. 143:3173 (1989)]. Mice may have developed relative resistance to toxic mitogens by deleting from their T cell repertoire those cells that display the most highly reactive V-β chains or by eliminating these V-β genes [Marrack and Kappler (1990) ibid.]. Such deletions have not been detected in humans, making them far more vulnerable.

The incapacitating and potentially lethal effects of SEB (and of exotoxins of the same family of superantigens) in humans, whether exerted on civilians or military personnel, create a need for prophylaxis against these toxins, and for treatment of toxin-exposed individuals.

Bacterial superantigens are among the most lethal of toxins, and they can be weaponized. These highly stable proteins resist boiling and are easy to produce and deliver. Bypassing the restricted presentation of conventional antigens, superantigens can activate up to 50% of T cells to divide and produce cytokines. Thus, superantigens activate the cellular immune response at least 5,000-fold more strongly than do ordinary antigens. Toxicity results from massive induction of Th1 cell-derived cytokines that include IL-2, IFN-γ and TNF. Death results within 24-48 hours, but even at concentrations several logs below lethal ones, these toxins severely incapacitate.

The family of superantigens produced by the common *S. aureus* and *Streptococcus pyogenes* ('flesh-eating bacteria') comprises well over 20 members, including staphylococcal enterotoxins SEA to SEE, among which SEB is most prominent, and toxic shock syndrome toxin 1 (TSST-1), and streptococcal pyrogenic exotoxins, inter alia SPEA. To compound the problem of protecting against superantigen-induced pathology, the amino acid sequences of superantigens are highly divergent: SEB and SEA have 28% homology, while TSST-1 exhibits only 6% sequence homology with SEB. The nature of toxins or toxin mixtures encountered during toxic shock, or in combat or bio-terrorism situations cannot be anticipated with certainty. The most likely scenarios of biological warfare entail not the use of a single, purified superantigen but rather of natural mixtures of superantigenic toxins, obtained by culturing the bacteria. This complexity demands the development of broad-spectrum countermeasures.

The inventors have previously explored the possibility of blocking superantigen action at the top of the toxicity cascade, before activation of T cells takes place. A purely intuitive approach has yielded the design of 12- or 14-amino acid peptide antagonists [p12A and p14A, also denoted by SEQ ID NO: 1 (daY N K K K A T V Q E L Dda) ("da" designates D-alaninedenoted by the 'A' in p12A) and SEQ ID NO: 2 (daV Q Y N K K K A T V Q E L Dda), respectively] that inhibit induction of human Th1 cytokine gene expression by widely different superantigens (SEB, SEA, TSST-1 and SPEA), protect mice from the lethal effects of these toxins while allowing rapid development of broad-spectrum immunity against toxin challenge [Arad et al., Nature Medicine 6:414-421 (2000); Arad et al., J. Leuk. Biol. 69:921-927 (2001)], and protects pigs from incapacitation symptoms as are seen in humans in early toxic shock [applicant's Japanese Application No. 2001-377682 JP, and applicant's U.S. application Ser. No. 10/172,425]. Because pigs are closer to humans in their immune system than are mice and, unlike mice, require no presensitization to the toxic effect of superantigens, these findings support the expectation that with proper effort, efficacy in humans can be reached. No side effects of antagonist peptide were detected in mice or pigs. Antibodies against the antagonist could not be found; indeed, the small size and relatively rapid clearance of a short peptide (12-14 amino acids) constitute therapeutic advantages. The antagonist blocks the action of a superantigen (but not of a conventional antigen) on human lymphoid cells at a molar excess of about 100-fold, and prevents lethal shock in mice and incapacitation in pigs at a molar excess of only about 20- to 40-fold, implying that it binds tightly to its cellular target and that this target is critical for the superantigen-mediated activation of T cells. The antagonist activity of this peptide identified a novel superantigen domain that is critical for the superantigen action [Arad (2000) ibid.]. This finding raised the possibility that superantigens may use this domain to bind to a third receptor.

CD28 and B7-2 serve as principal costimulatory ligands for conventional antigens [reviewed by Lenschow, D. J. et al., Annu. Rev. Immunol. 14:233-58 (1996); Salomon, B. and Bluestone, J. A. Annu. Rev. Immunol. 19:225-52 (2001); Acuto, O. and Michel, F. Nat. Rev. Immunol. 3(12):939-51 (2003)]. The present invention now shows that to deliver the signal for Th1 activation, a superantigen must bind directly to CD28. Signaling is blocked by peptide mimetics of the contact region in each ligand: the 6-strand-hinge-α-helix domain in superantigens [Arad (2000) ibid.; the 'antagonist domain'] and two noncontiguous domains in CD28 that form the predicted homodimerization interface. Thus, due to the surprising direct interaction of CD28 and the superantigen, which was shown to be essential for Th1 lymphocytes activation, CD28 became the first drug target for treatment of lethal toxic shock. Interaction of an antagonist agent with this receptor allows it to block the action of superantigen toxins. Insight into the nature of this receptor target and of its interaction with the antagonist or with superantigen now provides a novel approach to design yet more effective antagonists.

Full activation of T cells is not solely dependent on the interaction of MHC class II molecule, superantigen and TCR. Sustained TCR engagement, although essential for T cell activation, faces many barriers. First, the TCR has a low affinity for antigens. Second, the number of antigenic complexes between the antigen-presenting cell and T cell can be very low.

Third, the movement of T cells works against sustained recognition of antigen. Although superantigens are far superior to ordinary antigens in overcoming these limitations and bypass MHC restrictions while binding to many TCR Vβ chains, they still require costimulatory ligands for T cell activation, including those of the B7 family on the antigen-presenting cell and CD28 and CTLA-4 on T cells.

While several investigators have suggested a role for B7-1 and B7-2 in the activation of T cells by a superantigen, the results were contradictory. For example, Muraille et al. [Int. Immunol. 7:295-304 (1995)] reported that costimulation, by use of CD28- or B7-1-transfected cells, lowered the threshold for activation of naive T cells by bacterial superantigens. On the other hand, Muraille et al., [Cell. Immunol. 162:315-320 (1995a)] claimed that a combination of monoclonal antibodies to murine B7-1 and B7-2 molecules inhibits the in vitro response of naive T cells to SEA, SEB, and TSST-1. The inhibition of T cell responses required simultaneous blocking of B7-1 and B7-2, and they suggested that either B7-1 or B7-2 is sufficient to provide costimulatory signals to naive T cells in response to bacterial exotoxins. Inhibition of T cell activation by antibodies to B7-related molecules could be overcome by antibodies to CD28, raising the hypothesis that CD28-mediated signals participate in T cell activation by bacterial superantigens [Muraille (1995a) ibid.]. Yet another study by the same group, however, concluded that a single dose of anti-B7-2 antibodies, but not of anti-B7-1 antibodies, significantly inhibited T cell activation, and reduced the lethal effect of SEB in D-galactosamine-sensitized mice [Muraille et al., Eur. J. Immunol. 25:2111-2114 (1995b)]. Indeed, CTLA-4Ig or anti-B7-1 antibodies had little or no effect on superantigen-mediated activation of naïve T cells [reviewed by Muraille (1995b) ibid.]. These conclusions were subsequently rendered doubtful by a report, again from the same group, that blocking of CD80- or CD86-derived signals by specific monoclonal antibodies led to slower kinetics of IL-2 production in response to SEB [Muraille et al., Immunology 89:245-249 (1996)]. Krummel et al., [Int. Immunol. 8:519-523 (1996)] reported likewise that antibodies against B7-1/B7-2 or Fab fragments of anti-CD28 antibodies significantly inhibit the response of splenocytes to SEB. Mittrucker et al., [J. Exp. Med. 183: 2481-2488 (1996)] showed induction of unresponsiveness and impaired T cell expansion by SEB in CD28-deficient mice. The lack of expansion was not due to a failure of SEB to activate Vβ8$^+$ T cells, as Vβ8$^+$ T cells from both CD28$^{-/-}$ and CD28⁺/⁺ mice showed similar phenotypic changes within the first 24 h after SEB injection and cell cycle analysis showed that an equal percentage of Vβ8⁺ T cells started to proliferate. However, the phenotype and the state of proliferation of Vβ8⁺ T cells was different at later time points. They concluded that CD28 costimulation is crucial for the T cell-mediated toxicity of SEB. Protection against lethal toxic shock by targeted disruption of the CD28 gene was shown by Saha et al. [J. Exp. Med. 183:2675-2680 (1996)] who reported that CD28-deficient mice (CD28$^{-/-}$) were completely resistant to TSST-1-induced lethal TSS while CD28$^{+/-}$ littermate mice were partially resistant to TSST-1. The mechanism for the resistance of the CD28$^{-/-}$ mice was a complete abrogation of TNF-alpha accumulation in the serum and a nearly complete (90%) impairment of IFN-gamma secretion in response to TSST-1 injection. In contrast, the serum level of IL-2 was only moderately influenced by the variation of CD28 expression. The hierarchy of TSST-1 resistance among CD28 wild-type (CD28$^{+/+}$), CD28 heterozygous (CD28$^{+/-}$), and CD28$^{-/-}$ mice suggested a gene-dose effect, implying that the levels of T cell surface CD28 expression critically regulate superantigen-mediated costimulation. Although these results demonstrated a primary and non-redundant role of CD28 receptors in the initiation of the in vivo cytokine cascade, and suggested therapeutic approaches for superantigen-mediated immunopathology, no concrete approach was suggested. Wang et al. [J. Immunol. 158:2856-2861 (1997)] claimed that CD28 ligation prevents bacterial toxin-induced septic shock in mice by inducing IL-10 expression. They observed that septic shock syndrome and death mediated by SEB could be prevented by administration of anti-CD28 antibodies. Anti-CD28 antibody treatment, they claimed, stimulated the expression of IL-10, both in splenocytes and in T cell lines. Furthermore, injection of anti-IL-10 could abolish the protective effect of anti-CD28 on septic shock. In the light of the findings presented herein, the results of Wang et al. (op. cit.) can be accounted for as follows: anti-CD28 inhibited SEB action in their experiments not by inducing IL-10, as they claimed, but by blocking the direct binding of SEB to CD28 which, as the inventors have now shown, is obligatory for the induction of Th1 cytokine gene expression by SEB that in turn results in lethal shock, without interfering with the induction of the Th2 cytokine IL-10 by the superantigen which, as the inventors have shown, is independent of CD28 engagement. Thus, the action of SEB was apparent to Wang et al. (ibid.) only in elicitation of a Th2 response that was protective. Wang et al. neither showed nor suggested direct binding of SEB to CD28 and they neither showed nor suggested that such binding is needed selectively for a Th1 response but not for a Th2 response. Indeed, Wang et al. teach away from direct binding of SEB to CD28 and from the concept that such binding is needed selectively for a Th1 response but not for a Th2 response, as shown by the inventors. This is seen, for instance, from the title of Wang et al. "CD28 ligation prevents bacterial toxin-induced septic shock in mice by inducing IL-10 expression" and from their sentence "anti-CD28 Ab treatment stimulated the expression of IL-10, both in splenocytes and in T cell lines". In view of the prior art and Wang et al. [ibid.], the novel results obtained by the inventors are surprising. The present results do not bear out the claims of Wang et al. (ibid.). Indeed, as shown below in FIG. 10, anti-CD28 mAb (monoclonal antibody) fails to induce expression of IL-10 in human peripheral blood mononuclear cell (PBMC) populations. Moreover, antagonist peptide leaves the induction of IL-10 by superantigen intact (FIG. 3).

In summary, the prior art indicates that:
1. B7-1 and B7-2 engage T cells but the role of each coligand in terms of activating Th1 or Th2 cells has remained controversial;
2. The role of B7-1 and B7-2 in T cell activation by superantigen toxins has also remained controversial, with some reports claiming that either B7 ligand will costimulate superantigen action while other reports advocate a role for B7-2;
3. CD28 acts as a costimulatory ligand for superantigens, as it does for conventional antigens that are presented by the MHC class II molecule;
4. The mechanism of costimulation by CD28, in conjunction with B7-1 and/or B7-2, of superantigen-mediated T cell responses is not known but is thought to be similar for superantigens and conventional antigens, and more specifically, the prior art teaches away from the concept that the mechanism of costimulation of superantigens and of conventional antigens could be different;
5. The specific roles of B7-1 and B7-2, respectively, in the CD28-mediated activation of Th1 and Th2 responses by superantigens are unknown.

SEB binds to the MHC class II a chain with low affinity ($K_d$, 0.34 µM) [Papageorgiou, A. C. et al., *EMBO J.* 18:9-21 (1999)]. Superantigens bind even more weakly to the TCR, with affinities in the 1-100 µM range [Leder, L. et al., J. Exp. Med. 187:823-33 (1998); Andersen, P. S. et al., Biol. Chem. 276: 33452-7 (2001); Redpath, S. et al., J. Immunol. 163: 6-10 (1999)].

A low affinity and high off-rate, which determines the average time of ligand/receptor contact, is thought to determine the signaling strength through the TCR. Indeed, mutant forms of the staphylococcal superantigen SEC3 having increased affinity for TCR Vbeta8.2 domains also showed increased mitogenic potency on T cells [Andersen (2001) ibid.]. A direct correlation was found between the binding affinity of SEC3 variants for the TCR and the strength of the T cell response they evoke. This finding would suggest that superantigens could have evolved higher affinities for the TCR. That has not occurred in nature; instead, even a potent superantigen such as SEA retains a low affinity for the TCR [Kieke, M. C. et al., J. Mol. Biol. 307:1305-15 (2001)]. Surface plasmon resonance studies show that in absolute terms, the interaction of superantigens with either individual ligand, MHC class II molecule or TCR, is very weak [Redpath. (1999) ibid.; Seth, A. et al., Nature 369: 324-7 (1994)].

This suggests that to achieve T cell activation, superantigens may need to rely on additional ligand interactions, and the antagonist peptides described in the present application, block the interaction of superantigen with the CD28 receptor, an interaction that is critical for superantigen-mediated activation of the harmful Th1 cytokine response.

Occupation of the TCR binding domain on superantigens would be another strategy to block the action of superantigens. Using this approach, a soluble mutant form of the TCR Vbeta8 chain was selected that binds SEC3 1000-fold more tightly ($K_d$ of 7 nM) [Kieke (2001) ibid.]. This mutant Vbeta8 protein antagonized SEC3-mediated specific T cell activity. Unlike the short antagonist peptide described herein, the soluble Vbeta8 protein is of high molecular weight and thus will be more difficult to deliver. Even more problematic is the fact that different superantigens bind to the TCR with molecular surfaces that can differ widely. Moreover, each superantigen binds preferentially only to a narrow, individual subset of the Vbeta chain repertoire

[Kieke (2001) ibid.; Kline, J. B. et al., Mol. Microbiol. 24:191-202 (1997); Li, H. et al., Immunol. Rev. 163:177-86 (1998)].

Indeed, for different superantigens, highly efficient T cell activation may be achieved through structurally diverse strategies of TCR ligation [Sundberg, E. J. et al., Structure (Camb) 10:687-99 (2002)]. Hence, a soluble mutant Vbeta8 protein may exhibit limited specificity for superantigens.

As indicated above, CD28 belongs to a triad of costimulatory ligands whose genes are tightly linked: CD28, cytotoxic T-lymphocyte-associated protein 4 (CTLA4)(CD152) and inducible costimulator (ICOS) [reviewed by Sharpe, A. H. and Freeman, G. J., Nat. Rev. Immunol. 2(2):116-26 (2002); Carreno, B. M. and Collins, M. Annu. Rev. Immunol. 20:29-53 (2002)]. Via their coligands from the B7 family, these proteins function as costimulatory receptors that regulate signaling by ordinary antigens. CD28 acts as the critical early signal transducer for the innate immune response, balanced by ICOS and CTLA4 [reviewed by Rudd, C. E. and Schneider H. Nat. Rev. Immunol. 3(7):544-56 (2003)]. The present invention now further shows that through its β-strand-hinge-α-helix domain, the major superantigen staphylococcal enterotoxin B (SEB) binds with high affinity to each member of this conserved receptor family. Peptides derived from either rim of the bipartite dimer interface in CTLA4 [Schwartz, J. C. et al., Nature 410:604-608 (2001); Stamper, C. C. et al., Nature 410(6828):608-11 (2001)] or in CD28 and ICOS as predicted by sequence alignment, although unique for each costimulatory receptor, are potent antagonists that block superantigen-mediated induction of human Th1 cytokine gene expression and protect mice from lethal challenge with SEB. Apparently, the mode of action of these peptides is to compete with CD28 for its binding site in superantigens. SEB induces a vigorous expression of Th1 and Th2 cytokine genes but only induction of the Th1 response is dependent on CD28 signaling.

Direct binding to CD28 underlies the toxicity of the superantigens. The findings of the present invention reveal a mechanism of subversion of the innate immune response in which the superantigen co-opts a costimulatory ligand of the host for use as its obligatory receptor. This strategy may be used more widely by pathogens.

Therefore, it is an object of the invention to provide methods for inhibiting the activation of a T cell costimulatory pathway, preferably, the CD28/B7 pathway by a pathogenic agent, in a subject in need thereof. Such methods are based on the use of a substance which inhibits the direct interaction of a component derived from said pathogenic agent and a binding site within a T cell costimulatory pathway member molecule, which site is derived from the dimer interface of said T cell costimulatory pathway member.

Another object of the invention is to provide substances, preferably peptides, which inhibit the direct interaction of a component derived from the said pathogenic agent and a binding site within the dimer interface of a T cell costimulatory pathway member, preferably, CD28, CTLA4 and ICOS. Such peptides are provided by the invention and include peptides comprising an amino acid sequence derived from a dimer interface of a T cell costimulatory pathway member, for example the peptides of SEQ ID NO: 5, 15, 16, 18, 19, 20, 21, 59 and 60, and also peptides comprising an amino acid sequence which specifically binds to an amino acid sequence within the dimer interface of a T cell costimulatory pathway member, for example the peptides of SEQ ID NO: 12, 13, 14 and 27 to 58.

Another object of the invention is to provide compositions and method of treatment of immune-related disorders caused by a pathogenic agent, particularly, a superantigen exotoxin.

It is yet a further object of the present invention to use CD28 as a powerful novel target for the development of antidotes to superantigen-induced toxic shock symptoms, whether septic shock, toxic shock or incapacitation by toxin.

These, and other objects of the invention will become apparent as the description proceeds.

SUMMARY OF THE INVENTION

In a first aspect, the present invention relates to a superantigen binding site within a T cell costimulatory pathway member which specifically and directly binds to a superantigen. The specific binding site of the invention comprises an amino acid sequence derived from all or part of a dimer interface of a T cell costimulatory pathway member. Such T cell costimulatory pathway may be any one of the CD28/B7 T cell costimulatory pathway, the CD40 ligand/CD40, CD2/CD58 and the LFA-1 (CD18)/ICAM-1 (CD54) costimulatory pathway.

According to one embodiment, the T cell costimulatory pathway is the CD28/B7 pathway. Therefore, according to a specific embodiment, the CD28/B7 pathway member may be any one of CD28, CTLA4, ICOS and PD-1, B7-1, B7-2, ICOSL, PD-L1 and PD-L2.

In a specifically preferred embodiment, the invention relates to a superantigen binding site within the CD28 molecule. This specific binding site comprises an amino acid sequence derived from all or part of a dimer interface of CD28, which comprises amino acid residues 10-15 and 116-121 of the human CD28 amino acid sequence as denoted by SEQ ID NO: 22.

According to a specifically preferred embodiment, this binding site overlaps at least in part, with an epitope within the CD28 molecule that is recognized by an anti-CD28 monoclonal antibody, the mouse anti-CD28 monoclonal antibody designated MAB342, clone 37407.111 of R&D Systems, Inc., Minneapolis, Minn., USA. The particular epitope recognized by this antibody has the amino acid sequence as denoted by SEQ ID NO: 3 (H V K G K H L C P).

Direct binding between the CD28 molecule and the superantigen at the superantigen binding site in CD28 of the invention, facilitates the binding of a B7-2 ligand to CD28. More specifically, this specific binding is essential for activation of Th1 lymphocytes as defined by the induction of IL-2 and/or IFN-γ gene expression. However, binding of a B7-2 ligand to CD28 is not essential for activation of Th2 lymphocytes as defined by the induction of IL-4 and/or IL-10.

According to a preferred embodiment, the novel superantigen binding site in CD28, specifically and directly binds to a spatially conserved domain of a pyrogenic exotoxin. Preferably, this spatially conserved domain is not involved in the binding of any one of MHC Class II molecules and TCR. Most preferably, the said spatially conserved domain of pyrogenic exotoxin forms therein a central turn starting within β-strand 7 and connecting the β-strand 7, via short β-strand 8, to an α-helix 4, and ending within α-helix 4, based on the domain numbering of SEB. According to another specific embodiment, the invention relates to a superantigen binding site within the CTLA4 molecule. This specific binding site comprises an amino acid sequence derived from all or part of a dimer interface of CTLA4, which comprises amino acid residues 10-15 and 115-120 of the human CTLA4 amino acid sequence as denoted by SEQ ID NO: 23.

In another particular embodiment, the invention provides a superantigen binding site within the ICOS molecule. This specific binding site comprises an amino acid sequence derived from all or part of a dimer interface of ICOS, which comprises amino acid residues 10-15 and 119-124 of the human ICOS amino acid sequence as denoted by SEQ ID NO: 24.

As a second aspect, the invention relates to a method for the treatment of a superantigen-related disorder in a mammalian subject in need of such treatment. The method of the invention comprises inhibiting the interaction between T cell costimulatory pathway member molecule and said superantigen. According to a specifically preferred embodiment, the T cell costimulatory pathway may be the CD28/B7 pathway and said pathway member is the CD28 molecule.

According to a specific embodiment, inhibition of the direct binding between CD28 molecule and said superantigen may be performed by administering to said subject a therapeutically effective amount of a substance that inhibits the direct interaction between CD28 molecule and said superantigen or of a composition comprising said substance. The composition of the invention optionally further comprising pharmaceutically acceptable carrier, diluent, excipient and/or additive. More specifically, said substance inhibits the binding of the superantigen to the CD28 superantigen binding site of the invention.

More particularly, the inhibition of the direct interaction between CD28 molecule and the pyrogenic exotoxin leads to inhibition of exotoxin-mediated activation of Th1-lymphocytes, protection against toxic shock and optionally also leads to indirect elicitation of protective immunity against toxic shock induced by a pyrogenic exotoxin or by a mixture of at least two pyrogenic exotoxins.

In yet another preferred embodiment, the superantigen may be a pyrogenic exotoxin. Preferably, this pyrogenic exotoxin may be a bacterial exotoxin and most preferably, this exotoxin may be produced by any one of *Staphylococcus aureus* and *Streptococcus pyogenes*. The superantigen-related disorder treated by the method of the invention, may be according to a specific embodiment any one of toxic shock, incapacitation and death, induced by a pyrogenic exotoxin or by a mixture of at least two pyrogenic exotoxins.

The invention further provides a method of inhibiting pyrogenic exotoxin-mediated activation of Th1-lymphocytes and of protecting against toxic shock induced by a pyrogenic exotoxin or by a mixture of pyrogenic exotoxins, in a subject in need of such treatment. This method comprises administering to the subject a therapeutically effective amount of a substance that inhibits the direct interaction between a T cell costimulatory pathway member molecule and said pyrogenic exotoxin, or of a composition comprising said substance. The composition of the invention further optionally comprises pharmaceutically acceptable carrier, diluent, excipient and/or additive.

Still further, the invention provides for a method of eliciting protective immunity against toxic shock induced by a pyrogenic exotoxin in a subject in need of such treatment. Such method comprises administering to the subject a therapeutically effective amount of a substance that inhibits the direct interaction between a T cell costimulatory pathway member molecule and said pyrogenic exotoxin or of a composition comprising said substance, and further optionally comprising pharmaceutically acceptable carrier, diluent, excipient and/or additive. This inhibitor substance, by blocking the ability of the toxin to induce a cellular immune response leading to toxic shock, may potentially also allow the superantigen to induce a vigorous humoral immune response directed against itself, and therefore indirectly elicits protective immunity.

In yet another aspect, the present invention relates to a substance that inhibits the binding of a superantigen to the novel superantigen binding site in said T cell costimulatory pathway member, preferably, CD28. Specifically, said superantigen may be a pyrogenic exotoxin.

According to a preferred embodiment, inhibition of binding of the pyrogenic exotoxin to said CD28 superantigen binding site, by the substance of the invention, leads to antagonizing toxin-mediated activation of Th1 lymphocytes and therefore may indirectly lead to elicitation of protective immunity against toxic shock induced by said pyrogenic exotoxin or by a mixture of at least two pyrogenic exotoxins. More particularly, this binding is mediated by the novel superantigen binding site in CD28.

In another embodiment, the substance according to the invention is intended for use in the treatment of superantigen-related disorders.

The present invention further relates to the use of the substance of the invention, in the preparation of a pharmaceutical composition for the treatment of superantigen-related disorders.

In a fourth aspect, the present invention relates to a pharmaceutical composition for the treatment and/or prophylaxis of superantigen-related disorders. The composition of the invention comprises as an active ingredient a therapeutically effective amount of a substance that inhibits the direct interaction between a T cell costimulatory pathway member and said pyrogenic exotoxin. Such inhibition leads to antagonizing of toxin-mediated activation of Th1 lymphocytes. This composition of the invention optionally further comprises at least one of pharmaceutically acceptable carrier, diluent, excipient and/or additive.

In a further aspect, the invention relates to an isolated and purified peptide comprising an amino acid sequence derived from a dimer interface of a T cell costimulatory pathway member or comprising an amino acid sequence which specifically binds to an amino acid sequence within the dimer interface of a T cell costimulatory pathway member.

According to one embodiment, the T cell costimulatory pathway may be any one of the CD28/B7 T cell costimulatory pathway, the CD40 ligand/CD40, CD2/CD58 and the LFA-1 (CD18)/ICAM-1 (CD54) costimulatory pathway. Preferably, the T cell costimulatory pathway may be the CD28/B7 pathway, most preferably, the CD28/B7 pathway member may be any one of CD28, CTLA4, ICOS and PD-1, B7-1, B7-2, ICOSL, PD-L1 and PD-L2.

According to a specifically preferred embodiment, the peptide of the invention is an immunomodulatory peptide capable of modulating a T cell costimulatory pathway.

In one preferred embodiment, the peptide of the invention may comprise an amino acid sequence derived from the dimer interface of a T cell costimulatory pathway member, preferably, a CD28/B7 family member.

More specifically, the peptide of the invention comprises an amino acid sequence derived from all or part of the dimer interface of any one of CD28, CTLA4 and ICOS and the corresponding domains in PD-1.

According to one preferred embodiment, the peptide of the invention comprises an amino acid sequence derived from the dimer interface within the CD28 molecule, which dimer interface comprises amino acid residues 10-15 and 116-121 of the human CD28 amino acid sequence as denoted by SEQ ID NO: 22. More preferably, the peptide of the invention may comprise an amino acid sequence derived from any one of the amino acid sequence HVKGKHLCP as denoted by SEQ ID NO: 15 and the amino acid sequence SPMLVAYD, as denoted by SEQ ID NO: 16 or any functional fragments and derivatives thereof.

A specific preferred peptide of the invention is designated pTA and has the amino acid sequence $A_7$HVKGKHLCP as denoted by SEQ ID NO: 5 or any functional fragments and derivatives thereof.

Another specific preferred peptide of the invention is designated p1TA and has the amino acid sequence HVKG-KHLCP as denoted by SEQ ID NO: 15 or any functional fragments and derivatives thereof.

Another specific preferred peptide of the invention is designated p2TA and has the amino acid sequence SPM-LVAYD, as denoted by SEQ ID NO: 16 or any functional fragments and derivatives thereof.

Alternatively, the peptide of the invention may comprise an amino acid sequence derived from the dimer interface within the CTLA4 molecule, which dimer interface comprises amino acid residues 10-15 and 115-120 of the human CTLA4 amino acid sequence as denoted by SEQ ID NO: 23.

More specifically, such peptide comprises an amino acid sequence derived from any one of the amino acid sequence YVIDPEPCP as denoted by SEQ ID NO: 18 and the amino acid sequence PAVVLASS, as denoted by SEQ ID NO: 19 or any functional fragments and derivatives thereof.

Accordingly, one specific preferred peptide is designated p1TB and has the amino acid sequence YVIDPEPCP as denoted by SEQ ID NO: 18 or any functional fragments and derivatives thereof.

Another preferred specific peptide is designated p2TB and has the amino acid sequence PAVVLASS as denoted by SEQ ID NO: 19 or any functional fragments and derivatives thereof.

In yet another alternative, the peptide of the invention may comprise an amino acid sequence derived from the dimer interface within the ICOS molecule, which dimer interface comprises all or part of amino acid residues 10-15 and 119-124 of the human ICOS amino acid sequence as denoted by SEQ ID NO: 24.

More specifically, the peptide of the invention may comprise an amino acid sequence derived from any one of the amino acid sequence YESQLCCQL as denoted by SEQ ID NO: 20 and the amino acid sequence GEINGSAN, as denoted by SEQ ID NO: 21 or any functional fragments and derivatives thereof.

One specific example is peptide designated p1TC and has the amino acid sequence YESQLCCQL as denoted by SEQ ID NO: 20 or any functional fragments and derivatives thereof.

Another specific example is a peptide designated p2TC which has the amino acid sequence GEINGSAN, as denoted by SEQ ID NO: 21 or any functional fragments and derivatives thereof.

According to another specifically preferred embodiment, the peptide of the invention comprises an amino acid sequence which specifically binds to an amino acid sequence within the dimer interface of any one of CD28, CTLA4, ICOS and the corresponding domains in PD-1.

According to a specific embodiment, the peptide of the invention comprises an amino acid sequence as denoted by any one of SEQ ID NO: 62, 12, 13 and 14, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57 and 58.

Particular preferred peptides are any one of the peptide pe12 which has the amino acid sequence SHFTHNRH-GHST (SEQ ID NO: 12), the peptide pd7, which has the amino acid sequence WHAHPHKKPVVA (SEQ ID NO: 13), the peptide pc3 which has the amino acid sequence FHKHKNPGSPII (SEQ ID NO: 14), the peptide pe6 which has the amino acid sequence APMYHKHRLEKH (SEQ ID NO: 39) and the peptide pf8 which has the amino acid sequence IHKPHHHRTPLW (SEQ ID NO: 38) or any functional fragments and derivatives thereof.

According to another aspect, the invention relates to a composition for the modulation of a T cell costimulatory pathway, comprising as an active ingredient a purified peptide as defined by the invention or any combination, functional fragments and derivatives thereof and optionally further comprises pharmaceutically acceptable carrier, diluent, adjuvant and/or excipient.

The invention further provides a pharmaceutical composition for the treatment of immune disorders related to an imbalance in the Th1-Th2 response in a subject in need thereof comprising as an active ingredient any of the peptides of the invention or any combination, functional fragments and derivatives thereof and optionally further comprises pharmaceutically acceptable carrier, diluent, adjuvant and/or excipient.

According to a preferred embodiment, the invention provides a composition for the inhibition of a pyrogenic exotoxin-mediated activation of T-lymphocytes, which composition protects against toxic shock and optionally elicits protective immunity against toxic shock induced by a pyrogenic exotoxin or by a mixture of pyrogenic exotoxins. The composition of the invention comprises as an active ingredient any of the purified immunomodulatory peptides of the invention or any combination, functional fragments and derivatives thereof and optionally further comprises pharmaceutically acceptable carrier, diluent, adjuvant and/or excipient.

In a further aspect, the invention relates to a method for the modulation of a T cell costimulatory pathway in a subject in need thereof, comprising the step of administering to said subject an effective amount of an immunomodulatory peptide capable of modulating a T cell costimulatory pathway, which peptide comprises an amino acid sequence derived from a dimer interface of a T cell costimulatory pathway member or comprises an amino acid sequence which specifically binds to an amino acid sequence within the dimer interface of a T cell costimulatory pathway member, or of a composition comprising the same.

The invention further provides a method for the treatment of immune disorders related to an imbalance in the Th1-Th2 response in a subject in need thereof comprising the step of administering to said subject an effective amount of an immunomodulatory peptide as defined by the invention.

According to a specifically preferred embodiment, any of the peptides defined by the invention, or any combination, functional fragments derivatives, conjugates and composition thereof may be used in such methods.

In yet a further aspect, the invention relates to a method for inhibiting the activation or modulation of a T cell costimulatory pathway by a pathogenic agent, in a subject in need thereof. The method of the invention comprises the step of administering to the subject an inhibitory effective amount of a substance which inhibits the direct interaction of a component derived from said pathogenic agent and a binding site within a T cell costimulatory pathway member molecule, which site is derived from the dimer interface of said T cell costimulatory pathway member.

In one preferred embodiment, the substance used by the method of the invention for inhibiting the direct interaction between a component derived from said pathogenic agent, preferably, a superantigen, and a binding site within a T cell costimulatory pathway member molecule, may be a peptide as defined by the invention.

In a further aspect, the invention relates to a method for the treatment of pathological disorders related to an imbalance in the Th1-Th2 response caused by a pathogenic agent in a subject in need thereof. Such method comprises the step of administering to said subject an inhibitory effective amount of a substance, preferably, any of the peptides of the invention, which inhibits the direct interaction of a component derived from said pathogenic agent and a binding site within a T cell costimulatory pathway member molecule, which site is derived from the dimer interface of said T cell costimulatory pathway member.

Still further, the invention relates to a method of screening for a test substance which specifically binds to a T cell costimulatory pathway member and is capable of antagonizing pyrogenic exotoxin-mediated activation of Th1 lymphocytes and optionally of eliciting protective immunity against toxic shock induced by a pyrogenic exotoxin or by a mixture of at least two pyrogenic exotoxins, which screening method comprises the steps of: (a) obtaining candidate antagonist substances which bind to a T cell costimulatory pathway member; (b) selecting from the substances obtained in step (a), a substance that inhibits direct interaction between said T cell costimulatory pathway member and said superantigen; and (c) determining the antagonizing effect of the substance obtained in step (b) on the superantigen-mediated activation of Th1 lymphocytes.

The invention will be further described on the hand of the following figures, which are illustrative only and do not limit the scope of the invention which is defined by the appended claims.

Aliquots of $3 \times 10^7$ human PBMC were incubated with 0.1 (open circles), 1

(novel receptor), TCR (T cell receptor), Dea. (death), Antag. (antagonist), Surv. (survival), Prot. Imm. (protective immunity).

FIG. 6A-6D Effect of anti-B7 mAbs on SEB-induced expression of IL-2 and IFN-γ mRNA and of IL-10.

Figure 6D:
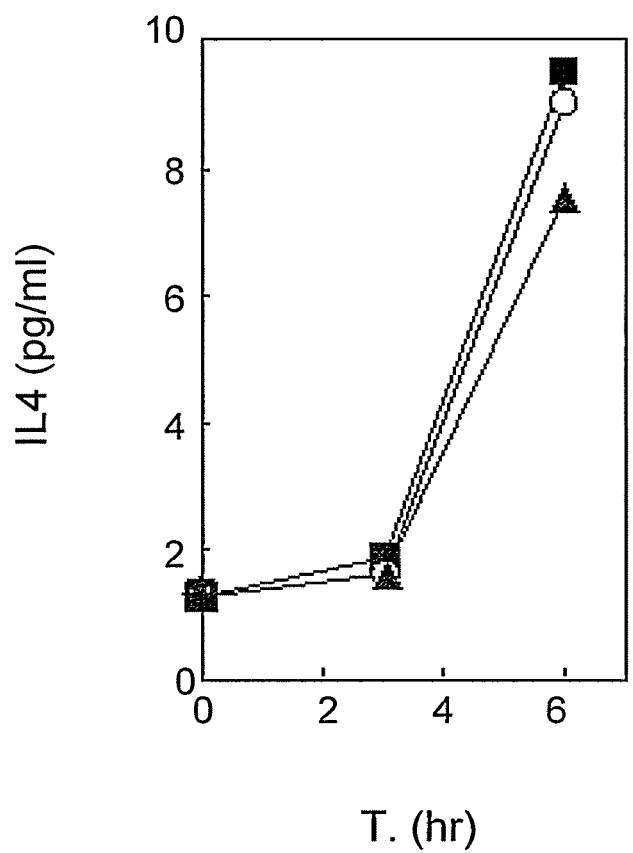

Human PBMC were incubated without SEB (open squares, open triangles) or with 0.1 μg/ml SEB (open circles, filled squares, filled triangles), either without mAb (open circles) or with 1:10$^4$-diluted anti-B7-1 (open squares, filled squares) or 1:10$^4$-diluted anti-B7-2 (open triangles, filled triangles). IL-2 RNA (FIG. 6A) and IFN-γ RNA (FIG. 6B) were analyzed by quantitative dot blot hybridization as in FIG. 2B (dots show 8-h values). IL-10 and IL-4 were assayed by ELISA in culture medium from the same cells (FIGS. 6C and 6D, respectively). Abbreviations: T (Time), h (hour), pg (picogram), ml (milliliter).

FIG. 7A-7F Effect of soluble CD28 receptor on the induction of IL-2 and IFN-γ mRNA and of IL-10 by SEB.

FIG. 7A-7C: Human PBMC were mixed and incubated with 100 ng/ml SEB (open squares), 1 μg/ml sCD28 (open triangles)(R&D Systems), or both (filled circles). At times indicated, IL-2 mRNA was determined by RNase protection analysis; actin mRNA served as loading control (FIG. 7A). (FIG. 7B) is a quantitation of the data in A, using NIH Image 1.61 software. IL-10 was assayed by ELISA in culture medium from the same cells (FIG. 7C). FIGS. 7D-7F: An experiment similar to (FIGS. 7A-7C), except that PBMC were incubated with 10 ng/ml SEB (open squares), 10 μg/ml sCD28 (open triangles), or both (filled circles). At times indicated, IFN-γ mRNA was analyzed by RNase protection analysis (FIG. 7D); FIG. 7E is a quantitation of the data in FIG. 7D. IL-10 was assayed by ELISA in culture medium from the same cells (FIG. 7F). Actin mRNA served as loading control (FIG. 7A and FIG. 7D). Abbreviations: T (Time), h (hour), pg (picogram), ml (milliliter), Un. (units).

FIG. 8A-8H Effect of soluble CD28 receptor and soluble B7-2 on the induction of IL-2 mRNA and IL-10 by SEB.

FIGS. 8A-8C: Human PBMC were incubated with 1 ng/ml SEB (open squares), and 0.1 (filled circles) or 10 μg/ml sCD28 (filled triangles). At times indicated, IL-2 mRNA was determined by RNase protection analysis (FIG. 8A) and quantitated (FIG. 8B); IL-10 was assayed by ELISA in culture medium from the same cells (FIG. 8C).

FIGS. 8D-8F: show a similar experiment (to the experiment shown in FIGS. 8A-8C), except that PBMC were incubated with 1 ng/ml SEB (open squares), and 10 μg/ml sCD28 (filled triangles) or 0.1 μg/ml sB7-2 (filled squares). IL2 (shown) and IFN-γ (not shown) mRNA were determined by RNase protection analysis with actin mRNA as loading control, and IL10 by ELISA.

Figure 8G:
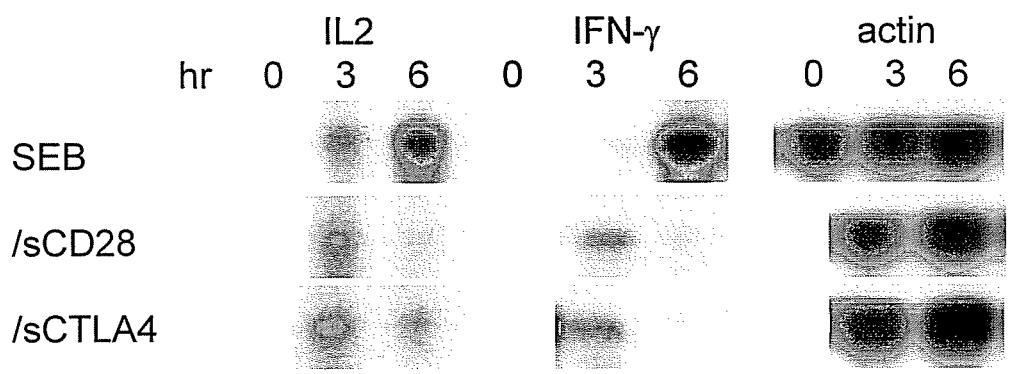
Figure 8H:
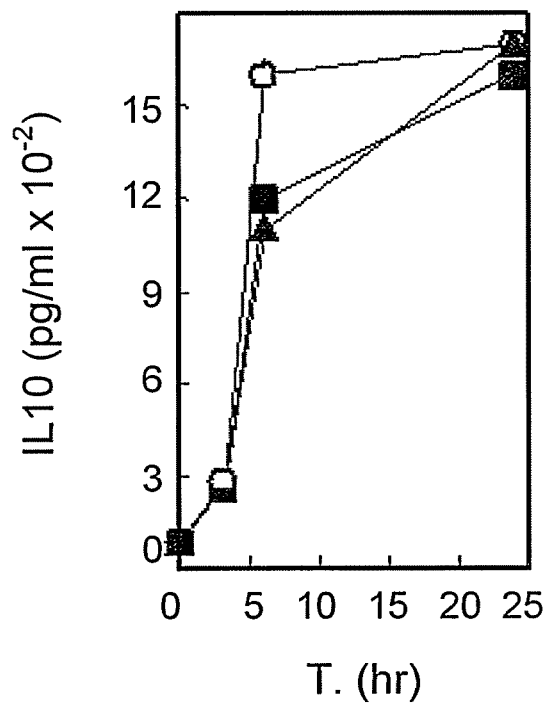

FIGS. 8G-8H: PBMC were induced with SEB alone (open circles) or with 10 ng/ml sCD28 (filled triangles) or 1 μg/ml sCTLA4 (filled squares); IL2 mRNA, IFN-γ mRNA (FIG. 8G) and IL10 (FIG. 8H) were determined. Abbreviations: T (Time), h (hour), pg (picogram), ml (milliliter), Un. (units), μg (microgram), ng (nanogram).

Figure 9A:
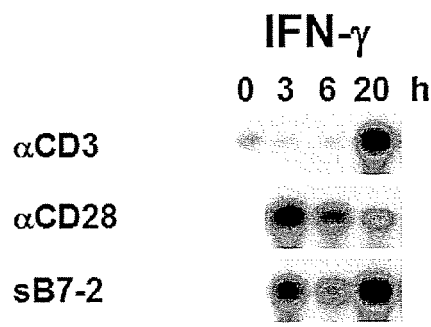
Figure 9B:
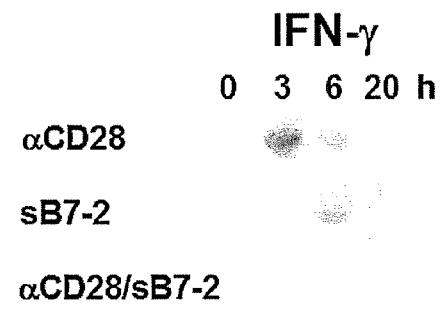

FIG. 9A-9B Induction of IFN-γ mRNA by anti-CD3, anti-CD28, or sB7-2.

Human PBMC were incubated with 0.1 μg/ml anti-CD3, 2.5 μg/ml anti-CD28 or 1 μg/ml sB7-2 (R&D Systems); at times indicated, IFN-γ mRNA was quantitated by RNase protection analysis (FIG. 9A). In (FIG. 9B), human PBMC were incubated with 2.5 μg/ml anti-CD28 or 1 μg/ml sB7-2, alone or in combination; at times indicated, IFN-γ mRNA was quantitated by RNase protection analysis. Abbreviations: h (hours).

Figure 10A:
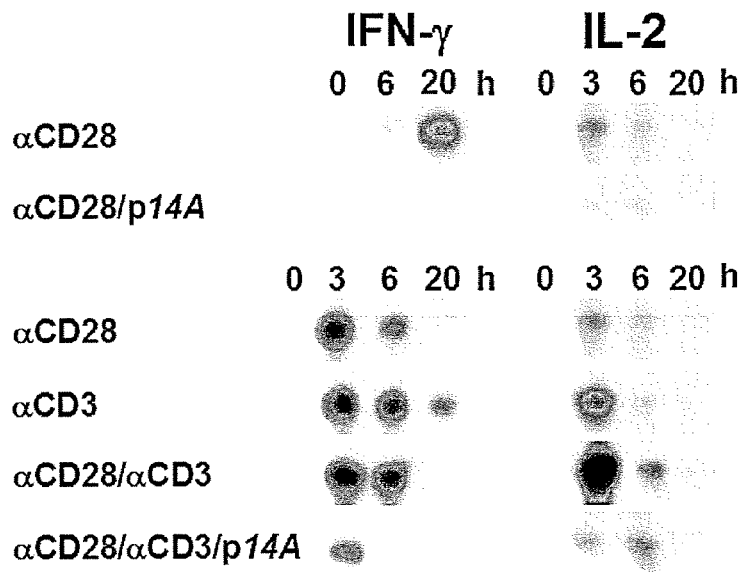
Figure 10B:
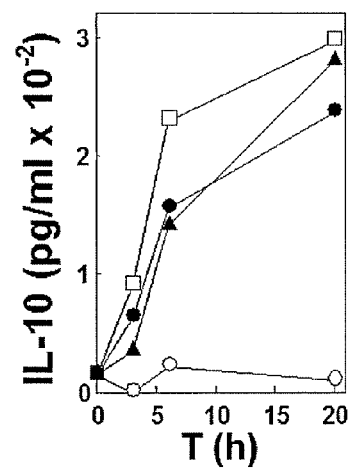
Figure 10C:
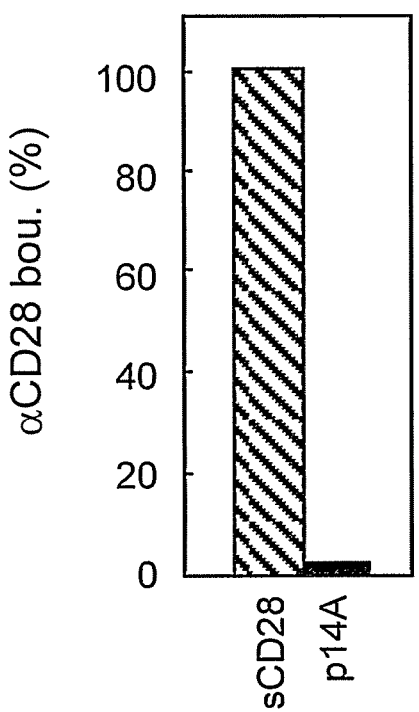

FIG. 10A-10C Induction of IFN-γ and IL-2 mRNA by anti-CD3/anti-CD28 and inhibition of this induction by p14A antagonist peptide.

Human PBMC were incubated with 2.5 μg/ml anti-CD28 (open circles) or 0.1 μg/ml anti-CD3 alone (open squares) or together, in the absence (filled triangles) or presence of 10 μg/ml p14A (filled circles). At times indicated, IL-2 mRNA and, in separate experiments, IFN-γ mRNA were quantitated by RNase protection analysis (FIG. 10A). IL-10 was assayed by ELISA in culture medium from the same cells used for determination of IL-2 mRNA (FIG. 10B). To show that αCD28 does not bind p14A, sCD28 or p14A was immobilized and binding of αCD28 was assayed by ELISA using alkaline phosphatase-coupled anti-mouse IgG (Jackson Laboratories) (FIG. 10C). Abbreviations: T (Time), h (hour), pg (picogram), ml (milliliter), Bou. (bound).

Figure 11A:
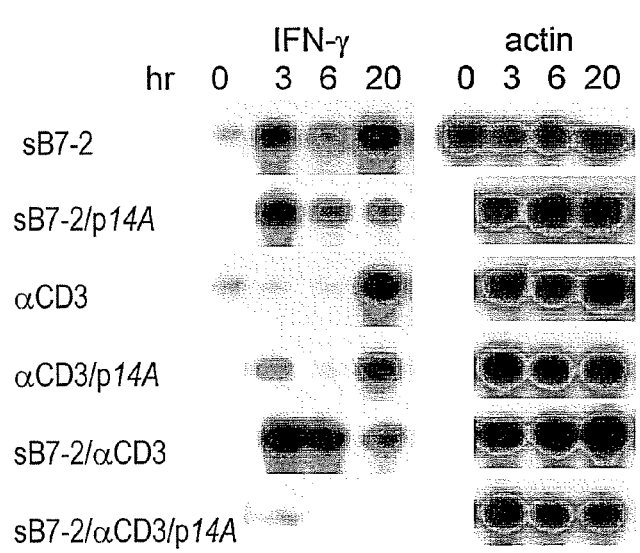
Figure 11B:
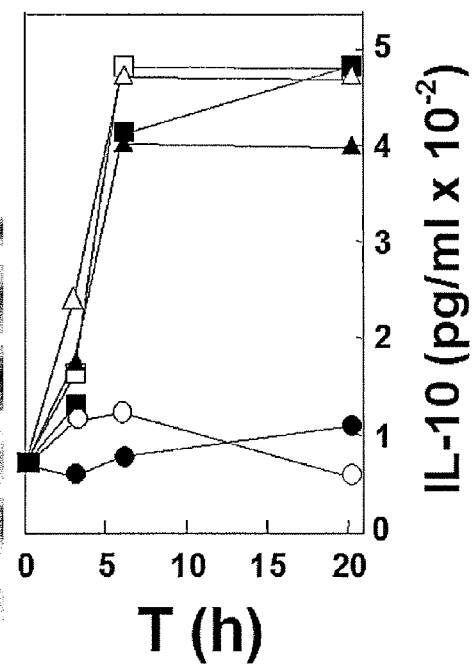

FIG. 11A-11B Effect of p14A antagonist peptide on the induction of IFN-γ mRNA and of IL-10 by anti-CD3 in combination with sB7-2.

Human PBMC were incubated with 0.1 μg/ml anti-CD3 (squares), 1 μg/ml sB7-2 (circles) or both (triangles), in the absence (open symbols) or presence of 10 μg/ml p14A (filled symbols). At times indicated, IFN-γ mRNA was determined by RNase protection analysis (FIG. 11A). IL-10 was assayed by ELISA in culture medium from the same cells (FIG. 11B). Abbreviations: T (Time), h (hour), pg (picogram), ml (milliliter).

Figure 12A:
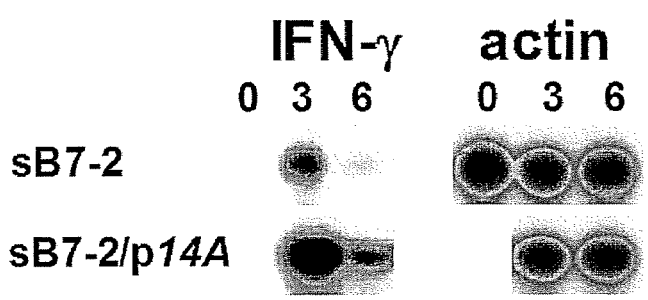
Figure 12B:
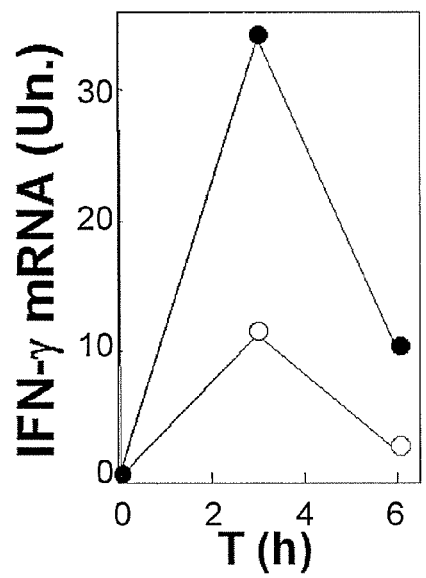

FIG. 12A-B sB7-2-induced expression of IFN-γ mRNA is enhanced by antagonist peptide.

Human PBMC were incubated with 1 μg/ml sB7-2 alone (open circles) or together with 10 μg/ml p14A (filled circles). At times indicated, IFN-γ mRNA was determined by RNase protection analysis (FIG. 12A) and quantitated (FIG. 12B). Actin mRNA served as loading control. Abbreviations: T (Time), h (hour), Un. (units).

Figures 13A, 13B, 13C:
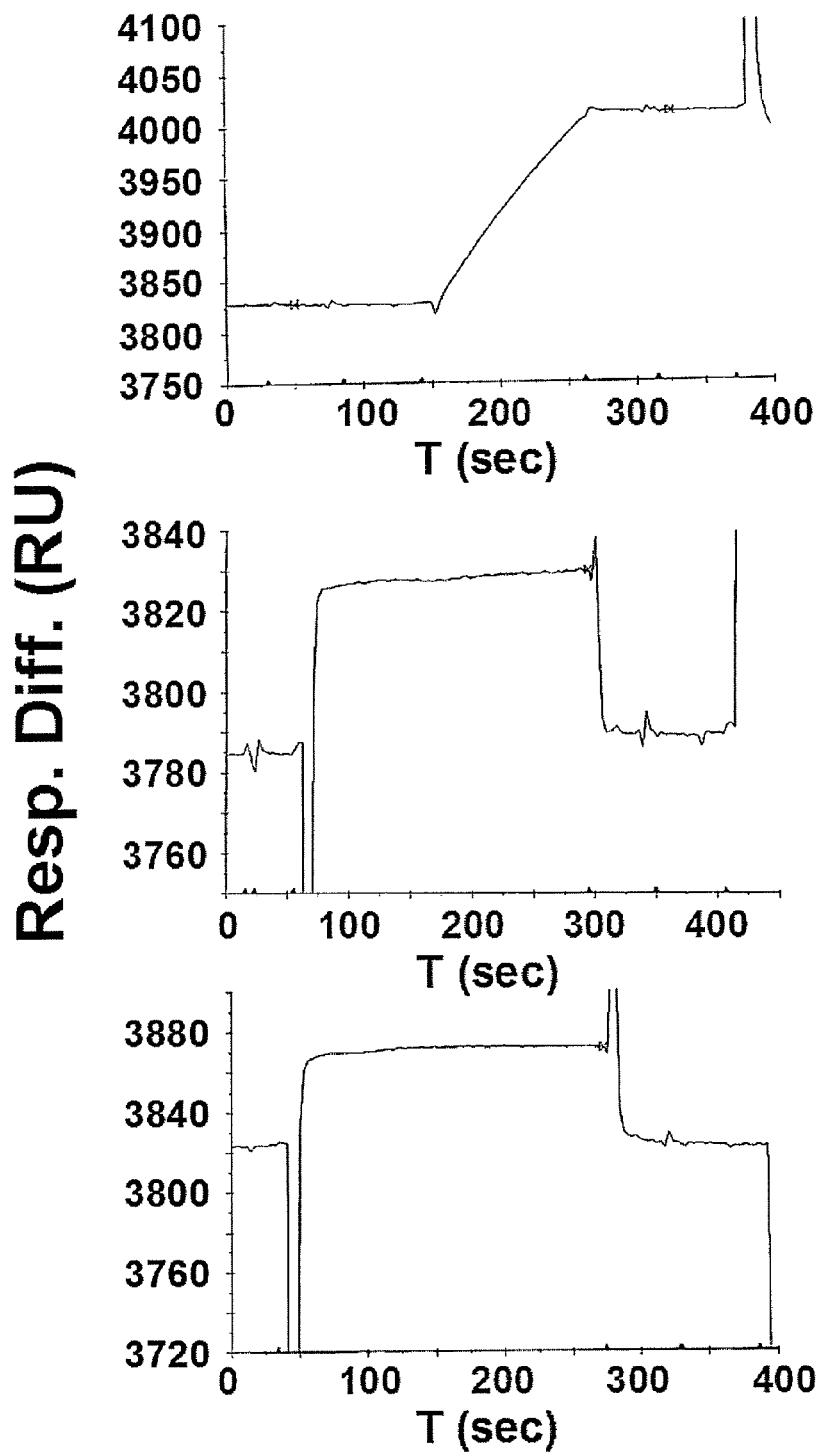

FIG. 13A-13C Plasmon resonance recordings of binding of SEB or antagonist peptide to sCD28.

An amount of 100 μg sCD28 was immobilized on a Biacore chip. Binding to the sCD28 chip was recorded separately for the analytes anti-CD28 (200 nM) (FIG. 13A), p14A (2 μM) (FIG. 13B), or SEB (200 nM) (FIG. 13C). The response is measured as resonance units (RU) indicating the difference in response to the analyte (Resp. Diff.) over time in seconds (sec.). Baseline is on the left, and binding is shown by the increase in RU over baseline. In B and C, regeneration of the baseline is shown on the right upon washing out of the analyte with 50 mM H$_3$PO$_4$. Abbreviations: T (time).

Figure 14:
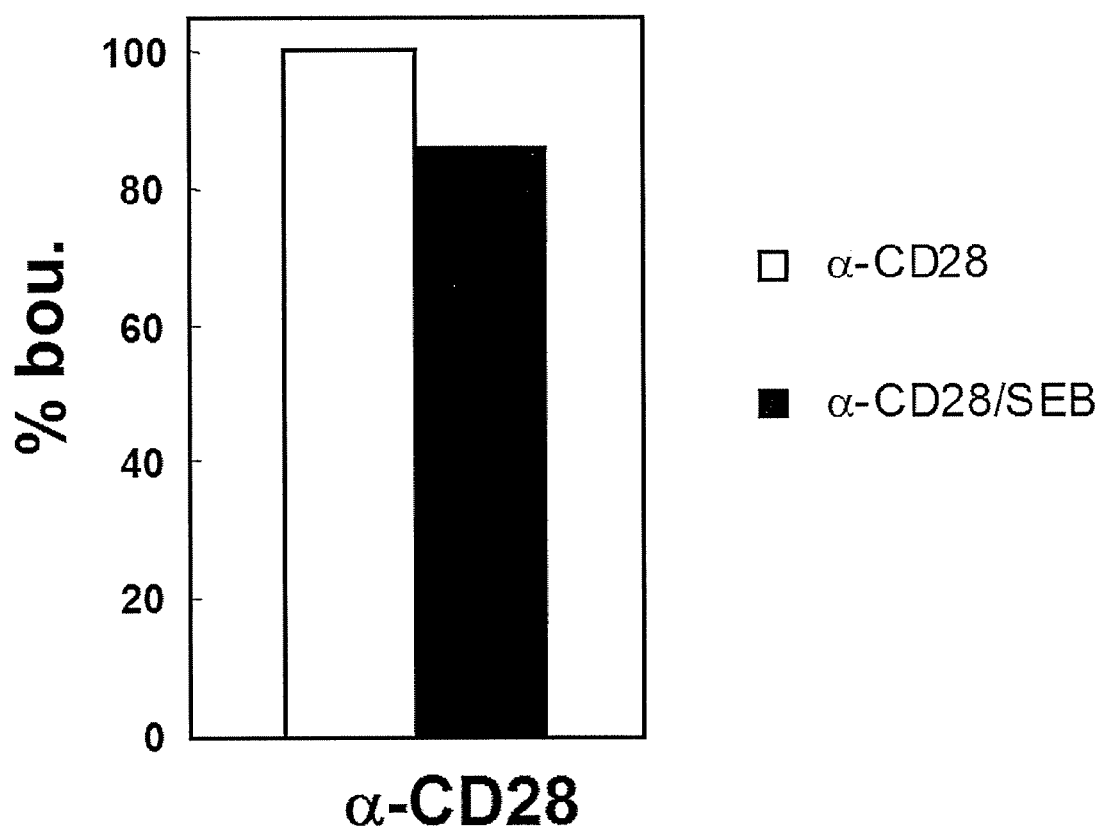

FIG. 14 High-affinity binding of anti-CD28 to sCD28 is inhibited by SEB: analysis by plasmon resonance.

An amount of 100 μg sCD28 was immobilized on a Biacore chip and plasmon resonance was recorded in the presence of 200 nM anti-CD28, in the absence or presence of 200 nM SEB as indicated. Bars depict the strength of the plasmon resonance signal. Abbreviations: bou. (bound), α (anti).

Figure 15:
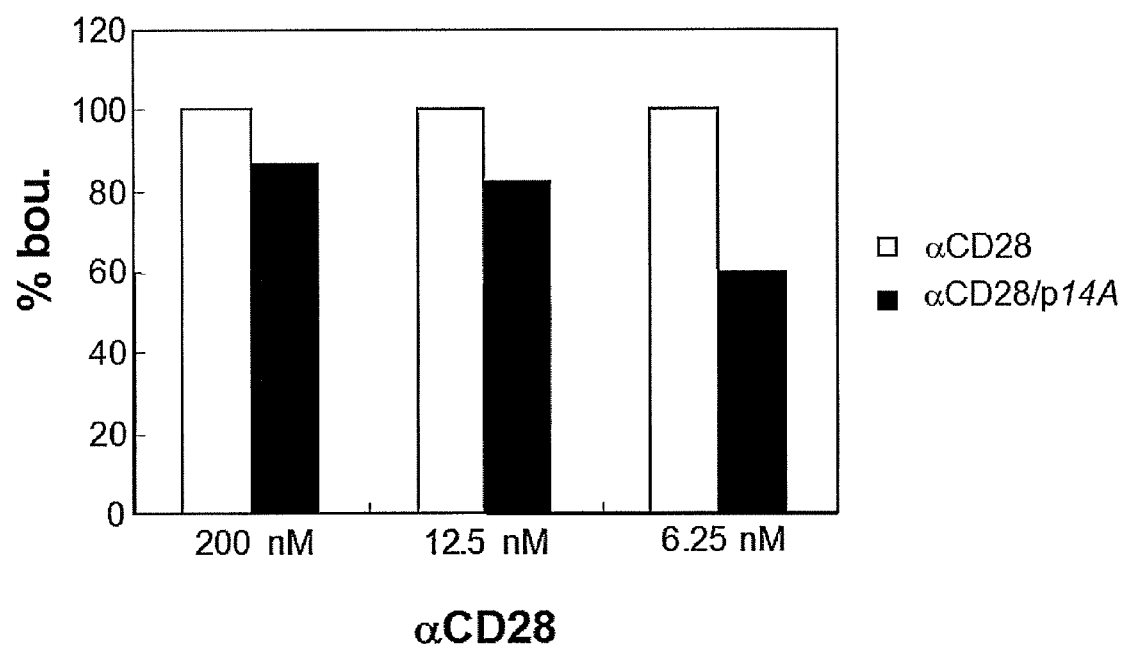

FIG. 15 High-affinity binding of anti-CD28 to sCD28 is inhibited by p14A: analysis by plasmon resonance.

An amount of 100 μg sCD28 was immobilized on a Biacore chip and plasmon resonance was recorded in the presence of anti-CD28 in the concentrations shown, in the absence or presence of 2 μM p14A as indicated. Bars depict the strength of the plasmon resonance signal. Abbreviations: bou. (bound), α (anti).

Figure 16:
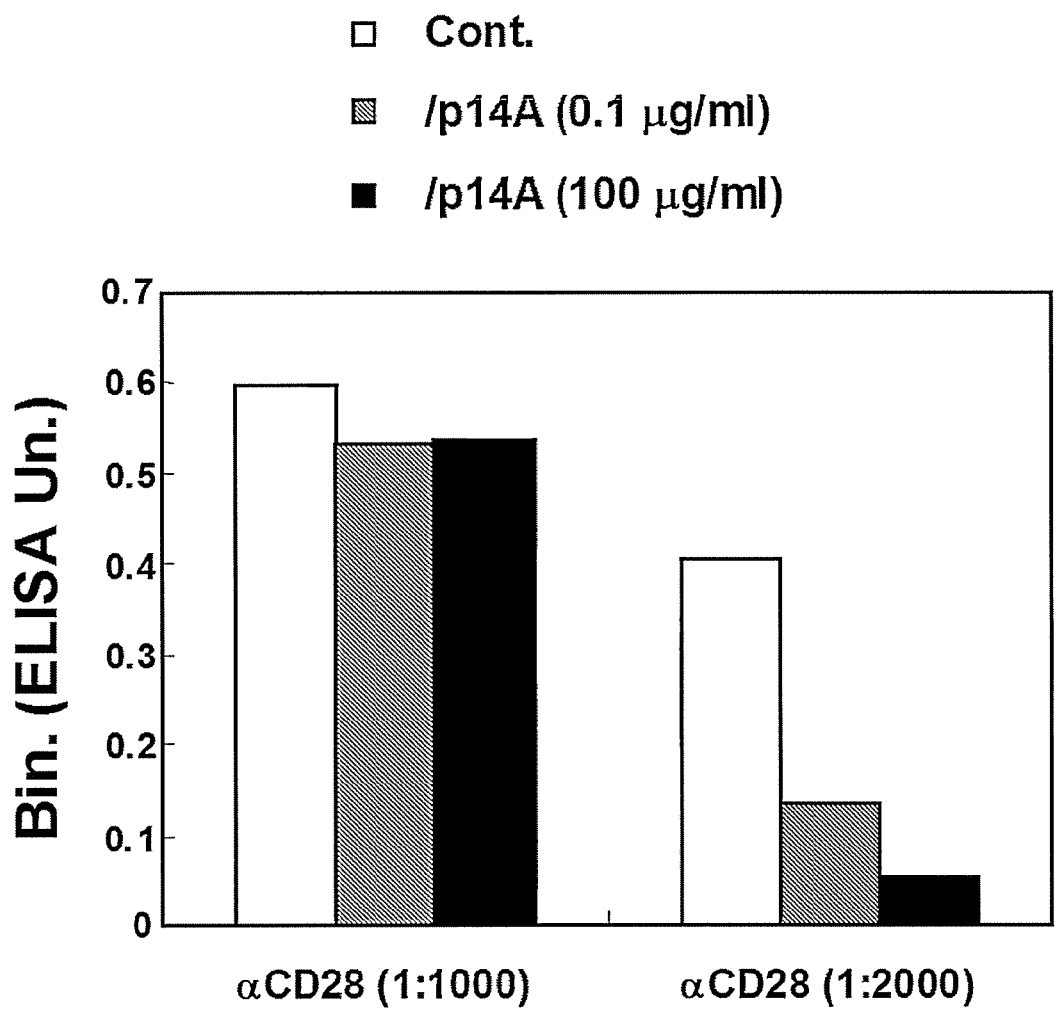

FIG. 16 High-affinity binding of anti-CD28 to sCD28 is inhibited by antagonist peptide: analysis by ELISA.

An amount of 250 ng sCD28 was immobilized on an ELISA microtiter plate and binding of anti-CD28 at the two indicated dilutions (corresponding to 250 and 125 ng/ml, respectively) was measured by use of a secondary antibody coupled to alkaline phosphatase, recording absorbency at 450 nm. p14A was either absent (Control) or present at the indicated concentrations. Abbreviations: bin. (binding), Un. (units), cont. (control), ml (milliliter), μg (microgram), α (anti).

FIG. 17A-17E Effect of CD28 or sB7-2 on the binding of anti-SEB to SEB: analysis by plasmon resonance.

(FIGS. 17A, 17B) An amount of 100 μg SEB was immobilized on a Biacore chip and plasmon resonance was recorded in the presence of 1:1,000-fold diluted polyclonal anti-SEB antibody (Sigma); (FIG. 17A) depicts the strength of the plasmon resonance signal. (FIG. 17B) shows percent anti-SEB/SEB complex formed as in (FIG. 17A), in the presence of increasing concentrations of sCD28 or of sB7-2 ligand. (FIG. 17C) shows binding of anti-SEB analyte (aSEB) to SEB or to sCD28, each immobilized in a distinct channel on the same Biacore chip. Bars denote relative complex formation. (FIG. 17D) shows plasmon resonance recordings for the binding of increasing concentrations of sB7-2 to sCD28 immobilized on a Biacore chip; the curves yield a Kd of 1.9e-8 M. In (FIG. 17E), the Biacore chip of (FIG. 17A) and (FIG. 17B), on which an amount of 100 μg SEB was immobilized, was used to record plasmon resonance in the presence of 1:1,000-fold diluted polyclonal anti-SEB antibody, in the presence of no competitor (CTRL), or in the presence of 250 nM sB7-2, 250 nM sCD28, or both added simultaneously; bars denote relative anti-SEB/SEB complex formation. Abbreviations: T (time), sec. (seconds), Resp. (response), Diff. (difference), bou. (bound), μg. (ligand), α (anti).

FIG. 18A-18B Effect of CD28 on the binding of anti-SEB to SEB: analysis by plasmon resonance.

FIG. 18A: An amount of 100 μg SEB was immobilized on a Biacore chip and plasmon resonance was recorded in the presence of 8 nM polyclonal rabbit anti-SEB antibody (Sigma) alone (open triangle) or in the presence of sCD28 at a concentration of 125 nM (open circle), 250 nM (open square), 500 nM (filled circle), 1 μM (filled triangle), or 2 μM (filled square). Strength of the plasmon resonance signal is shown (Resp. Diff., response difference; RU, response units);

FIG. 18B: In a separate experiment, an amount of 100 μg SEB was immobilized on a Biacore chip and plasmon resonance was recorded in the presence of increasing concentrations of polyclonal anti-SEB antibody (αSEB) as shown in the left column of the table. The table shows RU in the presence of αSEB alone or in the presence of a constant concentration of sCD28 (1 μM) and percent binding. Percent binding is plotted above the table as a function of αSEB concentration. Abbreviations: T (time), Sec. (seconds), bin. (binding).

FIG. 19A-19B Enzyme-linked immunoassay (ELISA) for the binding of SEB to anti-SEB and interference by sCD28.

ELISA plates were coated overnight at 4° C. with 0.5 μg SEB/well in phosphate-buffered saline (PBS), washed twice with PBS containing 0.05% Tween-20 and then blocked for 2 h with 5% bovine serum albumin in PBS. sCD28 at the concentrations indicated in the table were added together with rabbit anti-SEB antibodies that had been diluted 50,000-fold (FIGS. 19A; 19B, open squares) or 500,000-fold (FIG. 19B, filled squares). After 2-h incubation at room temperature, plates were washed twice and anti-rabbit IgG-AP (AP, alkaline phosphatase) was added for 1 h. After washing twice, the substrate PNPP was added and color was recorded at 405 nM after 10 min (circles) or 15 min (squares). Abbreviations: bin. (binding), conc. (concentration).

FIG. 20 Enzyme-linked immunoassay (ELISA) for the binding of p14A to anti-p14A and interference by sCD28.

ELISA plates were coated overnight at 4° C. with 0.5 μg p14A/well in PBS, washed twice with PBS containing 0.05% Tween-20 and then blocked for 2 h with 5% bovine serum albumin in PBS. sCD28 at the concentrations indicated were added together with rabbit anti-p14A antibodies that had been diluted 50,000-fold (filled circles) or 500,000-fold (filled squares). After 2-h incubation at room temperature, plates were washed twice and anti-rabbit IgG-AP (AP, alkaline phosphatase) was added for 1 h. After washing twice, the substrate PNPP was added and color was recorded at 405 nM. Percent binding is plotted (100%, without sCD28). Abbreviations: bin. (binding), pg/ml (pictogram/milliliter).

FIG. 21 Antagonist peptide enhances the binding of CD28 to sB7-2: analysis by plasmon resonance.

An amount of 100 μg sB7-2 was immobilized on a Biacore chip; sCD28 (200 nM) was the analyte (CTRL). Plasmon resonance was recorded in the absence or presence of 2 μM p14A or of 2 μM pSEB(41-61) as indicated. Bars depict the relative strength of the plasmon resonance signal. Abbreviations: Bou. (bound).

FIG. 22A-22L SEB binds to CD28, CTLA4 and ICOS through its antagonist domain.

FIGS. 22A-22D: Representative profiles of the relative surface plasmon resonance responses for binding of soluble CD28, CTLA4, ICOS and B7-2 in concentrations ranging from 0.25 μM in twofold increments to immobilized SEB (695 RU) were determined as described in Experimental Procedures;

FIGS. 22E-22H, 22J, 22K: Representative profiles of the relative surface plasmon resonance responses for binding of soluble CD28, PD-1, ubiquitin and human IgG in concentrations ranging from 0.125 and of soluble CTLA4 and ICOS from 0.063 in twofold increments to immobilized p12C (1,950 RU);

FIG. 22I: Representative profiles of the relative surface plasmon resonance responses for binding of soluble CD28 in concentrations ranging from 0.125 μM in twofold increments to immobilized p12Csc (930 RU);

FIG. 22L: Representative profiles of the relative surface plasmon resonance responses for binding of sB7-2 in concentrations ranging from 31.25 nM in twofold increments to immobilized sCD28 (3,400 RU). Abbreviations: Resp. Diff. (response difference), T (time), sec. (seconds).

FIG. 23 SEB induces a change in the CD28 receptor on human CD4 cells.

Starting with PBMC, CD4 cells were enriched to 90% and incubated at $4\times10^6$ cells/ml with 100 ng/ml of SEB and stained with anti-CD28 mAb (second antibody: cy-2, green) or with anti-CD28 Ab (second antibody: cy-3, red) at 0, 6 and 24 h after induction as indicated. Confocal fluorescence microscopy data are shown. Merge, double staining with anti-CD28 mAb and anti-CD28 Ab. Abbreviations: Mer. (merge), mAb (monoclonal antibody).

FIG. 24A-24C Peptide mimetics of the dimer interface predicted for CD28 are superantigen antagonists FIG. 24A: CTLA4/B7-2 complex and the dimer interface in CTLA4. In backbone diagram of the CTLA4/B7-2 complex [1I85.pdb; Schwartz et al., Nature 410:604-608 (2001)], generated with RasMol, one B7-2 monomer is shown in magenta, the other in grey and CTLA4 in blue, with MYPPPY (SEQ ID NO:8) in yellow, YVIDPE (SEQ ID NO:6) (HVKGKH in CD28, SEQ ID NO:4) in red, and VVLASS (SEQ ID NO:25) (MLVAYD in CD28, SEQ ID NO:26) in green, as in the sequence alignment of human (h) CD28 (residues 1-127 of SEQ ID NO:22), and CTLA4 (residues 1-126 of SEQ ID NO:23), and murine (m) CD28 (SEQ ID NO:64) and CTLA4 (SEQ ID NO:65) shown below; conserved residues appear in bold face.

Figure 24B:
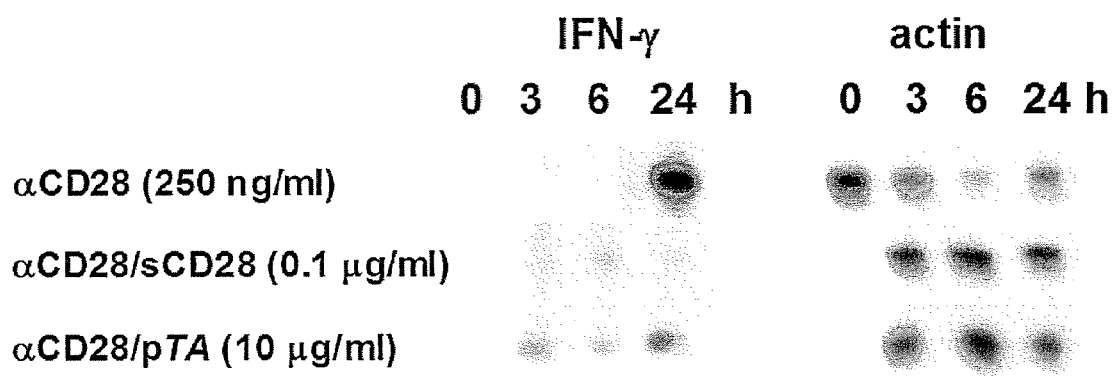
Figure 24C:
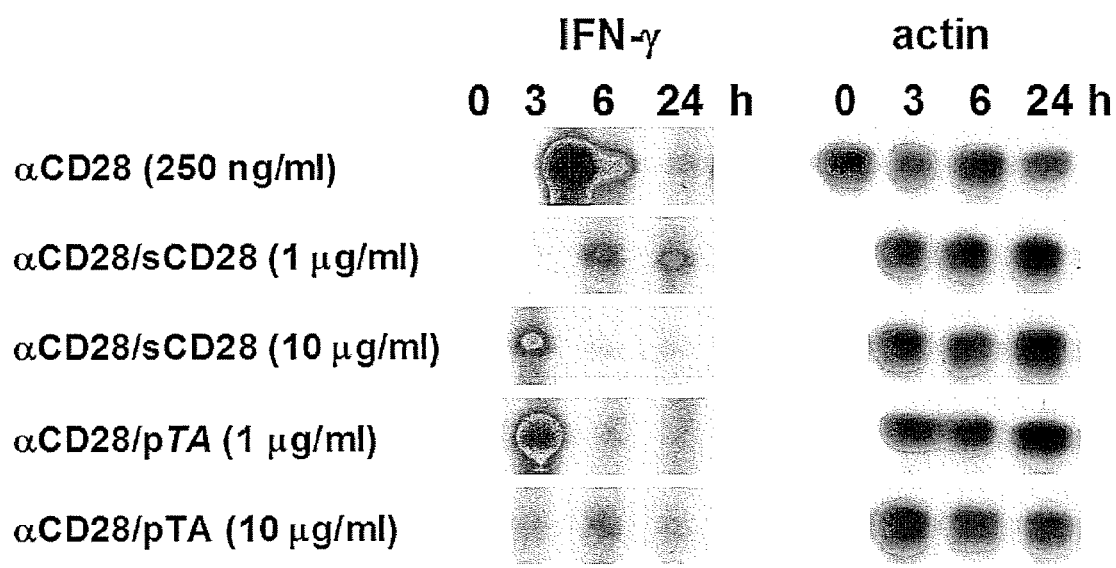

FIGS. 24B-24C: Human PBMC were incubated with 250 ng/ml anti-CD28 mAb alone or in the presence of 0.1 µg/ml sCD28 or 10 µg/ml of pTA. At times indicated, IFN-γ mRNA was determined by RNase protection analysis (FIG. 24B). (FIG. 24C) shows an experiment similar to (FIG. 24B), except that PBMC were incubated with 250 ng/ml anti-CD28 mAb alone or in the presence of 1 or 10 µg/ml sCD28 or 1 or 10 µg/ml pTA. Actin served as loading control for the RNase protection analyses. Abbreviations: h (hour), ml (milliliter), µg (microgram), ng (nanogram).

FIG. 25A-25F Effect of soluble CD28 receptor and peptide pTA on the induction of IFN-γ and IL-2 mRNA and of IL-10 by SEB.

FIGS. 25A-25B: Human PBMC were incubated with 100 ng/ml SEB (open squares) alone or in the presence of 1 µg/ml sCD28 (filled circles) or 10 µg/ml pTA (filled triangles). At times indicated, IFN-γ mRNA was determined by RNase protection analysis (FIG. 25A); IL-10 was assayed by ELISA in culture medium from the same cells (FIG. 25B).

FIGS. 25C-25D: show an experiment similar to (FIG. 25A-25B), except that PBMC were incubated with 100 ng/ml SEB (open squares) alone or in the presence of 0.1 µg/ml sCD28 (filled circles) or 10 µg/ml pTA (filled triangles). Actin served as loading control for the RNase protection analyses.

Figure 25E:
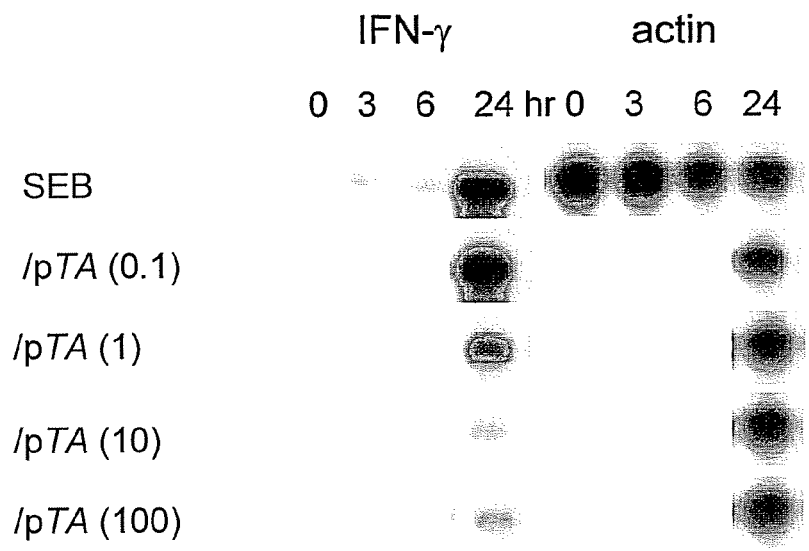
Figure 25F:
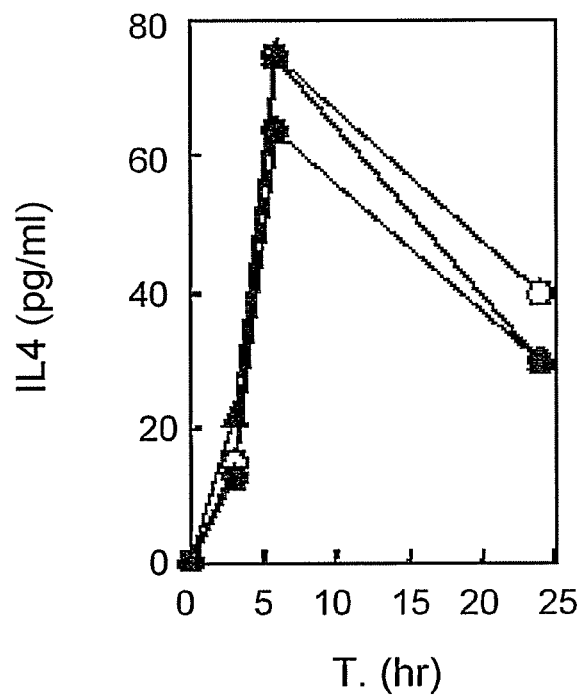

FIGS. 25E-25F: pTA antagonizes induction of Th1 cytokine mRNA by SEB. PBMC were induced by SEB alone (open circles) or with 0.1 µg/ml sCD28 (filled circles) or 10 µg/ml pTA (filled triangles). IL2, IFN-γ and actin mRNA, IL10 and IL4 were determined (FIG. 25F shows only IL4). In a separate experiment (FIG. 25F), pTA was added in increasing concentrations (µg/ml); IFN-γ and actin mRNA was determined.

Abbreviations: T (Time), h (hour), pg (picogram), ml (milliliter), µg (microgram), ng (nanogram).

Figure 26A:
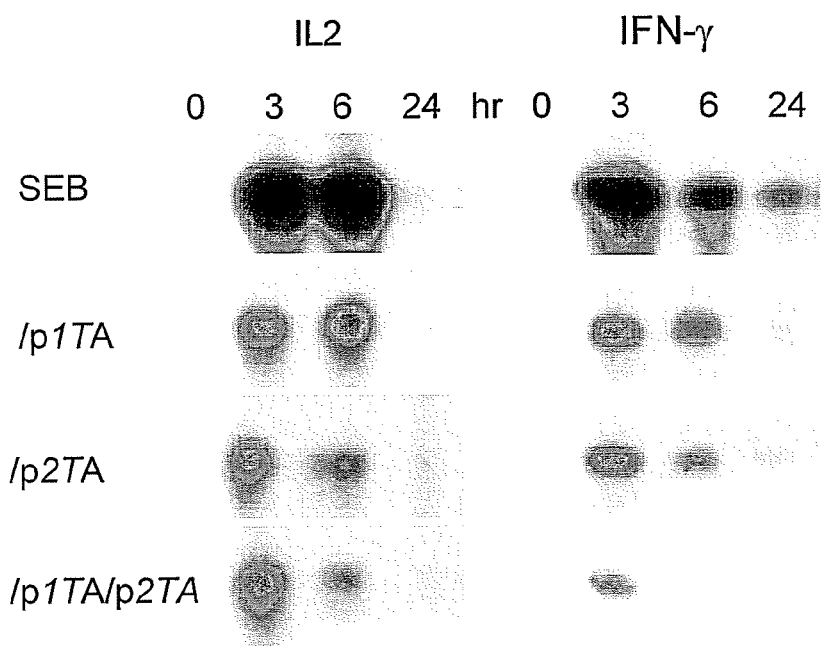
Figure 26B:
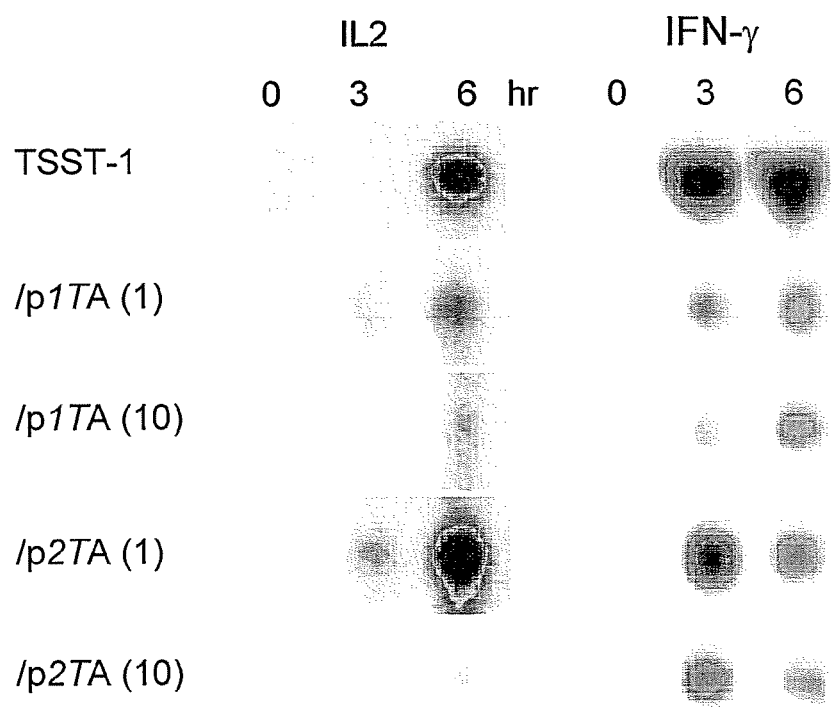

FIG. 26A-26C p1TA and p2TA antagonize induction of IL2 and IFN-γ mRNA by SEB or TSST-1.

FIG. 26A: PBMC were induced with SEB alone or with 0.1 µg/ml p1TA, p2TA or both.

FIG. 26B: PBMC were induced with TSST-1 (Sigma) alone or with p1TA or p2TA as shown, in µg/ml. IL2 and IFN-γ mRNA was determined; actin mRNA (not shown) served as loading control;

FIG. 26C: Sequence Alignment of ICOS with CD28 and CTLA4.

Amino acid sequences of the extracellular domains of human (h) ICOS (residues 1-130 of SEQ ID NO:24) (accession number Q9Y6W8), CD28 (residues 1-127 of SEQ ID NO:22) and CTLA4 (residues 1-125 of SEQ ID NO:23) and murine (m) ICOS (SEQ ID NO:66) (accession number NP_059508), CD28 (SEQ ID NO:64) and CTLA4 (SEQ ID NO:65) are shown. The CD28 sequence is numbered. Residues conserved between hICOS and hCD28 are shown in dark bluegreen; yellow marks B7 binding site. Conserved residues appear in bold face. A gap in CD28 used for the alignment with ICOS is shown in magenta. Sequences in ICOS colored cyan overlap with the two dimer interface sequences (red and green) in CD28 and CTLA4; the corresponding ICOS peptide p1TC aligns with CD28 peptide p1TA and CTLA4 peptide p1TB, and the corresponding ICOS peptide p2TC aligns with CD28 peptide p2TA and CTLA4 peptide p2TB. Abbreviations: hr. (hour).

FIG. 27A-27J CD28, CTLA4 and ICOS mimetic peptides protect mice from lethal shock.

Figures 27G, 27H, 27I:
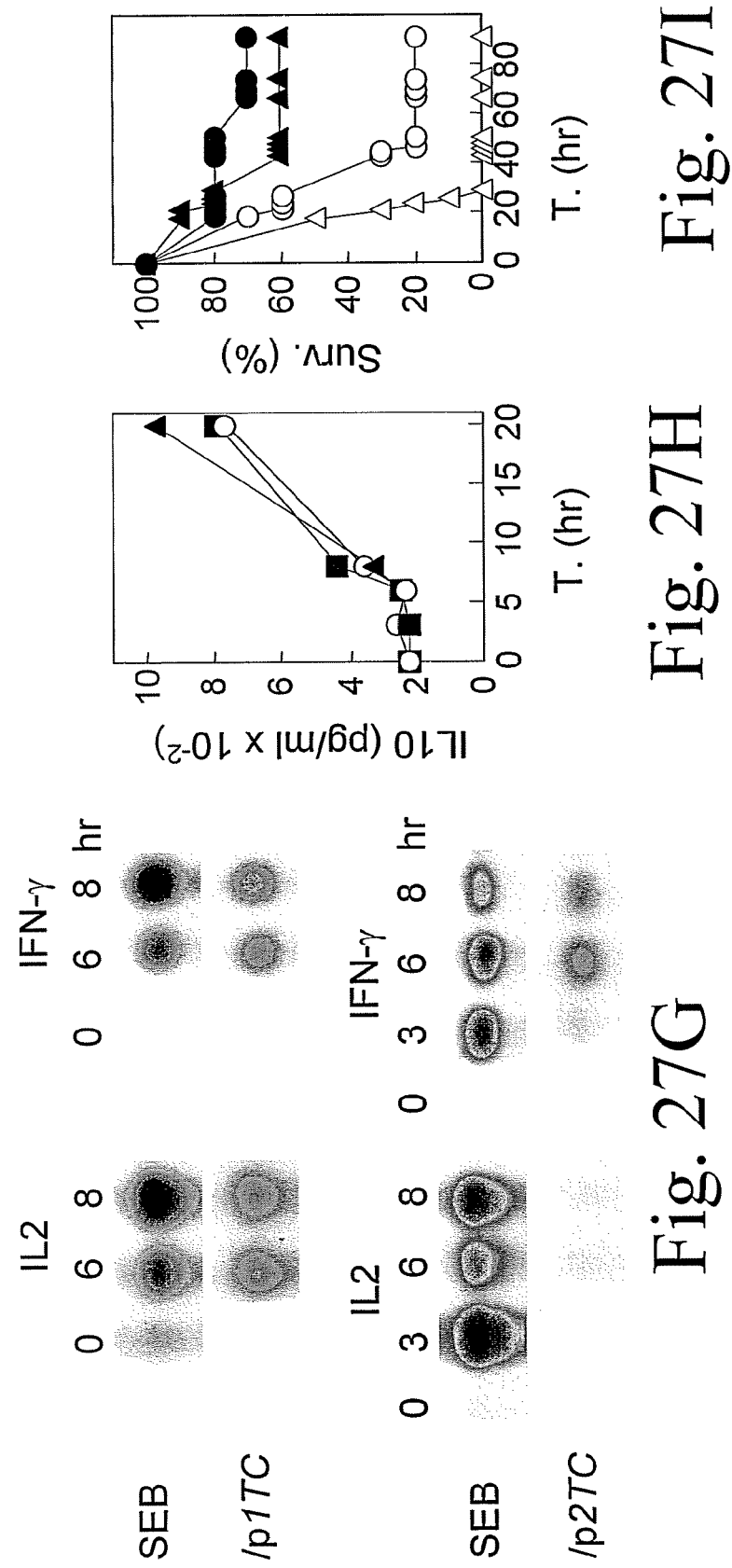

FIG. 27A: Antagonist activity of p1TA is sequence specific. PBMC were induced with SEB alone or with 1 µg/ml p1TA or its scrambled form p1TAsc (CHGHLVPKK, SEQ ID NO: 10). IFN-γ and actin mRNA was determined;

FIGS. 27B, 27C: CD28 mimetic peptides protect mice from lethal challenge with SEB. Groups of 10 mice were challenged with 6 µg SEB alone (open squares) or with p1TA (1 µg)(filled triangles), p14A (5 µg)(open circles) or p1TAsc (1 µg)(filled circles)(FIG. 27B), or with 0.2 µg p2TA (filled triangles) or its scrambled form p2TAsc (ASMDYPVL, SEQ ID NO: 11)(filled circles)(FIG. 27C). Controls received 25 µg of p1TA (FIG. 27B) or p2TA (FIG. 27C) 30 min before injection of D-galactosamine without SEB (open triangles);

FIGS. 27D-27F: Antagonist activity of CTLA mimetic peptides. PBMC were induced with SEB alone (open circles) or with 1 µg/ml p1TB (filled triangles) or p2TB (filled squares) (FIG. 27E). IL2, IFN-γ and actin mRNA and IL10 were determined (FIG. 27D). Groups of 10 mice were challenged with 6 µg SEB alone (open squares) or with 0.5 µg p1TB (filled triangles) or p2TB (filled squares) (FIG. 27F);

FIGS. 27G-27I: Antagonist activity of ICOS mimetic peptides. PBMC were induced with SEB alone (open circles) or with 1 µg/ml p1TC (filled triangles) or 0.1 µg/ml p2TC (filled squares). IL2, IFN-γ and actin mRNA and IL10 were determined. Groups of 10 mice were challenged with 5 µg SEB alone (open circles) or with 2.5 µg p1TC (filled circles) and with 6 µg SEB alone (open triangles) or with 0.2 µg p2TC (filled triangles).

Figure 27J:
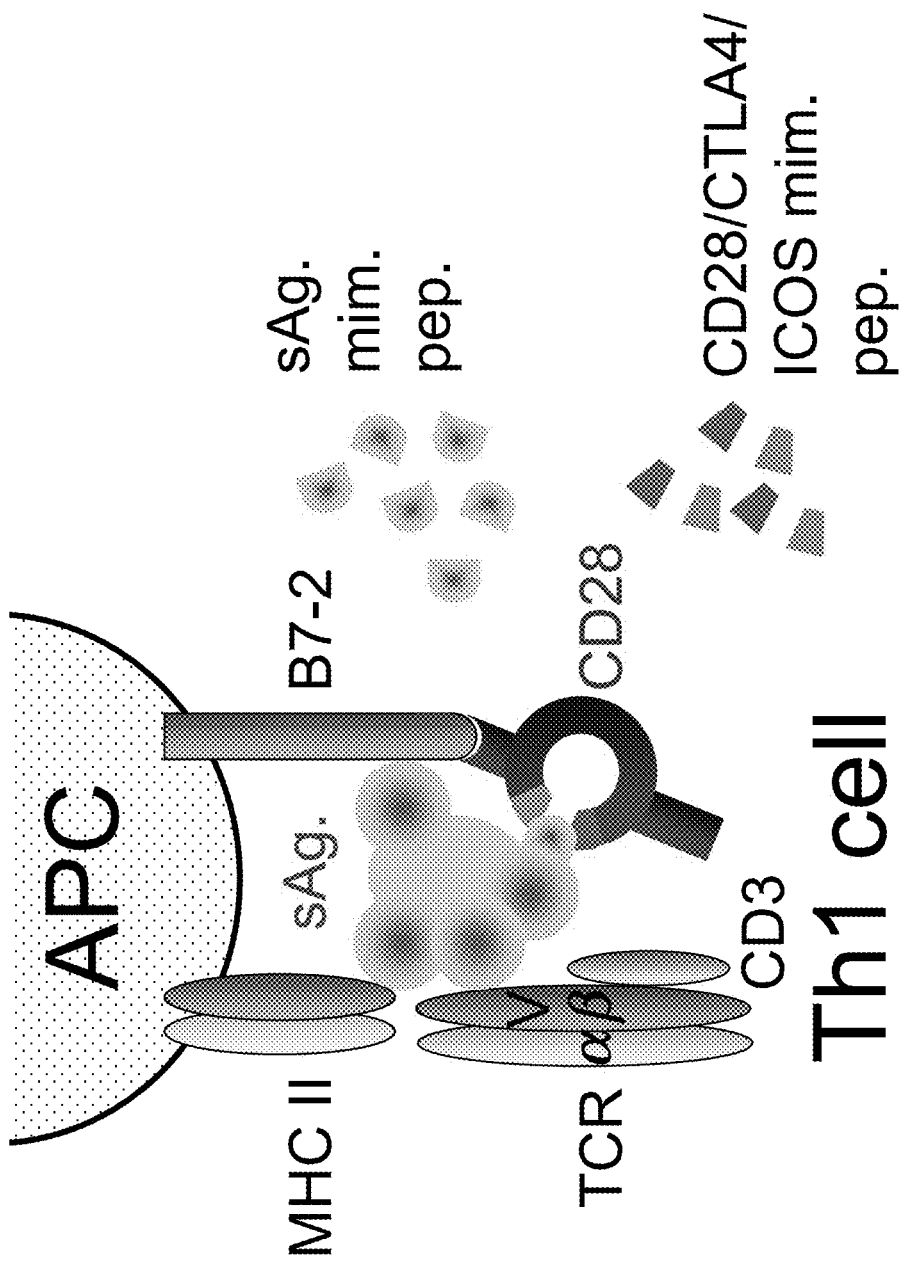

FIG. 27J: Schematic representation showing the interactions of SEB, antagonist peptides and CD28 target. Direct binding of superantigen to CD28 is required for activation and can be blocked by peptide mimetics of the contact region in each ligand: the antagonist domain in superantigens and the two rims (red and green) of the predicted dimer interface in CD28. Abbreviations: Surv. (survival), T (time), h (hour), sAg (superantigen), APC (antigen presenting cell), Ce. (cell), mim. Pep. (mimetic peptides).

FIG. 28A-28D: Screening assay for phages that bind tightly to sCD28.

Figure 28A:
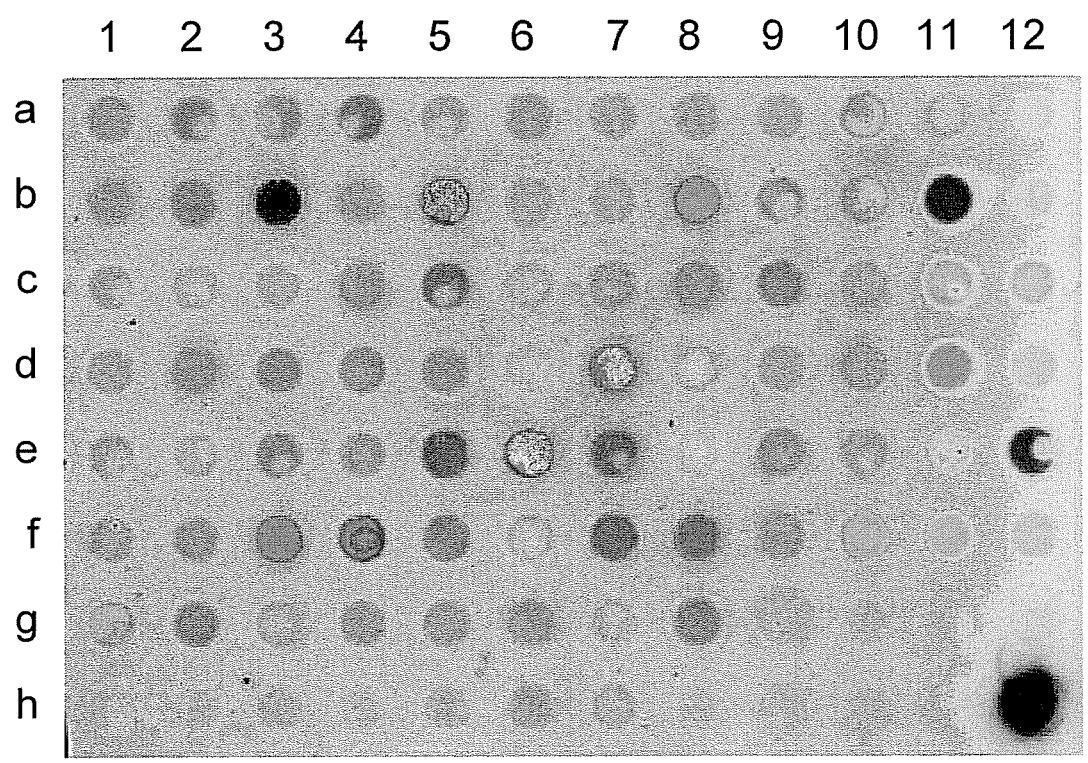

FIG. 28A: After 4 rounds of panning the PhD-12 phage display library on sCD28 and displacement with 100 µg/ml SEB, individual clones ($10^{10}$ phage/clone) were immobilized on ECL-plus membranes and binding of sCD28 was detected with 0.5 µg/ml HRP-conjugated sCD28 (R&D Systems). Positive control, αCD28 mAb (h12). Negative control, phage lacking insert (h5-h7);

FIG. 28B, 28C: Antagonist activity of pe12. PBMC were induced with 100 ng/ml SEB (open circles), 1 µg/ml pe12 or both (filled circles). IL2, IFN-γ and actin mRNA (FIG. 28B) and IL10 (FIG. 28C) were determined;

FIG. 28D: pe12 protects mice from killing by SEB. Groups of 10 mice were challenged with 6 µg SEB alone (open squares) or with 0.2 µg pe12 (filled triangles). Controls received 1 µg pe12 at 30 min before injection of D-galactosamine without SEB (open circles). Survival was monitored. Abbreviations: Surv. (survival), T (time), h (hour).

FIG. 29A-29C SEB antagonist activity of pc3 selected by affinity for CD28.

FIGS. 29A, 29B: Antagonist activity of pc3. PBMC was induced with 100 ng/ml SEB (open circles), 100 ng/ml pc3 (selected from another ECL assay) or both (filled circles). IL2, IFN-γ and actin mRNA (FIG. 29A) and IL10 (FIG. 29B) were determined;

FIG. 29C: pc3 protects mice from killing by SEB. Groups of 10 mice were challenged with 6 µg SEB alone (open squares) or with 0.5 µg pc3 (filled triangles). Controls received 1 µg pc3 at 30 min before injection of D-galactosamine without SEB (open circles). Survival was monitored. Abbreviations: Surv. (survival), T (time), h (hour), pg. (picogram).

FIG. 30A-30C SEB antagonist activity of pd7 selected by affinity for CD28.

FIGS. 30A, 30B: Ant of CTLA-4 [Ostrov et al., Science 290:816-819 (2000)], and B7-2 binds to CD28 and CTLA-4 with lower affinity than does B7-1 [Greenfield et al., Crit. Rev. Immunol. 18:389-418 (1998)]. The data in FIGS. 1-27 lead to the novel concept that effective B7-2/CD28 interaction becomes possible once the superantigen, held in place by its binding to TCR and MHC class II molecule, binds directly to CD28 on the Th1 cell. It is this latter binding step that is blocked by antagonists, particularly antagonist peptides. The Th2 cell, by contrast, is activated by superantigen without a need for the B7-2/CD28 interaction and thus the Th2 response is not inhibited by the antagonist peptide.

The superantigen and antagonist peptide each bind directly to CD28, CTLA4 and ICOS. The results show that the superantigen acts to provide a bridge that facilitates the functional interaction between CD28 and B7-2 needed for Th1 cell activation. This function is not needed for Th2 cell activation.

Therefore, in a preferred embodiment, direct binding between the CD28 molecule and the superantigen at the invention's superantigen binding site in CD28, facilitates the binding of a B7-2 ligand to CD28. More particularly, this specific binding is essential for activation of Th1 lymphocytes as defined by the induction of IL-2 and/or IFN-γ gene expression. However, as will be discussed below, binding of a B7-2 ligand to CD28 is not essential for activation of Th2 lymphocytes as defined by the induction of IL-4 and/or IL-10.

As shown by Example 1, the CD28 receptor is not required for the activation of a Th2 response by a superantigen, exemplified here for the induction of IL-10 by SEB. Indeed, both anti-CD28 and sB7-2 failed to induce expression of the Th2 cytokine IL-10 whereas they induced distinct Th1 responses. This unique dependence of the Th1 response to superantigen on CD28 signaling is new and surprising, same as the finding that the B7-2 ligand and not B7-1 is uniquely involved in the Th1 response to a superantigen.

The findings go a long way towards explaining the selective mode of action of the superantigen antagonist in blocking a Th1 response. Activation of Th2 cells by a superantigen occurs through the TCR without need for CD28 whereas the activation of Th1 cells exhibits an absolute requirement for not only the TCR but also the CD28/B7-2 complex that is used by ordinary antigens merely as a co-stimulatory ligand pathway. As a result, the activation of Th1 cells by a superantigen depends fully on a direct binding interaction between superantigen and CD28. This dependence renders the activation of Th1 cells selectively sensitive to any antagonist that acts to block the interaction between a superantigen and CD28.

The response to a superantigen entails a transient expression of Th1 cytokines within the first hours of a cellular immune response, as opposed to the more sustained and prolonged expression of Th2 cytokines which leads to B cell differentiation and the subsequent antibody response. The selective requirement for binding of a superantigen to CD28 and signaling through the CD28/B7-2 interaction in the activation of Th1 cells, divulged here, renders this response tightly regulated, because the superantigen must interact simultaneously with MHC class II molecule, TCR and CD28/B7-2 to activate. By contrast, the activation of Th2 cells bypasses the CD28/B7-2 requirement and therefore, is less stringently controlled.

The antagonist peptide does not block the activation of either a Th1 response or a Th2 response by anti-CD3, which signals through the TCR. Indeed, the antagonist peptide is homologous to a domain in superantigens that is well removed from the region that contacts the TCR [Arad et al., (2000) ibid]. The antagonist peptide does not block the superantigen-mediated Th2 response in conditions where the Th1 response is inhibited. The explanation is that the antagonist peptide blocks the binding of the superantigen to CD28 and thus prevents CD28/B7-2 signaling needed for the Th1 response but not for the Th2 response. The antagonist peptide does not block signaling through the TCR which is needed for both Th1 and Th2 responses.

Thus, according to a preferred embodiment, the invention's superantigen binding site in CD28 (as well as in CTLA4 and ICOS), specifically and directly binds to a spatially conserved domain of a pyrogenic exotoxin. Preferably, this spatially conserved domain is not involved in the binding of any one of MHC Class II molecules and TCR. Most preferably, the said spatially conserved domain of pyrogenic exotoxin forms therein a central turn starting within a β-strand 7 and connecting the β-strand 7, via short β-strand 8, to an α-helix 4, and ending within α-helix 4, based on the domain numbering of SEB [Arad et al., (2000), (2001) ibid.].

The results of Example 5 (FIGS. 12, 17 and 21) taken together, show that a superantigen, or an antagonist peptide, facilitate the binding of B7-2 to CD28. Indeed, because the anti-CD28-mediated activation of a Th1 response was sensitive to inhibition by antagonist peptide, the epitope in CD28 which is recognized by the antibody must overlap, at least in part, with the binding site for the antagonist peptide (and for superantigen). Anti-CD28-mediated activation of a Th1 response was also sensitive to inhibition by sB7-2, showing that the epitope in CD28 recognized by the antibody may be influenced through the binding site for B7-2, either by steric hindrance or by allosteric interaction. Thus, the binding sites for superantigen (or antagonist peptide) and sB7-2 within the folded CD28 protein molecule may interact, either by steric hindrance or by allosteric interaction. Therefore, according to a specifically preferred embodiment, the superantigen binding site in CD28 and the B7-2 binding site may interact within the folded CD28 molecule, either by steric hindrance or by allosteric interaction.

As shown by FIG. 22, SEB, as well as antagonist peptide clearly bind also to other CD28/B7 family members, CTLA4 and ICOS. Therefore, according to another specific embodiment, the invention relates to a superantigen binding site within the CTLA4 molecule. This specific binding site comprises an amino acid sequence derived from all or part of a dimer interface of CTLA4, which comprises amino acid residues 10-15 and 115-120 of the human CTLA4 amino acid sequence as denoted by SEQ ID NO: 23.

In yet another particular embodiment, the invention provides a superantigen binding site within the ICOS molecule. This specific binding site comprises an amino acid sequence derived from all or part of a dimer interface of ICOS, which comprises amino acid residues 10-15 and 119-124 of the human ICOS amino acid sequence as denoted by SEQ ID NO: 24.

In a second aspect, the invention relates to a method for the treatment of a superantigen-related disorder in a mammalian subject in need of such treatment. The method of the invention comprises the step of inhibiting the interaction between a T cell costimulatory pathway member molecule and said superantigen.

According to a specifically preferred embodiment, the T cell costimulatory pathway may be the CD28/B7 pathway and said pathway member is the CD28 molecule.

According to another specific embodiment, inhibition of the direct binding between CD28 molecule and said superantigen may be performed by administering to said subject a therapeutically effective amount of a substance that inhibits the direct interaction between CD28 molecule and said superantigen. More specifically, said substance inhibits the binding of the superantigen to the CD28 superantigen binding site according to the invention. Alternatively, a therapeutic effective amount of a composition comprising said substance, may be administered to said subject in need. Such composition optionally further comprises pharmaceutically acceptable carrier, diluent, excipient and/or additive.

In a specific embodiment, the substance used by the method of the invention may be selected from the group consisting of small molecules, enzymes, carbohydrates based, lipid based, natural organic based, synthetically derived organic based or inorganic based molecules, a T cell costimulatory pathway member molecule or any fragment thereof comprising the superantigen binding site.

According to another embodiment, said interaction is the binding of the superantigen to the superantigen binding site within the T cell costimulatory pathway member molecule as defined by the invention.

In another preferred embodiment, such superantigen is a pyrogenic exotoxin.

More particularly, the inhibition of the direct interaction between a T cell costimulatory pathway member molecule and the pyrogenic exotoxin leads to inhibition of exotoxin-mediated activation of Th1-lymphocytes, protection against toxic shock and may also leads to indirect elicitation of protective immunity against toxic shock induced by a pyrogenic exotoxin or by a mixture of at least two pyrogenic exotoxins.

The therapeutically 'effective amount' for purposes herein is that determined by such considerations as are known in the art. The amount must be sufficient to inhibit the direct interaction between a T cell costimulatory pathway member molecule and the pyrogenic exotoxin and to antagonize toxin-mediated activation of T cells.

It should be noted that although the method of the invention is particularly intended for the treatment of superantigen-related disorders in humans, other mammals are included. By way of non-limiting examples, mammalian subjects include monkeys, equines, cattle, canines, felines, rodents such as mice and rats, and pigs.

In yet another preferred embodiment, the superantigen may be a pyrogenic exotoxin. Preferably, the pyrogenic exotoxin may be a bacterial exotoxin and most preferably, this exotoxin may be produced by any one of *Staphylococcus aureus* and *Streptococcus pyogenes*. The superantigen-related disorder treated by the method of the invention, may be according to a specific embodiment any one of toxic shock, incapacitation and death, induced by a pyrogenic exotoxin or by a mixture of at least two pyrogenic exotoxins.

The invention further provides for a method of inhibiting pyrogenic exotoxin-mediated activation of Th1-lymphocytes and of protecting against toxic shock induced by a pyrogenic exotoxin or by a mixture of pyrogenic exotoxins, in a subject in need of such treatment. This method comprises administering to said subject a therapeutically effective amount of a substance that inhibits the direct interaction between a T cell costimulatory pathway member molecule, preferably, CD28, and said pyrogenic exotoxin or of a composition comprising said substance. The composition of the invention further optionally comprises pharmaceutically acceptable carrier, diluent, excipient and/or additive.

Still further, the invention provides for a method of eliciting protective immunity against toxic shock induced by a pyrogenic exotoxin in a subject in need of such treatment. Such method comprises administering to the subject an immunologically effective amount of a substance that inhibits the direct interaction between a T cell costimulatory pathway member molecule, preferably, CD28, and said pyrogenic exotoxin, or of a composition comprising said substance, which composition may further optionally comprise pharmaceutically acceptable carrier, diluent, excipient and/or additive.

By the term 'immunologically effective amount' is meant any amount sufficient to enhance the production of antibodies that block T cell activation induced by pyrogenic exotoxins, and confer immunity against toxic shock induced by a pyrogenic exotoxin or by a mixture of pyrogenic exotoxins.

In yet another aspect, the present invention relates to a substance that inhibits the binding of a superantigen to the superantigen binding site in a T cell costimulatory pathway member, preferably, CD28, as defined by the invention. Such substance may be selected for example, from the group consisting of small molecules, enzymes, carbohydrates based, lipid based, natural organic based, synthetically derived organic based or inorganic based molecules, a T cell costimulatory pathway member molecule or any fragment thereof comprising the superantigen binding site. Specifically, said superantigen may be a pyrogenic exotoxin According to a preferred embodiment of this aspect of the invention, inhibition of binding of said pyrogenic exotoxin to said CD28 superantigen binding site, by the substance of the invention, leads to antagonizing toxin-mediated activation of Th1 lymphocytes and may also lead to indirect elicitation of protective immunity against toxic shock induced by said pyrogenic exotoxin or by a mixture of at least two pyrogenic exotoxins. More particularly, this binding is mediated by the superantigen binding site in CD28 as defined by the invention.

The term toxin-mediated activation as used throughout this application can mean activation of T cells mediated by a single pyrogenic exotoxin or a mixture of such toxins.

In another embodiment, the substance according to the invention, is intended for use in the treatment of superantigen-related disorders.

The antagonist substance, and preferably antagonist peptide, can be used for both immediate treatment of acute toxic shock and of the harmful effects which may be due to, for example, accidental food poisoning, induced by pyrogenic exotoxins and for conferring long-term immunity against such toxic shock.

The present invention further relates to the use of the anatagonist substance of the invention, in the preparation of a pharmaceutical composition for the treatment of superantigen-related disorders. Such disorders may be any one of toxic shock, incapacitation and death, induced by a pyrogenic exotoxin or by a mixture of at least two pyrogenic exotoxins.

In a fourth aspect, the present invention relates to a pharmaceutical composition for the treatment and/or prophylaxis of superantigen-related disorders. The composition of the invention comprises as an active ingredient a therapeutically effective amount of a substance that inhibits the direct interaction between a T cell costimulatory pathway member molecule, preferably, CD28 and said pyrogenic exotoxin. Such inhibition leads to antagonizing of toxin-mediated activation of Th1 lymphocytes. This composition optionally further comprises at least one of pharmaceutically acceptable carrier, diluent, excipient and/or additive. It should be noted that such substance may be selected for example, from the group consisting of small molecules, enzymes, carbohydrates based, lipid based, natural organic based, synthetically derived organic based or inorganic based molecules, a T cell costimulatory pathway member molecule or any fragment thereof comprising the superantigen binding site.

It is known that CD28 acts as a costimulatory ligand for conventional antigens. In the present study, the inventors show that, in order to deliver the signal for Th1 activation, a superantigen must bind directly to CD28. Thus, as demonstrated by the following Examples, CD28 serves as the third superantigen receptor, in addition to the MHC II molecule and TCR.

Figure 5A:
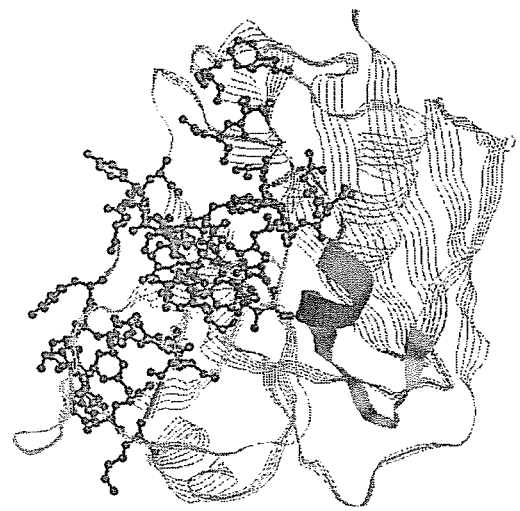

FIG. 24A shows that the binding site for superantigens in CD28 is the bipartite dimer interface predicted from alignment with CTLA4. The superantigen domain that engages CD28 is remote from the binding sites for both MHC class II molecule and TCR, leaving it accessible for interaction with the CD28 family molecules (FIG. 5A). This domain contains at least part of a β-strand-hinge-α-helix motif, which is conserved among the bacterial superantigens [Arad (2000) ibid.].

As shown by the inventors, SEB induces a vigorous and concomitant expression of Th1 and Th2 cytokine genes, but only induction of the Th1 response is dependent on CD28 signaling. The high affinity of superantigens for CD28 underlies their ability to elicit an excessive Th1 response. Thus, it seems that superantigens co-opt a costimulatory ligand of the host for use as their obligatory receptor, binding it directly. This strategy may be employed more widely by pathogens. Toll-like receptors recognize microbial components and thereby activate the innate immune response [Akira, S. et al. Nat. Immunol. 2:675-680 (2001); Janeway, C. A. Jr. and Medzhitov, R. Annu. Rev. Immunol. 20:197-216 (2002)]. In the present study, the inventors show that CD28 is a sensor of bacterial superantigens.

The present invention provides independent lines of evidence to support the concept that there is direct binding of superantigens to CD28. SPR (Surface Plasmon Resonance) equilibrium binding analysis showed that CD28 binds directly to SEB, with nanomolar affinity (FIG. 22A). Soluble CD28 blocked induction of Th1 cytokine mRNA by SEB (FIGS. 7A and 7D). Superantigen mimetic peptide p14A, homologous to the β-strand-hinge-α-helix 'antagonist domain' in SEB, and CD28 mimetic peptides p1TA and p2TA (SEQ ID NO: 15 and 16, respectively), corresponding to two noncontiguous sequences that form the predicted dimer interface in CD28, each blocked superantigen-mediated induction of IL2 and IFN-γ mRNA in human PBMC (FIGS. 3C, 26A, and 26B) and protected mice from lethal challenge with SEB (FIGS. 27B and 27C).

Novel peptide antagonists of SEB, effective in vivo, were selected from a random phage display library solely by their affinity for the SEB binding site in CD28 (FIG. 28). p14A blocked induction of Th1 cytokine gene expression by αCD28, alone or in combination with αCD3 (FIG. 10), apparently by interfering with binding of the mAb to its epitope in CD28. Indeed, in SPR kinetics, CD28 bound the p12 peptide with an affinity resembling that for SEB (FIG. 22D). Thus, SEB uses its antagonist domain to bind CD28.

Moreover, as shown by the following Examples, the soluble CD28 molecule (sCD28) may serve as an antagonist substance that inhibits the interaction between the superantigen (SEB) and the superantigen binding site within the membranal CD28 receptor molecule. More particularly, FIGS. 7 and 8, clearly indicate that the sCD28 molecule specifically inhibits SEB mediated activation of Th1 lymphocytes (IL-2 and IFN-γ) and not the Th2 activation (IL-10). Therefore, sCD28 or any fragments thereof comprising the superantigen binding site of CD28, may compete with the CD28 transmembranal receptor for binding to the superantigen.

Thus, sCD28, as well as fragments comprising the superantigen binding site of CD28 molecule, may be used as substances which inhibit the interaction between CD28 and the superantigen.

Particular example for such substance is therefore provided by a further aspect of the invention, which relates to an isolated and purified peptide comprising an amino acid sequence derived from a dimer interface of a T cell co-stimulatory pathway member. Alternatively, said peptide comprises an amino acid sequence which specifically binds to an amino acid sequence within the dimer interface of a T cell co-stimulatory pathway member.

According to one embodiment, the T cell co-stimulatory pathway may be any one of the CD28/B7 T cell co-stimulatory pathway, the CD40 ligand/CD40, CD2/CD58 and the LFA-1 (CD18)/ICAM-1 (CD54) co-stimulatory pathway.

In a preferred embodiment, the T cell co-stimulatory pathway may be the CD28/B7 pathway. Accordingly, the CD28/B7 pathway member may be any one of CD28, CTLA-4, ICOS and PD-1, B7-1, B7-2, ICOSL, PD-L1 and PD-L2.

According to one specifically preferred embodiment, the pathway member may be the CD28 molecule, and the dimer interface within CD28 comprises amino acid residues 10-15 and 116-121 of the human CD28 amino acid sequence, as denoted by SEQ ID NO: 22.

According to another preferred embodiment, the pathway member may be the CTLA-4 molecule, and the dimer interface within CTLA-4 comprises amino acid residues 10-15 and 115-120 of the human CTLA-4 amino acid sequence, as denoted by SEQ ID NO: 23.

In yet another embodiment, the pathway member may be the ICOS molecule and the dimer interface within ICOS comprises all or part of amino acid residues 10-15 and 119-124 of the human ICOS amino acid sequence as denoted by SEQ ID NO: 24.

Still further, the pathway member may be the PD-1 molecule. Although PD-1 is known as a monomer, the domains in PD-1 which overlap with the dimer interface of CTLA4 are folded similarly.

As described herein, the peptide of the invention is an immunomodulatory peptide capable of modulating a T cell costimulatory pathway.

In one preferred embodiment, the peptide of the invention may comprise an amino acid sequence derived from the dimer interface of a T cell co-stimulatory pathway member, preferably of a CD28/B7 family member.

More specifically, the peptide of the invention comprises an amino acid sequence derived from all or part of the dimer interface of any one of CD28, CTLA-4, ICOS and PD-1.

The structure of CD28 likely is similar to that of CTLA4 (FIG. 24A) [Schwartz (2001) ibid.; Luhder (2003) ibid.]. CD28 and CTLA4 show overall homology, with identity in their B7 binding domains, yet differ completely in two sequences that create the dimer interface in CTLA4, probably to prevent heterodimer formation [Schwartz (2001) ibid.; Collins (2002) ibid.]. In the folded CTLA4 protein, these remote sequences are juxtaposed (FIG. 24A). Peptides p1TA and p2TA derived from each rim of the dimer interface predicted for CD28 blocked the action of superantigens as widely different as SEB and TSST-1 and were protective in vivo when present in about equimolar ratio to SEB. These results provide strong evidence to the fact that to the superantigen binding site in CD28 and that it is the bipartite dimer interface.

CD28 belongs to a triad of costimulatory ligands: CD28, CTLA4, and ICOS that show up to 33% sequence identity [Carreno and Collins (2002) ibid.]. The inventors have shown that SEB bound directly to each one of them, with similar affinity (FIGS. 22A, 22B, and 22C). Binding occurs at the dimer interface of each costimulatory receptor. Peptides derived from either rim of the bipartite dimer interface in CTLA4 or that predicted for ICOS by alignment (FIG. 26C) are strong superantigen antagonists that, like CD28 mimetic peptides, protected mice from lethal challenge with SEB at a low molar ratio to the toxin (FIG. 27). Evidently, the mode of action of these antagonists is to compete with CD28 for its binding site in superantigens, the antagonist domain, since CD28, CTLA4 and ICOS bound directly to p12C, with nanomolar affinity (FIGS. 22D, 22E, and 22F).

The dimer interface in CTLA4 and those predicted for CD28 [Schwartz (2001) ibid.] and ICOS (present application) lack sequence homology, yet functional analyses (FIG. 27) of the present invention indicate that each uses this interface to bind SEB. Apparently, the three dimer interfaces are folded similarly. The antagonist domain in superantigens likewise shows spatial conservation despite sequence heterogeneity [Arad (2000) ibid.]. Thus, in both sets of ligands, the receptor triad and superantigens, structural features generate the contact surface.

Figure 4A:
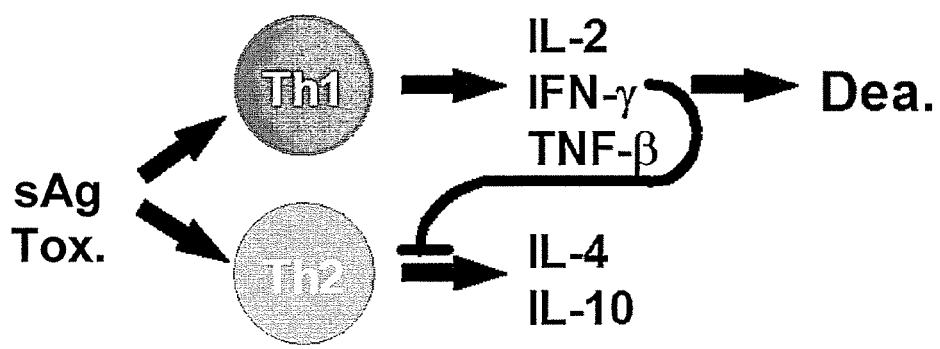
Figure 4B:
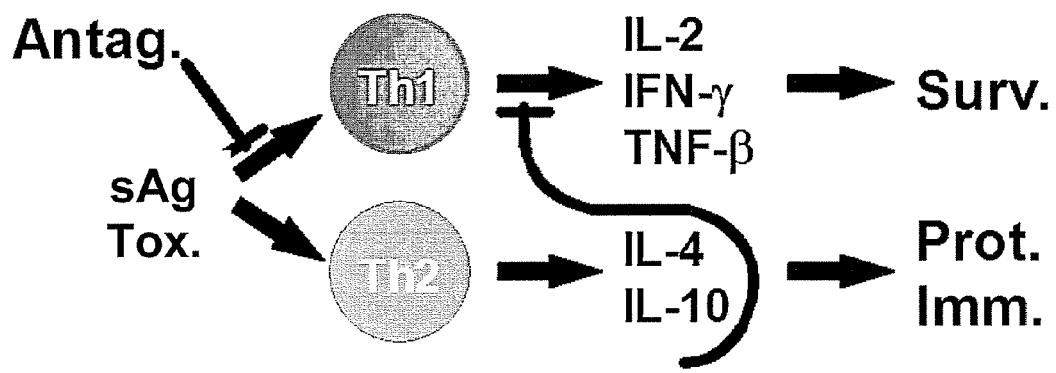

The structure of the costimulatory receptor programmed death-1 (PD-1) has been resolved and can be superimposed to the structure of CTLA4, allowing the alignment of their amino acid sequences [Zhang (2004) ibid.]. The sequences YVIDPEPCP (p1TB, SEQ ID NO: 18) and PAVVLASS (p2TB, SEQ ID NO: 19), related to the dimer interface in CTLA4, are aligned with the PD-1 sequences RVTERRAEV (p1TD, SEQ ID NO: 59) and PALLVVTE (p2TD, SEQ ID NO: 60), respectively. Although PD-1 is a monomer, the domains in PD-1 overlapping with p1TD and p2TD are folded similarly to those in CTLA4 overlapping with p1TB and p2TB [Zhang (2004) ibid.]. Therefore, peptides p1TD and p2TD derived from these two noncontiguous domains in PD-1 are potential competitors for the binding site for CD28 in a superantigen, which will result in the inhibition of superantigen action. However, although PD-1 and CTLA4 show high overall structural similarity, extending to the domains that correspond to the dimer interface in CTLA4 (Zhang et al., 2004). Yet, PD-1 did not bind effectively to the antagonist domain in SEB (FIG. 4H). Because PD-1 is monomeric in nature whereas CD28, CTLA4 and ICOS are dimers, a functional dimer interface may be needed for binding of a costimulatory receptor to the antagonist domain.

In a specifically preferred embodiment, the peptide of the invention is derived from a dimer interface within the CD28 molecule which comprises residues 10-15 and 116-121 of the human CD28 amino acid sequence as denoted by SEQ ID NO: 22. It should be noted that the human CD28 amino acid sequence shown by FIG. 24A and denoted by SEQ ID NO: 22 represents only the extracellular part of the human CD28 sequence according to GenBank Accession No. P10747. As shown by FIG. 24A, the predicted CD28 dimer interface corresponds to the CTLA-4 dimer interface, in position but not in sequence (positions 10-15 and 115-120 of CTLA-4). It should be further noted that the human CTLA-4 amino acid sequence shown by FIG. 24A represents only the extracellular part of the human CTLA-4 sequence according to GenBank Accession No. P16410. Preferably, the peptides of the invention comprise the CD28 dimer interface and additional flanking residues, i.e. amino acid residues 8-15 and 116-124 of CD28.

A specific preferred peptide of the invention is designated p1TA and has the amino acid sequence HVKGKHLCP as denoted by SEQ ID NO: 15 or any functional fragments and derivatives thereof.

Another specific preferred peptide of the invention is designated p2TA and has the amino acid sequence SPMLVAYD, as denoted by SEQ ID NO: 16 or any functional fragments and derivatives thereof.

Alternatively, the peptide of the invention may comprise an amino acid sequence derived from the dimer interface within the CTLA-4 molecule, which dimer interface comprises amino acid residues 10-15 and 115-120 of the human CTLA-4 amino acid sequence as denoted by SEQ ID NO: 23.

More specifically, such peptide comprises an amino acid sequence derived from any one of the amino acid sequence YVIDPEPCP as denoted by SEQ ID NO: 18, the amino acid sequence PAVVLASS, as denoted by SEQ ID NO: 19, and any functional fragments and derivatives thereof.

Accordingly, one specific preferred peptide is designated p1TB and has the amino acid sequence YVIDPEPCP, as denoted by SEQ ID NO: 18 or any functional fragments and derivatives thereof.

Another preferred specific peptide is designated p2TB and has the amino acid sequence PAVVLASS as denoted by SEQ ID NO: 19 or any functional fragments and derivatives thereof.

In yet another alternative, the peptide of the invention may comprise an amino acid sequence derived from the dimer interface within the ICOS molecule, which dimer interface comprises all or part of amino acid residues 10-15 and 119-124 of the human ICOS amino acid sequence as denoted by SEQ ID NO: 24.

More specifically, the peptide of the invention may comprise an amino acid sequence derived from any one of the amino acid sequence YESQLCCQL as denoted by SEQ ID NO: 20, the amino acid sequence GEINGSAN, as denoted by SEQ ID NO: 21, and any functional fragments and derivatives thereof.

One specific example peptide is designated p1TC and has the amino acid sequence YESQLCCQL, as denoted by SEQ ID NO: 20 or any functional fragments and derivatives thereof.

Another specific example is a peptide designated p2TC which has the amino acid sequence GEINGSAN, as denoted by SEQ ID NO: 21 or any functional fragments and derivatives thereof.

According to another preferred embodiment, the peptide of the invention comprises an amino acid sequence derived from domains in the PD-1 molecule that correspond to the dimer interface in CTLA4, comprising amino acid residues 8-13 and 110-116 [Zhang (2004) ibid.] of the human PD-1 sequence as denoted by SEQ ID NO: 61.

More specifically, the peptide of the invention may comprise an amino acid sequence derived from any one of the amino acid sequences RVTERRAEV (as denoted by SEQ ID NO: 59), PALLVVTE (as denoted by SEQ ID NO: 60) and any functional fragments and derivatives thereof.

A specific preferred peptide of the invention is designated p1TD and has the amino acid sequence RVTERRAEV, as denoted by SEQ ID NO: 59 or any functional fragments and derivatives thereof.

Another specific preferred peptide of the invention is designated p2TD and has the amino acid sequence PALL- VVTE, as denoted by SEQ ID NO: 60 or any functional fragments and derivatives thereof.

It should be noted that peptides derived from the dimer interface of any of the CD28 family molecules may comprise all or part of the amino acid sequence of any of the dimer interface rims. Therefore, the homology or similarity between any peptide of the present invention and the corresponding dimer interface within the CD28 molecule may range between 10% to 100% homology, preferably, 20% to 90% homology, and most preferably, between 30% to 80% homology.

According to another specifically preferred embodiment, the peptide of the invention comprises an amino acid sequence which specifically binds to an amino acid sequence within the dimer interface of any one of CD28, CTLA-4, ICOS and PD-1.

In one preferred embodiment, such peptide may specifically bind to an amino acid sequence within the dimer interface of the CD28 molecule, which dimer interface comprises amino acid residues 10-15 and 116-121 of the human CD28 amino acid sequence, as denoted by SEQ ID NO: 22.

Alternatively, the peptide of the invention may specifically bind to an amino acid sequence within the dimer interface of CTLA-4 molecule, which dimer interface comprises amino acid residues 10-15 and 115-120 of the human CTLA-4 amino acid sequence, as denoted by SEQ ID NO: 23.

In yet another alternative, the peptide of the invention specifically binds to an amino acid sequence within the dimer interface of the ICOS molecule, which dimer interface comprises all or part of amino acid residues 10-15 and 119-124 of the human ICOS amino acid sequence as denoted by SEQ ID NO: 24.

It should be further appreciated that the peptides of the invention may bind to sequences within the PD-1 molecule which are folded similarly to the dimer interface of CTLA4, comprising all or part of amino acid residues 8-13 and 110-116 of the human PD-1 amino acid sequence, as denoted by SEQ ID NO: 61.

Although a peptide derived from the spatially conserved domain of a pyrogenic exotoxin which forms therein a central turn starting within a β-strand 7 and connecting the β-strand 7, via short β-strand 8, to an α-helix 4, and ending within α-helix 4, based on the domain numbering of SEB, for example p12A and p14A (SEQ ID NO: 1 and 2, respectively) specifically binds to the dimer interface of the CD28 family molecules, such peptides are out of the ambit of the application. However, these peptides may be used for some of the methods of the invention, as will be described hereinafter.

Therefore, according to a preferred embodiment the invention relates to peptides which bind to the dimer interface of all three members of the CD28 family, CD28, CTLA-4 and ICOS, as well as to PD-1, provided that said peptide is not derived from the spatially conserved domain of a pyrogenic exotoxin which forms therein a central turn starting within a β-strand 7 and connecting the β-strand 7, via short β-strand 8, to an α-helix 4, and ending within α-helix 4, based on the domain numbering of SEB [Arad (2000) ibid.]

As described by Example 12 and FIG. 28A, the inventors have performed screening of phage display library on immobilized sCD28, which comprises the dimer interface of CD28 and displaced bound phages with SEB. In this screening different peptides were isolated and further analyzed for their antagonist activity. Therefore, the peptide of the invention comprises an amino acid sequence as denoted by any one of SEQ ID NO: 12, 13, 14, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57 and 58.

According to a specifically preferred embodiment, the peptide of the invention is designated pe12 and has the amino acid sequence SHFTHNRHGHST, as denoted by SEQ ID NO: 12 or any functional fragments and derivatives thereof.

Another specific peptide is designated pd7. This peptide has the amino acid sequence WHAHPHKKPVVA, as denoted by SEQ ID NO: 13 or any functional fragments and derivatives thereof.

In yet another example, the peptide of the invention is designated pc3 and has the amino acid sequence FHKHKNPGSPII, as denoted by SEQ ID NO: 14 or any functional fragments and derivatives thereof.

According to another specifically preferred embodiment, the peptide of the invention is designated pe6 and has the amino acid sequence APMYHKHRLEKH, as denoted by SEQ ID NO: 39 or any functional fragments and derivatives thereof.

According to another example, the peptide of the invention is designated pf8 and has the amino acid sequence IHKPHHHRTPLW, as denoted by SEQ ID NO: 38 or any functional fragments and derivatives thereof.

According to a preferred embodiment, any of the peptides of the invention may inhibit the direct interaction between a T cell costimulatory pathway member, preferably, the CD28 molecule and a pyrogenic exotoxin. Therefore, these peptides serve as antagonists of toxin-mediated activation of T lymphocytes, and protect against toxic shock induced by a pyrogenic exotoxin or by a mixture of pyrogenic exotoxins.

The terms derivatives and functional derivatives as used herein mean peptides comprising the amino acid sequence of any one of SEQ ID NO: 12, 13, 14, 15, 16, 18, 19, 20, 21, and 27 to 60, with any insertions, deletions, substitutions and modifications to the peptide that do not interfere with their ability to inhibit the interaction between T cell co-stimulatory pathway member and component of a pathogenic agent, preferably, an exotoxin, to elicit protective immunity against toxic shock induced by the exotoxins and/or antagonizing toxin-mediated activation of T cells or the ability to inhibit the interaction between a T cell costimulatory pathway member, preferably, CD28, and the superantigen, or to modulate a T cell costimulatory pathway, preferably the CD28/B7 pathway (hereafter referred to as "derivative/s"). A derivative should maintain its ability to bind the sAg binding site within the particular T cell costimulatory pathway member, preferably, CD28.

It should be appreciated that by the term "insertions", as used herein it is meant any addition of amino acid residues to the peptides of the invention, of between 1 to 50 amino acid residues, preferably between 20 to 1 amino acid residues, and most preferably, between 1 to 10 amino acid residues.

It is to be appreciated that the present invention also includes longer peptides which comprise part or all of the amino acid sequence of the peptides of the invention, or in which the basic peptidic sequence of any of the peptides of the invention is repeated from about 2 to about 100 times.

The lack of structure of linear peptides renders them vulnerable to proteases in human serum and acts to reduce their affinity for target sites, because only few of the possible conformations may be active. Therefore, it is desirable to optimize antagonist peptide structure, for example by creating different derivatives of the various peptides of the invention.

In order to improve peptide structure, the peptides of the invention can be coupled through their N-terminus to a lauryl-cysteine (LC) residue and/or through their C-terminus to a cysteine (C) residue, or to other residue/s suitable for linking the peptide to adjuvant/s for immunization, as will be described in more detail hereafter.

The peptides of the invention, as well as derivatives thereof may all be positively charged, negatively charged or neutral. In addition, they may be in the form of a dimer, a multimer or in a constrained conformation, which can be attained by internal bridges, short-range cyclizations, extension or other chemical modifications.

Further, the peptides of the invention may be extended at the N-terminus and/or C-terminus thereof with various identical or different amino acid residues. As an example for such extension, the peptide may be extended at the N-terminus and/or C-terminus thereof with identical or different hydrophobic amino acid residue/s which may be naturally occurring or synthetic amino acid residue/s. A preferred synthetic amino acid residue is D-alanine.

An additional example for such an extension may be provided by peptides extended both at the N-terminus and/or C-terminus thereof with a cysteine residue. Naturally, such an extension may lead to a constrained conformation due to Cys-Cys cyclization resulting from the formation of a disulfide bond.

Another example may be the incorporation of an N-terminal lysyl-palmitoyl tail, the lysine serving as linker and the palmitic acid as a hydrophobic anchor.

In addition, the peptides may be extended by aromatic amino acid residue/s. A preferred aromatic amino acid residue may be tryptophan. Alternatively, the peptides can be extended at the N-terminus and/or C-terminus thereof with amino acids present in corresponding positions of the amino acid sequence of the naturally occurring pyrogenic exotoxin or T cell costimulatory pathway member.

Further, according to the invention, the peptides of the invention may be extended at the N-terminus and/or C-terminus thereof with various identical or different organic moieties which are not a naturally occurring or synthetic amino acids. As an example for such extension, the peptide may be extended at the N-terminus and/or C-terminus thereof with an N-acetyl group.

For every single peptide sequence used by the invention and disclosed herein, this invention includes the corresponding retro-inverso sequence wherein the direction of the peptide chain has been inverted and wherein all the amino acids belong to the D-series.

It is to be appreciated that the present invention also encompasses longer peptides in which the basic peptidic sequence which comprises part or all of the amino acid sequence as denoted by SEQ ID NO: 12, 13, 14, 15, 16, 18, 18, 20, 21, 27 to 58, 59 and 60, or in which the basic peptidic sequence of any one of these peptides is repeated from about 2 to about 100 times.

According to another aspect, the invention relates to a composition for the modulation of a T cell costimulatory pathway, comprising as an active ingredient a purified peptide as defined by the invention or any combination, functional fragments and derivatives thereof, optionally further comprising pharmaceutically acceptable carrier, diluent, adjuvant and/or excipient.

The invention further provides a pharmaceutical composition for the treatment of immune disorders related to an imbalance in the Th1-Th2 response in a subject in need thereof comprising as an active ingredient any of the peptides of the invention or any combination, functional fragments and derivatives thereof and optionally further comprises pharmaceutically acceptable carrier, diluent, adjuvant and/or excipient.

The compositions of the invention may also comprise additional active agents, e.g. protease inhibitors.

More specifically, immune disorders related to an imbalance in the Th1-Th2 response immune-related disorder may be for example, an autoimmune disease, (for example, multiple sclerosis (MS), Type-1 diabetes, lupus, Graves disease and thyroiditis), malignant and non-malignant proliferative disorders, graft rejection pathology and graft versus host disease, and disorders induced by a pyrogenic exotoxin or by a mixture of at least two pyrogenic exotoxins (such as toxic shock, incapacitation and death, septic shock and severe sepsis).

According to a preferred embodiment, the invention provides a composition for the inhibition of a pyrogenic exotoxin-mediated activation of T-lymphocytes. Said composition protects against toxic shock, which may be induced by a pyrogenic exotoxin or by a mixture of pyrogenic exotoxins. The composition of the invention comprises as an active ingredient any of the purified immunomodulatory peptides of the invention or any combination, functional fragments and derivatives thereof in an amount effective to inhibit exotoxin-induced expression of an RNA encoded by the IL2 and/or IFN-γ genes, and optionally further comprises pharmaceutically acceptable carrier, diluent, adjuvant and/or excipient.

In one specifically preferred embodiment, such composition may comprise as an active ingredient a peptide selected from the group consisting of pTA (as denoted by SEQ ID NO: 5), p1TA (as denoted by SEQ ID NO: 15), p2TA (as denoted by SEQ ID NO: 16), p1TB (as denoted by SEQ ID NO: 18), p2TB (as denoted by SEQ ID NO: 19), p1TC (as denoted by SEQ ID NO: 20), p2TC (as denoted by SEQ ID NO: 21), pe12 (as denoted by SEQ ID NO: 12), pd7 (as denoted by SEQ ID NO: 13), pc3 (as denoted by SEQ ID NO: 14), pa2 (as denoted by SEQ ID NO: 27), pb11.1 (as denoted by SEQ ID NO: 28), pc11 (as denoted by SEQ ID NO: 29), pf11 (as denoted by SEQ ID NO: 30), pg3 (as denoted by SEQ ID NO: 31), pb12 (as denoted by SEQ ID NO: 32), pa8.1 (as denoted by SEQ ID NO: 33), pb3 (as denoted by SEQ ID NO: 34), pb5 (as denoted by SEQ ID NO: 35), pb11.2 (as denoted by SEQ ID NO: 36), p13 (as denoted by SEQ ID NO: 37), pf8 (as denoted by SEQ ID NO: 38), pe6 (as denoted by SEQ ID NO: 39), p14 (as denoted by SEQ ID NO: 40), pa8.2 (as denoted by SEQ ID NO: 41), pb3 (as denoted by SEQ ID NO: 42), pb2 (as denoted by SEQ ID NO: 43), pc2 (as denoted by SEQ ID NO: 44), pc8 (as denoted by SEQ ID NO: 45), pc9 (as denoted by SEQ ID NO: 46), pf12 (as denoted by SEQ ID NO: 47), pc4 (as denoted by SEQ ID NO: 48), pe11.1 (as denoted by SEQ ID NO: 49), pb5 (as denoted by SEQ ID NO: 50), pe11.2 (as denoted by SEQ ID NO: 51), pg7 (as denoted by SEQ ID NO: 52), pa12 (as denoted by SEQ ID NO: 53), pb8 (as denoted by SEQ ID NO: 54), pb12 (as denoted by SEQ ID NO: 55), pc8 (as denoted by SEQ ID NO: 56), pd8 (as denoted by SEQ ID NO: 57), pg6 (as denoted by SEQ ID NO: 58), p1TD (as denoted by SEQ ID NO: 59), p2TD (as denoted by SEQ ID NO: 60) and any combination, functional fragments and derivatives thereof.

Still further, the invention relates to a composition for inhibiting the direct interaction between a superantigen and a superantigen binding site in any one of CD28, CTLA4, ICOS and PD-1. This composition comprises as active ingredient an isolated and purified peptide, in an amount effective to inhibit said interaction.

The pharmaceutical composition of the invention may comprise the active substance in free form and be administered directly to the subject to be treated. Alternatively, depending on the size of the active molecule, it may be desirable to conjugate it to a carrier prior to administration. Therapeutic formulations may be administered in any conventional dosage formulation. Formulations typically comprise at least one active ingredient, as defined above, together with one or more acceptable carriers thereof.

Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intraperitoneal (IP), intravenous (IV) and intradermal) administration.

The pharmaceutical forms suitable for injection use include sterile aqueous solutions or dispersions and sterile powders for the extemporaneous preparation of sterile injectable solutions or dispersions. In all cases the form must be sterile and must be fluid to the extent that easy syringeability exists. It must be stable under the conditions of manufacture and storage and must be preserved against the contaminating action of microorganisms, such as bacteria and fungi.

The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

In the case of sterile powders for the preparation of the sterile injectable solutions, the preferred method of preparation are vacuum-drying and freeze drying techniques which yield a powder of the active ingredient plus any additional desired ingredient from a previously sterile-filtered solution thereof.

The pharmaceutical compositions of the invention generally comprise a buffering agent, an agent which adjusts the osmolarity thereof, and optionally, one or more pharmaceutically acceptable carriers, excipients and/or additives as known in the art. Supplementary active ingredients can also be incorporated into the compositions. The carrier can be solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants.

As used herein "pharmaceutically acceptable carrier" includes any and all solvents, dispersion media, coatings, antibacterial and antifungal agents and the like. The use of such media and agents for pharmaceutical active substances is well known in the art. Except as any conventional media or agent is incompatible with the active ingredient, its use in the therapeutic composition is contemplated.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

The pharmaceutical compositions of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers. The pharmaceutical compositions of the present invention also include, but are not limited to, emulsions and liposome-containing formulations.

The nature, availability and sources, and the administration of all such compounds including the effective amounts necessary to produce desirable effects in a subject are well known in the art and need not be further described herein. The preparation of pharmaceutical compositions is well known to the skilled man of the art and has been described in many articles and textbooks, see e.g., Remington's Pharmaceutical Sciences, Gennaro A. R. ed., Mack Publishing Co., Easton, Pa., 1990, and especially pp. 1521-1712 therein.

The ability to discriminate between self and non-self is perhaps the most fundamentally important aspect of immune regulation. This property translates into the immune recognition and destruction of infectious invaders while normal host tissues are left untouched. This highly selective response is characterized by a complicated set of T cell regulatory mechanisms that have been described over the past decades. One such mechanism designed to maintain the fidelity of the immune response is the requirement of two distinct signals for effective activation of antigen-specific T cells: an antigen-specific signal via the T cell receptor (Signal 1) and a noncognate costimulatory signal (Signal 2) that is provided by soluble factors or cell-surface molecules on the antigen presenting cell (APC). The integration of these two signals triggers cell division and differentiation of effectors and regulators of the immune response. Aside from the critical biological implications of costimulation, the identification of a costimulatory signal has important implications for clinical intervention as the effects of costimulation blockade would be restricted to only those T cells whose antigen-specific receptors have already been engaged, i.e. T cells already receiving signal 1. Thus, in principle, the selective blockade of T cell costimulation offers an antigen-specific mode of targeting immune responses without actual knowledge of the specific antigen involved. In fact, in some instances, costimulatory pathway antagonists can induce antigen-specific tolerance that prevents the progression of autoimmune diseases and organ graft rejection.

Therefore, in a further aspect, the invention relates to a method for the modulation of a T cell costimulatory pathway in a subject in need thereof. Said method comprises the step of administering to said subject an effective amount of an immunomodulatory peptide capable of modulating a T cell costimulatory pathway, which peptide comprises an amino acid sequence derived from a dimer interface of a T cell co-stimulatory pathway member. Alternatively, said peptide comprises an amino acid sequence which specifically binds to an amino acid sequence within the dimer interface of a T cell co-stimulatory pathway member or of a composition comprising the same.

Current evidence supports the concept that costimulatory ligands of the CD28/CTLA4/ICOS family have major role in the generation of autoimmune diseases [Salomon and Bluestone, Ann. Rev. Immunol. 19: 225-252 (2001); Chang et al., in Altman, A. (Ed): Signal Transduction Pathways in Autoimmunity. Curr. Dir. Autoimmun. Basel, Karger, vol. 5, pp 113-130 (2002); Khoury and Sayegh, Immunity 20:529-538 (2004)]. Multiple mechanisms contribute to CD28/B7-mediated T cell costimulation in disease settings that include expansion of activated pathogenic T cells, differentiation of Th1/Th2 cells, and the migration of T cells into target tissues. This is most apparent in regulation of the $CD4^+$ $CD25^+CTLA4^+$ immunoregulatory T cells that control multiple autoimmune diseases [Salomon and Bluestone (2001) ibid.; Kohm et al., J. Immunol. 169:4712-4716 (2002)]. The pleiotropic activities of CD28 support the potential clinical usefulness of CD28/B7 blockade in immune intervention [Salomon and Bluestone (2001) ibid.]. Understanding the mechanisms of these pathways has implications for development of novel treatment strategies for autoimmune disease, transplantation, tumor immunotherapy, and vaccine development [Khoury and Sayegh (2004) ibid.]. Interference in the CD28/B7 signaling pathway, whether by peptide mimetics of contact domains critical for signal transduction or other means, will therefore have promise in therapy of such diseases. Autoimmune diseases can be exacerbated by superantigens [Brocke et al., Nature 365:642-644 (1993)], enhancing the potential value of superantigen antagonist peptides for treatment, quite independent of their mechanism of action.

As shown by the present application, the inventors have found that peptide mimetics of the contact domains involved in the direct binding of a superantigen to CD28 are potent superantigen antagonists, including peptide mimetics of a domain that is conserved within the broad family of super-antigens and peptide mimetics of the dimer interface in each of the costimulatory ligands CD28, CTLA4 and ICOS. Thus, such peptides may have a broader therapeutic value for autoimmune diseases.

The invention thus further provides a method for the treatment of immune disorders related to an imbalance in the Th1-Th2 response in a subject in need thereof. Said method comprises the step of administering to said subject an effective amount of an immunomodulatory peptide capable of modulating a T cell costimulatory pathway or of a composition comprising the same, which peptide comprises an amino acid sequence derived from a dimer interface of a T cell co-stimulatory pathway member. Alternatively, said peptide comprises an amino acid sequence which specifically binds to an amino acid sequence within the dimer interface of a T cell co-stimulatory pathway member or of a composition comprising the same.

The therapeutically 'effective amount' for purposes herein is that determined by such considerations as are known in the art. The amount must be sufficient to inhibit the direct interaction between a T cell co-stimulatory pathway member, such as the CD28, CTLA-4, ICOS and PD-1 molecules and a component of a pathogenic agent, such as the pyrogenic exotoxin and to antagonize toxin-mediated activation of T cells.

According to one embodiment, the invention relates to a method for the treatment of immune disorders related to an imbalance in the Th1-Th2 response. Examples of said disorders are autoimmune diseases (for example, multiple sclerosis (MS), Type-1 diabetes, lupus, Graves disease and thyroiditis), malignant and non-malignant proliferative disorders, graft rejection pathology and graft versus host disease.

In general, the composition as well as the methods of the present invention may be used in the treatment of any autoimmune disease such as for example, but not limited to, Eaton-Lambert syndrome, Goodpasture's syndrome, Greave's disease, Guillain-Barr syndrome, autoimmune hemolytic anemia (AIHA), hepatitis, insulin-dependent diabetes mellitus (IDDM), systemic lupus erythematosus (SLE), multiple sclerosis (MS), myasthenia gravis, plexus disorders e.g. acute brachial neuritis, polyglandular deficiency syndrome, primary biliary cirrhosis, rheumatoid arthritis, scleroderma, thrombocytopenia, thyroiditis e.g. Hashimoto's disease, Sjogren's syndrome, allergic purpura, psoriasis, mixed connective tissue disease, polymyositis, dermatomyositis, vasculitis, polyarteritis nodosa, polymyalgia rheumatica, Wegener's granulomatosis, Reiter's syndrome, Behget's syndrome, ankylosing spondylitis, pemphigus, bullous pemphigoid, dermatitis herpetiformis, insulin dependent diabetes, inflammatory bowel disease, ulcerative colitis and Crohn's disease.

As used herein to describe the present invention, the terms "malignant proliferative disorder", "cancer", "tumor" and "malignancy" all relate equivalently to a hyperplasia of a tissue or organ. If the tissue is a part of the lymphatic or immune systems, malignant cells may include non-solid tumors of circulating cells. Malignancies of other tissues or organs may produce solid tumors. In general, the composition as well as the methods of the present invention may be used in the treatment of non-solid and solid tumors, for example, carcinoma, melanoma, leukemia, and lymphoma.

Therefore, according to a preferred embodiment, the immunomodulatory peptide of the invention or a composition comprising the same, can be used for the treatment or inhibition of non-solid cancers, e.g. hematopoietic malignancies such as all types of leukemia, e.g. acute lymphocytic leukemia (ALL), acute myelogenous leukemia (AML), chronic lymphocytic leukemia (CLL), chronic myelogenous leukemia (CML), myelodysplastic syndrome (MDS), mast cell leukemia, hairy cell leukemia, Hodgkin's disease, non-Hodgkin's lymphomas, Burkitt's lymphoma and multiple myeloma, as well as for the treatment or inhibition of solid tumors such as tumors in lip and oral cavity, pharynx, larynx, paranasal sinuses, major salivary glands, thyroid gland, esophagus, stomach, small intestine, colon, colorectum, anal canal, liver, gallbladder, extraliepatic bile ducts, ampulla of Vater, exocrine pancreas, lung, pleural mesothelioma, bone, soft tissue sarcoma, carcinoma and malignant melanoma of the skin, breast, vulva, vagina, cervix uteri, corpus uteri, ovary, fallopian tube, gestational trophoblastic tumors, penis, prostate, testis, kidney, renal pelvis, ureter, urinary bladder, urethra, carcinoma of the eyelid, carcinoma of the conjunctiva, malignant melanoma of the conjunctiva, malignant melanoma of the uvea, retinoblastoma, carcinoma of the lacrimal gland, sarcoma of the orbit, brain, spinal cord, vascular system, hemangiosarcoma and Kaposi's sarcoma.

According to a specifically preferred embodiment, any of the peptides defined by the invention, or any combination, functional fragments derivatives, conjugates and composition thereof may be used for such methods.

It should be noted that also peptides derived from the "antagonist domain" (such as p12A, p14A and p12C), may be used by the method of the invention.

More specifically, the method of the invention may use a peptide, that may be selected from the group consisting of p12A (as denoted by SEQ ID NO:1), p14A (as denoted by SEQ ID NO: 2), p12C (as denoted by SEQ ID NO:62) pTA (as denoted by SEQ ID NO: 5), p1TA (as denoted by SEQ ID NO: 15), p2TA (as denoted by SEQ ID NO: 16), p1TB (as denoted by SEQ ID NO: 18), p2TB (as denoted by SEQ ID NO: 19), p1TC (as denoted by SEQ ID NO: 20), p2TC (as denoted by SEQ ID NO: 21), pe12 (as denoted by SEQ ID NO: 12), pd7 (as denoted by SEQ ID NO: 13), pc3 (as denoted by SEQ ID NO: 14), pa2 (as denoted by SEQ ID NO: 27), pb11.1 (as denoted by SEQ ID NO: 28), pc11 (as denoted by SEQ ID NO: 29), pf11 (as denoted by SEQ ID NO: 30), pg3 (as denoted by SEQ ID NO: 31), pb12 (as denoted by SEQ ID NO: 32), pa8.1 (as denoted by SEQ ID NO: 33), pb3 (as denoted by SEQ ID NO: 34), pb5 (as denoted by SEQ ID NO: 35), pb11.2 (as denoted by SEQ ID NO: 36), pf3 (as denoted by SEQ ID NO: 37), pf8 (as denoted by SEQ ID NO: 38), pe6 (as denoted by SEQ ID NO: 39), pf4 (as denoted by SEQ ID NO: 40), pa8.2 (as denoted by SEQ ID NO: 41), pb3 (as denoted by SEQ ID NO: 42), pb2 (as denoted by SEQ ID NO: 43), pc2 (as denoted by SEQ ID NO: 44), pc8 (as denoted by SEQ ID NO: 45), pc9 (as denoted by SEQ ID NO: 46), pf12 (as denoted by SEQ ID NO: 47), pc4 (as denoted by SEQ ID NO: 48), pe11.1 (as denoted by SEQ ID NO: 49), pb5 (as denoted by SEQ ID NO: 50), pe11.2 (as denoted by SEQ ID NO: 51), pg7 (as denoted by SEQ ID NO: 52), pa12 (as denoted by SEQ ID NO: 53), pb8 (as denoted by SEQ ID NO: 54), pb12 (as denoted by SEQ ID NO: 55), pc8 (as denoted by SEQ ID NO: 56), pd8 (as denoted by SEQ ID NO: 57), pg6 (as denoted by SEQ ID NO: 58), p1TD (as denoted by SEQ ID NO: 59), p2TD (as denoted by SEQ ID NO: 60) and any combination, functional fragments derivatives and composition thereof.

Still further, the invention provides the use of an immunomodulatory peptide capable of modulating a T cell costimulatory pathway for the preparation of a composition for modulation of a T cell co-stimulatory pathway in a subject in need thereof, which peptide comprises an amino acid sequence derived from a dimer interface of a T cell co-stimulatory pathway member or an amino acid sequence which specifically binds to an amino acid sequence within the dimer interface of a T cell co-stimulatory pathway member.

In yet another embodiment, the invention relates to the use of an immunomodulatory peptide capable of modulating a T cell costimulatory pathway for the preparation of a pharmaceutical composition for the treatment of immune disorders related to an imbalance in the Th1-Th2 response in a subject in need thereof. The peptide used for such composition may comprises an amino acid sequence derived from a dimer interface of a T cell co-stimulatory pathway member or an amino acid sequence which specifically binds to an amino acid sequence within the dimer interface of a T cell co-stimulatory pathway member.

According to a specifically preferred embodiment, such composition may be useful for the treatment of immune disorders related to an imbalance in the Th1-Th2 response an autoimmune disease an autoimmune disease, (for example, multiple sclerosis (MS), Type-1 diabetes, lupus, Graves disease and thyroiditis), malignant and non-malignant proliferative disorders, graft rejection pathology and graft versus host disease.

According to a specifically preferred embodiment, any of the peptides defined by the invention or any combination, functional fragments and derivatives thereof may be use for the preparation of such compositions.

According to a specific embodiment, a peptide used for the preparation of these compositions may be selected from the group consisting of p12A (as denoted by SEQ ID NO:1), p12C (as denoted by SEQ ID NO:62), p14A (as denoted by SEQ ID NO: 2), pTA (as denoted by SEQ ID NO: 5), p1TA (as denoted by SEQ ID NO: 15), p2TA (as denoted by SEQ ID NO: 16), p1TB (as denoted by SEQ ID NO: 18), p2TB (as denoted by SEQ ID NO: 19), p1TC (as denoted by SEQ ID NO: 20), p2TC (as denoted by SEQ ID NO: 21), pe12 (as denoted by SEQ ID NO: 12), pd7 (as denoted by SEQ ID NO: 13), pc3 (as denoted by SEQ ID NO: 14), pa2 (as denoted by SEQ ID NO: 27), pb11.1 (as denoted by SEQ ID NO: 28), pc11 (as denoted by SEQ ID NO: 29), pf11 (as denoted by SEQ ID NO: 30), pg3 (as denoted by SEQ ID NO: 31), pb12 (as denoted by SEQ ID NO: 32), pa8.1 (as denoted by SEQ ID NO: 33), pb3 (as denoted by SEQ ID NO: 34), pb5 (as denoted by SEQ ID NO: 35), pb11.2 (as denoted by SEQ ID NO: 36), p13 (as denoted by SEQ ID NO: 37), pf8 (as denoted by SEQ ID NO: 38), pe6 (as denoted by SEQ ID NO: 39), pf4 (as denoted by SEQ ID NO: 40), pa8.2 (as denoted by SEQ ID NO: 41), pb3 (as denoted by SEQ ID NO: 42), pb2 (as denoted by SEQ ID NO: 43), pc2 (as denoted by SEQ ID NO: 44), pc8 (as denoted by SEQ ID NO: 45), pc9 (as denoted by SEQ ID NO: 46), pf12 (as denoted by SEQ ID NO: 47), pc4 (as denoted by SEQ ID NO: 48), pe11.1 (as denoted by SEQ ID NO: 49), pb5 (as denoted by SEQ ID NO: 50), pe11.2 (as denoted by SEQ ID NO: 51), pg7 (as denoted by SEQ ID NO: 52), pa12 (as denoted by SEQ ID NO: 53), pb8 (as denoted by SEQ ID NO: 54), pb12 (as denoted by SEQ ID NO: 55), pc8 (as denoted by SEQ ID NO: 56), pd8 (as denoted by SEQ ID NO: 57), pg6 (as denoted by SEQ ID NO: 58), p1TD (as denoted by SEQ ID NO: 59), p2TD (as denoted by SEQ ID NO: 60) and any combination, functional fragments and derivatives thereof.

Figure 23:
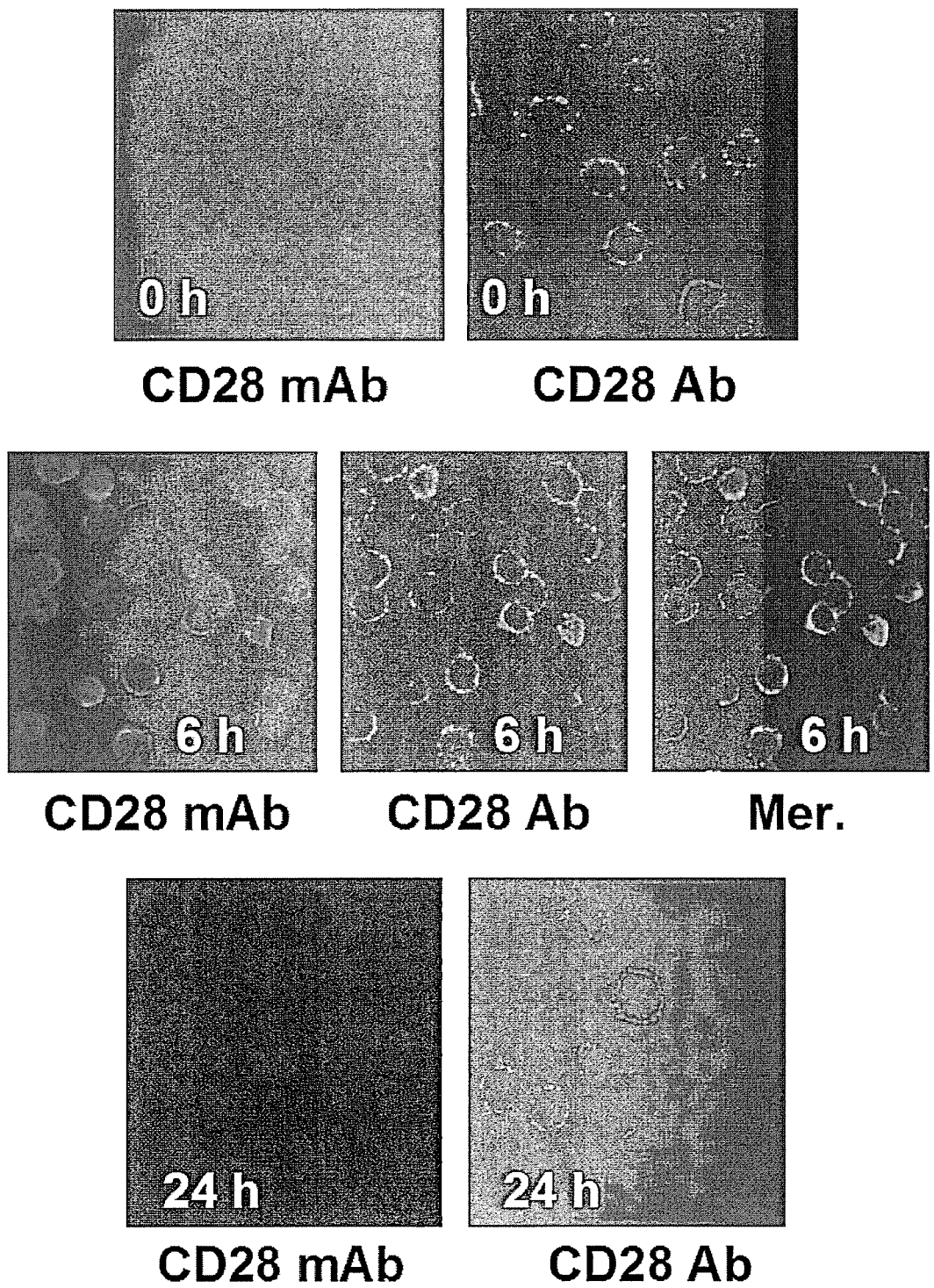

Engagement of MHC II molecule and TCR by a superantigen is insufficient for induction of Th1 cytokines that mediate lethal toxic shock. SPR affinity studies showed that in absolute terms, the interaction of superantigens with either ligand is very weak [Seth (1994) ibid.; Redpath (1999) ibid.]. By contrast, the affinity of SEB for CD28 is far greater, giving this interaction a pivotal role the formation of a stable immunological synapse. By engaging the three ligands simultaneously, the superantigen is able to deliver the signal Th1 activation. Peptide mimetics that interfere with binding of the superantigen to CD28 will disrupt synapse formation, preventing induction of a Th1 response (FIG. 27J).

CD28 exists as a dimer on the cell surface but dimerization of CD28 and of CTLA4 is not required for B7 binding, nor is it sufficient to trigger signaling by conventional antigens [Linsley, P. S. et al., J. Biol. Chem. 270(25):15417-24 (1995)]. Only one B7-2 monomer is thought to engage the CD28 dimer [Collins (2002) ibid.]. SEB induced a transient change in cell surface presentation of CD28, rendering it accessible to a αCD28 mAb specific for one rim of the predicted dimer interface (FIGS. 23, 24A, 24B, and 24C). The finding that this mAb alone can trigger a Th1 response (FIGS. 10A, 24B, and 24C) supports the existence of an equilibrium between states of accessibility of the CD28 epitope that can be shifted by SEB (FIG. 23). The inventors have shown that SEB engages CD28 at both rims of the dimer interface. When it interacts with one CD28 monomer, the superantigen likely displaces the other monomer, which now becomes accessible to the mAb.

CD28 has a unique role as early signal transducer for innate immunity. Whereas CD28 is expressed constitutively and is essential for an immediate Th1 response, ICOS is induced later in dependence on CD28 and promotes primarily a Th2 response. The late induction of CTLA4, also dependent on CD28, acts to shut off these earlier responses [reviewed by Rudd and Schneider (2003) ibid.]. Thus, early engagement of superantigens will be selectively with CD28. Without being bound by any theory, the inventors hypothesize that because SEB has the potential to bind not only CD28 but also ICOS and CTLA4 (FIG. 22), it may use the latter ligands to modulate the Th1 response induced via CD28.

During their convergent evolution, superantigens from *S. aureus* and *S. pyogenes* acquired structures designed to recognize receptors critical for their function, among them TCR and MHC II molecules. Yet, individual superantigens exhibit wide diversity in the way they interact with these two ligands [Sundberg (2002a,b) ibid.]. By contrast, binding of superantigen to CD28 not only is with higher affinity but involves a conserved structure in both molecules, rendering both SEB and TSST-1 sensitive to mimetics of the antagonist domain [Arad (2000) ibid.] and of the dimer interface in CD28 (FIGS. 26A and 26B).

The CD28 coligand B7-2 is expressed constitutively and induced rapidly during the innate immune response [reviewed by Sharpe and Freeman (2002) ibid.]. The action depends totally on B7-2 (FIGS. 6A and 6B). sB7-2 bound SEB directly, with an affinity resembling that for sCD28 but with lower avidity (FIG. 22). Simultaneous engagement of B7-2 and CD28 by A superantigen may stabilize binding of B7-2 to CD28 and trigger extensive costimulation. The results of the present invention lead to the novel concept that by directly engaging CD28 and B7-2 in addition to MHC II and TCR, the superantigen recruits four ligands in an unconventional manner, two from the antigen-presenting cell and two from the T cell, to create an unusually stable immunological synapse leading to an excessive Th1 response.

Induction of IL2 and IFN-γ gene expression by αCD3 jointly with sB7-2 or with αCD28, which engage the TCR and CD28 to mimic immunological synapse formation, was blocked by p14A (FIGS. 10A and 11A). Apparently, such signaling occurs mainly through the superantigen binding site in CD28, rendering it sensitive to p14A. By contrast, p14A did not inhibit IL2 and IFN-γ gene expression induced by signaling through the TCR, with αCD3 alone (FIG. 11A). Moreover, p14A did not inhibit induction of IL10, whether by SEB (FIG. 3C) or αCD3 (FIG. 11B), implying that it does not interfere with binding of SEB to the TCR.

Induction of Th1 cytokine genes by SEB was strongly attenuated by a concomitant induction of IL4 and IL10 (FIG. 2). However, in addition to signaling through the TCR, induction of a Th1 response by a superantigen requires CD28 engagement whereas induction of a Th2 response does not. αCD28 or sB7-2 failed to induce IL10 (FIGS. 10B and 11B). In all cases where the Th1 response was blocked by soluble ligands or by peptide mimetics of superantigen or of CD28, CTLA4 and ICOS, the Th2 response, measured through IL10 or IL4, remained unabated. Inhibition of the CD28-dependent Th1 response by superantigen antagonist peptides thus leaves the Th2 response intact, with the concomitant induction of protective immunity (FIG. 5B; [Arad (2000) ibid.]). The selective requirement for CD28 signaling in Th1 cytokine gene expression renders this response more sensitive to regulation. By contrast, activation of the Th2 response bypasses the CD28 requirement and therefore, is less stringently controlled.

Therefore, in a further aspect, the invention relates to a method for inhibiting the activation or the modulation of a T cell co-stimulatory pathway by a pathogenic agent, in a subject in need thereof. The method of the invention comprises the step of administering to the subject an inhibitory effective amount of a substance which inhibits the direct interaction of a component derived from said pathogenic agent and a binding site within a T cell co-stimulatory pathway member molecule, which site is derived from the dimer interface of said T cell co-stimulatory pathway member.

According to a preferred embodiment, the T cell co-stimulatory pathway may be any one of the CD28/B7, the CD40 ligand/CD40, CD2/CD58 and the LFA-1 (CD18)/ICAM-1 (CD54) co-stimulatory pathways. Preferably, the T cell co-stimulatory pathway may be the CD28/B7 pathway.

According to another embodiment, the invention relates to a method for the inhibition of activation of a T cell co-stimulatory pathway by a pathogenic agent. Pathogenic agents include prokaryotic microorganisms, lower eukaryotic microorganisms, complex eukaryotic organisms, viruses, fungi, prions, parasites, yeasts, toxins and venoms.

A prokaryotic microorganism includes bacteria such as Gram positive, Gram negative and Gram variable bacteria and intracellular bacteria. Examples of bacteria contemplated herein include the species of the genera *Treponema* sp., *Borrelia* sp., *Neisseria* sp., *Legionella* sp., *Bordetella* sp., *Escherichia* sp., *Salmonella* sp., *Shigella* sp., *Klebsiella* sp., *Yersinia* sp., *Vibrio* sp., *Hemophilus* sp., *Rickettsia* sp., *Chlamydia* sp., *Mycoplasma* sp., *Staphylococcus* sp., *Streptococcus* sp., *Bacillus* sp., *Clostridium* sp., *Corynebacterium* sp., *Proprionibacterium* sp., *Mycobacterium* sp., *Ureaplasma* sp. and *Listeria* sp.

Particular species include *Treponema pallidum, Borrelia burgdorferi, Neisseria gonorrhea, Neisseria meningitidis, Legionella pneumophila, Bordetella pertussis, Escherichia coli, Salmonella typhi, Salmonella typhimurium, Shigella dysenteriae, Klebsiella pneumoniae, Yersinia pestis, Vibrio cholerae, Hemophilus influenzae, Rickettsia rickettsii, Chlamydia trachomatis, Mycoplasma pneumoniae, Staphylococcus aureus, Streptococcus pneumoniae, Streptococcus pyogenes, Bacillus anthracis, Clostridium botulinum, Clostridium tetani, Clostridium perfringens, Corynebacterium diphtheriae, Proprionibacterium acnes, Mycobacterium tuberculosis, Mycobacterium leprae* and *Listeria monocytogenes.*

A lower eukaryotic organism includes a yeast or fungus such as but not limited to *Pneumocystis carinii, Candida albicans, Aspergillus, Histoplasma capsulatum, Blastomyces dermatitidis, Cryptococcus neoformans, Trichophyton* and *Microsporum.*

A complex eukaryotic organism includes worms, insects, arachnids, nematodes, aemobe, *Entamoeba histolytica, Giardia lamblia, Trichomonas vaginalis, Trypanosoma brucei gambiense, Trypanosoma cruzi, Balantidium coli, Toxoplasma gondii, Cryptosporidium* or *Leishmania*.

The term "viruses" is used in its broadest sense to include viruses of the families adenoviruses, papovaviruses, herpesviruses: simplex, varicella-zoster, Epstein-Barr, CMV, pox viruses: smallpox, vaccinia, hepatitis B, rhinoviruses, hepatitis A, poliovirus, rubella virus, hepatitis C, arboviruses, rabies virus, influenza viruses A and B, measles virus, mumps virus, HIV, HTLV I and II.

The term "fungi" includes for example, fungi that cause diseases such as ringworm, histoplasmosis, blastomycosis, aspergillosis, cryptococcosis, sporotrichosis, coccidioidomycosis, paracoccidio-idoinycosis, and candidiasis.

The term parasite includes, but not limited to, infections caused by somatic tapeworms, blood flukes, tissue roundworms, ameba, and *Plasmodium, Trypanosoma, Leishmania*, and *Toxoplasma* species.

According to a preferred embodiment, the method of the invention is particularly useful for inhibiting the activation of a T cell co-stimulatory pathway by a pathogenic bacterium selected from the group consisting of *Staphylococcus aureus* and *Streptococcus pyogenes*.

In yet another preferred embodiment, a component of said bacterium is a superantigen which may be a pyrogenic exotoxin. Preferably, the pyrogenic exotoxin may be a bacterial exotoxin and most preferably, this exotoxin may be produced by any one of *Staphylococcus aureus* and *Streptococcus pyogenes*. The superantigen-related disorder treated by the method of the invention, may be according to a specific embodiment any one of toxic shock, incapacitation and death, induced by a pyrogenic exotoxin or by a mixture of at least two pyrogenic exotoxins.

Accordingly, a preferred component of such pathogenic agent may be a superantigen, preferably a pyrogenic exotoxin.

According to another preferred embodiment, the method of the invention is based on the use of a substance which inhibits the binding of such superantigen to a specific site within a molecule belonging to the CD28/B7 pathway. Examples of such molecules may be CD28, CTLA-4, ICOS and PD-1, B7-1, B7-2, ICOSL, PD-L1 and PD-L2.

According to one specific embodiment, the superantigen binding site may be within the dimer interface of the CD28 which comprises amino acid residues 10-15 and 116-121 of the human CD28 amino acid sequence as denoted by SEQ ID NO: 22.

According to another embodiment, the superantigen binding site may be within the dimer interface of the CTLA-4 molecule which comprises amino acid residues 10-15 and 115-120 of the human CTLA-4 amino acid sequence as denoted by SEQ ID NO: 23.

Alternatively, the superantigen binding site may be within the dimer interface of the ICOS molecule, which comprises part or all of amino acid residues 10-15 and 119-124 of the human ICOS amino acid sequence as denoted by SEQ ID NO: 24.

Alternatively, the superantigen binding site may be within the domains in the PD-1 molecule that correspond to the dimer interface in CTLA4, comprising amino acid residues 8-13 and 110-116 of the human PD-1 sequence as denoted by SEQ ID NO: 61.

As shown by the Examples, the superantigen specifically binds to its binding site within the dimer interface of CD28, CTLA4 and ICOS. FIG. 22 further indicates that the superantigen binds to a yet undefined site within the B7-2 molecule.

As shown by the inventors, the dimer interface of the CD28 family members, specifically and directly binds to a spatially conserved domain of a pyrogenic exotoxin. Preferably, this spatially conserved domain is not involved in the binding of any one of MHC Class II molecules and TCR. Most preferably, the said spatially conserved domain of pyrogenic exotoxin forms therein a central turn starting within a β-strand 7 and connecting the β-strand 7, via short β-strand 8, to an α-helix 4, and ending within α-helix 4, based on the domain numbering of SEB [Arad et al., (2000), (2001) ibid.].

In one preferred embodiment, the substance used by the method of the invention for inhibiting the direct interaction between a component derived from said pathogenic agent, preferably, a superantigen, and a binding site within a T cell co-stimulatory pathway member molecule, may be a peptide derived from the dimer interface of a T cell co-stimulatory pathway member or alternatively, a peptide which specifically binds to an amino acid sequence within the dimer interface of a T cell co-stimulatory pathway member.

According to a specific embodiment, the method of the invention may use for inhibiting the specific interaction between the superantigen and the CD28 family member, a peptide derived from the dimer interface of a T cell co-stimulatory pathway member. Particular examples for such peptides are the peptides having the amino acid sequence of any one of SEQ ID NO: 5, 15, 16, 18-21 and 59 and 60.

In an alternative embodiment, inhibition of the direct binding of the superantigen to its specific site within the dimer interface of any of the CD28 family molecules, may be achieved by using a peptide which specifically binds to an amino acid sequence within the dimer interface of a T cell co-stimulatory pathway member. As shown by Example 12, such peptides were isolated by the screening method of the invention and include, but are not limited to peptides having the amino acid sequence of any one of SEQ ID NO: 12-14 and 27-58.

It should be noted that the peptides used by this method are peptides which bind to the dimer interface of a CD28 family member provided that said peptides are not derived from the spatially conserved domain of a pyrogenic exotoxin which forms therein a central turn starting within a β-strand 7 and connecting the β-strand 7, via short β-strand 8, to an α-helix 4, and ending within α-helix 4, based on the domain numbering of SEB.

According to a specifically preferred embodiment, the peptide used by this method may be any of the peptides defined by the invention.

According to a preferred embodiment, the peptide used by the method of the invention inhibits the direct interaction between CD28/B7 family molecules and said pyrogenic exotoxin. According to a preferred embodiment of this aspect of the invention, inhibition of binding of said component of a pathogenic agent. Preferably said component is a pyrogenic exotoxin to said T cell co-stimulatory pathway member, preferably of the CD28/B7 family, by the substance of the invention, leads to antagonizing toxin-mediated activation of Th1 lymphocytes and may also lead to indirect elicitation of protective immunity against toxic shock induced by said pyrogenic exotoxin or by a mixture of at least two pyrogenic exotoxins. More particularly, this binding is mediated by the superantigen binding site in CD28 as defined by the invention.

Therefore, an antagonist of a toxin-mediated activation of T lymphocytes, protects against toxic shock induced by a pyrogenic exotoxin or by a mixture of pyrogenic exotoxins and may also indirectly elicit protective immunity against toxic shock induced by a pyrogenic exotoxin or by a mixture of pyrogenic exotoxins. By blocking the ability of the toxin to induce a cellular immune response leading to toxic shock, the antagonist peptides of the invention may allow the superantigen to induce a vigorous humoral immune response directed against itself. Therefore, the treated subject may acquire protective immunity against further toxin challenges, and develop protective antitoxin antibodies. Thus, the antagonist peptide of the invention can be used for immediate treatment of acute toxic shock and of the harmful effects which may be due to, for example, accidental food poisoning, induced by pyrogenic exotoxins. In addition, it may indirectly confer long-term immunity against such toxic shock, as described above.

Where the peptide that inhibits the direct interaction between a T cell co-stimulatory pathway member, for example, CD28 and a component of a pathogenic agent, preferably, a superantigen, is for example a peptide having low immunogenicity and relative rapid clearance, antibodies against such antagonist peptide may not be detected. However, by blocking the ability of the toxin to induce a cellular immune response leading to toxic shock, the antagonist peptide allows the superantigen to induce a vigorous humoral immune response directed against itself. Under these conditions, the superantigen acts as its own adjuvant. Thus, when lethal toxic shock is prevented by antagonist peptide during exposure to a superantigen (by inhibiting the CD28-superantigen interaction), the treated subject may acquire protective immunity against further toxin challenges, even with different toxins, and develop protective antitoxin antibodies. Therefore, the use of the peptide of the invention that inhibits the direct interaction between CD28 molecule and a superantigen toxin, may indirectly elicit protective immunity against toxic shock induced by said pyrogenic exotoxin, and confer long term immunity against such toxic shock.

In a further aspect, the invention relates to a method for the treatment of pathological disorders related to an imbalance in the Th1-Th2 response caused by a pathogenic agent in a subject in need thereof. Such method comprises the step of administering to said subject an inhibitory effective amount of a substance which inhibits the direct interaction of a component derived from said pathogenic agent and a binding site within a T cell co-stimulatory pathway member molecule, which site is derived from the dimer interface of said T cell co-stimulatory pathway member. According to one embodiment, the method of the invention is intended for the treatment of pathologies such as malignant and non-malignant proliferative disorder, and an immune related disorder, for example, inflammation, autoimmune disease, and also exotoxin related disorders.

Inflammation includes any inflammatory conditions wherein said inflammatory conditions may be any one of rheumatoid arthritis, adult respiratory distress syndrome (ARDS), asthma, rhinitis, idiopathic pulmonary fibrosis, peritonitis, cardiovascular inflammation, myocardial ischemia, reperfusion injury, atherosclerosis, sepsis, trauma, diabetes type II, retinopathy, psoriasis, gastrointestinal inflammation, cirrhosis and inflammatory bowel disease.

According to another embodiment, the T cell co-stimulatory pathway may be any one of the CD28/B7 T cell co-stimulatory pathway, the CD40 ligand/CD40, CD2/CD58 and the LFA-1 (CD18)/ICAM-1 (CD54) co-stimulatory pathways, preferably, the CD28/B7 pathway.

More specifically, the CD28/B7 pathway member may be any one of CD28, CTLA-4, ICOS and PD-1, B7-1, B7-2, ICOSL, PD-L1 and PD-L2.

In one embodiment, the pathway member may be the CD28 molecule and the dimer interface within CD28 comprises amino acid residues 10-15 and 116-121 of the human CD28 amino acid sequence as denoted by SEQ ID NO: 22.

In another embodiment, the pathway member may be the CTLA-4 molecule and the dimer interface within CTLA-4 comprises amino acid residues 10-15 and 115-120 of the human CTLA-4 amino acid sequence as denoted by SEQ ID NO: 23.

Alternatively, the pathway member may be the ICOS molecule, and the dimer interface within ICOS comprises all or part of amino acid residues 10-15 and 119-124 of the human ICOS amino acid sequence as denoted by SEQ ID NO: 24.

Alternatively, the pathway member may be the PD-1 molecule and the domains within the PD-1 molecule that correspond to the dimer interface in CTLA4 and comprises amino acid residues 8-13 and 110-116 of the human PD-1 sequence as denoted by SEQ ID NO: 61.

In yet another embodiment, the method of the invention is intended for the treatment of pathologies caused by a pathogenic agents such as bacterial pathogens, viruses, fungi, prions, parasites, yeast, toxins and venoms.

In a specifically preferred embodiment, such pathogenic agent may be a pathogenic bacterium selected from the group consisting of *Staphylococcus aureus* and *Streptococcus pyogenes*. Accordingly, a component of said bacteria which specifically binds to a specific binding site within a T cell co-stimulatory pathway member, may be a superantigen, preferably a pyrogenic exotoxin.

More particularly, the inhibition of the direct interaction between the T cell co-stimulatory pathway member, preferably the CD28 molecule and the pyrogenic exotoxin leads to inhibition of exotoxin-mediated activation of Th1-lymphocytes, protection against toxic shock and may also leads to indirect elicitation of protective immunity against toxic shock induced by a pyrogenic exotoxin or by a mixture of at least two pyrogenic exotoxins.

According to a preferred embodiment, the method of the invention is particularly useful for the treatment of toxic shock, incapacitation and death, induced by a pyrogenic exotoxin or by a mixture of at least two pyrogenic exotoxins.

By the term 'immunologically effective amount' is meant any amount sufficient to enhance the production of antibodies that block T cell activation, preferably, Th1 response induced by pyrogenic exotoxins, and confer immunity against toxic shock induced by a pyrogenic exotoxin or by a mixture of pyrogenic exotoxins.

The term toxin-mediated activation as used throughout this application can mean activation of T cells mediated by a single pyrogenic exotoxin or a mixture of such toxins.

The antagonist peptide of the invention can be used for immediate treatment of acute toxic shock and of the harmful effects which may be due to, for example, accidental food poisoning, induced by pyrogenic exotoxins, as indicated above. In addition, by blocking the ability of the toxin to induce a cellular immune response may indirectly confer long-term immunity against such toxic shock.

In humans for example, toxic shock resulting from exposure to pyrogenic exotoxins has two distinct components: (1) incapacitation and (2) death. Even at concentrations several logs below lethal ones, pyrogenic exotoxins severely incapacitate, causing high morbidity [USAMRIID Manual, (1998) Eitzen, E. Pavlin, J. Cieslak, T. Christopher, G. Culpepper, R. eds. Medical Management of Biological Casualties Handbook. 3rd ed. Fort Detrick, Md.: United States Army Medical Research Institute of Infectious Diseases, 1998]. Incapacitation response observed, e.g. in food poisonings, which may be mass poisonings, affects large numbers of people. Moreover, the incapacitation response may be a military threat and a national security threat.

According to one embodiment, the method of the invention uses as a substance which inhibits the direct interaction between a component derived from said pathogenic agent and a binding site within a T cell co-stimulatory pathway member molecule, a peptide derived from the dimer interface of a T cell co-stimulatory pathway member or alternatively, a peptide which specifically binds to an amino acid sequence within the dimer interface of a T cell co-stimulatory pathway member.

According to a specifically preferred embodiment, inhibition of the interaction of a pathogenic agent, such as a pyrogenic exotoxin and a CD28 family member, may be performed by a peptide derived from the dimer interface of a T cell co-stimulatory pathway member.

More specifically, such peptide may be any of the peptides defined by the invention.

One particular example for such substance is provided by a further aspect of the invention, which relates to an isolated and purified peptide having an amino acid sequence derived from the dimer interface of a T cell co-stimulatory pathway member, preferably, of the CD28/B7 pathway molecules.

According to an alternative embodiment, inhibition of the direct interaction between a component of a pathogenic agent and a T cell co-stimulatory pathway member may be performed via the method of the invention by using a peptide which specifically binds to an amino acid sequence within the dimer interface of a T cell co-stimulatory pathway member. Specifically, such peptide may be any peptide defined by the invention.

According to a specifically preferred embodiment, the peptide used by the method of the invention inhibits the direct interaction between CD28 molecule and said pyrogenic exotoxin.

In another preferred embodiment, the peptide used by the method of the invention is an antagonist of a toxin-mediated activation of T lymphocytes and protects against toxic shock induced by a pyrogenic exotoxin or by a mixture of pyrogenic exotoxins.

The pharmaceutical composition of the invention can be administered and dosed in accordance with good medical practice. Various methods of administration may be used for delivering the peptides or the compositions of the invention to a subject in need. Peptides may be delivered via intravenous (i.v.), intramuscular (i.m.) intraperitoneal (i.p.) injections, orally (in liquid form or prepared as dosage unit forms like capsules, pills, lozenges, etc.). In order to be effective therapeutically, peptides should be prepared in a way that would enable their stability in the system following injection, or yet more preferably, following oral administration. Alternatively, the peptides of the invention may also be delivered via transdermal delivery using patches, ointment or cream.

The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular administration.

As described by the present, the cellular target of the superantigen is CD28. The present invention further demonstrates that all the three members of the CD28 family binds to the sAg (FIG. 22). This finding provides cellular drug targets for the design of antagonists that will inhibit toxic shock and other outcomes of superantigen-mediated overstimulation of the cellular immune response (and in particular, the Th1 response), such as death and toxic incapacitation (manifested by nausea, vomiting, and diarrhea). Most importantly, the invention now allows the design of novel antagonists of the interaction between superantigens and the CD28 receptor, whether by antagonist peptides as illustrated herein (FIGS. 28 to 32) or by small molecules or enzymes or proteins. The invention provides a new strategy for discovery of toxic shock antagonists, through use of the peptides of the invention which derived from the dimer interface within the CD28, CTLA-4 and ICOS molecules as bait for binding of antagonist molecules. The latter may be selected, for example, through phage display from random or dedicated peptide libraries, positional scanning of peptide libraries, or from libraries of cyclic peptidomimetics, as demonstrated by Examples 11 and 12.

Thus, in a further aspect, the present invention relates to a method of screening for a test substance which specifically binds to a T cell co-stimulatory pathway member, for example, any one of the CD28, ICOS, PD-1 and CTLA-4 molecules, and is capable of antagonizing pyrogenic exotoxin-mediated activation of Th1 lymphocytes. Additionally, said test substance may potentially be capable of specifically and indirectly eliciting protective immunity against toxic shock induced by a pyrogenic exotoxin or by a mixture of at least two pyrogenic exotoxins. The screening method of the invention comprises the steps of: (a) obtaining candidate antagonist substances which bind to a T cell co-stimulatory pathway member; (b) selecting from the substances obtained in step (a), a substance that inhibits direct interaction between said T cell co-stimulatory pathway member and said superantigen; and (c) determining the antagonizing effect of the substance obtained in step (b) on the superantigen-mediated activation of Th1 lymphocytes.

Key to the application of high-throughput screening for high-affinity binding of antagonist peptides generated by positional scanning and cyclization chemistry is the development of a sensitive and convenient screening assay.

Development of a robust screening assay for antagonist substances through their affinity for any one of CD28, CTLA-4, ICOS and PD-1 target in the domain recognized by superantigens, will be the first step in said screening method.

Therefore, in a preferred embodiment, the candidate antagonist substance utilized by the screening method of the invention may be obtained by the steps of:

(a) providing a mixture comprising a T cell co-stimulatory pathway member molecule or any fragment thereof; specifically, a preferred fragment may be for example, the soluble extracellular domain or a portion thereof containing the binding site as defined by the invention. More specifically, a fragment may be any of the peptides derived from the dimer interface of said T cell co-stimulatory pathway member, particularly, the peptides of the invention (for example, peptides having the amino acid sequence of any one of SEQ ID NO: 5, 15, 16 and 18-21);

(b) contacting the mixture of (a) with a test substance under suitable conditions for said binding; conditions may optimized for example, for interaction of CD28 with an interactor molecule such as the antagonist peptides p12A, p12C and p14A), and may be also optimized for any of the peptides that bind the sAg binding site within CD28, shown by the invention (Example 12); and (c) determining the effect of the test substance on an end-point indication, whereby modulation of said end point is indicative of binding of said T cell co-stimulatory pathway member molecule to said test substance.

According to a specific embodiment, the end point indication may be the binding of an anti-T cell co-stimulatory pathway member antibody to the T cell co-stimulatory pathway member molecule. This binding leads to a visually detectable signal. Preferably, said T cell co-stimulatory pathway member is the CD28 molecule. In such case, an increase in this end point is indicative of binding of said test substance to the CD28 molecule.

More particularly, each candidate substance, or preferably, peptide, may be placed in a well and direct binding of the peptides of the invention is detected preferably by an antibody specific for said peptides. Conditions for effective binding of the CD28 molecule of the invention, any fragments thereof or the peptides of the invention to a candidate antagonist peptide on the plate may be optimized involving study of pH, salt and buffer composition and, carrier proteins such as BSA. This robust screening yields substances, preferably peptides that bind to the superantigen binding site within the dimer interface of any one of CTLA-4, ICOS, CD28 and PD-1. Substances (particularly peptides) that bind to the peptides of the invention, are pooled and then assayed as described below.

According to one preferred embodiment, where the T cell costimulatory pathway member used is CD28, or where the peptide used by the screening method of the invention is any one of a peptide designated pTA and p1TA (SEQ ID NO: 5, and 15, respectively), the antibody that should be used for detection may be the mouse anti-CD28 monoclonal antibody designated MAB342, clone 37407.111 of R&D Systems, Inc., Minneapolis, Minn., USA.

Alternatively, where the peptide used for the screening method is p2TA, p1TB, p2TB, p1TC, p2TC, p1TD and p2TD which has an amino acid sequence as denoted by SEQ ID NO: 16, 18, 19, 20, 21, 59 and 60, a specific antibody, preferably monoclonal antibody, should be used for detection.

The anti peptides antibody used for this first step of the screening method of the invention may be any one of polyclonal and monoclonal antibody. Generation of polyclonal antibodies against proteins is described in, for example, Chapter 2 of Current Protocols in Immunology, Wiley and Sons Inc.

Monoclonal antibodies may be prepared from B cells taken from the spleen or lymph nodes of immunized animals, in particular rats or mice, by fusion with immortalized B cells under conditions which favor the growth of hybrid cells. The technique of generating monoclonal antibodies is described in many articles and textbooks, such as the above-noted Chapter 2 of Current Protocols in Immunology.

The term "antibody" is meant to include intact molecules as well as fragments thereof, such as, for example, Fab and $F(ab')_2$, which are capable of binding antigen [Wahl et al., J. Nucl. Med. 24:316-325 (1983)].

It will be appreciated that Fab and $F(ab')_2$ and other fragments of the antibodies useful in the present invention may be used for the detection and quantitation of the bound CD28, CTLA-4, ICOS and PD-1 molecules, according to the methods disclosed herein for intact antibody molecules. Such fragments are typically produced by proteolytic cleavage, using enzymes such as papain (to produce Fab fragments) or pepsin (to produce $F(ab')_2$ fragments).

In the second step of the screening method of the invention, the candidate antagonist substances which bind a T cell co-stimulatory pathway member molecule (preferably, CD28), that were preferably obtained as described above, may be further selected for their ability to specifically bind to the T cell co-stimulatory pathway member molecule at the novel superantigen binding site of the invention. Such selected substances will desirably be capable of preventing the interaction between said T cell co-stimulatory pathway member, preferably, CD28 molecule and said superantigen. According to this embodiment, selection of such substances may be performed by the steps of: (a) providing a mixture comprising a T cell co-stimulatory pathway member molecule or any fragment thereof comprising the sAg binding site; (b) contacting said mixture with said candidate test substance under suitable conditions for specific interaction with the T cell co-stimulatory pathway member molecule by the superantigen binding site in said T cell co-stimulatory pathway member; and (c) determining the effect of the test substance on an end-point indication, whereby modulation of said end point is indicative of binding of the T cell co-stimulatory pathway member molecule to the test substance by said superantigen binding site.

According to one preferred embodiment, the T cell costimulatory pathway may be the CD28/B7 pathway and the T cell costimulatory pathway member therefore, may be selected from the group consisting of CD28, CTLA4, ICOS and PD-1, B7-1, B7-2, ICOSL, PD-L1 and PD-L2, more preferably, CD28.

According to another preferred embodiment, the mixture used by the screening method of the invention comprises a peptide derived from the dimer interface of any of the T cell co-stimulatory pathway members as defined by the invention. More particularly, such peptides may be selected from any of the peptides having the amino acid sequence of any one of SEQ ID NO: 5, 15, 16 and 18-21.

According to a specifically preferred embodiment, the mixture used for the selection process comprises: (a) CD28 molecule or any fragment thereof, being fragment, for example, the soluble extracellular domain or a portion thereof containing the binding site of the invention, preferably, a binding site comprising at least part of the dimer interface of CD28, as defined by the invention; (b) an interactor molecule, which is a known molecule that specifically binds to CD28, at the superantigen binding site in CD28 of the invention; and (c) optionally solutions, buffers and compounds which provide suitable conditions for interaction of such interactor molecules with the CD28 molecule and for the detection of an end-point indication for the interaction of the interactor molecule with the CD28 molecule.

The terms fragments and functional fragments used herein mean the T cell costimulatory pathway member, preferably, CD28 target molecule or any fragment thereof, with any insertions, deletions, substitutions and modifications, that include the superantigen binding site and is capable of binding the superantigen and by facilitating the binding of the B7-2 molecule and thereby inducing specific activation of Th1 cells (hereafter referred to as "fragment/s"). As indicated above, a fragment of CD28 may be any peptide which comprises the amino acid sequence of at least part of the dimer interface in CD28, which dimer interface comprises amino acid residues 10-15 and 116-121 of the human CD28 amino acid sequence as denoted by SEQ ID NO: 22. Non limiting examples of such peptides are peptides having the amino acid sequence of SEQ ID NO: 5, 15 or 16.

In a particular embodiment, the interactor molecule may be any one of anti-CD28 monoclonal antibody, including but not limited to the mouse anti-CD28 antibody designated MAB342, clone 37407.111 of R&D Systems, antagonist peptide p12A as denoted by SEQ ID NO: 1, antagonist peptide p14A as denoted by SEQ ID NO: 2, antagonist peptide p12C as denoted by SEQ ID NO: 62, as well as any of the peptides shown by the invention as binding to the sAg binding site within CD28 (Example 12, preferably, peptides of SEQ ID NO: 12-14 and 27-58) and a pyrogenic exotoxin or any functional fragments thereof. As demonstrated by the present invention, such interactor molecules display specific affinity to the invention's superantigen binding site in CD28.

The antagonist peptides used by the screening method of the invention (p12 and p14 and peptides of SEQ ID NO: 5, 12-16, 18-21, 27-58 and 62), as well as the derivatives thereof, may all be positively charged, negatively charged or neutral and may be in the form of a dimer, a multimer or in a constrained conformation. A constrained conformation can be attained by internal bridges, short-range cyclizations, extension or other chemical modification.

The end point indication may be, according to one embodiment, the binding of the interactor molecule to the CD28 molecule, which leads to a visually detectable signal. Inhibition or reduction in this end point is indicative of direct binding of the test substance to the invention's superantigen binding site in CD28. This binding competes with the binding of the interactor molecule to said site. For performing this competition assay, the interactor molecule may be directly labeled, for example by biotinylation or by addition of fluorescein, or alternatively may be indirectly labeled by a secondary antibody.

The mixture used for obtaining and selecting candidate substances by the screening method of the invention may be a cell mixture or a cell-free mixture.

According to one alternative embodiment, the mixture utilized by the method of the invention may be a cell-free mixture. Such mixture comprises the CD28 molecule or any functional fragment thereof (preferably, comprising the sAg binding site), that may be provided as any one of a peptide, a purified recombinant protein, a fusion protein and a cell lysate or membrane preparation of a transformed host cell expressing the said CD28 molecule.

A particular and non-limiting example for a purified recombinant CD28 protein used herein, as described by Example 11, is a chimeric sCD28/Fc homodimer molecule comprising the extracellular domain of CD28 molecule. The sCD28 is from R&D Systems (Minneapolis) and consists of a chimeric sCD28/Fc homodimer, each monomer having 42.2 kDa of protein before glycosylation but reaching 60-70 kDa in the heavily glycosylated form that is actually expressed. Another particular example may be a fragment of CD28 which comprises the sAg binding site that has an amino acid sequence comprising part or all of the dimer interface in CD28.

In a particular and non limiting example, such selection step of the screening method of the present invention may be performed, where sCD28 is bound onto the wells of a microplate. Conditions for effective binding of antagonist peptide to sCD28 on the plate may be optimized first using antagonist peptides p12 and p14. Then, each well is incubated with a limiting amount of anti-CD28 mAb as the interactor molecule, in the presence of antagonist substance, preferably, peptide (alone or a pool). Supernatant is collected from each well. Unbound mAb is detected in the supernatant by secondary antibody ELISA. Should antagonist substance bind tightly to sCD28 in the domain recognized by the mAb, it will compete in the binding of anti-CD28 to sCD28 and release free mAb that can be detected over a zero background, rendering the assay sensitive. Candidate antagonist substance or peptides binding outside the domain involved in the anti-CD28/CD28 interaction will be eliminated by this approach. The data of the present invention indicate that the monoclonal anti-CD28 used by the inventors recognizes an epitope that overlaps at least in part the binding site for superantigen.

An alternative approach is to use biotinylated SEB (Toxin Technologies) as the interactor molecule and assay for the ability of peptides to displace labeled SEB from binding to sCD28 on the plate. Yet another alternative is to use as the interactor molecule, labeled p12A, p14A and p12C and assay for the ability of peptides to displace label from binding to sCD28 on the plate. Cysteine-tagged p12A, p14A and p12C may be used to couple biotin or fluorescein. Though specific and at first sight convenient, these one-step screening methods may be less sensitive as they measure a decrease from 100% binding in the control.

Alternatively, the mixture utilized for the selection step by the method of the invention may be a cell mixture. Preferably, the cell mixture may be a transfected cell culture.

In a particular preferred embodiment, the transfected cells are BHK-21 cells transfected with an expression vector comprising a nucleic acid sequence coding for CD28 molecule or any fragment thereof (preferably, any fragment comprising the sAg binding site). CD28 cDNA is cloned under the powerful myeloproliferative sarcoma virus promoter and upstream of the SV40 polyadenylation signal in a vector that has been routinely used in the inventors' laboratory for transient expression in transfected BHK-21 cells [Ben-Asouli et al., Cell 106:221-232 (2002)]. Alternatively, CD28 cDNA is expressed transiently in transfected COS cells [Aruffo & Seed, Proc Natl Acad Sci USA 84:8573-8577 (1987)].

In this particular embodiment, each candidate antagonist, preferably a peptide, is placed in a well and the well is then blocked with BSA or fetal calf serum. Binding of BHK-21 cells that express CD28 on their cell surface is scored visually, or by anti-CD28 ELISA. Alternatively, cell membranes prepared from the CD28-expressing cells may be used and binding is detected using anti-CD28 antibody. Positive candidate antagonist substances are then re-examined in the presence of the interactor molecules, e.g. SEB, p12A, p14A or p12C, as competitor.

"Vectors", as used herein, encompass plasmids, viruses, bacteriophage, integratable DNA fragments, and other vehicles, which enable the integration of DNA fragments into the genome of the host. Expression vectors are typically self-replicating DNA or RNA constructs containing the desired gene or its fragments, and operably linked genetic control elements that are recognized in a suitable host cell and effect expression of the desired genes. These control elements are capable of effecting expression within a suitable host. Generally, the genetic control elements can include a prokaryotic promoter system or a eukaryotic promoter expression control system. This typically includes a transcriptional promoter, an optional operator to control the onset of transcription, transcription enhancers to elevate the level of RNA expression, a sequence that encodes a suitable ribosome binding site, RNA splice junctions, sequences that terminate transcription and translation and so forth. Expression vectors usually contain an origin of replication that allows the vector to replicate independently of the host cell.

A vector may additionally include appropriate restriction sites, antibiotic resistance or other markers for selection of vector-containing cells. Plasmids are the most commonly used form of vector but other forms of vectors which serve an equivalent function and which are, or become, known in the art are suitable for use herein. See, e.g., Pouwels et al., Cloning Vectors: a Laboratory Manual (1985 and supplements), Elsevier, N.Y.; and Rodriquez, et al. (eds.) Vectors: a Survey of Molecular Cloning Vectors and their Uses, Buttersworth, Boston, Mass. (1988), which are incorporated herein by reference.

According to a preferred embodiment, a candidate substance suitable for screening by the method of the invention may be selected from the group consisting of: protein based, carbohydrates based, lipid based, natural organic based, synthetically derived organic based, inorganic based, and peptidomimetics based substances.

Preferably, such substance may be a product of any one of positional scanning of combinatorial libraries of peptides, libraries of cyclic peptidomimetics, and random or dedicated phage display libraries.

In a specifically preferred embodiment, the candidate antagonist substance obtained and selected by the screening method of the invention, may be a peptide. Therefore, combinatorial phage libraries may be used to screen for superantigen antagonist peptides with nanomolar affinity for any one of the CD28, CTLA-4, ICOS and PD-1 receptors, preferably, CD28. In a particular and non-limiting example, the PhD-12 library of New England Biolabs may be used.

Panning may be performed in two stages, in the first stage, bound phage are eluted from microplate-bound sCD28, pTA, p1TA, p2TA, p1TB, p2TB, p1TC, p2TC, p1TD and p2TD of the invention using elution at pH 2.2. This will select all phages that bind the superantigen binding site of CD28. In the second stage, phage selected as above are bound to pTA, p1TA, p2TA, p1TB, p2TB, p1TC, p2TC, p1TD and p2TD or to sCD28, sICOS, sCTLA-4 and sPD-1 and eluted specifically with an excess of free SEB. Bound phages are eluted and subjected to between two and three further cycles of panning. Then, direct binding of phage to immobilized pTA, p1TA, p2TA, p1TB, p2TB, p1TC, p2TC, p1TD, p2TD, sCD28, sICOS, sCTLA-4, sPD-1 or to any fragment thereof comprising the superantigen binding site, may be detected by phage ELISA, scoring for M13 on the plate. Positive phage clones are amplified and sequenced, before synthesis of the peptides in linear form.

In an alternative panning strategy, CD28 cDNA transiently overexpressed in transfected BHK-21 cells as described above, may be used. Cells may be immobilized on the plate. Panning of phage-displayed peptides may be done first on vector-transfected BHK-21 cells to eliminate non-specific binders, and then on BHK-21 cells that overexpress CD28 (or cells that overexpress a fragment of CD28 comprising the sAg binding site) on their cell surface. Alternatively, whole cell membrane preparations may be substituted for cells. CD28-bound phage are eluted with an excess of free interactor molecules, such as p12A, p14A and p12C or SEB.

The candidate antagonist substances which bind to the peptides of the invention and therefore to the superantigen binding site within CD28, that were preferably obtained as described above, may be further selected for their ability to prevent the interaction between any one of the CD28, ICOS, CTLA-4, PD-1 molecules and the superantigen.

One possible approach to examine the ability of the candidate substance to inhibit the interaction between the superantigen and any one of the CD28, ICOS, CTLA-4, PD-1 molecules, is to use biotinylated SEB (Toxin Technologies) and assay for the ability of peptides to displace labeled SEB from binding to sCD28, sICOS, sCTLA-4 or sPD-1 on a plate.

The candidate antagonist peptide obtained and selected by the screening method of the invention may be further analyzed and improved by positional scanning.

In a pepscan positional scan, the start affinity can be as low as $10^{-3}$ M and the peptide length can easily be 15 residues. Lead peptides may be derived from any type of peptide library, including random combinatorial libraries or peptide libraries derived from given protein sequences. A sound signal-to-noise ratio allows detection of specific low-affinity interactions. It can be used on a solid support [Schroeijers et al., Cancer Res. 60:1104-1110 (2000)] or after split of the peptides from the support and their use in soluble form [Kast et al., Cell 59:603-614 (1989); Kast et al., Proc. Natl. Acad. Sci. U.S.A. 88:2283-2287 (1991); De Samblanx et al., Pept. Res. 9:262-268 (1996); Oosterom et al., J. Biol. Chem. 274:16853-16860 (1999)]. In constrained positional scanning, all candidate peptides are synthesized as non-reducable loops; it is used to further improve the affinity of lead peptides. Thus, peptides are linked to a solid support (pepscan-I) or assayed as free soluble peptides (pepscan-II) to optimize the affinity of lead peptides.

An alanine scan may be performed on a candidate antagonist peptide to identify residues critical for binding to the receptor and, separately, for superantigen antagonist activity in vitro. The in vitro antagonist activity may be evaluated according to the evaluation step of the screening method of the invention, described below. Peptides are synthesized in soluble form with N-terminal acetyl and C-terminal —CONH$_2$ and retain flanking D-alanines for greater protease resistance in in vitro assays with PBMC as an evaluating step. Further rounds of alanine scan may be performed on identified lead peptides. Because lysine is prominent in the superantigen antagonist domain, a lysine-scan of the peptide may likewise be performed.

Once residues critical for antagonist activity are identified by the alanine scan, 2 such positions are chosen for a fully permuted pepscan of all 20 amino acids (400 peptides) and then 2 additional positions are scanned likewise (400 peptides). Peptides are first in releasable form but held on the chip. Binding of any one of sCD28, sICOS, sCTLA-4 or sPD-1, preferably, sCD28, to each peptide is scored by ELISA using commercial polyclonal antibodies or monoclonal antibodies to this receptor. Next, positive peptides are released and pooled into groups for assay of binding the receptor in the screening assay ELISA format (see above) and also for antagonist activity in vitro in PBMC assays (detailed below) and the groups are then deconvoluted. In stepwise fashion, the resulting improved leads are subjected to additional rounds of positional scanning. In total, four rounds of positional scanning may be performed, and further rounds of constrained positional scanning, on the peptide with highest affinity for the receptor.

For cyclization scan, a linker such as m-maleinimidobenzoic acid N-hydroxy-succinimide (MBS) ester may be used to react via its active ester with the N-terminus of a given peptide and via its maleinimide group with a free thiol group from cysteine. The cysteine is part of the peptide.

For loop scan, the N-terminus of each peptide may be linked with MBS to a free SH group from a cysteine that is coupled separately to the bottom of the same well. In this way, a constrained loop is formed.

Cyclic peptidomimetics are synthesized individually and evaluated for antagonist activity in PBMC.

Backups, whether obtained by positional scan, phage display or cyclic peptidomimetic synthesis, may be compared with p12A, p12C and p14A antagonist peptides as the interactor molecules, in terms of their ability to bind the target receptor, using plasmon resonance measurements as well as ELISA assays. Both direct binding and ability to compete with SEB for sCD28 are assayed. Ability of antagonist peptide to interfere with the binding of sCD28 to anti-CD28 antibodies for example, may be also tested. Ability of the antagonist peptide to promote complex formation between sCD28 and B7-2 may be studied as well, as an evaluating step as described below.

It should be noted that a candidate antagonist selected and characterized by the screening method of the invention shown by Example 12, is a substance which binds to the superantigen binding site within any one of CD28, ICOS, CTLA-4 or PD-1, and as shown by FIGS. 28 to 32, should be further evaluated for its ability of to antagonize toxin-mediated activation of Th1 lymphocytes and optionally its ability to elicit protective immunity against toxic shock induced by a pyrogenic exotoxin or by a mixture of such pyrogenic exotoxins.

Thus, the third step of the screening method of the invention, is evaluation of the selected candidate substance. As indicated above, in this stage, the candidate antagonist substance is evaluated for its capability to antagonize toxin-mediated activation of Th1 lymphocytes and may be also evaluated for its potential capability of eliciting protective immunity against toxic shock induced by a pyrogenic exotoxin or by a mixture of such pyrogenic exotoxins. Evaluation of the selected substances, preferably resulting from the selection method of the invention, may be performed by the steps of: (a) providing a test system comprising a T cell costimulatory pathway member, preferably, the CD28 molecule or any fragments thereof comprising the sAg binding site of the invention; (b) contacting said system with a candidate antagonist, preferably obtained and selected by the method according to the invention, which contacting is performed under conditions suitable for interaction; and (c) determining the effect of the evaluated candidate antagonist on an end-point indication as compared to a control, which effect is indicative of the capability of said candidate to inhibit the direct interaction between the T cell costimulatory pathway member molecule and a pyrogenic exotoxin which leads to antagonizing of toxin-mediated activation of Th1 lymphocytes. Preferably, the T cell costimulatory pathway member is the CD28 molecule.

The test system used for evaluating the candidate antagonist isolated by the screening method of the invention may be an in-vitro/ex-vivo cell culture, or an in-vivo animal model. Such test system optionally further comprises endogenous and/or exogenous compounds which provide suitable conditions for the superantigen-induced activation of T cells and for the detection of an end-point indication for determining the antagonizing effect of the candidate antagonist. More specifically, the T cells are Th1 lymphocytes and said activation is determined by the induction of IL2 and/or IFN-γ gene expression.

As shown by Example 4, the antagonist peptide alone does not act as a superantigen agonist on human PBMC [Arad (2000) ibid.] but rather it interferes with the binding of superantigen to CD28. However, the antagonist peptide shares the ability of a superantigen to stimulate signaling by sB7-2 (Example 5). The activation of T cells by a superantigen requires antigen presenting cells and will not occur in the presence of T cells alone [Marrack and Kappler, Science 248:705-711 (1990)]. Thus, in nature, the action of superantigens involves predominantly cell-anchored B7-2 and CD28 [see Salomon and Bluestone, Annu. Rev. Immunol. 19:225-252 (2001)], brought into proximity by superantigen-mediated crosslinking of the MHC class II molecule on the antigen presenting cell with the TCR on the T cell. In that context, the antagonist peptide will block the ability of a superantigen to bind to CD28, thereby preventing the superantigen from promoting B7-2/CD28-mediated signaling. The antagonist does not interact with the TCR, as shown by a lack of antagonist activity when Th1 cell stimulation is by anti-CD3.

Thus, according to a specific embodiment, the test system used for evaluation of the antagonist candidates may be a cell-free system comprising soluble CD28, CTLA4, ICOS, PD-1 molecules, and preferably, soluble CD28 molecule (sCD28) or any fragments thereof comprising the sAg binding site, and soluble B7-2 molecule (sB7-2).

In a specifically preferred embodiment, the end point indication for such cell-free system may be the binding of sCD28 molecule to the sB7-2 molecule, which is detected by a suitable means. For example, by ELISA and plasmon resonance, as was also utilized for demonstrating the direct binding in Example 5. More specifically, an increase in the interaction between CD28 molecule and the sB7-2 in the presence of a candidate antagonist is indicative of the ability of said candidate to specifically antagonize and inhibit the interaction between the superantigen and CD28 molecule.

Alternatively, the test system utilized by the screening method of the invention for evaluation may be an in-vitro/ex-vivo cell culture comprising an endogenously expressed CD28, ICOS, CTLA-4 or PD-1 molecules. In a particular example, the cell culture used as the test system may be a PBMC culture isolated from a mammalian donor. Such mammal may preferably be any one of human and rhesus monkey.

The end point indication in this particular test system may therefore be the superantigen-induced expression of IL2 and/or of IFN-γ, which leads to a visually detectable signal. Thus, any inhibition or even reduction of said end point is indicative of the ability of the candidate substance to specifically antagonize and inhibit the interaction of a superantigen with CD28 molecule. Such inhibition leads to antagonizing toxin-mediated activation of Th1 lymphocytes. The superantigen-induced expression of IL2 and/or of IFN-γ may be detected, for example, by quantitative dot blot hybridization and RNAase protection assay.

As demonstrated by the following Examples, the inventors developed a powerful in vitro screening tool for superantigen antagonist activity based on the ability of an antagonist peptide to inhibit the superantigen-induced expression of Th1 cytokine mRNA in freshly isolated whole human PBMC populations that contain all cell subsets that participate in a cellular immune response [Arad et al., (2000) ibid.]. The inventors have shown that this system closely reflects the human immune response in a variety of diseases where it detected dysregulation of that response [Gerez et al., Clin. Immunol. Immunopathol. 58:152-266 (1991); Gerez et al., Kidney International 40:266-272 (1991); Gerez et al., Clin. Exp. Immunol. 109:296-303 (1997); Kaempfer et al., J. Clin. Oncol. 14:1778-1786 (1996)], thus providing an excellent surrogate marker. This PBMC assay proved effective in the discovery of the antagonist peptides p12 and p14 by the present inventors [Arad et al., (2000), (2001) ibid.] and for showing lack of toxin agonist activity [Arad et al., (2000) ibid.]. This system therefore may be efficiently used for evaluating the antagonist activity of the candidate antagonist substances obtained by the screening method of the invention.

The inventors devised a sensitive, quantitative method for measuring expression of IL2 and IFN-γ mRNA induced in human PBMC, quantitating their low-abundancy mRNA species in small numbers of cells. The method allows for convenient processing of large numbers of samples, and as such, is suitable for screening potential toxin antagonists. Moreover, it allows study of responses of PBMC from several different human donors at once, for a large number of parameters. This creates an effective tool for showing antagonist activity in a reproducible manner. Measurements of IL2 and IFN-γ protein are less informative than of mRNA because these proteins appear only gradually during induction and are sequestered by binding to their cellular receptors, while mRNA is expressed promptly and can be assayed accurately. Determination of IL2 and IFN-γ mRNA gives dynamic information on the primary response of these genes within hours after immune stimulation. The assay is linear over a wide range. Information obtained from such analysis is verified by RNase protection analysis.

An essential property of the desired antagonist peptide is that it leaves the Th2 response intact. This is also a requirement for backups, and may be tested by ELISA for IL10, using culture medium from PBMC in which toxin-induced expression of Th1 cytokine mRNA is inhibited by the antagonist peptide.

In yet another alternative, the test system utilized by the screening method of the invention for evaluating candidate antagonists, may be an in-vivo system, particularly an animal model.

According to one specific embodiment, the animal model may be a D-galactosamine-sensitized mouse challenged with a superantigen, preferably a pyrogenic exotoxin. The end point indication for such test system may be the protection and rescue of said mouse from lethal toxic shock. An increase in said end point is indicative of the ability of said candidate substance to specifically antagonize and inhibit the interaction between the superantigen and CD28 molecule, to antagonize the pyrogenic toxin-mediated activation of Th1 lymphocytes, to protect against toxic shock and may also indicate the ability of said candidate to indirectly elicit protective immunity against toxic shock induced by a pyrogenic exotoxin or by a mixture of at least two pyrogenic exotoxins.

An alternative animal model may be a pig challenged with a pyrogenic exotoxin. In such method the end point indication may be the protection and rescue of said pig from toxic shock and incapacitation. An increase in such end point is indicative of the capability of said candidate substance to specifically antagonize and inhibit the interaction between the superantigen and CD28 molecule, to antagonize the pyrogenic exotoxin mediated activation of Th1 lymphocytes, to protect against toxic shock and incapacitation and optionally to elicit protective immunity against toxic shock induced by a pyrogenic exotoxin or by a mixture of at least two pyrogenic exotoxins.

The present invention further provides a method of preparing a therapeutic composition for the treatment of a superantigen-related disorder in a mammalian subject. This method comprises the steps of:

(a) identifying an antagonist substance that is capable of antagonizing superantigen-mediated activation of Th1 lymphocytes and preferably further capable of eliciting protective immunity against toxic shock induced by a pyrogenic exotoxin or by a mixture of at least two pyrogenic exotoxins; and (b) admixing said antagonist substance with at least one of a pharmaceutically acceptable carrier, diluent, excipient and/or additive.

The antagonist substance used by the method of preparing a therapeutic composition may preferably be identified by the screening method of the invention, as exemplified by Examples 11 and 12.

The invention further relates to the use of the CD28 molecule or fragment thereof, particularly, a fragment comprising the superantigen binding site which most preferably, comprises all or part of the amino acid sequence of CD28 dimer interface, in the preparation of a pharmaceutical composition for the treatment of superantigen-related disorders by the method of the invention.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures

Cell Culture and Induction of Human Cytokine Gene Expression

PBMC from healthy human donors were separated on Ficoll Paque (Pharmacia), washed twice with 50 ml of RPMI 1640 medium, resuspended at a density of $4\times10^6$/ml and cultured in this medium supplemented with 2% fetal calf serum, 2 mM glutamine, 10 mM MEM nonspecific amino acids, 100 mM Na-pyruvate, 10 mM Hepes pH 7.2, $5\times10^{-5}$ M 2-mercapto-ethanol, 100 u/ml penicillin, 100 μg/ml streptomycin and 5 μg/ml nystatin. SEB (lot 14-30, from the Department of Toxinology, U.S. Army Medical Research Institute of Infectious Diseases), SEA or TSST-1 (Sigma) were added to 100 ng/ml.

RNase Protection Analysis

Total RNA was extracted with guanidinium isothiocyanate [Chomczynski and Sacchi, Anal. Biochem. 162:156 (1987)]. RNase protection analysis was done [Arad et al.

(1995) ibid.] using genomic antisense RNA probes transcribed with α-[$^{32}$P]UTP in vitro from DNA inserted into pBS (Promega). The IL-2 probe (600 nucleotides (nt)), transcribed from the T7 promoter, is complementary to the third exon and a portion of the third intron of the IL-2 gene; in 8 M urea-polyacrylamide gels, it yields an RNA fragment of 117 nt protected by IL-2 mRNA. The IFN-γ probe (274 nt), transcribed from the T3 promoter, is complementary to the third exon and a portion of the third intron of the IFN-γ gene and yields an RNA fragment of 183 nt protected by IFN-γ mRNA. The TNF-β probe (700 nt), transcribed from the T3 promoter, is complementary to part of exon 1, exon 2, exon 3, and portions of intron 3 and exon 4; TNF-β mRNA protects 2 fragments of 274 and 263 nt. Sense RNA transcripts yielded no detectable signal upon hybridization. Antisense RNA probes for 18S rRNA (protecting 90 nt) or β-actin (protecting 415 nt) served as loading controls.

Quantitative Dot Blot Hybridization of IL-2 and IFN-γ RNA

PBMC from 1-ml cultures were collected and lysed in 7.5 M guanidinium-HCl. RNA, precipitated overnight in ethanol at −20° C., was dissolved into formaldehyde and incubated for 15 min at 60° C. Four serial 2-fold dilutions, made in 10× saline sodium citrate, were applied in duplicate to nitrocellulose sheets, using a 96-well dot blot apparatus. After baking in a vacuum oven at 80° C., sheets were hybridized separately with $^{32}$P-labeled antisense RNA probes for human IL-2 and IFN-γ, respectively. Exposed autoradiograms were scanned at 630 nm in an ELISA reader. RNA levels are expressed in units of $A_{630}$. Serial twofold dilutions of a given RNA sample yield a linear optical density response over a 200-fold range of intensities of gene expression that is proportional to the concentration of specific RNA present in each sample [Arad et al. (1995) ibid.; Gerez et al., Clin. Immunol. Immunopathol. 58:251 (1991); Kaempfer et al., J. Clin. Oncol. 14:1778 (1996)].

Synthesis of SEB-Related Peptides

Peptides were generally synthesized as described in WO98/29444, incorporated by reference.

Briefly, peptides were synthesized using fluoronylmethoxycarbonyl chemistry, cleaved and the side chain deprotected with trifluoroacetic acid. Peptides were >95% pure by high-pressure liquid chromatography and their molecular weight was verified by MALDI-TOF mass spectrometry. All peptides except p72C were abutted with D-Ala residues for greater protease resistance. Scrambled sequences were obtained using a true random number generator (random.ota).

Surface Plasmon Resonance (SPR)

Protein-protein interactions are detected by surface plasmon resonance (BIAcore instrument, Pharmacia) where increase in resonance units (RU) indicates binding of injected protein to protein immobilized on surface. The protein to be immobilized was coupled to the dextran matrix by standard amine chemistry as reported by Seth et al. [Nature 369:324-327 (1994)]. A flow of HBS (10 mM HEPES, 150 mM NaCl, 3.4 mM EDTA, 0.05% surfactant Tween 20 pH 7.4) was maintained over the sensor surface at 10 μl/min. Samples were injected at 10 μl/min for 2 or 4 min depending on their volume, 20 or 40 μl; 40 μl was used for antagonist peptide only. Between injections, the surface was regenerated with 50 mM $H_3PO_4$. The immobilization level was 3,000-4,000 RU. Sensorgrams show resonance signal before the injection, at the height of the response, during the injection, and towards the end of the wash. More specifically, SEB, sCD28 and p12C (also denoted by SEQ ID NO: 62) were diluted to 100 μg/ml in 10 mM Na acetate pH 4.0 and immobilized on a CM5 sensorchip (BIAcore) by amine-thiol coupling using the manufacturer's kit (BIAcore). Soluble CD28, CTLA4, ICOS, PD-1, B7-2, ubiquitin (R&D Systems) or human IgG (Jackson Laboratories) were injected at 10 μl/min in 25 mM HEPES pH 7.4, 150 mM NaCl, 3.4 mM EDTA, and 0.005% surfactant P20 under conditions showing no mass transfer limitation. Affinity and kinetic analyses were performed at 25° C. in a BIAcore 3000 instrument, using BIAevaluation 3.0 software.

Soluble CD28, CTLA4, ICOS, PD-1 and B7-2

Carrier-free CTLA4 (R&D Systems) expressed in Sf21 cells using baculovirus, and CD28, ICOS, PD-1 and B7-2 (R&D Systems) expressed in mouse myeloma NS0 cells, comprise the extracellular 37-162, 19-152, 21-141, 24-167 and 20-239 amino acid, respectively, of the mature human ligands domain (the sequence locations refer to the amino acid sequence of GenBank Accession Nos., P16410, P10747, Q9Y6W8, NP_005009, and P42081, respectively) fused to C-terminal human IgG1 Fc and are homodimers, disulfide-linked in the Fc domain. CD28, CTLA4 and B7-2 carry a $His_6$-tag.

Phage Display

For epitope mapping, the PhD-12 combinatorial phage display library in M13KE (New England Biolabs) was panned on immobilized αCD28 mAb (MAB342, clone 37407.111, R&D Systems) following instructions of the manufacturer; displacement was with 100 μg/ml sCD28. Phages from the fourth panning were immobilized on ECL-plus membranes (Pharmacia). Binding of αCD28 was detected with horseradish peroxidase (HRP)-linked anti-mouse IgG (Jackson Laboratories). Sequences of 19 distinct inserts were aligned with CD28, without gaps. For CD28 affinity selection, the same library was panned on immobilized sCD28; displacement was with SEB.

Protection of Mice Against Toxic Shock

Female BALB/c mice (10-12 wk; Harlan) were challenged by intraperitoneal injection of SEB (Sigma) and 20 mg D-galactosamine (Sigma). Antagonist peptides were injected intraperitoneally 30 min before challenge. Survival was monitored. Viability remained constant beyond 72 hr for as long as followed, two weeks. Experiments involving mice were approved by the institutional animal care and use committee.

Protection of Pigs Against Toxic Shock

Five-day old mixed breed pigs (mainly Yorkshire; 2.5 kg) in randomized groups of 6 piglets for each test condition, each group under its own sow, were injected IP with SEA (25 μg). Antagonist peptide was administered IP, 30 min before SEA, and 1, 2, 3, 4 and 5 h post-SEA. Vomiting and diarrhea were scored at hourly intervals until 8 h and then every 3 h until 12 h, and again at 21 and 24 h.

Example 1

A Superantigen, Exemplified by SEB, Induces the Early and Concomitant Expression of Th1 Cytokines, IL-2 and IFN-γ, and of Th2 Cytokines, IL-4 and IL-10

SEB Induces the Early Expression of Th2 Cytokines IL-4 and IL-10

Superantigens are thought to exert their toxic effects by overstimulating the Th1 response, involving the expression of IL-2, IFN-γ and TNF-β. It is also commonly believed that the Th2 response, which involves the expression of immunosuppressive cytokines, in particular IL-10, is a later event that acts to shut off the earlier Th1 response. In lymph nodes [Litton et al., J. Immunol. Methods 175:47-58, (1994)] or freshly isolated CD4 cells [Cardell et al., Eur. J. Immunol. 23:523-529, (1993); Nagelkerken et al., Eur. J. Immunol. 23:2306-2310, (1993)] from SEB-treated mice, there was rapid induction of mRNA for IL-2 and IFN-γ but not for IL-4 and IL-10. In murine CD4 cells, significant induction of IL-10 by SEB was seen in the presence of IL-2 and IL-4 but not in their absence [Cardell et al., op. cit.]. In human peripheral blood mononuclear cells (PBMC), SEB and SEA induced expression of IL-2 and IFN-γ, yet induction of IL-4 or IL-10 was not detected [Krakauer, J. Leukoc. Biol. 57:450-454, (1995), Litton et al., op. cit.]. These findings led to the view that during a primary response to superantigen, expression of Th2 cytokines lags well behind that of Th1 cytokines.

Figures 1A, 1B:
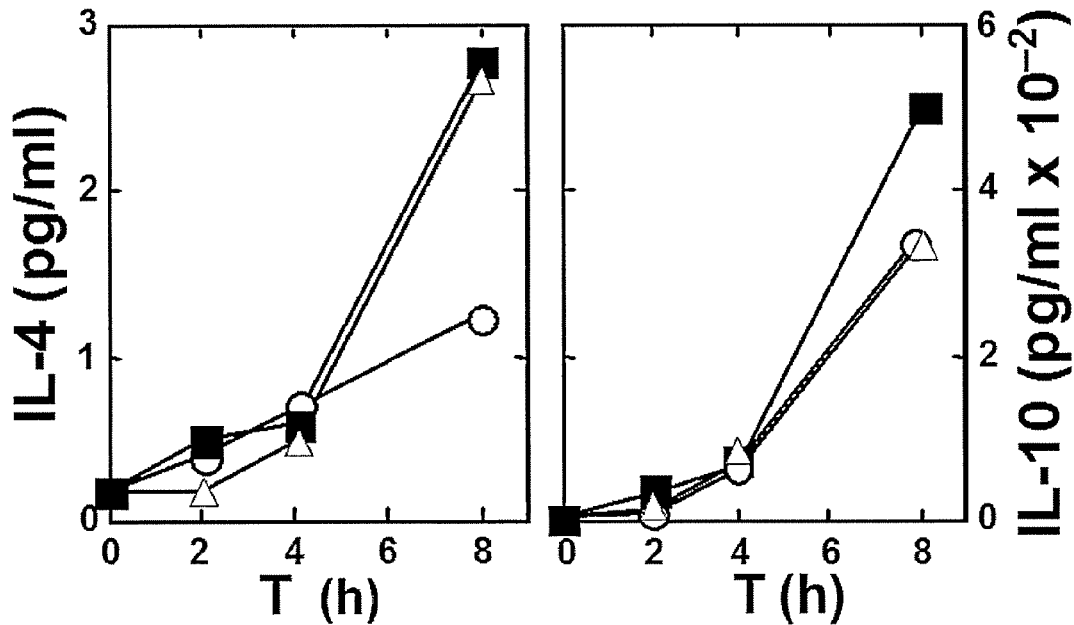
FIG. 1A-1C Early induction of IL-4 and IL-10 by SEB.

The inventors have studied the kinetics of SEB-induced expression of a Th2 response in human PBMC. As can be seen in FIG. 1, within 2 to 4 h SEB induces a low yet significant level of IL-4 (FIG. 1A) and likewise it induces the production of IL-10 (FIG. 1B). The induction increased with SEB dose.

Figure 1C:
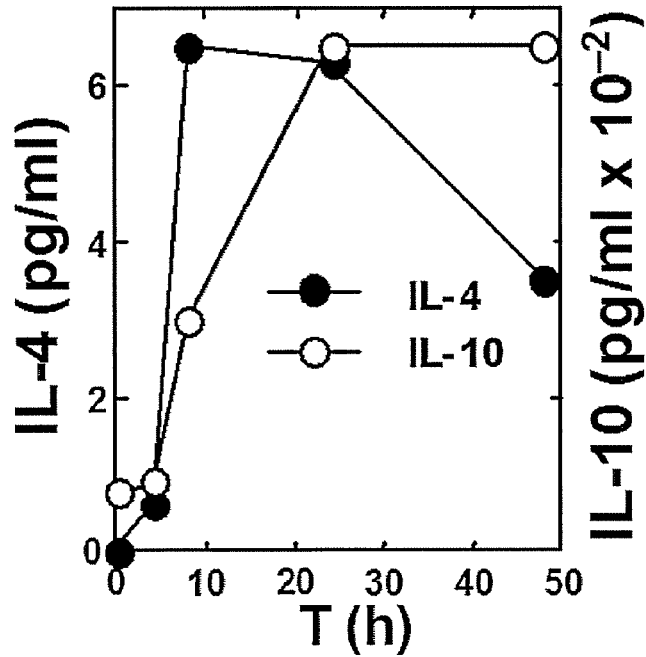
Figure 3D:
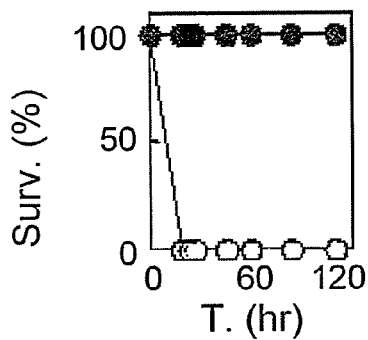
Figure 3E:
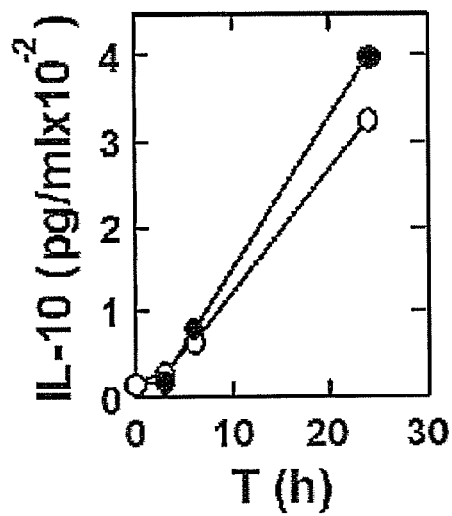
Figure 3F:
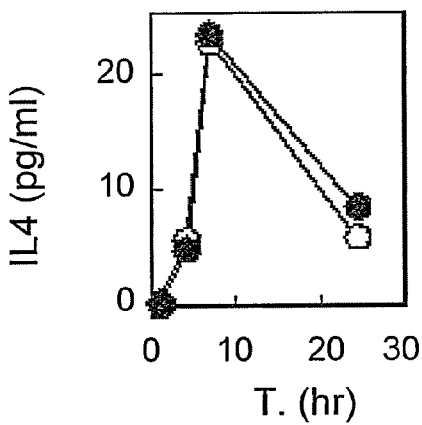

FIG. 1C shows kinetics of induction over the longer term and it is seen clearly that SEB induces maximal levels of these Th2 cytokines within 8 to 20 h and that the expression of IL-4 and IL-10 is sustained. The levels of IL-4 and IL-10 were, however, far lower (pg/ml) than those reported for sera of SEB-treated mice (ng/ml) [see Florquin et al., Autoimmun. 9:609-615, (1996)]; indeed, in other studies, such early induction of IL-4 or IL-10 by SEB escaped detection [see Cardell et al., op. cit; Litton et al., op. cit; Nagelkerken et al, op. cit.; Krakauer, op. cit.].

Induction of Th1 Cytokine mRNA by SEB is Attenuated by Concomitant Induction of Th2 Cytokines In a search for the novel toxin receptor, the inventors next investigated whether the observed early induction of Th2 type cytokines has a role in the powerful, SEB-mediated induction of Th1 cytokines that leads to toxic shock. The findings indicated that concomitant with the induction of IL-2 and IFN-γ gene expression, SEB induces the early appearance of IL-4 and IL-10 to low levels that nevertheless suffice to severely inhibit the induction of IL-2 and IFN-γ gene expression, by at least 10- to 20-fold. SEB-induced expression of IL-2 and IFN-γ mRNA is enhanced greatly in the presence of antibodies (Abs) that neutralize IL-4 or IL-10; these Abs had no inductive effect in the absence of SEB (FIG. 2). Thus, from the outset of induction by SEB, expression of IL-2 and IFN-γ genes is downregulated by concomitantly induced IL-4 and IL-10. Induction of these Th2 type cytokines is a primary response that begins to regulate the expression of IL-2 and IFN-γ genes as soon as they are induced (FIG. 2). Without this built-in suppressive mechanism, their harmful induction would be even greater.

To assess the effect of SEB-mediated induction of IL-4 and IL-10 (FIG. 1) on SEB-induced expression of IL-2 and IFN-γ genes, neutralizing Abs αIL-4 or αIL-10 were used to block the action of IL-4 or IL-10. Within 4-6 hr, the amplitude of the induced IL2 mRNA wave increased significantly when neutralizing Abs against IL4 or IL10 were present, whereas isotype-matched control IgG had no effect (FIG. 2A). The IFN-γ gene responded even more extensively to depletion of IL-4 or IL-10. As seen in FIG. 2C, depletion of either IL-4 or IL-10 with Abs not only enhanced both amplitude and duration of the induced IFN-γ mRNA wave but also led to a far earlier expression. It was thus shown by using neutralizing Abs, that from the outset of induction by SEB, expression of IL-2 and IFN-γ genes is reduced greatly (20-fold) by a concomitant induction of IL-4 and IL-10. Thus, although superantigens such as SEB induce an excessive Th1 cytokine gene expression, this response remains below its full potential because it is attenuated by concomitant induction of IL4 and IL10. Early expression of these Th2 cytokines forms an integral part of the primary response to superantigen.

Selective Inhibition of the Th1 Response by a Superantigen Mimetic Peptide

Figure 5B:
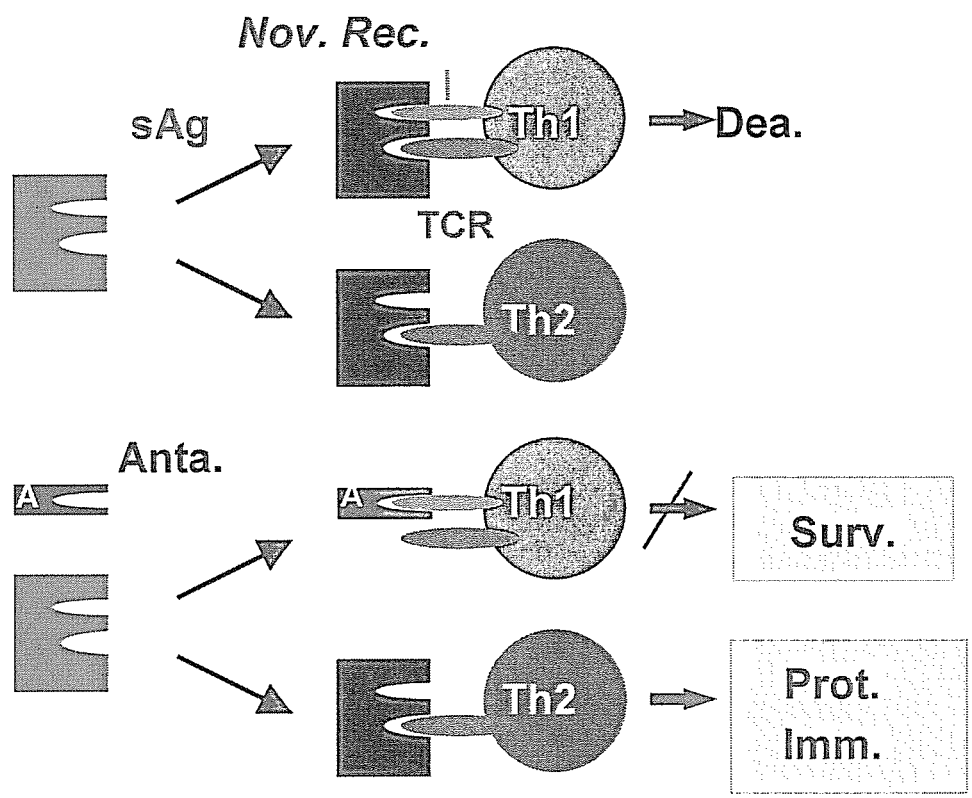

Mice that were protected against lethal toxin challenge by antagonist peptide, through blocking of the Th1 cytokine response, rapidly develop protective immunity against further toxin challenges, even with different toxins [Arad et al., (2000) ibid.; Arad et al., (2001) ibid.]. Such immunity, which involves protective antibodies [Arad et al., (2000) ibid.], might be mediated through a vigorous induction of Th2 cytokines by superantigen in conditions where a lethal Th1 response is blocked by antagonist peptide. Indeed, whereas the antagonist peptide p14A (SEQ ID NO: 2) blocked induction of Th1 cytokine gene expression by SEB (FIG. 3A for IL-2; FIG. 3B for IFN-γ and FIG. 3C, for both), it left induction of the Th2-type cytokines IL-10 and IL-4 intact (FIGS. 3E and 3F, respectively). This expression of IL-10 flags immunocompetence, with the concomitant helper function for B cells.

This result points to Th1 cells as a likely carrier of an antagonist peptide receptor that is essential for superantigen action. The data in FIGS. 2 and 3 suggest a model as depicted in FIG. 4. An excessive Th1 response induced by a superantigen toxin leads to lethal shock, where IFN-γ suppresses the Th2 response. Supported by the data of FIGS. 2 and 3, it was hypothesized that the antagonist peptide elicits a selective block in Th1 cell activation by toxin yet does not interfere with the concomitant and vigorous induction of Th2 cytokines (IL-4, IL-10) that act not only to suppress any residual Th1 response but also to promote a rapid development of protective immunity—as is in fact observed [Arad et al., (2000), (2001) ibid.].

There is clinical evidence that the activation of T cells by a superantigen is predominantly a Th1 response. The massive, toxin-induced release of IFN-γ interferes with development of protective neutralizing antibodies. For example, 85% of women who develop menstrual staphylococcal toxic shock syndrome fail to develop antibodies against TSST-1 after recovering, and many have recurrences [Schlievert, Nature Medicine 6:378-379. (2000)].

In the absence of antagonist (FIG. 4A), toxin induces a powerful production of the Th1 cytokines IL-2, IFN-γ, and TNF that on one hand will act to inhibit the Th2 response and on the other, will lead to organ failure and death. In the presence of antagonist, however, the Th1 response is inhibited while the Th2 response proceeds unabated (FIG. 4B). Now, high levels of IL-4 and IL-10 will suppress any residual Th1 response and at the same time induce protective immunity.

It is suggested that the antagonist peptide acts as an adjuvant that switches a lethal Th1 response to a protective Th2 response. Consistent with a key role of the antagonist domain in superantigen function, αp14A Ab was fully protective against SEB in the D-galactosamine-sensitized mouse (FIG. 3D), an established model for the lethality of superantigens [Arad et al. (2000) ibid.]. Whereas p14A blocked the SEB-mediated induction of IL2 and IFN-γ mRNA, it did not inhibit induction of IL4 and IL10 (FIGS. 3A-3C, 3E and 3F). This result was reproducible and shows that the balance between Th1 and Th2 responses induced by SEB is modulated by the antagonist peptide. Interaction of SEB with the TCR and MHC class II molecule leaves the antagonist domain accessible (FIG. 5A).

Without being bound by theory, an attractive concept as to how the antagonist causes a selective block in Th1 cell activation by toxin is that the novel toxin receptor is selectively utilized for the activation of Th1 cells. The inventors working hypothesis was that in order to activate Th1 cells, a superantigen toxin must engage not only the T cell receptor but also the novel receptor, whereas this receptor is not required for a Th2 response (FIG. 5B upper panel). Accordingly, binding of antagonist peptide to the novel receptor will result in a selective block in Th1 cell activation by toxin and thus permit survival (FIG. 5B, lower panel).

Full activation of Th1 cells is not solely dependent on the interaction of MHC class II molecule, superantigen and TCR. Sustained TCR engagement, although essential for T cell activation, faces many barriers. First, the TCR has a low affinity for antigenic MHC-peptide. Second, the number of antigenic complexes on the antigen-presenting cell can be very low. Third, the movement of T cells works against sustained recognition of antigen [Grakoui et al., Science 285:221-227 (1999)]. Although superantigens are far superior to ordinary antigens in overcoming these limitations and bypass MHC restrictions, they still require costimulatory ligands for T cell activation, including those of the B7 family on the antigen-presenting cell and CD28 on T cells delayed [reviewed by Lenschow et al., (1996) ibid.].

Example 2

Specific Involvement/Requirement of B7-2 in Superantigen Activation of Th1 Cells Anti-B7-2 Blocks the Th1 Response to SEB Yet Fails to Block the Th2 Response to SEB Whereas Anti-B7-1 Fails to Block Th1 or Th2 Responses The inventors have now found that mAbs against B7-2 block the induction of IL-2 and IFN-γ mRNA by SEB in human PBMC, whereas mAbs against B7-1 have no such effect (FIGS. 6A for IL-2 and 6B for IFN-γ). By contrast, the concomitant induction of IL10 and IL4 was resistant to either mAb (FIGS. 6C and 6D, respectively). These results were reproducible and show that as for conventional antigens [reviewed by Carreno, B. M. and Collins, M. Annu. Rev. Immunol. 20:29-53 (2002); Collins, A. V. et al., Immunity 17:201-210 (2002)], induction of a Th1 response by SEB relies selectively on signaling via B7-2/CD28.

This correlation between the lack of inhibition of IL-10 production by antagonist peptide on one hand and by anti-B7-2 on the other, in conditions where the Th1 response is inhibited, supports involvement of the B7-2 coligand in the mode of action of superantigens. Based on these results, the inventors have investigated whether SEB binds to the B7-2 ligand or to the CD28 costimulatory receptor that engages these B7 ligands and whether such binding is sensitive to inhibition by antagonist peptide.

Without being bound by any theory, the results detailed below support the following interpretation. Although activation of Th1 cells to express the cytokines that mediate lethal toxic shock depends strictly on the interaction of the superantigen with the MHC class II and TCR ligands, this interaction by itself is insufficient for activation. Once bound, a superantigen acts via the antagonist domain to allow for B7-2/CD28 ligand interaction and it is the strong facilitation of this inherently weak interaction that is the key signal driving Th1 cell activation. Without this interaction, a superantigen cannot activate Th1 cells. Critically, the superantigen binds directly to CD28 and facilitates the binding of B7-2 to the latter. The superantigen binds also to B7-2, although more weakly. Remarkably, the superantigen forms a ternary complex with CD28 and B7-2 and thereby uses the CD28/B7-2 ligand interaction as its essential, indeed obligatory pathway for Th1 cell activation. Thus, the utilization of CD28 and B7-2 by superantigens differs fundamentally from that of conventional antigens, which are presented as processed peptides within the MHC class II pocket to the TCR such that these peptides cannot engage B7-2 and CD28 and instead, merely use these ligands in an indirect manner, as costimulatory rather than obligatory ligands.

As shown in Example 3 below, the superantigen SEB binds directly to the CD28 receptor on the Th1 cell. These results show that the target of the antagonist peptide, the novel receptor, is CD28. Antagonist peptide blocks Th1 cell activation by binding to the CD28 molecule and thus preventing access of the superantigen to this receptor. Moreover, the inventors show that in contrast to activation of Th1 cells, the activation of Th2 cells is independent of the B7-2/CD28 ligand interaction. Thus, activation of Th1 cells by a superantigen uniquely requires the B7-2/CD28 ligand interaction.

Example 3

Superantigen-Mediated Activation of Th1 Cells, but not Activation of Th2 Cells, is Dependent Upon the CD28 Receptor which Serves as the Antagonist Target Soluble CD28 Receptor Blocks the SEB-Mediated Induction of Th1 Cytokine Gene Expression Yet Fails to Block the Th2 Response to SEB The following set of observations provides strong evidence that the CD28 receptor is the antagonist target. Human PBMC were induced by various protocols. Expression of IL-2 and IFN-γ mRNA was used as readout for a Th1 response and expression of IL-10 protein as readout for a Th2 response.

Recombinant soluble CD28 receptor (sCD28) is a chimeric molecule composed of the extracellular 1 to 152-amino acid domain of the human CD28 molecule fused to the C-terminal, histidine-6-tagged Fc region of human IgG (catalogue no. 342-CD of R&D Systems, Inc., Minneapolis, Minn., USA). Induction of IL-2 mRNA by SEB was inhibited 3.5-fold by sCD28 which by itself did not induce this gene (FIGS. 7A and B). By contrast, the induction of IL-10 by SEB in the same cell culture was essentially unaffected by sCD28 (FIG. 7C). Induction of IFN-γ mRNA by SEB was inhibited about twenty fold by sCD28 at 6 h, the time of maximal expression; by itself, sCD28 did not induce IFN-γ mRNA (FIGS. 7D and E). By contrast, the induction of IL-10 by SEB in the same cell culture was essentially unaffected by sCD28 (FIG. 7F).

sCD28 inhibited the SEB-mediated induction of IL-2 mRNA in a dose-dependent manner (FIGS. 8A and B). By contrast, the induction of IL-10 in the same cell population was not inhibited even at the highest concentration of sCD28 used and instead, was stimulated significantly (FIG. 8C). The distinct and opposite responses of Th1 and Th2 cytokine-producing cells, manifested by expression of IL-2 or IFN-γ genes and of IL-10, respectively, are a recurrent theme throughout these experiments.

Alternative splicing generates a natural soluble form of the B7-2 ligand, lacking the transmembrane domain, that is detected in human serum and appears to be a functional costimulatory molecule [Jeannin et al., Immunity 13:303-312 (2000)]. The costimulatory activity of this soluble form of B7-2 was shown by its ability to enhance the induction of Th1 cytokines by anti-CD3 [Jeannin et al. (2000) ibid.]. Here, the inventors used a soluble recombinant form of B7-2 (sB7-2) comprising the extracellular 1 to 239 amino acid domain of the B7-2 molecule fused to the C-terminal, histidine-6-tagged Fc region of human IgG (catalogue no. 141-B2 of R&D Systems, Inc., Minneapolis, Minn., USA). The possibility that sB7-2, through an interaction with CD28, could inhibit the action of SEB was then examined. As seen in FIGS. 8D and 8E, sB7-2 strongly inhibited the induction of IL-2 mRNA and on a molar basis was far more effective in this respect than sCD28. Induction of IL-10, by contrast, was inhibited neither by sCD28 nor by sB7-2 (FIG. 8F).

CTLA4 and CD28 are structurally homologous and interact with the same B7 coligands to deliver opposite signals [reviewed by Collins (2002) ibid.; Sansom, D. M. et al., Trends Immunol. 24:314-319 (2003)]. The inventors examined the effect of sCTLA4 on expression of IL2 and IFN-γ mRNA induced by SEB. sCTLA4 blocked this expression (FIG. 8G) yet as for sCD28, left the induction of IL10 intact (FIG. 8H). sCTLA4 could inhibit the action of SEB by competing for B7-2 [Zhou, T. et al., Eur. J. Immunol. 24:1019-1025 (1994)] but the inventors considered the possibility that by binding to SEB it might impede the interaction of the superantigen with cell surface CD28.

Anti-CD28 and sB7-2 Each Induce Strong Th1 Cytokine Gene Expression Yet No Significant Th2 Cytokine Gene Expression So far, SEB was used as inducer of the Th1 and Th2 responses. To dissect the specific role of CD28 and its co-ligand B7-2, anti-CD28 mAb (catalogue no. MAB342, clone 37407.111, of R&D Systems, Inc., Minneapolis, Minn., USA) or sB7-2, have been used as sole activator of these responses, and their inductive effect was compared to that of anti-CD3, which signals through the TCR. CD3 forms an essential part of the TCR and anti-CD3 mAbs strongly activate T cells [Schlossman et al., Leukocyte Typing V: White cell differentiation antigens. Oxford University press, NY, (1995); Sancho et al., J. Biol. Chem. 267:7871-7879 (1992)]. Anti-CD3 induced expression of IFN-γ mRNA (FIG. 9A). Anti-CD28 and sB7-2 each elicited a vigorous induction of IFN-γ mRNA that occurred earlier than that with anti-CD3.

More generally, the inventors have observed a consistent link between the responses to anti-CD28 and to sB7-2 in the same PBMC population. That is, where anti-CD28 induces a Th1 response, sB7-2 also induces that response. In the PBMC population illustrated in FIG. 9B, anti-CD28 or sB7-2 each yielded induction of IFN-γ mRNA yet the combination of anti-CD28 with sB7-2 resulted in a mutual inhibition. This result confirms the concept that sB7-2 interacts with CD28 to deliver the signal for the induction of IFN-γ gene expression in Th1 cells.

Example 4

Superantigen Mimetic Peptide Blocks Signaling Through CD28

To examine the role of CD28 in activation of Th1 cytokine genes independently of other ligands, the inventors induced IL2 and IFN-γ mRNA with αCD28 alone. This induction was blocked by superantigen mimetic peptide p14A (FIG. 10A, top two rows).

Stimulation of T cells by a combination of anti-CD3 and anti-CD28 has been employed widely to activate T cell populations [e.g., Jeannin et al., ibid.]. The combination of αCD28 and αCD3 elicited a higher expression than did either mAb alone; this induction was eliminated virtually in full by p14A (FIG. 10A, bottom). By contrast, induction of IL10 by αCD28/αCD3 was resistant to p14A (FIG. 10B). Thus, in the absence of a superantigen, the antagonist peptide selectively blocked activation of a Th1 response transduced by CD28. Therefore, the antagonist peptide is a specific inhibitor of Th1 cytokine gene expression whether induced by anti-CD28 alone or by the combination of anti-CD3/anti-CD28. αCD28 bound sCD28 as expected but failed to bind to p14A (FIG. 10C), indicating that the peptide competes with αCD28 for CD28.

An Anti-CD3/sB7-2-Induced Th1 Response, but not the Th2 Response, is Blocked by Antagonist Peptide The inventors postulated that dual stimulation of T cells with a combination of anti-CD3 with sB7-2 might mimic stimulation by a superantigen. Indeed, this combination yielded a strong and early induction of IFN-γ mRNA and this induction was abrogated by p14A (FIG. 11A). By contrast, p14A did not inhibit the induction of IFN-γ mRNA by anti-CD3 alone, and it shifted the induction by sB7-2 alone to earlier times.

This result shows that the antagonist peptide is specific in its inhibitory action, which requires B7-2 and thus its coligand on the Th1 cell, CD28. sB7-2 alone gave an earlier induction of IFN-γ mRNA than anti-CD3. By contrast, sB7-2 alone failed to give an induction of IL-10 comparable to that seen with anti-CD3, nor did the combination of CD3 with sB7-2 yield a significantly enhanced induction over that by CD3 alone (FIG. 11B). Induction of IL-10 by sB7-2/anti-CD3 proved largely resistant to inhibition by p14A antagonist peptide (FIG. 11B). The finding that anti-CD28 failed to induce IL-10 (FIG. 10B) and sB7-2 failed to induce IL-10 to levels comparable to those obtained in the presence of anti-CD3 (FIG. 11B) supports the concept, first advanced by the data of FIG. 6, that neither the B7-2 molecule nor CD28 have a role in IL-10 induction.

Dual stimulation with anti-CD3/sB7-2 mimics the stimulation by superantigens via TCR and CD28 and thus it is consistent that here, the antagonist peptide will inhibit (FIGS. 11A and B).

Antagonist Peptide Stimulates the sB7-2-Mediated Induction of Th1 Cytokine Gene Expression In the PBMC population used in FIG. 12, sB7-2 yielded only a brief and transient induction of IFN-γ mRNA. In this limiting condition, addition of p14A not only failed to inhibit this induction, consistent with the results of FIG. 11A, but the antagonist peptide even stimulated induction significantly.

This result supports the concept that the binding of a superantigen to CD28 facilitates the interaction between the coligands B7-2 and CD28 and that p14A, in the absence of a superantigen, mimics the superantigen in this respect.

These functional studies show that induction of IL10 is independent of CD28. This provides an explanation for the resistance of the SEB-mediated induction of IL10 to p14A and to anti-B7-2, sB7-2, sCD28 and sCTLA4 (FIGS. 3C, 3D, 3E, 3F and 7). Signaling through CD28 is needed selectively for the Th1 response to superantigen. The finding that even in the absence of SEB, a superantigen mimetic peptide blocked CD28-mediated Th1 activation led the inventors to examine whether superantigens use the antagonist domain to bind to CD28.

Example 5

Direct Binding of Superantigen to the CD28 Target Receptor

Plasmon Resonance Equilibrium Binding Studies Show Binding of SEB and of Antagonist Peptide to Recombinant Soluble CD28

Thus far the evidence for an interaction between superantigen and CD28, and of the inhibition of this interaction by antagonist peptide, is based on functional studies of Th1 cytokine gene induction in human PBMC. There is therefore a need to show direct binding of the superantigen or the antagonist peptide to the CD28 target receptor. To quantitate the binding of these molecules in solution, plasmon resonance measurements were employed. This method has been used to demonstrate complex formation between a superantigen, the MHC class II molecule, and the TCR [Seth et al., Nature 369:324-327 (1994) ibid.]. It should be noted that these Surface Plasmon Resonance (SPR) equilibrium binding studies have shown that the interaction of superantigens with the TCR or MHC II molecule is weak, with dissociation constants in the micromolar range [Seth et al., (1994) ibid.; Redpath (1999) ibid.]. In the experiment of FIG. 13, sCD28 was immobilized on a Biacore chip and anti-CD28, SEB or p14A were used as analyte for complex formation, which is measured in resonance units (RU). The binding of anti-CD28 to sCD28 is monitored in FIG. 13A through a rise in RU. Binding of SEB is shown in FIG. 13B and binding of p14A is shown in FIG. 13C. This binding is of low affinity, as would be expected for SEB, which depends on binding to multiple ligands, MHC class II, TCR and CD28, for its function as T cell activator.

Since plasmon resonance measures binding under equilibrium conditions in real time, these results demonstrate that SEB and p14A each bind directly to CD28.

Biacore Plasmon Resonance Equilibrium Binding Studies Show that High-Affinity Binding of Anti-CD28 to sCD28 is Inhibited by SEB The plasmon resonance signal for binding of anti-CD28 to sCD28 is shown in FIG. 14. This binding was reduced by SEB, even when present in equimolar ratio to the anti-CD28 antibody. The ability of SEB to compete with the anti-CD28 mAb is surprising since anti-CD28, being a monoclonal antibody, was selected for its high affinity for CD28, whereas the superantigen binds to sCD28 with lower affinity (cf. the increase of about 200 RU for anti-CD28 in FIG. 13A with about 30 RU for SEB in FIG. 13B). This result again shows that SEB interacts directly with sCD28.

Biacore Plasmon Resonance Equilibrium Binding Studies Show that High-Affinity Binding of Anti-CD28 to sCD28 is Inhibited by p14A The plasmon resonance signal for binding of anti-CD28 to sCD28 was reduced by antagonist peptide p14A, the extent of inhibition increasing progressively with decreasing CD28 antibody concentration (FIG. 15). The ability of antagonist peptide to compete with anti-CD28 mAb is surprising since the mAb has a higher affinity for its ligand, sCD28, than does the antagonist peptide (FIG. 13A vs. FIG. 13C). This result shows that the toxin antagonist peptide interacts directly with sCD28.

Binding Studies in ELISA Format Show that High-Affinity Binding of Anti-CD28 to sCD28 is Inhibited by Antagonist Peptide Yet another assay was devised to show a direct interaction between antagonist peptide and sCD28. The inventors developed an enzyme-linked immune sorbent assay (ELISA) in which sCD28 is immobilized in the wells of a microtiter ELISA plate and binding of anti-CD28 is measured by use of a secondary antibody coupled to alkaline phosphatase. It is seen in FIG. 16 that binding of 1,000-fold diluted anti-CD28 to the plate was inhibited by p14A even at a concentration of only 0.1 µg per ml. Higher levels of p14A did not yield higher levels of inhibition, which was only partial. However, when the concentration of anti-CD28 was reduced twofold, p14A had a pronounced inhibitory effect on the binding to sCD28, and this inhibition increased progressively with p14A concentration. Thus, antagonist peptide p14A is a powerful inhibitor of the interaction between anti-CD28 and sCD28. This shows, in reinforcement of the conclusion based on the data in FIG. 13C, that p14A binds directly to sCD28.

Plasmon Resonance Equilibrium Binding Studies Show that SEB Interacts with sCD28 and, More Weakly, with sB7-2

Figure 17A:
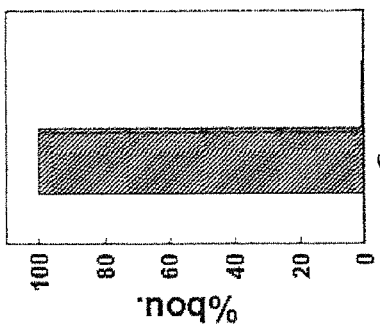
Figure 17B:
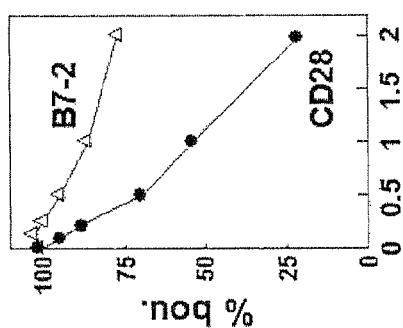
Figure 17C:
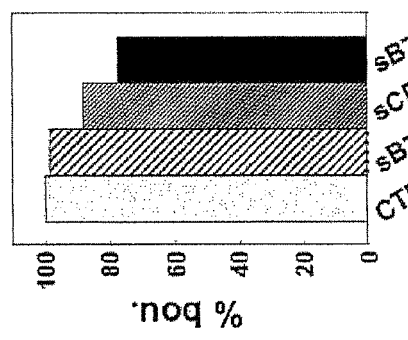

The plasmon resonance signal for binding of anti-SEB to immobilized SEB is shown in FIG. 17A. In the experiment of FIG. 17B, this binding was studied in the presence of increasing concentrations of sCD28. sCD28 effectively inhibited the interaction of anti-SEB with SEB, reducing the binding by about 5-fold. sB7-2 also inhibited this interaction, although more weakly. Although anti-SEB bound well to SEB (FIGS. 17A and C), it failed to bind to CD28 (FIG. 17C). Hence, the results of FIG. 17B demonstrate a direct interaction between CD28 and SEB. They also show that a direct interaction occurs between sB7-2 and SEB.

Figure 17D:
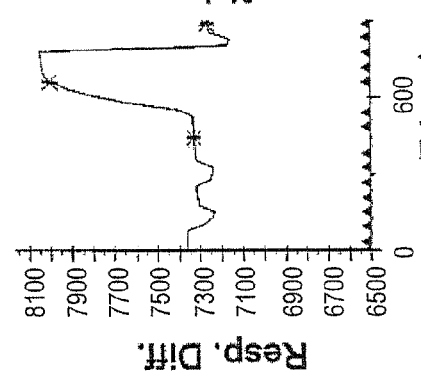
Figure 17E:
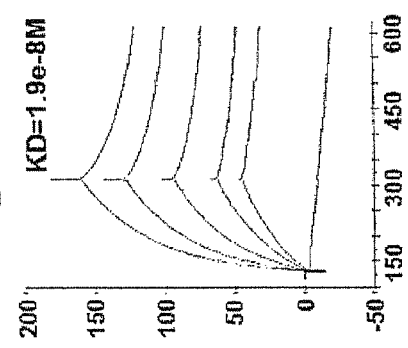

The plasmon resonance signal for the binding of sB7-2 to immobilized CD28 is shown in FIG. 17D, yielding a Kd of 19 nM. To analyze whether the B7-2/CD28 complex is able to bind to SEB, sB7-2 and sCD28 were introduced in equimolar amounts into the assay system of FIG. 17A. Whereas sB7-2 alone was not inhibitory at the concentration tested, it enhanced the inhibitory effect of sCD28, indicating that the two ligands cooperate in their interaction with the superantigen (FIG. 17E).

To further study the binding of sCD28 to SEB, an extended plasmon resonance analysis was employed (FIG. 18). Binding of anti-SEB as analyte to SEB immobilized on the chip was inhibited progressively by increasing concentrations of sCD28 (FIG. 18A). The inhibition of 84% caused by 1 µM sCD28 on binding of 4 nM anti-SEB Ab to SEB could be relieved progressively by increasing concentrations of the anti-SEB Ab (FIG. 18B depicts percent binding). This result shows that despite the strong interaction between anti-SEB Ab and SEB, sCD28 is able to compete. By contrast, when sCD28 was immobilized on the chip and the chip was then exposed to anti-SEB Ab, no signal could be observed (FIG. 17C above). Therefore, sCD28 binds to SEB with sufficient affinity to displace the antibodies.

Figure 19A:
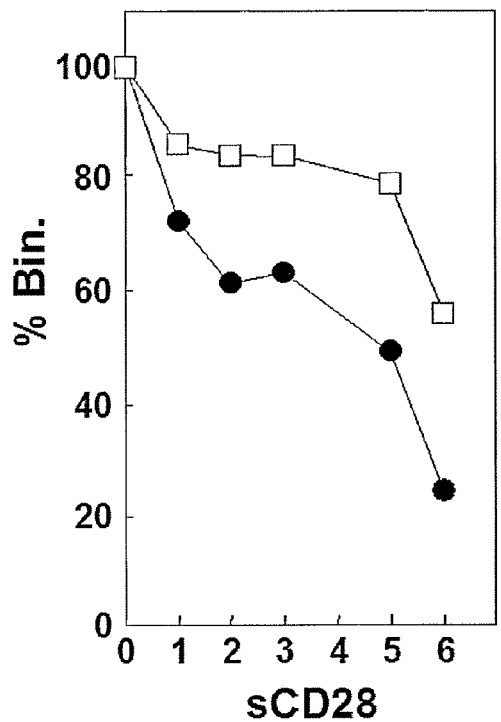
Figure 19B:
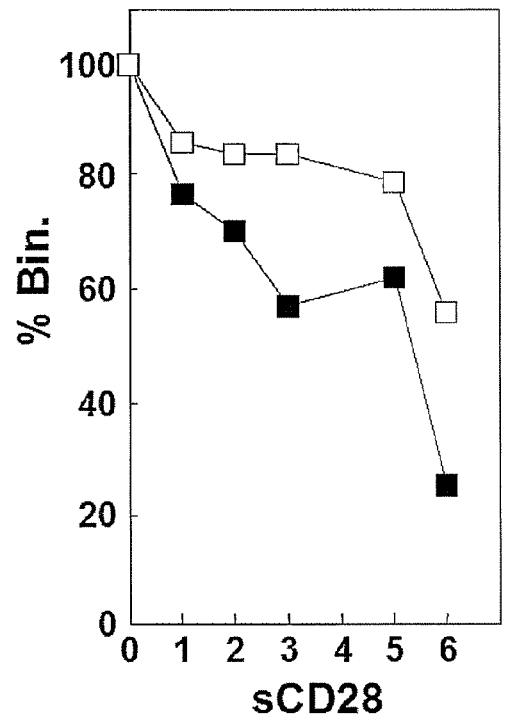

Independent evidence for the interaction of sCD28 with SEB is provided by ELISA. In the experiment of FIG. 19, binding of anti-SEB Ab to SEB immobilized on the ELISA plate was assayed. This binding could be competed effectively by increasing concentrations of sCD28, up to about 75% (FIGS. 19A and 19B). The earliest time for readout of the assay showed a stronger inhibitory effect (FIG. 19A). Extent of inhibition was greater when the antibodies were diluted more extensively (FIG. 19B), in accordance with the plasmon resonance data in FIG. 18B. Therefore, experimental evidence based on ELISA also shows that sCD28 binds to SEB with sufficient affinity to displace the antibodies.

By contrast, when sCD28 was used to coat the ELISA plate and the plate was then exposed to anti-SEB antibodies, no signal could be observed. Therefore, sCD28 binds to SEB in order to interfere with the binding of anti-SEB to SEB.

ELISA Studies Show that p14A Interacts with CD28

Figure 20:
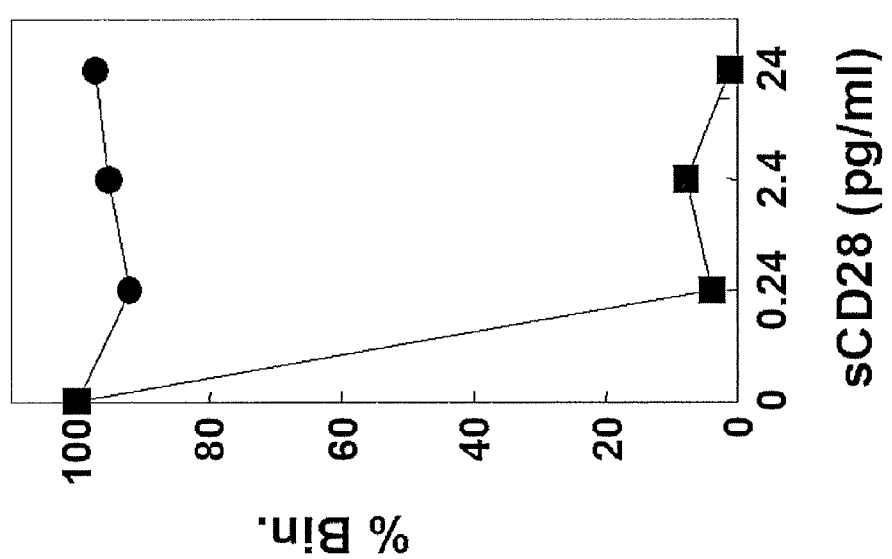

Evidence for the interaction of sCD28 with p14A is further provided by ELISA in FIG. 20. Binding of anti-p14A Ab to p14A immobilized on the ELISA plate was assayed. This binding could be competed effectively by increasing concentrations of sCD28, to yield an inhibition of over 90%. Extent of inhibition was greater when the antibodies were diluted more extensively. Therefore, sCD28 binds to p14A with sufficient affinity to displace the anti-p14A antibodies.

Because p14A is homologous to a domain in SEB and because sCD28 inhibits both the binding of p14A to anti-p14A Ab and the binding of SEB to anti-SEB Ab, it follows that SEB interacts with sCD28 through the domain having homology with p14A. This conclusion receives support from the ability of sCD28 to inhibit the induction of Th1 cytokine gene expression by SEB (FIGS. 7 and 8 and FIGS. 25 and 26 below) and from the ability of p14A to inhibit the induction of Th1 cytokine gene expression by anti-CD28 mAb (FIG. 10A) and to inhibit the binding of the anti-CD28 mAb to sCD28 (FIG. 16).

Figure 21:
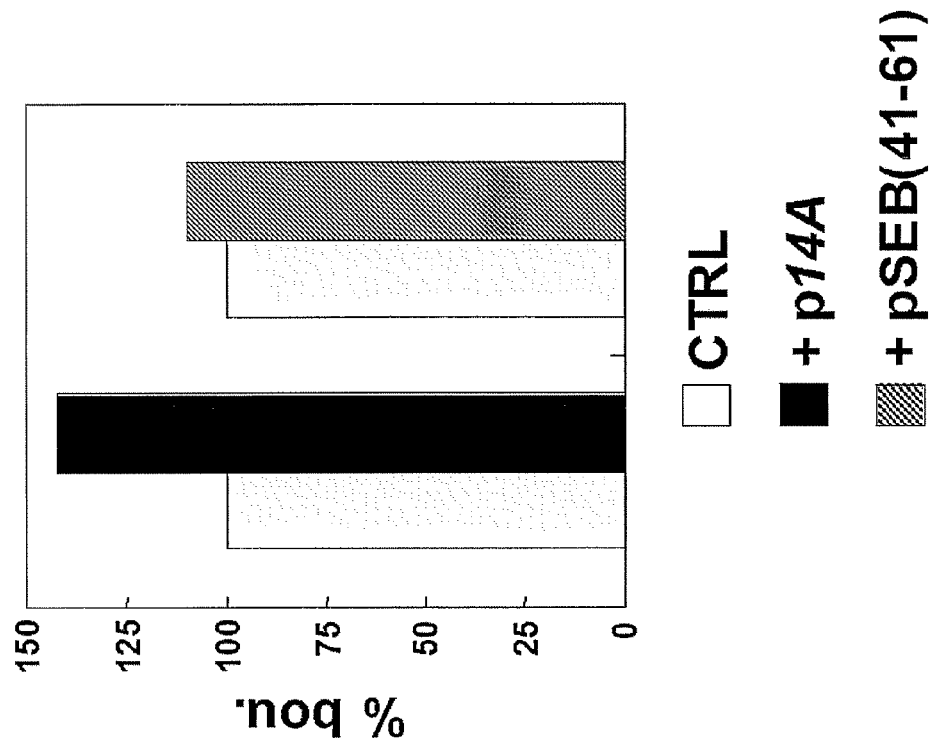

Plasmon Resonance Equilibrium Binding Studies Show that Binding of sCD28 to sB7-2 is Enhanced by Antagonist Peptide The plasmon resonance signal for binding of sCD28 to sB7-2 was enhanced significantly by antagonist peptide p14A but only slightly by pSEB(41-61), a peptide that lacks antagonist activity [Arad et al., (2000) ibid.](FIG. 21). This result can explain the observation (FIG. 12) that the antagonist peptide is able to enhance the early induction of IFN-γ mRNA by sB7-2.

It is thus seen that there exists a direct correlation between the binding measured by plasmon resonance, and functional assays for induction of a Th1 response in PBMC.

SEB Binds CD28, CTLA4 and ICOS Through its Antagonist Domain

The inventors further analyzed direct interaction of the superantigen with the CD28 costimulatory receptor family members. When SEB was immobilized on a Biacore chip, direct binding of soluble CD28, CTLA4 or ICOS was detected, with $K_D$ values of 28, 31 and 21 nM, respectively (FIGS. 22A, 22B, and 22C) but not of human IgG (not shown). Thus, SEB binds directly to each member of the triad of costimulatory receptors, CD28, CTLA4 and ICOS, with an affinity well above that for the TCR or MHC II molecule.

The inventors next immobilized p12C (p12 abutted by terminal cysteines, C-YNKKKATVQELD-C, also denoted by SEQ ID NO: 62). This peptide was as active as p14A in blocking SEB-mediated induction of IL2 and IFN-γ mRNA in human PBMC (not shown). Soluble CD28, CTLA4 and ICOS bound directly to p12C, with $K_D$ values of 76, 33 and 42 nM, respectively (FIGS. 22E, 22F, and 22G). Affinities for the p12C peptide did not differ significantly from those for intact SEB. By contrast, PD-1, another member of the CD28/CTLA4/ICOS costimulatory receptor family, failed to bind significantly (FIG. 22H). Binding was not mediated by a His-tag because ICOS bound tightly yet lacked this tag whereas His-tagged ubiquitin did not bind (FIGS. 22G and 22J). The soluble ligands were presented as fusions with IgG1 Fc yet no binding was detected for free human IgG (FIG. 22K); the Fc portion has no effect on B7-2 binding affinity of CD28 [Collins (2002) ibid.]. Thus, binding of the coligands CD28, CTLA4 and ICOS is specific. Although CTLA4 and PD-1 have very similar overall structures, PD-1 is monomeric [Zhang, Z. Y., et al., Immunity 20:337-347 (2004)] whereas CD28, CTLA4 and ICOS exist as dimers. Randomly scrambled p12Csc (C-EKAKYTQLVKDN-C, also denoted by SEQ ID NO: 63) failed to bind CD28 (FIG. 22I), showing sequence specificity for the p12C peptide (SEQ ID NO. 62). The inventors conclude that SEB uses its antagonist domain to bind CD28, CTLA4 and ICOS.

As was also shown above, the CD28 coligand sB7-2 also bound directly to SEB, with a $K_D$ of 25 nM (FIG. 22D). This affinity was similar to that of sCD28 for SEB (FIG. 22A) and of sCD28 for sB7-2 ($K_D$, 19 nM; FIG. 22L) but association and dissociation rates of sB7-2 to SEB were greater, attesting to lower avidity. Collins et al. [Collins (2002) ibid.,] reported a far lower affinity of sCD28 for sB7-2 ($K_D$, 20 µM at 37° C.). Most plausibly, the discrepancy results from the temperature, method of sCD28 presentation and activity of the recombinant sCD28 preparations used. By comparison, αCD28 mAb reproducibly bound to sCD28 with a $K_D$ of 2 nM (not shown).

The results from Th1 cytokine gene expression analysis (FIGS. 3C, 3D, 3E, 3F, 6, 7, and 10) are readily accommodated by the finding that SEB interacts directly with CD28 and that this binding occurs through the antagonist domain in the superantigen.

The data presented herein led the inventors to the novel concept that the activation of a Th1 cell response by superantigens depends totally on the B7-2/CD28 interaction, which is known as a very weak interaction (20-fold weaker than the B7-1/CD28 interaction and 100-fold weaker than the B7-1/CTLA-4 interaction), and that effective B7-2/CD28 interaction becomes possible once the superantigen, held in place by its binding to TCR and MHC class II molecule, binds directly to CD28 on the Th1 cell. It is this latter binding step that is blocked by antagonist peptide. The Th2 cell, by contrast, is activated by superantigen without a need for the B7-2/CD28 interaction and thus the Th2 response is not inhibited by the antagonist peptide.

Example 6

SEB Induces Transient Change in the CD28 Molecule that Exposes the Epitope for the Anti-CD28 mAb Mouse anti-human CD28 mAb (MAB342 of R&D Systems, Minneapolis, Minn.) and a goat anti-human polyclonal antibody against CD28 (CD28 Ab) were used to stain CD4-enriched human PBMC. Enrichment of CD4-positive cells was achieved by means of a cocktail of antibodies (RosetteSep, StemCell Technologies, Vancouver, Canada), following instructions of the manufacturer. CD4 cells constituted 18% of total PBMC before enrichment and 90% after enrichment. The enriched CD4 cells were induced with 100 ng/ml of SEB and stained with anti-CD28 mAb or with anti-CD28 Ab at 0, 6 and 24 h after induction. Although anti-CD28 Ab could stain the cells at all times examined, the anti-CD28 mAb stain was detected on cells induced by SEB for 6 h but not on resting cells at 0 h nor on cells that had been induced with SEB for 24 h (FIG. 23). Therefore, although the CD28 receptor was present on the cells at all these times as shown by staining with the anti-CD28 Ab, it was recognized by the mAb only after induction of the cells with SEB. This result supports the interpretation that SEB induces a transient change in the CD28 receptor that renders it accessible to the mAb.

Example 7

The Binding Site for SEB in CD28/CTLA4 Maps to the Dimer Interface and the CD28 Epitope is Recognized by Antagonist Peptide The antagonist peptide inhibits the binding of anti-CD28 mAb to sCD28. The inventors have taken advantage of the specificity of this mAb to map the CD28 epitope that is recognized by the antibody. This epitope must overlap, at least in part, with the binding site for superantigen and thus for antagonist peptide. To this end, an epitope mapping was done using the PhD-12 combinatorial phage display library (New England Biolabs), by repeated panning of phages on immobilized anti-CD28 mAb MAB342 and displacement by means of sCD28, followed by screening for those phages that bound most readily to the anti-CD28 mAb. When peptide sequences obtained from 22 phages thus selected were aligned without allowing for gaps, they yielded a single consensus sequence that overlaps with the sequence $CD28_{116-124}$, H V K G K H L C P motif (FIG. 24A and also denoted by SEQ ID NO: 3), in which HVKGKH (also denoted by SEQ ID NO. 4) corresponds to the dimerization domain in CTLA4, YVIDPE (SEQ ID NO: 6) [Schwartz (2001) ibid.,] (FIG. 24A). Though they are highly homologous and thought to fold similarly [Luhder, F. et al., J. Exp. Med. 197:955-966 (2003)], CD28 and CTLA4 sequences differ in this domain as well as in residues 10-15; in the folded CTLA4 protein, the two domains are juxtaposed, creating the dimer interface (FIG. 24A, red and green). The conserved B7 binding domain in residues 97-105 is located on the opposite side of CTLA4 (FIG. 24A, yellow), leaving the dimer interface accessible.

Example 8

Peptide Mimetics of the Predicted Dimer Interface in CD28 Block Induction of a Th1 Response by Superantigens To evaluate the function of the H V K G K H L C P (SEQ ID NO: 3) motif of human CD28 in superantigen action, and to verify the CD28 epitope mapping, a 16-mer peptide was synthesized containing this motif and having the sequence AAAAAAAHVKGKHLCP (pTA, also denoted by SEQ ID NO: 5), in which the N-terminal alanine residues were added merely in order to create a peptide of the same length as p14A.

Induction of PBMC with anti-CD28 mAb MAB342 yielded expression of IFN-γ mRNA, prominent at 24 h. This expression was inhibited not only by sCD28 but also by pTA (FIG. 24B). In an experiment with another PBMC population, induction of IFN-γ mRNA by anti-CD28 mAb occurred earlier, being prominent by 3 h and subsiding later. This induction was inhibited, as expected, by sCD28 and it was also inhibited by pTA in a dose-dependent manner (FIG. 24C). Therefore, pTA is a functional antagonist of the anti-CD28 mAb.

The action of the anti-CD28 mAb on PBMC is abrogated by CD28 as well as by pTA (SEQ ID NO: 5). Whether upon induction by anti-CD28 expression of IFN-γ mRNA is early, as in FIG. 24C, or late, as in FIG. 24B, pTA is inhibitory. This result shows that like the soluble CD28 receptor, pTA is able to compete with the cellular CD28 receptor in binding to the anti-CD28 mAb and that the CD28 sequence motif in pTA is a functional epitope of the mAb. The analysis of Th1 cytokine gene induction by anti-CD28 mAb reinforces the validity of the epitope mapping (FIG. 24A). This provides functional evidence that the mAb engages the $CD28_{116-124}$ domain, which most likely includes part of the CD28 dimer interface.

When induction of PBMC was done with SEB, expression of IFN-γ mRNA was clearly observed at 3-24 h and SEB-induced expression of IL-2 mRNA in PBMC was most prominent at 6 h. As shown by FIG. 25, pTA blocked the induction of IL2 and IFN-γ mRNA by SEB (FIGS. 25A and 25C), in a dose-dependent manner (FIG. 25E). By contrast, it left the induction of IL10 and IL4 intact (FIGS. 25B and 25F), reflecting the Th1 specificity of superantigen mimetic peptide p14A (FIGS. 3 and 9-11).

Therefore, the peptide pTA (also denoted by SEQ ID NO: 5), carrying at least part of the epitope of CD28 recognized by the mAb MAB342, is an antagonist of SEB. This is the result expected if SEB binds to the cellular CD28 receptor through the H V K G K H L C P motif (SEQ ID NO: 3) in whole or in part in this receptor and if this binding is essential for toxin-mediated activation of the Th1 cytokine response. This defines CD28 as a critical target for superantigen-mediated activation of the harmful cellular immune response that can lead to toxic shock.

The binding site for SEB in CD28 comprises part or all of the sequence H V K G K H L C P (SEQ ID NO:15) which is present in pTA.

The finding that pTA is an antagonist of SEB and of anti-CD28 mAb provides strong support for the concept that SEB must interact directly with CD28 in order to induce Th1 cytokine gene expression, and that this interaction occurs through a site which comprises all or part of the HVKGKHLCP (SEQ ID NO: 3) motif.

Indeed, when the peptide AAAAAAAAAAMYPPPY (denoted by SEQ ID NO: 7) was tested in the same manner, containing another motif in the sCD28 molecule (FIG. 24A), it did not show antagonist activity for SEB. Neither pTA nor AAAAAAAAAAMYPPPY (SEQ ID NO:7) alone were active as inducer of Th1 cytokine mRNA expression or IL-10 expression in human PBMC.

The finding that a peptide carrying a sequence motif from CD28 can act as a superantigen antagonist, extends the work with antagonist peptides having homology to a superantigen domain, exemplified by p12A and p14A. In principle, two distinct types of superantigen antagonist peptides can be generated: one competes with the superantigen for its CD28 target receptor (exemplified by p12A, p14A, denoted by SEQ ID NOs: 1 and 2, respectively) and the other (exemplified by pTA, denoted by SEQ ID NO: 5) competes with the CD28 target receptor for the superantigen.

The inventors next synthesized CD28 mimetic peptides HVKGKHLCP (p1TA, also denoted by SEQ ID NO: 15) and SPMLVAYD (p2TA; $CD28_{8-15}$, also denoted by SEQ ID NO: 16). Based merely on epitope mapping, p2TA would not be expected to act as SEB antagonist. The inventors posited that p2TA might be an antagonist if, to induce a Th1 response, the superantigen must contact both rims of the dimer interface predicted for CD28 (FIG. 24A). Indeed, p1TA (SEQ ID NO: 15) and p2TA (SEQ ID NO: 16) each antagonized SEB-induced expression of IL2 and IFN-γ mRNA (FIG. 26A). The combination of p1TA and p2TA was not significantly more potent. p1Tasc (SEQ ID NO: 10), which contains the amino acids of p1TA in a randomly scrambled order, lacked antagonist activity (FIG. 27A). These results provide strong evidence that the functional superantigen binding site in CD28 is composite, formed from sequences in p1TA and p2TA.

Within the bacterial superantigen family, toxic shock syndrome toxin-1 (TSST-1) differs most extensively from the other members, showing only 6% overall sequence homology with SEB. Although TSST-1 exhibits in its antagonist domain FDKKQLAISTLD (also denoted by SEQ ID NO: 17) far less sequence homology than other superantigens to SEB domain TNKKKVTAQELD (also denoted by SEQ ID NO: 9), this domain nonetheless shows spatial conservation [Arad (2000) ibid.]. Indeed, p1TA and p2TA inhibited induction of IL2 and IFN-γ mRNA by TSST-1 (FIG. 26B). Like p12A, therefore, p1TA and p2TA exhibit broad-spectrum activity as superantigen antagonists. Most likely, they act by competing with cell surface CD28 for the antagonist domain in superantigens.

Example 9

CD28 Mimetic Peptides from the Dimer Interface Protect Mice from Lethal Shock

The inventors used the mouse model to examine whether p1TA and p2TA exhibit SEB antagonist activity in vivo. Whereas none of the controls (0/10) survived SEB challenge, 7/10 mice survived that had received a single dose of p1TA shortly before SEB (FIG. 27B). p1TA was protective when present in 3.6-fold molar excess over SEB. By contrast, p1TAsc failed to provide protection. In 12-fold molar excess over SEB, p14A also gave 70% protection. Moreover, p2TA, but not p2TAsc, protected mice from lethal shock (FIG. 27C). Whereas none of the controls (0/10) survived SEB challenge, 8/10 mice survived that also received a single dose of p2TA. p2TA was effective as antagonist in vivo in only 0.8-fold molar ratio to SEB. These results were reproducible. Alone, p1TA and p2TA lacked detectable toxicity even at concentrations 25- and 125-fold greater, respectively, than needed for protection (FIGS. 27B and 27C).

The ability of p1TA and p2TA to protect mice from SEB-induced lethal shock in very low molar excess over the toxin and to block induction of Th1 cytokine mRNA (FIGS. 26A and 26B) shows that each of the two rims of the predicted CD28 dimer interface plays a critical role in the activation of a deleterious Th1 response by a superantigen.

Example 10

Peptide Mimetics of the Dimer Interface in CTLA4 or ICOS are SEB Antagonists

As shown in FIG. 22, SEB bound not only to CD28 but also to the related receptors CTLA4 and ICOS. The inventors examined whether interaction with CTLA4 also takes place at the dimer interface. Indeed, peptides derived from each of the two rims of the CTLA4 dimer interface, YVIDPEPCP (p1TB, also denoted by SEQ ID NO; 18) and PAVVLASS (p2TB, also denoted by SEQ ID NO; 19), were potent SEB antagonists that inhibited the induction of IL2 and IFN-γ genes yet left induction of IL10 intact (FIGS. 27D and 27E). When present in 3.6 and 2 fold molar excess over SEB, respectively, p1TB and p2TB protected mice from lethal challenge (FIG. 27F).

ICOS, the third member of the coreceptor triad [Hutloff, A. et al., Nature 397(6716):263-6 (1999); Coyle, A. J. et al., Immunity 13(1):95-105 (2000)], uses a different coligand, ICOSL [reviewed by Sharpe and Freeman, (2002) ibid.] and thus appears to function distinctly from CD28 and CTLA4. As shown by FIG. 26C, the inventors aligned human ICOS with CD28 and synthesized two peptides, YESQLCCQL (p1TC, also denoted by SEQ ID NO: 20) and GEINGSAN (p2TC, also denoted by SEQ ID NO: 21), postulating that they correspond to the bipartite dimer interface in CTLA4/CD28. Indeed, p1TC and p2TC inhibited the Th1 cytokine response to SEB but not the induction of IL10 (FIGS. 27G and 27H) and protected mice from lethal challenge with the superantigen (FIG. 27I).

It can be concluded that SEB has the potential to bind directly not only to the (predicted) dimer interface in CD28 but also in CTLA4 and ICOS. Peptides derived from the dimer interfaces in the CD28/CTLA4/ICOS triad, though totally lacking in homology, are potent superantigen antagonists that block the induction of a Th1 cytokine response and protect against lethal toxic shock. Thus, two distinct classes of antagonist peptides define a critical role for the direct engagement of superantigen and CD28: superantigen mimetics that compete with superantigen for CD28 and mimetics of the coreceptor triad that compete with CD28 for superantigen (FIG. 27J).

Example 11

Development of Screening Assay for High-Affinity Antagonist

The cellular target of superantigen antagonist peptides thus is CD28. This provides, for the first time, a cellular drug target for the design of antagonists that will inhibit toxic shock and other outcomes of superantigen-mediated overstimulation of the cellular immune response (and in particular, the Th1 response), such as toxin incapacitation including nausea, vomiting, and diarrhea. Most importantly, the invention now allows the design of novel antagonists of the interaction between superantigens and the CD28 receptor, whether by antagonist peptides as illustrated here or by small molecules, enzymes or proteins. The invention provides a new strategy for discovery of toxic shock antagonists, through use of soluble recombinant CD28 or any fragments thereof comprising the sAg binding site (preferably comprising all or part of the amino acid sequence of SEQ ID NO: 3), as bait for binding of antagonist molecules, for example, by phage display or positional scanning or cyclic peptidomimetics.

Use of Soluble CD28 or Fragments Thereof Comprising the sAg Binding Site, as Target Each of the candidate test substances, and more preferably, test peptides is placed in a well and direct binding of soluble recombinant CD28 (sCD28) is detected by tagged Ab against sCD28. Conditions for effective binding of sCD28 to a known antagonist peptide, such as p12 and p14, on the plate are first optimized, including study of pH, salt and buffer composition, and carrier proteins such as BSA. This screening yields all peptides or substances that bind to sCD28.

In order to select peptides or candidate substances which bind to CD28 specifically in the superantigen binding site, peptides or substances that bind sCD28 are pooled and then assayed in different competition assays as follows. sCD28 or any fragment thereof comprising the sAg binding site (preferably comprising all or part of the amino acid sequence of SEQ ID NO: 3), is bound into the wells of a microplate. Conditions for effective binding of antagonist peptide to sCD28 (or to fragments comprising the sAg binding site) on the plate are first optimized using a known antagonist peptide, such as p12 and p14. Then, each well is incubated with a limiting amount of anti-CD28 mAb, in the presence of the test antagonist peptide or substance (alone or a pool). Supernatant is collected from each well. Unbound mAb is detected in the supernatant by secondary antibody ELISA. This selection should yield specific candidate substances, and preferably peptides blocking either the binding site of the antagonist domain of superantigens on CD28 or the adjacent B7-2 binding site. This is resolved by competition with antagonist peptide or superantigen in the next round. Biotinylated SEB may also be used in assay for the ability of peptides to displace labeled SEB from binding to sCD28 on the plate. Yet another alternative is to use labeled known antagonist peptide, such as p12 and p14, and to assay for the ability of test peptides to displace label from binding to sCD28 (or fragments thereof comprising the sAg binding site), on the plate. For example, cysteine-tagged p12 may be used to couple biotin or fluorescein.

Use of Cells Overexpressing CD28 as Target

CD28 cDNA is cloned into an expression vector suitable for mammalian cells, for example, under the myeloproliferative sarcoma virus promoter and upstream of the SV40 polyadenylation signal as described by Ben-Asouli et al. [Cell 108:221-232 (2002)]. Alternatively, CD28 cDNA is expressed transiently in transfected COS cells [Aruffo & Seed (1987) ibid.]. Each peptide is placed in a well and the well is then blocked with BSA or fetal calf serum. Binding of cells, for example, BHK-21 cells, that express CD28 on their cell surface is scored visually, or by anti-CD28 ELISA. Alternatively, cell membranes prepared from the CD28-expressing cells are used and binding is detected using anti-CD28. Positive peptides are then re-examined in the presence of SEB or a known antagonist peptide, such as p12 and p14, as competitor.

It should be noted that cells expressing any fragment of CD28 comprising the sAg binding site (preferably comprising all or part of the amino acid sequence of SEQ ID NO: 3), may be used as described above.

Phage Display

Random library—Combinatorial phage libraries are used to screen for superantigen antagonist peptides with high affinity for the CD28 receptor (preferably subnanomolar). Specifically, the PhD library of New England Biolabs is first used, typically, for about 4-6 rounds of panning. Panning is performed in two stages. In the first stage, bound phages are eluted from microplate-bound sCD28 (or any fragment thereof comprising the sAg binding site) using elution at a low pH, preferably pH 2.2. In the second stage, phages selected as above are bound to sCD28 and eluted specifically with an excess of known antagonist peptide, such as p12 and p14, or SEB. Bound phages are eluted and subjected to further cycles (2-3) of similar panning. Then, direct binding of individual phage clones to immobilized sCD28 is detected by phage ELISA, scoring for, in this case, M13 phage on the plate. A total of, for example, 1,000 positive phage clones are amplified and sequenced, before synthesis of selected peptides in linear form and assay for antagonist activity in PBMC.

An alternative panning strategy is followed in the event that use of sCD28 as immobilized target does not yield to experimentation. CD28 cDNA is overexpressed transiently in transfected cells, for example, BHK-21 cells, and these cells are then immobilized on the plate. Panning of phage-displayed peptides is done first on vector-transfected cells to eliminate nonspecific binders, and then on cells that overexpress CD28 on their cell surface. Alternatively, whole cell membrane preparations may be substituted for cells. CD28-bound phage are eluted with an excess of a known antagonist peptide, such as p12 and p14, or with SEB.

Dedicated library—In the second stage, a dedicated library in which several residues of the displayed peptide are held constant is constructed. Small-scale synthesis of peptides selected from the random and dedicated libraries is performed for evaluation of antagonist activity.

Candidate peptides, whether isolated during phage display screening or generated by positional scanning or cyclization chemistry are subjected to high-throughput screening for high-affinity binding to CD28, to sCD28 or to the sAg binding site within the CD28 molecule which preferably comprises part or all of the amino acid sequence as denoted by SEQ ID NO: 3, as described above.

Alanine Scan

An alanine scan is first done on a known antagonist peptide, e.g. p12 or p14, to identify residues critical for binding to the receptor or on the antagonist pTA of the invention, in order to identify residues critical for binding to the sAg and, separately, for superantigen antagonist activity in vitro. Peptides are synthesized in soluble form with N-terminal acetyl and C-terminal —$CONH_2$ and retain flanking D-alanines for greater protease resistance in in vitro assays with PBMC. Further rounds of alanine scan are performed on identified backup antagonist peptides. A lysine-scan of the peptide is performed likewise. Further rounds of lysine scan are performed on identified backup peptides.

Positional Scan

Once residues critical for antagonist activity are identified by the alanine scan, 2 such positions are chosen for a fully permutated pepscan of all 20 amino acids (400 peptides) and then 2 additional positions are scanned likewise (400 peptides). Peptides are first in releasable form but held on the chip (Pepscan I, see below). Binding of sCD28 or fragment thereof comprising the sAg binding site, to each peptide is scored by ELISA using commercial rabbit polyclonal antibodies to this receptor. Next, positive peptides are released (Pepscan II, see below) and pooled into groups for assay of binding the receptor in the screening assay ELISA format according to the selection step of the screening method of the invention as described above, and also evaluated for antagonist activity in vitro in PBMC assays and the groups will then be deconvoluted. In stepwise fashion, the resulting improved leads are then subjected to additional rounds of positional scanning. Preferably, in total, 4 rounds of positional scanning are performed, and two rounds of constrained positional scanning, on the peptide with highest affinity for the receptor.

Pepscan-I: Peptides Remain Attached to Bottom of Miniwell

Pepscan libraries are synthesized and screened using polyethylene cards containing the covalently linked peptides [as described, for example, by Slootstra et al., Molecular Diversity 1:87-96 (1995)]. Peptides may be synthesized in solid phase with the N-terminus acetylated and with C-terminus linked to the miniwell. Binding of sCD28 (or fragment thereof comprising the sAg binding site) to each peptide is scored by ELISA using commercial rabbit polyclonal antibodies to this receptor. After washing the cards, they are incubated with goat antirabbit peroxidase and then, after washing, peroxidase substrate 2,2'-azino-di-3-ethylbenzthiazoline sulfonate and $H_2O_2$ are added. Color development is quantified, for example, with a CCD camera and image processing software.

Pepscan-II: Peptides are Released from Bottom of Miniwell

Pepscan libraries are synthesized as above with the exception that an acid-labile linker is placed between the peptide and the bottom of the miniwell. At low pH, the peptide is released from the bottom of the miniwell and transferred to a 96-well microtiter plate. This plate is used in a competition ELISA format, using methods described above. Two formats are used: miniwells (1 μg/well, ≤15 residues) and pins (1,000 μg/pin, ≤15 residues). In pepscan-II format it is possible to pool sets of peptides. For example, a complete single positional scan of a 12-mer peptide will yield 240 peptides including 12 controls. These can be pooled for assay into 12 groups each having one position changed (with the control peptide left out). The 12 groups are assayed for binding the receptor in the ELISA format and also for antagonist activity in vitro and then are deconvoluted.

Cyclization Scan (Pepscan I)

A linker such as MBS (m-maleinimidobenzoic acid N-hydroxy-succinimide ester) is used to react via its active ester (succinimide) with the N-terminus of a given peptide and via its maleinimide group with a free thiol group from cysteine [cf. Langeveld et al., J. Virol. 68:4506-4513 (1994)]. The cysteine is part of the peptide (e.g. positioned at the C-terminus). This linkage is not sensitive to reducing agents, an advantage compared to a disulfide bridge.

Loop Scan (Pepscan I)

The N-terminus of each peptide is linked with a linking agent such as MBS to a free SH group from a cysteine that is coupled separately to the bottom of the same well. In this way, a constrained loop is formed. Synthesis of a peptide and the separate coupling of a cysteine in the same well is done with a combination of standard FMOC- and BOC-peptide chemistry (cf. Schnolzer et al. Int. J. Pept. Protein Res. 40:180-193 (1992); Guy and Fields, Method Enzymol. 289: 67-83 (1997)]. FMOC is cleaved off with 20% piperidine while BOC is cleaved off with 100% trifluoroacetic acid (TFA); piperidine will not cleave off BOC while TFA will not cleave off FMOC. Thus, a peptide is synthesized with FMOC-chemistry and cysteine is coupled independently to the same well with BOC-chemistry. After each coupling, FMOC is removed selectively and another amino acid is added. Since BOC is not removed from the cysteine, additional amino acids cannot be coupled to it. At the end of FMOC synthesis, when the peptide is complete, the BOC-cysteine is deprotected. Then, the N-terminus of the peptide can be linked to the single cysteine as described above.

Once peptides have been selected by positional scanning and by phage display as described above, it will be possible to synthesize shorter versions to attain a minimal length antagonist peptide. When the inventors reduced the dodecamer p12 to a decamer by removing two N-terminal amino acids, this led to a decline in antagonist activity [Arad et al., (2000) ibid.], but more potent antagonists, once identified, may remain active upon shortening. Shortening will be guided by the data of positional scanning.

Small-scale synthesis of selected peptides is then performed for evaluation of toxin antagonist activity in PBMC.

Truncation

Once peptides have been selected by positional scanning and by phage display (see above), shorter versions are then synthesized to attain a minimal length antagonist peptide.

D-Enantiomer of Antagonist

To obtain high affinity D-peptides as potential drugs (Schumacher et al., Science, 271:1854-1856 (1996); Miller et al., J. Molec. Struct. 423:137-152 (1998); Eckhart et al., Cell 99:103-115 (1999), a preferred stepwise program is to:

(1) Make a mirror-image of the target molecule, i.e. make a D-amino acid enantiomer with the same sequence;

(2) Select an L-peptide antagonist (using phage display) which binds to the D-enantiomer target;

(3) Synthesize the D-peptide enantiomer of the L-antagonist ligand that bound. This will bind to the natural L-target.

Reverse-inverso D-analogues of L-peptides are not mirror image (enantiomer) structures even though side chains appear in a cartoon presentation to be oriented at the same angles. The backbone needs to be mirror image, not just the side chains.

The D-peptide is resistant to acid and proteases and can be considered as a good bioavailable oral drug candidate directly. Cyclosporin is a natural D-peptide. D-peptides have low, almost non-existent immunogenicity as they cannot be digested to a form that can be presented on the MHC complex (wrong C-alpha backbone orientation disrupts binding) and thus they cannot elicit B and T cell activation [Dintzis et al., Proteins 16:306-308 (1993)]. D-peptides have a half-life in serum of days rather than a few hours as seen for L-peptides [Dintzis et al., (1993) ibid.] and they can be adsorbed directly from the gut (Ptachcinski et al., Clin. Pharmacokinet. 11:107-132 (1986); Pappenheimer, et al. Proc. Natl. Acad. Sci. U.S.A. 91:1942-1945 (1994)]. They have shown no discernable toxicity in animal models and in cell culture, even at 100 μM concentration.

To efficiently produce a D-enantiomer protein, peptide ligation technology, as developed, for example, by Gryphon Biosciences, San Francisco, is used.

A requirement for this approach is that the target (CD28 receptor in soluble form or fragment thereof comprising the sAg binding site) is available and its amino acid sequence verified and that this molecule can be denatured reversibly to regain its binding activity. This latter requirement is based on the fact that synthesis of the D-enantiomer target will yield a chain that has to fold spontaneously into its active shape before it can be used to screen for high-affinity L-antagonist peptides. Therefore, the D-antagonist approach is an option that can be realized only if the target renaturation requirement is fulfilled. This is tested using sCD28. A series of denaturation and renaturation protocols is used, with ability to bind a known antagonist peptide, such as p12 and p14, as readout.

Cyclic Peptidomimetics

Assay of SEB antagonist activity on human PBMC in vitro has shown that backbone cyclic peptides based on $SEB^{150-161}$ with a ring between positions 152 and 159 act as superior SEB antagonists to the linear analogs and that residues with positive charge, $Lys^{153}$ and $Lys^{154}$, are important for antagonist activity, a point that is examined directly in the alanine and lysine scans indicated above.

Optimal constraint is achieved only through successive cycles of design and evaluation. Antagonist peptide sequences selected for a higher affinity than p12A or p14A for the CD28 receptor by phage display or positional scanning are subjected to a similar strategy.

Peptide Synthesis

Peptides are synthesized using fluoronyl-methoxycarbonyl (FMOC) chemistry [Arad et al., (2000) ibid.]. D-Ala is linked using the same procedure. High-pressure liquid chromatography is used to show that peptides are >95% pure [Arad et al., (2000) ibid.]. Peptidomimetics are synthesized carrying short-range cyclizations via internal bridges. Short-range cyclizations via internal bridges, using $N^{\alpha}$-ω-functionalized derivatives of amino acids to provide non-peptidic linkages [Toniolo, Int. J. Peptide Protein Res. 35:287-300 (1990); Gilon et al., (1991); Chorev et al., Biopolymers 31:725-733 (1991)], have been successful in enhancing the activity of peptidomimetics for substance P [Bitan et al., J. Pept. Sci. 2:261-269 (1996); Byk et al., J. Med. Chem. 39:3174-3178 (1996)], HIV Tat NLS [Friedler et al., J. Biol. Chem. 275:23783-23789 (2000)], HIV matrix protein NLS [Friedler et al., Biochemistry 37:5616-5622 (1998)], and an insect pheromone antagonist [Altstein et al., J. Biol. Chem. 274:17573-17579 (1999)]. The fact that frequently only a small number of 4-8 amino acid side chains of the peptide are responsible for recognition of the ligand by the receptor turns out to be favorable for the short-range cyclization approach. In such cases, the rest of the molecular framework serves to fix the pharmacophore in a specific spatial arrangement. An added advantage of the cyclic constraint approach is that fewer amino acids may be used, to generate smaller antagonist molecules. Peptidomimetics are purified by HPLC and purity is assessed by mass spectrometry.

Evaluation of Antagonist Backups-Affinity for Novel Receptor

The backups are compared with p12 and p14 antagonist peptides in terms of their ability to bind the CD28 receptor, using plasmon resonance measurements as well as ELISA assays. Both direct binding and ability to compete with SEB for soluble recombinant CD28 (sCD28) or fragment thereof comprising the sAg binding site, are assayed. Ability of antagonist peptide to interfere with the binding of sCD28 (or fragment thereof comprising the sAg binding site which has an amino acid sequence comprising all or part of the sequence as denoted by SEQ ID NO: 3) to anti-CD28 antibodies is also tested. It should be noted that the ability of the tested antagonist peptide to interfere with the interaction of anti-CD28 with its epitope which comprises all or part of the amino acid sequence as denoted by SEQ ID NO: 3, may be also tested. Ability of the antagonist peptide to promote complex formation between sCD28 and B7-2 is studied as described in Example 5. Using p12 and p14, pH and buffers were varied first to obtain optimal binding conditions for each ligand combination.

Therefore, candidate antagonists peptides obtained and selected by their high affinity for the CD28 receptor may be synthesized in the linear form with D-alanine termini for greater protease resistance [Arad et al., (2000) ibid.], or as cyclic peptides or peptidomimetics, and then tested for the ability to inhibit the superantigen-induced expression of Th1 cytokine mRNA in freshly isolated whole human PBMC, using PBMC from different healthy donors [Arad et al., (2000) ibid.].

Briefly, PBMC from healthy human donors are induced with 100 ng/ml of SEB lot 14-30 from the Department of Toxinology at USAMRIID, SPEA (Toxin Technology, Sarasota, Fla.), SEA or TSST-1 (Toxin Technology; Sigma) [Arad et al., (2000) ibid.]. When present, antagonist peptides are used preferably at 0.01-10 μg/ml. PBMC from single donors tend to give a lower induction of Th1 cytokine gene expression than mixed PBMC from 3-4 donors. This higher response in the mixed PBMC population is most likely due to expression of cell surface receptors needed for toxin action to a higher density, resulting from the mixed lymphocyte response. Cyclic peptides or peptidomimetics, or candidate backups that are synthesized in the linear form with D-alanine termini, are tested for their ability to inhibit the superantigen-induced expression of Th1 cytokine mRNA, using PBMC from 10 different healthy donors. Peptides showing strong antagonist activity with SEB are retested with SEB, SEA, TSST-1 and SPEA. Both single and mixed-donor PBMC are used for the evaluation assays.

Quantitative Dot Blot Hybridization of RNA.

This method requires only small amounts of PBMC and thus is suitable for first-level screening of a larger number of candidate backups, before verification by RNase protection analysis. RNA is isolated from 1-ml cultures of PBMC by collecting the cells and lysing them in 7.5 M guanidinium-HCl. RNA is precipitated and serial twofold dilutions are applied in duplicate to nitrocellulose sheets using a 96-well dot blot apparatus. To detect expression of human Th1 cytokine genes, sheets are hybridized with the $^{32}$P-labeled antisense RNA probes and subjected to autoradiography or read in a phosphoimager. RNA levels are quantitated. Hybridization intensity is linear with amount of RNA and number of cells and can be quantitated accurately over a 200-fold range. As analyzed by Northern blotting, over 85% of the IL-2 and IFN-γ hybridization signals thus detected consists of mature mRNA [Arad et al., (2000) ibid.].

Ribonuclease Protection Analysis of Th1 Cytokine mRNA

Though laborious and costly, ribonuclease protection analysis yields the most direct quantitative measurement of spliced mRNA. Total RNA, extracted from 30-ml cultures of PBMC with guanidinium isothiocyanate, is subjected to RNase protection analysis using antisense RNA probes transcribed with [α-$^{32}$P]UTP in vitro from DNA inserted into pBS (Promega). The IL-2 probe (600 nt), transcribed from the T7 promoter, is complementary to the third exon and a portion of the third intron; in 8 M urea-polyacrylamide gels, it yields an RNA fragment of 117 nt protected by mRNA. The IFN-γ probe (274 nt), transcribed from the T3 promoter, is complementary to the third exon and a portion of the third intron and yields an RNA fragment of 183 nt protected by mRNA. The TNF-β probe (700 nt), transcribed from the T3 promoter, is complementary to part of exon 1, exon 2, exon 3, and portions of intron 3 and exon 4; mRNA protects 2 fragments of 274 and 263 nt. Sense RNA transcripts yield no detectable hybridization signal. Analysis with an antisense RNA probe for 18S rRNA, yielding a protected fragment of 90 nt, serves as loading control [Arad et al., (2000) ibid.]. Gels are quantitated by densitometry.

Assay of the Th2 Response

An essential property of the current antagonist peptide is that it leaves the Th2 response intact. This is also a requirement for backups that are tested by ELISA for IL-10, using culture medium from PBMC in which toxin-induced expression of Th1 cytokine mRNA is inhibited by antagonist peptide. The inventors found that superantigen-induced IL-4 levels tend to be below the sensitivity of the available ELISA kits whereas IL-10 can be measured reliably.

Antagonist Efficacy in Primate PBMC Functional Assay

The approach described in the previous section is also applicable to assay of antagonist activity using PBMC from rhesus monkeys. This is useful in order to establish a correlation between the efficacy of antagonist peptide in a surrogate marker system derived from this animal model, approved by the FDA for in vivo efficacy study, with data from in vivo protection. Such a correlation cannot be achieved in humans, where in vitro efficacy has already been demonstrated for the current antagonist leads p12 and p14.

At the Hebrew University of Jerusalem, a rhesus monkey has been approved by IACUC for the collection of 15-ml samples of blood that suffice for analysis of antagonist activity, using the quantitative dot blot hybridization assay (see above). Rhesus and human IL-2 and IFN-γ cDNA show 95% nucleotide sequence homology, and the inventors have shown that induction of the monkey lL-2 and IFN-γ genes is readily detected with the human riboprobes in the dot blot assay, which does not measure protection against nuclease attack but merely the ability to anneal with cellular mRNA.

In Vivo Test Models for Evaluation of the Protective Activity of the Candidate Antagonist Potent Protecting Activity of a Candidate Antagonist on Lethally Challenged Mice:

Using D-galactosamine-sensitized mice, an accepted animal model for studying lethality of the superantigens, the protective activity of the different antagonist candidates is investigated. The antagonist candidate is administered just before lethal challenge with the superantigen, preferably, SEB, SEA, TSST-1 or SPEA, and the survival of mice is examined.

Protecting Activity of a Candidate Antagonist from SEA-Induced Incapacitation in Pigs:

Human T cells are at least two orders of magnitude more sensitive to staphylococcal superantigens than murine ones and while humans are sensitive to developing toxic shock syndrome, mice are resistant, apparently because cells that display the most highly reactive Vβ chains of the TCR were deleted from the murine T cell repertoire or the relevant Vβ genes eliminated [see Arad et al., (2000), ibid.]. Mice thus have acquired a natural resistance to superantigen toxins and must be sensitized before they will undergo toxic shock. Moreover, mice are remote from humans in terms of weight and immune system. It is thus important to demonstrate efficacy of an antagonist also in an animal model closer to man.

The inventors addressed both issues: toxin incapacitation and use of a higher animal model. Pigs have an immune system similar to humans; thus, between pigs and humans the nucleotide sequence homology of mRNA encoding the Th1 cytokine IFN-γ that mediates shock is in the order of 85%, whereas there is no detectable similarity between the human and mouse mRNAs.

Pigs are sensitive to acute superantigen exposure without need for sensitization, and develop incapacitation symptoms similar to those seen in humans. A reproducible pig model for the early incapacitation symptoms of toxic shock that include nausea and vomiting (a neuronal response) as well as severe diarrhea (an intestinal immune response) was established.

As was previously indicated by the inventors, using five-day old mixed breed pigs (mainly Yorkshire; 2.5 kg) in randomized groups of 6 piglets for each test condition, each group under its own sow, SEA (25 μg) caused a severe incapacitation that became apparent within 2 h and subsided by 24-36 h, with similar kinetics and intensity whether given by the IV or IP route. IP administration of SEA was used for incapacitation studies in pigs because this route is less traumatizing yet similarly effective to IV. This result confirms that pigs are especially sensitive to SEA [Taylor et al., Infect. Immun. 36:1263 (1982)]. The reason for this selective sensitivity may be that SEA also uses its beta-grasp to bind the MHC II molecule at an independent second site, binding it far more tightly and allowing crosslinking to occur between MHC II molecules [Hudson et al., J. Exp. Med. 182:711 (1995); Schad et al., EMBO J. 14:3292 (1995); Abrahmsen et al., EMBO J. 14:2978 (1995)]. The domain targeted by toxin antagonist is remote from both of the binding sites for MHC II and from the binding site for TCR in SEA.

The following criteria are used to quantitate incapacitation in pigs: vomiting (score of 4); diarrhea, scored for mild (score of 1), regular (score of 2), severe (score of 4), and watery diarrhea (score of 6) (data not shown).

Example 12

Selection of SEB Antagonist Peptides by Affinity for CD28

Figures 31, 32:
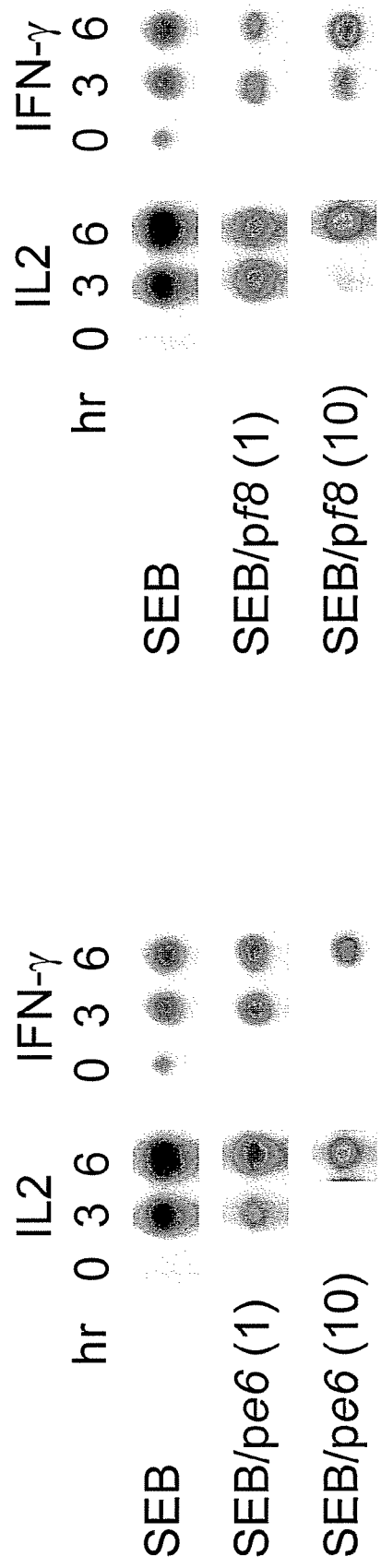

To obtain independent evidence for a direct interaction between superantigen and CD28, the inventors repeatedly panned a random 12-mer phage display library on immobilized sCD28, displacing bound phages with SEB. Over 10% of selected phages bound tightly to sCD28 (FIG. 28A), and more then 40 peptides were isolated from these phages (as denoted by SEQ ID NO: 27 to 58). Peptides from five phages were analyzed for antagonist activity. Peptide pe12 (SHFTHNRHGHST, also denoted by SEQ ID NO: 12) strongly inhibited induction of IL2 and IFN-γ mRNA by SEB yet lacked superantigen agonist activity (FIG. 28B) and failed to inhibit induction of IL10 (FIG. 28C). Likewise, pc3 (FHKHKNPGSPII, also denoted by SEQ ID NO: 14) inhibited induction of IL2 and IFN-γ mRNA by SEB yet lacked superantigen agonist activity (FIG. 29A) and failed to inhibit induction of IL10 (FIG. 29B). Furthermore, pd7 (WHAHPHKKPVVA, also denoted by SEQ ID NO: 13) also inhibited induction of IL2 and IFN-γ mRNA by SEB yet lacked superantigen agonist activity and failed to inhibit induction of IL10 (FIG. 30A). These peptides exhibited SEB antagonist activity also in vivo. When present in about equimolar ratio to SEB, pe12 and pc3 protected 8/10 and 7/10 mice, respectively, from lethal challenge that left no survivors in the control group (FIGS. 28D and 29C). Whereas 1/10 controls survived SEB challenge, 4/10 mice survived that also received a single dose of pd7 (FIG. 30B). Alone, pe12, pc3 and pd7 each lacked detectable toxicity even when administered at concentrations well above those that sufficed for protection (FIGS. 28D, 29C and 30B). In the same manner, pe6 (APMYHKHRLEKH, also denoted by SEQ ID NO: 39) and pf8 (IHKPHHHRTPLW, also denoted by SEQ ID NO: 38) each inhibited induction of IL2 and IFN-γ mRNA by SEB (FIGS. 31 and 32). Thus, novel superantigen antagonists can be selected from random peptide sequences solely by their affinity for the SEB binding site in CD28.

The invention claimed is:

1. An isolated and purified peptide consisting of the amino acid sequence of SEQ ID NO:16 extended at each of the N-terminus and the C-terminus thereof by a single D-Ala residue.

2. A composition comprising a purified peptide as defined in claim 1 and a pharmaceutically acceptable carrier, diluent, adjuvant and/or excipient.

3. A method for the inhibition of a T cell costimulatory pathway in a subject in need thereof, comprising the step of administering to said subject an effective amount of a peptide consisting of the amino acid sequence of SEQ ID NO:16 or a peptide in accordance with claim 1.

* * * * *

SEQUENCE LISTING

```
<160> NUMBER OF SEQ ID NOS: 66

<210> SEQ ID NO 1
<211> LENGTH: 14
<212> TYPE: PRT
<213> ORGANISM: Artificial Sequence
<220> FEATURE:
<223> OTHER INFORMATION: Synthetic peptide p12A
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (14)..(14)
<223> OTHER INFORMATION: Xaa can be any naturally occurring amino acid

<400> SEQUENCE: 1

Xaa Tyr Asn Lys Lys Lys Ala Thr Val Gln Glu Leu Asp Xaa
1               5                   10
```

```
<210> SEQ ID NO 2
<211> LENGTH: 16
<212> TYPE: PRT
<213> ORGANISM: Artificial Sequence
<220> FEATURE:
<223> OTHER INFORMATION: Synthetic peptide p14A
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid

<400> SEQUENCE: 2

Xaa Val Gln Tyr Asn Lys Lys Ala Thr Val Gln Glu Leu Asp Xaa
1               5                   10                  15

<210> SEQ ID NO 3
<211> LENGTH: 9
<212> TYPE: PRT
<213> ORGANISM: Artificial Sequence
<220> FEATURE:
<223> OTHER INFORMATION: Consensus amino acid sequence

<400> SEQUENCE: 3

His Val Lys Gly Lys His Leu Cys Pro
1               5

<210> SEQ ID NO 4
<211> LENGTH: 6
<212> TYPE: PRT
<213> ORGANISM: Artificial Sequence
<220> FEATURE:
<223> OTHER INFORMATION: Synthetic peptide of CD28 dimerization domains

<400> SEQUENCE: 4

His Val Lys Gly Lys His
1               5

<210> SEQ ID NO 5
<211> LENGTH: 16
<212> TYPE: PRT
<213> ORGANISM: Artificial Sequence
<220> FEATURE:
<223> OTHER INFORMATION: Synthetic peptide

<400> SEQUENCE: 5

Ala Ala Ala Ala Ala Ala Ala His Val Lys Gly Lys His Leu Cys Pro
1               5                   10                  15

<210> SEQ ID NO 6
<211> LENGTH: 6
<212> TYPE: PRT
<213> ORGANISM: Artificial Sequence
<220> FEATURE:
<223> OTHER INFORMATION: Synthetic peptide of CTLA4 dimer interface

<400> SEQUENCE: 6

Tyr Val Ile Asp Pro Glu
1               5

<210> SEQ ID NO 7
<211> LENGTH: 16
<212> TYPE: PRT
<213> ORGANISM: Artificial sequence
<220> FEATURE:
<223> OTHER INFORMATION: Synthetic peptide
```

<400> SEQUENCE: 7

Ala Ala Ala Ala Ala Ala Ala Ala Ala Ala Met Tyr Pro Pro Pro Tyr
1 5 10 15

<210> SEQ ID NO 8
<211> LENGTH: 6
<212> TYPE: PRT
<213> ORGANISM: Homo sapiens

<400> SEQUENCE: 8

Met Tyr Pro Pro Pro Tyr
1 5

<210> SEQ ID NO 9
<211> LENGTH: 12
<212> TYPE: PRT
<213> ORGANISM: Artificial sequence
<220> FEATURE:
<223> OTHER INFORMATION: Synthetic peptide derived from residues 150-161 of SEB

<400> SEQUENCE: 9

Thr Asn Lys Lys Lys Val Thr Ala Gln Glu Leu Asp
1 5 10

<210> SEQ ID NO 10
<211> LENGTH: 9
<212> TYPE: PRT
<213> ORGANISM: Artificial sequence
<220> FEATURE:
<223> OTHER INFORMATION: Synthetic scrambled control peptide p1TAsc

<400> SEQUENCE: 10

Cys His Gly His Leu Val Pro Lys Lys
1 5

<210> SEQ ID NO 11
<211> LENGTH: 8
<212> TYPE: PRT
<213> ORGANISM: Artificial sequence
<220> FEATURE:
<223> OTHER INFORMATION: Synthetic scrambled control peptide p2TAsc

<400> SEQUENCE: 11

Ala Ser Met Asp Tyr Pro Val Leu
1 5

<210> SEQ ID NO 12
<211> LENGTH: 12
<212> TYPE: PRT
<213> ORGANISM: Artificial sequence
<220> FEATURE:
<223> OTHER INFORMATION: Synthetic Peptide pe12

<400> SEQUENCE: 12

Ser His Phe Thr His Asn Arg His Gly His Ser Thr
1 5 10

<210> SEQ ID NO 13
<211> LENGTH: 12
<212> TYPE: PRT
<213> ORGANISM: Artificial sequence
<220> FEATURE:
<223> OTHER INFORMATION: Synthetic peptide

```
<400> SEQUENCE: 13

Trp His Ala His Pro His Lys Lys Pro Val Val Ala
1               5                   10

<210> SEQ ID NO 14
<211> LENGTH: 12
<212> TYPE: PRT
<213> ORGANISM: Artificial sequence
<220> FEATURE:
<223> OTHER INFORMATION: Synthetic peptide pc3

<400> SEQUENCE: 14

Phe His Lys His Lys Asn Pro Gly Ser Pro Ile Ile
1               5                   10

<210> SEQ ID NO 15
<211> LENGTH: 9
<212> TYPE: PRT
<213> ORGANISM: Artificial sequence
<220> FEATURE:
<223> OTHER INFORMATION: Synthetic peptide p1TA

<400> SEQUENCE: 15

His Val Lys Gly Lys His Leu Cys Pro
1               5

<210> SEQ ID NO 16
<211> LENGTH: 8
<212> TYPE: PRT
<213> ORGANISM: Artificial sequence
<220> FEATURE:
<223> OTHER INFORMATION: Synthetic peptide p2TA

<400> SEQUENCE: 16

Ser Pro Met Leu Val Ala Tyr Asp
1               5

<210> SEQ ID NO 17
<211> LENGTH: 12
<212> TYPE: PRT
<213> ORGANISM: Artificial sequence
<220> FEATURE:
<223> OTHER INFORMATION: Synthetic peptide TSST-1 antagonist domain

<400> SEQUENCE: 17

Phe Asp Lys Lys Gln Leu Ala Ile Ser Thr Leu Asp
1               5                   10

<210> SEQ ID NO 18
<211> LENGTH: 9
<212> TYPE: PRT
<213> ORGANISM: Artificial sequence
<220> FEATURE:
<223> OTHER INFORMATION: Synthetic peptide p1TB

<400> SEQUENCE: 18

Tyr Val Ile Asp Pro Glu Pro Cys Pro
1               5

<210> SEQ ID NO 19
<211> LENGTH: 8
<212> TYPE: PRT
<213> ORGANISM: Artificial sequence
<220> FEATURE:
<223> OTHER INFORMATION: Synthetic peptide p2TB
```

<400> SEQUENCE: 19

Pro Ala Val Val Leu Ala Ser Ser
1               5

<210> SEQ ID NO 20
<211> LENGTH: 9
<212> TYPE: PRT
<213> ORGANISM: Artificial sequence
<220> FEATURE:
<223> OTHER INFORMATION: Synthetic peptide p1TC

<400> SEQUENCE: 20

Tyr Glu Ser Gln Leu Cys Cys Gln Leu
1               5

<210> SEQ ID NO 21
<211> LENGTH: 8
<212> TYPE: PRT
<213> ORGANISM: Artificial sequence
<220> FEATURE:
<223> OTHER INFORMATION: Synthetic peptide p2TC

<400> SEQUENCE: 21

Gly Glu Ile Asn Gly Ser Ala Asn
1               5

<210> SEQ ID NO 22
<211> LENGTH: 202
<212> TYPE: PRT
<213> ORGANISM: Homo sapiens

<400> SEQUENCE: 22

Asn Lys Ile Leu Val Lys Gln Ser Pro Met Leu Val Ala Tyr Asp Asn
1               5                   10                  15

Ala Val Asn Leu Ser Cys Lys Tyr Ser Tyr Asn Leu Phe Ser Arg Glu
                20                  25                  30

Phe Arg Ala Ser Leu His Lys Gly Leu Asp Ser Ala Val Glu Val Cys
            35                  40                  45

Val Val Tyr Gly Asn Tyr Ser Gln Gln Leu Gln Val Tyr Ser Lys Thr
    50                  55                  60

Gly Phe Asn Cys Asp Gly Lys Leu Gly Asn Glu Ser Val Thr Phe Tyr
65                  70                  75                  80

Leu Gln Asn Leu Tyr Val Asn Gln Thr Asp Ile Tyr Phe Cys Lys Ile
                85                  90                  95

Glu Val Met Tyr Pro Pro Pro Tyr Leu Asp Asn Glu Lys Ser Asn Gly
            100                 105                 110

Thr Ile Ile His Val Lys Gly Lys His Leu Cys Pro Ser Pro Leu Phe
        115                 120                 125

Pro Gly Pro Ser Lys Pro Phe Trp Val Leu Val Val Val Gly Gly Val
    130                 135                 140

Leu Ala Cys Tyr Ser Leu Leu Val Thr Val Ala Phe Ile Ile Phe Trp
145                 150                 155                 160

Val Arg Ser Lys Arg Ser Arg Leu Leu His Ser Asp Tyr Met Asn Met
                165                 170                 175

Thr Pro Arg Arg Pro Gly Pro Thr Arg Lys His Tyr Gln Pro Tyr Ala
            180                 185                 190

Pro Pro Arg Asp Phe Ala Ala Tyr Arg Ser
        195                 200

-continued

<210> SEQ ID NO 23
<211> LENGTH: 188
<212> TYPE: PRT
<213> ORGANISM: Homo sapiens

<400> SEQUENCE: 23

```
Lys Ala Met His Val Ala Gln Pro Ala Val Val Leu Ala Ser Ser Arg
1               5                   10                  15

Gly Ile Ala Ser Phe Val Cys Glu Tyr Ala Ser Pro Gly Lys Ala Thr
                20                  25                  30

Glu Val Arg Val Thr Val Leu Arg Gln Ala Asp Ser Gln Val Thr Glu
            35                  40                  45

Val Cys Ala Ala Thr Tyr Met Met Gly Asn Glu Leu Thr Phe Leu Asp
        50                  55                  60

Asp Ser Ile Cys Thr Gly Thr Ser Ser Gly Asn Gln Val Asn Leu Thr
65                  70                  75                  80

Ile Gln Gly Leu Arg Ala Met Asp Thr Gly Leu Tyr Ile Cys Lys Val
                85                  90                  95

Glu Leu Met Tyr Pro Pro Pro Tyr Tyr Leu Gly Ile Gly Asn Gly Thr
                100                 105                 110

Gln Ile Tyr Val Ile Asp Pro Glu Pro Cys Pro Asp Ser Asp Phe Leu
            115                 120                 125

Leu Trp Ile Leu Ala Ala Val Ser Ser Gly Leu Phe Phe Tyr Ser Phe
        130                 135                 140

Leu Leu Thr Ala Val Ser Leu Ser Lys Met Leu Lys Lys Arg Ser Pro
145                 150                 155                 160

Leu Thr Thr Gly Val Tyr Val Lys Met Pro Pro Thr Glu Pro Glu Cys
                165                 170                 175

Glu Lys Gln Phe Gln Pro Tyr Phe Ile Pro Ile Asn
            180                 185
```

<210> SEQ ID NO 24
<211> LENGTH: 156
<212> TYPE: PRT
<213> ORGANISM: Homo sapiens

<400> SEQUENCE: 24

```
Leu Arg Ile Lys Val Leu Thr Gly Glu Ile Asn Gly Ser Ala Asn Tyr
1               5                   10                  15

Glu Met Phe Ile Phe His Asn Gly Gly Val Gln Ile Leu Cys Lys Tyr
                20                  25                  30

Pro Asp Ile Val Gln Gln Phe Lys Met Gln Leu Leu Lys Gly Gly Gln
            35                  40                  45

Ile Leu Cys Asp Leu Thr Lys Thr Lys Gly Ser Gly Asn Thr Val Ser
        50                  55                  60

Ile Lys Ser Leu Lys Phe Cys His Ser Gln Leu Ser Asn Asn Ser Val
65                  70                  75                  80

Ser Phe Phe Leu Tyr Asn Leu Asp His Ser His Ala Asn Tyr Tyr Phe
                85                  90                  95

Cys Asn Leu Ser Ile Phe Asp Pro Pro Pro Phe Lys Val Thr Leu Thr
                100                 105                 110

Gly Gly Tyr Leu His Ile Tyr Glu Ser Gln Leu Cys Cys Gln Leu Lys
            115                 120                 125
```

```
Phe Trp Leu Pro Ile Gly Cys Ala Ala Phe Val Val Cys Ile Leu
            130                 135                 140
Gly Cys Ile Leu Ile Cys Trp Leu Thr Lys Lys Met
145                 150                 155

<210> SEQ ID NO 25
<211> LENGTH: 6
<212> TYPE: PRT
<213> ORGANISM: Artificial sequence
<220> FEATURE:
<223> OTHER INFORMATION: Synthetic peptide

<400> SEQUENCE: 25

Val Val Leu Ala Ser Ser
1               5

<210> SEQ ID NO 26
<211> LENGTH: 6
<212> TYPE: PRT
<213> ORGANISM: Artificial sequence
<220> FEATURE:
<223> OTHER INFORMATION: Synthetic peptide

<400> SEQUENCE: 26

Met Leu Val Ala Tyr Asp
1               5

<210> SEQ ID NO 27
<211> LENGTH: 12
<212> TYPE: PRT
<213> ORGANISM: Artificial sequence
<220> FEATURE:
<223> OTHER INFORMATION: Synthetic peptide pa2

<400> SEQUENCE: 27

Phe His Lys His Ser Pro Arg Ser Pro Ile Phe Ile
1               5                   10

<210> SEQ ID NO 28
<211> LENGTH: 12
<212> TYPE: PRT
<213> ORGANISM: Artificial sequence
<220> FEATURE:
<223> OTHER INFORMATION: Synthetic peptide pb11.1

<400> SEQUENCE: 28

Ser Trp Pro His His His Arg Met Pro Leu Leu Ala
1               5                   10

<210> SEQ ID NO 29
<211> LENGTH: 12
<212> TYPE: PRT
<213> ORGANISM: Artificial sequence
<220> FEATURE:
<223> OTHER INFORMATION: Synthetic peptide pc11

<400> SEQUENCE: 29

Phe His Lys Thr Pro Arg Ile Ala Pro Pro Pro Leu
1               5                   10

<210> SEQ ID NO 30
<211> LENGTH: 12
<212> TYPE: PRT
<213> ORGANISM: Artificial sequence
<220> FEATURE:
<223> OTHER INFORMATION: Synthetic peptide pf11
```

<400> SEQUENCE: 30

His Ser Ser His His Ser His Arg Ala Pro Thr Thr
1               5                   10

<210> SEQ ID NO 31
<211> LENGTH: 12
<212> TYPE: PRT
<213> ORGANISM: Artificial sequence
<220> FEATURE:
<223> OTHER INFORMATION: Synthetic peptide pg3

<400> SEQUENCE: 31

His Asn Ser Tyr His His Gln His Lys Pro Thr Ser
1               5                   10

<210> SEQ ID NO 32
<211> LENGTH: 12
<212> TYPE: PRT
<213> ORGANISM: Artificial sequence
<220> FEATURE:
<223> OTHER INFORMATION: Synthetic peptide pb12

<400> SEQUENCE: 32

Tyr His Arg Pro His Glu His Lys Met Phe Gln Pro
1               5                   10

<210> SEQ ID NO 33
<211> LENGTH: 12
<212> TYPE: PRT
<213> ORGANISM: Artificial sequence
<220> FEATURE:
<223> OTHER INFORMATION: Synthetic peptide pa8.1

<400> SEQUENCE: 33

Ala His Lys Ala His Lys His Met Pro Trp Ile Asn
1               5                   10

<210> SEQ ID NO 34
<211> LENGTH: 12
<212> TYPE: PRT
<213> ORGANISM: Artificial sequence
<220> FEATURE:
<223> OTHER INFORMATION: Synthetic peptide pb3

<400> SEQUENCE: 34

Ala Pro Trp Thr His His Ser Lys His Ser His Pro
1               5                   10

<210> SEQ ID NO 35
<211> LENGTH: 12
<212> TYPE: PRT
<213> ORGANISM: Artificial sequence
<220> FEATURE:
<223> OTHER INFORMATION: Synthetic peptide pb5

<400> SEQUENCE: 35

Lys Pro Phe His His Asp His Ser Lys Gln His Gln
1               5                   10

<210> SEQ ID NO 36
<211> LENGTH: 12
<212> TYPE: PRT
<213> ORGANISM: Artificial sequence
<220> FEATURE:
<223> OTHER INFORMATION: Synthetic peptide pb11.2

```
<400> SEQUENCE: 36

Ala Arg Leu His Thr His Gln His Ser Asn Met Arg
1               5                   10

<210> SEQ ID NO 37
<211> LENGTH: 12
<212> TYPE: PRT
<213> ORGANISM: Artificial sequence
<220> FEATURE:
<223> OTHER INFORMATION: Synthetic peptide pf3

<400> SEQUENCE: 37

Gly Gln Thr His His His His Arg Phe Phe Gly Ser
1               5                   10

<210> SEQ ID NO 38
<211> LENGTH: 12
<212> TYPE: PRT
<213> ORGANISM: Artificial sequence
<220> FEATURE:
<223> OTHER INFORMATION: Synthetic peptide pf8

<400> SEQUENCE: 38

Ile His Lys Pro His His His Arg Thr Pro Leu Trp
1               5                   10

<210> SEQ ID NO 39
<211> LENGTH: 12
<212> TYPE: PRT
<213> ORGANISM: Artificial sequence
<220> FEATURE:
<223> OTHER INFORMATION: Synthetic peptide pe6

<400> SEQUENCE: 39

Ala Pro Met Tyr His Lys His Arg Leu Glu Lys His
1               5                   10

<210> SEQ ID NO 40
<211> LENGTH: 12
<212> TYPE: PRT
<213> ORGANISM: Artificial sequence
<220> FEATURE:
<223> OTHER INFORMATION: Synthetic peptide pf4

<400> SEQUENCE: 40

Trp His Lys Ile Pro Gln Lys Ala Pro Leu Asn Pro
1               5                   10

<210> SEQ ID NO 41
<211> LENGTH: 12
<212> TYPE: PRT
<213> ORGANISM: Artificial sequence
<220> FEATURE:
<223> OTHER INFORMATION: Synthetic peptide pa8.2

<400> SEQUENCE: 41

Tyr Pro His Ile His Thr His Arg Pro Pro Val His
1               5                   10

<210> SEQ ID NO 42
<211> LENGTH: 12
<212> TYPE: PRT
<213> ORGANISM: Artificial sequence
<220> FEATURE:
<223> OTHER INFORMATION: Synthetic peptide pb3
```

```
<400> SEQUENCE: 42

Ala Trp Asn Ser Pro His Gln His His His Arg Lys
1               5                   10

<210> SEQ ID NO 43
<211> LENGTH: 12
<212> TYPE: PRT
<213> ORGANISM: Artificial sequence
<220> FEATURE:
<223> OTHER INFORMATION: Synthetic peptide pb2

<400> SEQUENCE: 43

Trp Pro Arg His His His Ser Gly Glu Leu Lys Thr
1               5                   10

<210> SEQ ID NO 44
<211> LENGTH: 12
<212> TYPE: PRT
<213> ORGANISM: Artificial sequence
<220> FEATURE:
<223> OTHER INFORMATION: Synthetic peptide pc2

<400> SEQUENCE: 44

Ser His Trp His Ser Lys Leu Arg Tyr Phe Pro Pro
1               5                   10

<210> SEQ ID NO 45
<211> LENGTH: 12
<212> TYPE: PRT
<213> ORGANISM: Artificial sequence
<220> FEATURE:
<223> OTHER INFORMATION: Synthetic peptide pc8

<400> SEQUENCE: 45

Leu Pro His His Lys His Arg Pro Asn Leu Pro Ser
1               5                   10

<210> SEQ ID NO 46
<211> LENGTH: 12
<212> TYPE: PRT
<213> ORGANISM: Artificial sequence
<220> FEATURE:
<223> OTHER INFORMATION: Synthetic peptide pc9

<400> SEQUENCE: 46

Phe His Lys His Asn Tyr Lys Ser Pro Pro Ile Ile
1               5                   10

<210> SEQ ID NO 47
<211> LENGTH: 12
<212> TYPE: PRT
<213> ORGANISM: Artificial sequence
<220> FEATURE:
<223> OTHER INFORMATION: Synthetic peptide pf12

<400> SEQUENCE: 47

Trp Pro Met Lys His His His Leu Val Thr Ala Arg
1               5                   10

<210> SEQ ID NO 48
<211> LENGTH: 12
<212> TYPE: PRT
<213> ORGANISM: Artificial sequence
<220> FEATURE:
<223> OTHER INFORMATION: Synthetic peptide pc4
```

```
<400> SEQUENCE: 48

His Ile Lys His Leu Ser His Trp Thr Pro Lys Pro
1               5                   10

<210> SEQ ID NO 49
<211> LENGTH: 12
<212> TYPE: PRT
<213> ORGANISM: Artificial sequence
<220> FEATURE:
<223> OTHER INFORMATION: Synthetic peptide pe11.1

<400> SEQUENCE: 49

Ala His Arg His Gln His Gln His Pro His Ala Gln
1               5                   10

<210> SEQ ID NO 50
<211> LENGTH: 12
<212> TYPE: PRT
<213> ORGANISM: Artificial sequence
<220> FEATURE:
<223> OTHER INFORMATION: Synthetic peptide pb5

<400> SEQUENCE: 50

Leu Pro Trp His Arg His Gly Pro Ala Pro Ser Phe
1               5                   10

<210> SEQ ID NO 51
<211> LENGTH: 12
<212> TYPE: PRT
<213> ORGANISM: Artificial sequence
<220> FEATURE:
<223> OTHER INFORMATION: Synthetic peptide pe11.2

<400> SEQUENCE: 51

Ala Pro Trp Ser His His His Gly Lys Leu Pro Arg
1               5                   10

<210> SEQ ID NO 52
<211> LENGTH: 12
<212> TYPE: PRT
<213> ORGANISM: Artificial sequence
<220> FEATURE:
<223> OTHER INFORMATION: Synthetic peptide pg7

<400> SEQUENCE: 52

Gly Leu Trp His Ala Pro His Pro Ala His Arg His
1               5                   10

<210> SEQ ID NO 53
<211> LENGTH: 12
<212> TYPE: PRT
<213> ORGANISM: Artificial sequence
<220> FEATURE:
<223> OTHER INFORMATION: Synthetic peptide pa12

<400> SEQUENCE: 53

Thr Gln Gly His His His His Arg His Pro Arg Ile
1               5                   10

<210> SEQ ID NO 54
<211> LENGTH: 12
<212> TYPE: PRT
<213> ORGANISM: Artificial sequence
<220> FEATURE:
<223> OTHER INFORMATION: Synthetic peptide pb8
```

```
<400> SEQUENCE: 54

Ser Pro His Asn His Thr His Lys Pro Lys Ser
1               5                   10

<210> SEQ ID NO 55
<211> LENGTH: 12
<212> TYPE: PRT
<213> ORGANISM: Artificial sequence
<220> FEATURE:
<223> OTHER INFORMATION: Synthetic peptide pb12

<400> SEQUENCE: 55

Leu Pro Met Lys His Ser Trp His Ser His Thr Leu
1               5                   10

<210> SEQ ID NO 56
<211> LENGTH: 12
<212> TYPE: PRT
<213> ORGANISM: Artificial sequence
<220> FEATURE:
<223> OTHER INFORMATION: Synthetic peptide pc8

<400> SEQUENCE: 56

Ala Val Lys His His Tyr His Arg His Pro Ile Ile
1               5                   10

<210> SEQ ID NO 57
<211> LENGTH: 12
<212> TYPE: PRT
<213> ORGANISM: Artificial sequence
<220> FEATURE:
<223> OTHER INFORMATION: Synthetic peptide pd8

<400> SEQUENCE: 57

Thr His Pro His Leu His His Arg His Leu Ala Pro
1               5                   10

<210> SEQ ID NO 58
<211> LENGTH: 12
<212> TYPE: PRT
<213> ORGANISM: Artificial sequence
<220> FEATURE:
<223> OTHER INFORMATION: Synthetic peptide pg6

<400> SEQUENCE: 58

Gly Lys Met His Leu His His Pro His Ser Gln Pro
1               5                   10

<210> SEQ ID NO 59
<211> LENGTH: 9
<212> TYPE: PRT
<213> ORGANISM: Artificial Sequence
<220> FEATURE:
<223> OTHER INFORMATION: Synthetic Peptide p1TD

<400> SEQUENCE: 59

Arg Val Thr Glu Arg Arg Ala Glu Val
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Peptide p2TD
```

<400> SEQUENCE: 60

Pro Ala Leu Leu Val Val Thr Glu
1               5

<210> SEQ ID NO 61
<211> LENGTH: 255
<212> TYPE: PRT
<213> ORGANISM: Homo sapiens

<400> SEQUENCE: 61

Pro Pro Thr Phe Phe Pro Ala Leu Leu Val Val Thr Glu Gly Asp Asn
1               5                   10                  15

Ala Thr Phe Thr Cys Ser Phe Ser Asn Thr Ser Glu Ser Phe Val Leu
            20                  25                  30

Asn Trp Tyr Arg Met Ser Pro Ser Asn Gln Thr Asp Lys Leu Ala Ala
        35                  40                  45

Phe Pro Glu Asp Arg Ser Gln Pro Gly Gln Asp Cys Arg Phe Arg Val
    50                  55                  60

Thr Gln Leu Pro Asn Gly Arg Asp Phe His Met Ser Val Val Arg Ala
65                  70                  75                  80

Arg Arg Asn Asp Ser Gly Thr Tyr Leu Cys Gly Ala Ile Ser Leu Ala
                85                  90                  95

Pro Lys Ala Gln Ile Lys Glu Ser Leu Arg Ala Glu Leu Arg Val Thr
            100                 105                 110

Glu Arg Arg Ala Glu Val Pro Thr Ala His Pro Ser Pro Ser Pro Arg
        115                 120                 125

Pro Ala Gly Gln Phe Gln Thr Leu Val Val Gly Val Val Gly Gly Leu
    130                 135                 140

Leu Gly Ser Leu Val Leu Leu Val Trp Val Leu Ala Val Ile Cys Ser
145                 150                 155                 160

Arg Ala Ala Arg Gly Thr Ile Gly Ala Arg Arg Thr Gly Gln Pro Leu
                165                 170                 175

Lys Glu Asp Pro Ser Ala Val Pro Val Phe Ser Val Asp Tyr Gly Glu
            180                 185                 190

Leu Asp Phe Gln Trp Arg Glu Lys Thr Pro Glu Pro Pro Val Pro Cys
        195                 200                 205

Val Pro Glu Gln Thr Glu Tyr Ala Thr Ile Val Phe Pro Ser Gly Met
    210                 215                 220

Gly Thr Ser Ser Pro Ala Arg Arg Gly Ser Ala Asp Gly Pro Arg Ser
225                 230                 235                 240

Ala Gln Pro Leu Arg Pro Glu Asp Gly His Cys Ser Trp Pro Leu
                245                 250                 255

<210> SEQ ID NO 62
<211> LENGTH: 14
<212> TYPE: PRT
<213> ORGANISM: Artificial Sequence
<220> FEATURE:
<223> OTHER INFORMATION: Sequence of artificial peptide p12C

<400> SEQUENCE: 62

Cys Tyr Asn Lys Lys Ala Thr Val Gln Glu Leu Asp Cys
1               5                   10

<210> SEQ ID NO 63
<211> LENGTH: 14
<212> TYPE: PRT
<213> ORGANISM: Artificial Sequence

```
<220> FEATURE:
<223> OTHER INFORMATION: Sequence of artificial peptide p12Csc

<400> SEQUENCE: 63

Cys Glu Lys Ala Lys Tyr Thr Gln Leu Val Lys Asp Asn Cys
1               5                   10

<210> SEQ ID NO 64
<211> LENGTH: 127
<212> TYPE: PRT
<213> ORGANISM: murine
<220> FEATURE:
<221> NAME/KEY: misc_feature
<223> OTHER INFORMATION: mCD28

<400> SEQUENCE: 64

Asn Lys Ile Leu Val Lys Gln Ser Pro Leu Leu Val Val Asp Ser Asn
1               5                   10                  15

Glu Val Ser Leu Ser Cys Arg Tyr Ser Tyr Asn Leu Leu Ala Lys Glu
            20                  25                  30

Phe Arg Ala Ser Leu Tyr Lys Gly Val Asn Ser Asp Val Glu Val Cys
        35                  40                  45

Val Gly Asn Gly Asn Phe Thr Tyr Gln Pro Gln Phe Arg Ser Asn Ala
    50                  55                  60

Glu Phe Asn Cys Asp Gly Asp Phe Asp Asn Glu Thr Val Thr Phe Arg
65                  70                  75                  80

Leu Trp Asn Leu His Val Asn His Thr Asp Ile Tyr Phe Cys Lys Ile
                85                  90                  95

Glu Phe Met Tyr Pro Pro Pro Tyr Leu Asp Asn Glu Arg Ser Asn Gly
            100                 105                 110

Thr Ile Ile His Ile Lys Glu Lys His Leu Cys His Thr Gln Ser
        115                 120                 125

<210> SEQ ID NO 65
<211> LENGTH: 126
<212> TYPE: PRT
<213> ORGANISM: murine
<220> FEATURE:
<221> NAME/KEY: misc_feature
<223> OTHER INFORMATION: mCTLA4

<400> SEQUENCE: 65

Glu Ala Ile Gln Val Thr Gln Pro Ser Val Val Leu Ala Ser Ser His
1               5                   10                  15

Gly Val Ala Ser Phe Pro Cys Glu Tyr Ser Pro Ser His Asn Thr Asp
            20                  25                  30

Glu Val Arg Val Thr Val Leu Arg Gln Thr Asn Asp Gln Met Thr Glu
        35                  40                  45

Val Cys Ala Thr Thr Phe Thr Glu Lys Asn Thr Val Gly Phe Leu Asp
    50                  55                  60

Tyr Pro Phe Cys Ser Gly Thr Phe Asn Glu Ser Arg Val Asn Leu Thr
65                  70                  75                  80

Ile Gln Gly Leu Arg Ala Val Asp Thr Gly Leu Tyr Leu Cys Lys Val
                85                  90                  95

Glu Leu Met Tyr Pro Pro Pro Tyr Phe Val Gly Met Gly Asn Gly Thr
            100                 105                 110

Gln Ile Tyr Val Ile Asp Pro Glu Pro Cys Pro Asp Ser Asp
        115                 120                 125
```

```
<210> SEQ ID NO 66
<211> LENGTH: 130
<212> TYPE: PRT
<213> ORGANISM: murine
<220> FEATURE:
<221> NAME/KEY: misc_feature
<223> OTHER INFORMATION: mICOS

<400> SEQUENCE: 66

Phe Leu Ile Arg Leu Leu Thr Gly Ile Asn Gly Ser Ala Asp His Arg
1               5                   10                  15

Met Phe Ser Phe His Asn Gly Gly Val Gln Ile Ser Cys Lys Tyr Pro
            20                  25                  30

Glu Thr Val Gln Gln Leu Lys Met Arg Leu Phe Arg Glu Arg Glu Val
            35                  40                  45

Leu Cys Glu Leu Thr Lys Thr Lys Gly Ser Gly Asn Ala Val Ser Ile
    50                  55                  60

Lys Asn Pro Met Leu Cys Leu Tyr His Leu Ser Asn Asn Ser Val Ser
65                  70                  75                  80

Phe Phe Leu Asn Asn Pro Asp Ser Ser Gln Gly Ser Tyr Tyr Phe Cys
                85                  90                  95

Ser Leu Ser Ile Phe Asp Pro Pro Phe Gln Glu Arg Asn Leu Ser
            100                 105                 110

Gly Gly Tyr Leu His Ile Tyr Glu Ser Gln Leu Cys Cys Gln Leu Lys
            115                 120                 125

Leu Trp
    130
```